(12) United States Patent
Handique et al.

(10) Patent No.: US 9,040,288 B2
(45) Date of Patent: *May 26, 2015

(54) INTEGRATED SYSTEM FOR PROCESSING MICROFLUIDIC SAMPLES, AND METHOD OF USING THE SAME

(75) Inventors: Kalyan Handique, Ypsilanti, MI (US); Sundaresh N. Brahmasandra, Ann Arbor, MI (US); Karthik Ganesan, Ann Arbor, MI (US); Betty Wu, Canton, MI (US); Nikhil Phadke, Ann Arbor, MI (US); Gene Parunak, Saline, MI (US); Jeff Williams, Chelsea, MI (US)

(73) Assignee: HandyLab, Inc., Franklin Lakes, NJ (US)

( * ) Notice: Subject to any disclaimer, the term of this patent is extended or adjusted under 35 U.S.C. 154(b) by 932 days.

This patent is subject to a terminal disclaimer.

(21) Appl. No.: 11/728,964

(22) Filed: Mar. 26, 2007

(65) Prior Publication Data
US 2007/0292941 A1    Dec. 20, 2007

Related U.S. Application Data

(60) Provisional application No. 60/786,007, filed on Mar. 24, 2006, provisional application No. 60/859,284, filed on Nov. 14, 2006.

(51) Int. Cl.
C12M 1/00      (2006.01)
C12M 1/34      (2006.01)
(Continued)

(52) U.S. Cl.
CPC ......... B01L 3/5027 (2013.01); B01L 3/502715 (2013.01); B01L 3/50273 (2013.01);
(Continued)

(58) Field of Classification Search
CPC .................. B01L 2200/027; B01L 2300/021; B01L 2300/1827; B01L 3/502715; B01L 3/502738; B01L 7/52; B01L 9/527; B01L 2200/10; B01L 2200/147; B01L 2300/0816; B01L 2300/0867; B01L 2300/087; B01L 2300/0887; B01L 2300/1822; B01L 2200/025; B01L 2300/046; B01L 2300/0861; B01L 2300/1805; B01L 3/5027; C12Q 1/686; C12Q 2565/629; F16K 2099/0084; G01N 2035/00881; G01N 21/6428; H05B 3/02; H05B 3/22
USPC ................. 435/6, 285.1–285.2, 287.1–287.3, 435/288.5–288.7, 303.1
See application file for complete search history.

(56) References Cited

U.S. PATENT DOCUMENTS 1,434,314 A    10/1922    Raich
1,616,419 A     2/1927    Wilson
(Continued)

FOREIGN PATENT DOCUMENTS

CA    2294819    1/1999
DE    19929734   12/1999
(Continued)

OTHER PUBLICATIONS

Handylab, Inc., International Search Report and the Written Opinion of PCT/US2007/07513 dated Apr. 4, 2008, 11 pages.
(Continued)

*Primary Examiner* — Michael Marcheschi
*Assistant Examiner* — Shanta G Doe
(74) *Attorney, Agent, or Firm* — Knobbe, Martens, Olson & Bear, LLP

(57) ABSTRACT

This patent application describes an integrated apparatus for processing polynucleotide-containing samples, and for providing a diagnostic result thereon. The apparatus is configured to receive a microfluidic cartridge that contains reagents and a network for processing a sample. Also described are methods of using the apparatus.

52 Claims, 78 Drawing Sheets

(51) Int. Cl.
*C12M 3/00* (2006.01)
*B01L 3/00* (2006.01)
*B01L 9/00* (2006.01)
*F16K 99/00* (2006.01)
*B01L 7/00* (2006.01)
*G01N 35/00* (2006.01)

(52) U.S. Cl.
CPC .............. *B01L3/502738* (2013.01); *B01L 7/52* (2013.01); *B01L 9/527* (2013.01); *B01L 2200/027* (2013.01); *B01L 2200/10* (2013.01); *B01L 2200/147* (2013.01); *B01L 2200/148* (2013.01); *B01L 2200/16* (2013.01); *B01L 2300/021* (2013.01); *B01L 2300/0681* (2013.01); *B01L 2300/0816* (2013.01); *B01L 2300/0867* (2013.01); *B01L 2300/087* (2013.01); *B01L 2300/0887* (2013.01); *B01L 2300/1827* (2013.01); *B01L 2300/1861* (2013.01); *B01L 2400/0442* (2013.01); *B01L 2400/0481* (2013.01); *B01L 2400/0487* (2013.01); *B01L 2400/0611* (2013.01); *B01L 2400/0677* (2013.01); *B01L 2400/0683* (2013.01); *F16K 99/0001* (2013.01); *F16K 99/003* (2013.01); *F16K 99/0032* (2013.01); *F16K 99/0044* (2013.01); *F16K 99/0061* (2013.01); *F16K 2099/0084* (2013.01); *G01N 2035/00881* (2013.01)

(56) References Cited

U.S. PATENT DOCUMENTS

| | | | |
|---|---|---|---|
| 1,733,401 A | 8/1930 | Lovekin | |
| D189,404 S | 12/1960 | Nicolle | |
| 3,528,449 A | 9/1970 | Witte et al. | |
| 3,813,316 A | 5/1974 | Chakrabarty et al. | |
| 3,985,649 A | 10/1976 | Eddelman | |
| 4,018,089 A | 4/1977 | Dzula et al. | |
| 4,018,652 A | 4/1977 | Lanham et al. | |
| 4,038,192 A | 7/1977 | Serur | |
| 4,055,395 A * | 10/1977 | Honkawa et al. | 422/82.09 |
| D249,706 S | 9/1978 | Adamski | |
| 4,139,005 A | 2/1979 | Dickey | |
| D252,157 S | 6/1979 | Kronish et al. | |
| D252,341 S | 7/1979 | Thomas | |
| D254,687 S | 4/1980 | Fadler et al. | |
| 4,212,744 A | 7/1980 | Oota | |
| D261,033 S | 9/1981 | Armbruster | |
| D261,173 S | 10/1981 | Armbruster | |
| 4,301,412 A | 11/1981 | Hill et al. | |
| 4,439,526 A | 3/1984 | Columbus | |
| 4,457,329 A | 7/1984 | Werley et al. | |
| 4,466,740 A | 8/1984 | Kano et al. | |
| 4,504,582 A | 3/1985 | Swann | |
| 4,522,786 A | 6/1985 | Ebersole | |
| D279,817 S | 7/1985 | Chen et al. | |
| D282,208 S | 1/1986 | Lowry | |
| 4,599,315 A | 7/1986 | Teraski et al. | |
| 4,612,873 A | 9/1986 | Eberle | |
| 4,612,959 A | 9/1986 | Costello | |
| D288,478 S | 2/1987 | Carlson et al. | |
| 4,647,432 A | 3/1987 | Wakatake | |
| 4,654,127 A | 3/1987 | Baker et al. | |
| 4,673,657 A | 6/1987 | Christian | |
| 4,683,195 A | 7/1987 | Mullis et al. | |
| 4,683,202 A | 7/1987 | Mullis | |
| D292,735 S | 11/1987 | Lovborg | |
| 4,720,374 A | 1/1988 | Ramachandran | |
| 4,724,207 A | 2/1988 | Hou et al. | |
| 4,798,693 A | 1/1989 | Mase et al. | |
| 4,800,022 A | 1/1989 | Leonard | |
| 4,841,786 A | 6/1989 | Schulz | |
| D302,294 S | 7/1989 | Hillman | |
| 4,871,779 A | 10/1989 | Killat et al. | |
| 4,895,650 A | 1/1990 | Wang | |
| 4,919,829 A | 4/1990 | Gates et al. | |
| 4,921,809 A | 5/1990 | Shiff et al. | |
| 4,935,342 A | 6/1990 | Seligson et al. | |
| 4,946,562 A | 8/1990 | Guruswamy | |
| 4,949,742 A | 8/1990 | Rando et al. | |
| D310,413 S | 9/1990 | Bigler et al. | |
| 4,963,498 A | 10/1990 | Hillman | |
| 4,967,950 A | 11/1990 | Legg et al. | |
| D312,692 S | 12/1990 | Bradley | |
| 4,978,502 A | 12/1990 | Dole et al. | |
| 4,978,622 A | 12/1990 | Mishell et al. | |
| 4,989,626 A | 2/1991 | Takagi et al. | |
| 5,001,417 A | 3/1991 | Pumphrey et al. | |
| 5,004,583 A | 4/1991 | Guruswamy et al. | |
| 5,048,554 A | 9/1991 | Kremer | |
| 5,053,199 A | 10/1991 | Keiser et al. | |
| 5,060,823 A | 10/1991 | Perlman | |
| 5,061,336 A | 10/1991 | Soane | |
| 5,064,618 A | 11/1991 | Baker et al. | |
| 5,071,531 A | 12/1991 | Soane | |
| 5,091,328 A | 2/1992 | Miller | |
| D324,426 S | 3/1992 | Fan et al. | |
| 5,096,669 A | 3/1992 | Lauks et al. | |
| D325,638 S | 4/1992 | Sloat et al. | |
| 5,126,002 A | 6/1992 | Iwata et al. | |
| 5,126,022 A | 6/1992 | Soane et al. | |
| D328,135 S | 7/1992 | Fan et al. | |
| D328,794 S | 8/1992 | Frenkel et al. | |
| 5,135,627 A | 8/1992 | Soane | |
| 5,135,872 A | 8/1992 | Pouletty et al. | |
| 5,147,606 A | 9/1992 | Charlton et al. | |
| 5,169,512 A | 12/1992 | Wiedenmann et al. | |
| D333,522 S | 2/1993 | Gianino | |
| 5,186,339 A | 2/1993 | Heissler | |
| 5,192,507 A | 3/1993 | Taylor et al. | |
| 5,208,163 A | 5/1993 | Charlton et al. | |
| 5,223,226 A | 6/1993 | Wittmer et al. | |
| D338,275 S | 8/1993 | Fischer et al. | |
| 5,250,263 A | 10/1993 | Manz | |
| 5,252,743 A | 10/1993 | Barrett et al. | |
| 5,256,376 A | 10/1993 | Callan et al. | |
| 5,275,787 A | 1/1994 | Yuguchi et al. | |
| 5,282,950 A | 2/1994 | Dietze et al. | |
| 5,296,375 A | 3/1994 | Kricka et al. | |
| 5,304,477 A | 4/1994 | Nagoh et al. | |
| 5,304,487 A | 4/1994 | Wilding et al. | |
| D347,478 S | 5/1994 | Pinkney | |
| 5,311,896 A | 5/1994 | Kaartinen | |
| 5,311,996 A | 5/1994 | Duffy et al. | |
| 5,316,727 A | 5/1994 | Suzuki et al. | |
| 5,327,038 A | 7/1994 | Culp | |
| 5,339,486 A | 8/1994 | Persic, Jr. | |
| D351,475 S | 10/1994 | Gerber | |
| D351,913 S | 10/1994 | Hieb et al. | |
| 5,364,591 A | 11/1994 | Green et al. | |
| 5,372,946 A | 12/1994 | Cusak et al. | |
| 5,374,395 A | 12/1994 | Robinson | |
| 5,389,339 A | 2/1995 | Petschek et al. | |
| D356,232 S | 3/1995 | Armstrong et al. | |
| 5,397,709 A | 3/1995 | Berndt | |
| 5,401,465 A | 3/1995 | Smethers et al. | |
| 5,411,708 A | 5/1995 | Moscetta et al. | |
| 5,414,245 A | 5/1995 | Hackleman | |
| 5,416,000 A | 5/1995 | Allen et al. | |
| 5,422,271 A | 6/1995 | Chen et al. | |
| 5,422,284 A | 6/1995 | Lau | |
| 5,427,946 A | 6/1995 | Kricka et al. | |
| 5,443,791 A | 8/1995 | Cathcart et al. | |
| 5,474,796 A | 12/1995 | Brennan | |
| D366,116 S | 1/1996 | Biskupski | |
| 5,486,335 A | 1/1996 | Wilding et al. | |
| 5,494,639 A | 2/1996 | Grzegorzewski | |
| 5,498,392 A | 3/1996 | Wilding et al. | |
| 5,503,803 A | 4/1996 | Brown | |
| 5,516,410 A | 5/1996 | Schneider et al. | |
| 5,519,635 A | 5/1996 | Miyake et al. | |
| 5,529,677 A | 6/1996 | Schneider et al. | |

(56) References Cited

U.S. PATENT DOCUMENTS

| | | |
|---|---|---|
| 5,559,432 A | 9/1996 | Logue |
| 5,565,171 A | 10/1996 | Dovichi et al. |
| 5,569,364 A | 10/1996 | Hooper et al. |
| 5,578,270 A | 11/1996 | Reichler et al. |
| 5,578,818 A | 11/1996 | Kain et al. |
| 5,579,928 A | 12/1996 | Anukwuem |
| 5,580,523 A | 12/1996 | Bard |
| 5,582,884 A | 12/1996 | Ball et al. |
| 5,585,069 A | 12/1996 | Zanucchi et al. |
| 5,585,089 A | 12/1996 | Queen et al. |
| 5,585,242 A | 12/1996 | Bouma et al. |
| 5,587,128 A | 12/1996 | Wilding et al. |
| 5,589,136 A | 12/1996 | Northrup et al. |
| 5,593,838 A | 1/1997 | Zanzucchi et al. |
| 5,595,708 A | 1/1997 | Berndt |
| 5,599,432 A | 2/1997 | Manz et al. |
| 5,599,503 A | 2/1997 | Manz et al. |
| 5,599,667 A | 2/1997 | Arnold, Jr. et al. |
| 5,601,727 A | 2/1997 | Bormann et al. |
| 5,603,351 A | 2/1997 | Cherukuri et al. |
| 5,605,662 A | 2/1997 | Heller et al. |
| D378,782 S | 4/1997 | LaBarbera et al. |
| 5,628,890 A | 5/1997 | Carter et al. |
| 5,630,920 A | 5/1997 | Friese et al. |
| 5,631,337 A | 5/1997 | Sassi et al. |
| 5,632,876 A | 5/1997 | Zanzucchi et al. |
| 5,632,957 A | 5/1997 | Heller et al. |
| 5,635,358 A | 6/1997 | Wilding et al. |
| 5,637,469 A | 6/1997 | Wilding et al. |
| 5,639,423 A | 6/1997 | Northrup et al. |
| 5,643,738 A | 7/1997 | Zanzucchi et al. |
| 5,646,039 A | 7/1997 | Northrup et al. |
| 5,646,049 A | 7/1997 | Tayi |
| 5,647,994 A | 7/1997 | Tuunanen et al. |
| 5,651,839 A | 7/1997 | Rauf |
| 5,652,141 A | 7/1997 | Henco et al. |
| 5,652,149 A | 7/1997 | Mileaf et al. |
| D382,346 S | 8/1997 | Buhler et al. |
| D382,647 S | 8/1997 | Staples et al. |
| 5,667,976 A | 9/1997 | Van Ness et al. |
| 5,671,303 A | 9/1997 | Shieh et al. |
| 5,674,394 A | 10/1997 | Whitmore |
| 5,674,742 A | 10/1997 | Northrup et al. |
| 5,681,484 A | 10/1997 | Zanzucchi et al. |
| 5,681,529 A | 10/1997 | Taguchi et al. |
| 5,683,657 A | 11/1997 | Mian |
| 5,699,157 A | 12/1997 | Parce |
| 5,700,637 A | 12/1997 | Southern |
| 5,705,813 A | 1/1998 | Apffel et al. |
| 5,726,026 A | 3/1998 | Wilding et al. |
| 5,726,404 A | 3/1998 | Brody |
| 5,726,944 A | 3/1998 | Taft et al. |
| 5,731,212 A | 3/1998 | Gavin et al. |
| 5,744,366 A | 4/1998 | Kricka et al. |
| 5,747,666 A | 5/1998 | Willis |
| 5,750,015 A | 5/1998 | Soane et al. |
| 5,755,942 A | 5/1998 | Zanzucchi et al. |
| 5,763,262 A | 6/1998 | Wong et al. |
| 5,770,029 A | 6/1998 | Nelson et al. |
| 5,770,388 A | 6/1998 | Vorpahl |
| 5,772,966 A | 6/1998 | Maracas et al. |
| 5,779,868 A | 7/1998 | Parce et al. |
| 5,787,032 A | 7/1998 | Heller et al. |
| 5,788,814 A | 8/1998 | Sun et al. |
| 5,800,600 A | 9/1998 | Lima-Marques et al. |
| 5,800,690 A | 9/1998 | Chow et al. |
| 5,804,436 A | 9/1998 | Okun et al. |
| D399,959 S | 10/1998 | Prokop et al. |
| 5,827,481 A | 10/1998 | Bente et al. |
| 5,842,106 A | 11/1998 | Thaler et al. |
| 5,842,787 A | 12/1998 | Kopf-Sill et al. |
| 5,846,396 A | 12/1998 | Zanzucchi et al. |
| 5,846,493 A | 12/1998 | Bankier et al. |
| 5,849,208 A | 12/1998 | Hayes et al. |
| 5,849,486 A | 12/1998 | Heller et al. |
| 5,849,489 A | 12/1998 | Heller |
| 5,849,598 A | 12/1998 | Wilson et al. |
| 5,852,495 A | 12/1998 | Parce |
| 5,856,174 A | 1/1999 | Lipshutz et al. |
| 5,858,187 A | 1/1999 | Ramsey et al. |
| 5,858,188 A | 1/1999 | Soane et al. |
| 5,863,502 A | 1/1999 | Southgate et al. |
| 5,863,708 A | 1/1999 | Zanzucchi et al. |
| 5,863,801 A | 1/1999 | Southgate et al. |
| 5,866,345 A | 2/1999 | Wilding et al. |
| 5,869,004 A | 2/1999 | Parce et al. |
| 5,869,244 A | 2/1999 | Martin et al. |
| 5,872,010 A | 2/1999 | Karger et al. |
| 5,872,623 A | 2/1999 | Stabile et al. |
| 5,874,046 A | 2/1999 | Megerle |
| 5,876,675 A | 3/1999 | Kennedy |
| 5,880,071 A | 3/1999 | Parce et al. |
| 5,882,465 A | 3/1999 | McReynolds |
| 5,883,211 A | 3/1999 | Sassi et al. |
| 5,885,432 A | 3/1999 | Hooper et al. |
| 5,885,470 A | 3/1999 | Parce et al. |
| 5,895,762 A | 4/1999 | Greenfield et al. |
| 5,900,130 A | 5/1999 | Benregnu et al. |
| 5,912,124 A | 6/1999 | Kumar |
| 5,912,134 A | 6/1999 | Shartle |
| 5,916,522 A | 6/1999 | Boyd et al. |
| 5,916,776 A | 6/1999 | Kumar |
| 5,919,646 A | 7/1999 | Okun et al. |
| 5,919,711 A | 7/1999 | Boyd et al. |
| 5,922,591 A | 7/1999 | Anderson et al. |
| 5,927,547 A | 7/1999 | Papen et al. |
| 5,928,880 A | 7/1999 | Wilding et al. |
| 5,929,208 A | 7/1999 | Heller et al. |
| D413,391 S | 8/1999 | Lapeus et al. |
| 5,932,799 A | 8/1999 | Moles |
| 5,935,401 A | 8/1999 | Amigo |
| 5,939,291 A | 8/1999 | Loewy et al. |
| 5,942,443 A | 8/1999 | Parce et al. |
| D413,677 S | 9/1999 | Dumitrescu et al. |
| 5,948,227 A | 9/1999 | Dubrow |
| 5,955,028 A | 9/1999 | Chow |
| 5,955,029 A | 9/1999 | Wilding et al. |
| 5,957,579 A | 9/1999 | Kopf-Sill et al. |
| 5,958,203 A | 9/1999 | Parce et al. |
| 5,958,694 A | 9/1999 | Nikiforov |
| 5,959,221 A | 9/1999 | Boyd et al. |
| 5,959,291 A | 9/1999 | Jensen |
| 5,964,995 A | 10/1999 | Nikiforov et al. |
| 5,964,997 A | 10/1999 | McBride |
| 5,965,001 A | 10/1999 | Chow et al. |
| 5,965,410 A | 10/1999 | Chow et al. |
| 5,965,886 A | 10/1999 | Sauer et al. |
| 5,968,745 A | 10/1999 | Thorp et al. |
| 5,972,187 A | 10/1999 | Parce et al. |
| D417,009 S | 11/1999 | Boyd |
| 5,976,336 A | 11/1999 | Dubrow et al. |
| 5,980,704 A | 11/1999 | Cherukuri et al. |
| 5,980,719 A | 11/1999 | Cherukuri et al. |
| 5,981,735 A | 11/1999 | Thatcher et al. |
| 5,989,402 A | 11/1999 | Chow et al. |
| 5,992,820 A | 11/1999 | Fare et al. |
| 5,993,611 A | 11/1999 | Moroney, III et al. |
| 5,993,750 A | 11/1999 | Ghosh et al. |
| 5,997,708 A | 12/1999 | Craig |
| 6,001,229 A | 12/1999 | Ramsey |
| 6,001,231 A | 12/1999 | Kopf-Sill |
| 6,001,307 A | 12/1999 | Naka et al. |
| 6,004,515 A | 12/1999 | Parce et al. |
| 6,007,690 A | 12/1999 | Nelson et al. |
| 6,010,607 A | 1/2000 | Ramsey |
| 6,010,608 A | 1/2000 | Ramsey |
| 6,010,627 A | 1/2000 | Hood, III |
| 6,012,902 A | 1/2000 | Parce |
| D420,747 S | 2/2000 | Dumitrescu et al. |
| D421,130 S | 2/2000 | Cohen et al. |
| 6,024,920 A | 2/2000 | Cunanan |
| D421,653 S | 3/2000 | Purcell |
| 6,033,546 A | 3/2000 | Ramsey |
| 6,043,080 A | 3/2000 | Lipshutz et al. |

(56) References Cited

U.S. PATENT DOCUMENTS

| | | | |
|---|---|---|---|
| 6,046,056 A | 4/2000 | Parce et al. |
| 6,048,734 A | 4/2000 | Burns et al. |
| 6,054,034 A | 4/2000 | Soane et al. |
| 6,054,277 A | 4/2000 | Furcht et al. |
| 6,056,860 A | 5/2000 | Amigo et al. |
| 6,057,149 A | 5/2000 | Burns et al. |
| 6,062,261 A | 5/2000 | Jacobson et al. |
| 6,063,341 A | 5/2000 | Fassbind et al. |
| 6,063,589 A | 5/2000 | Kellogg et al. |
| 6,068,752 A | 5/2000 | Dubrow et al. |
| 6,071,478 A | 6/2000 | Chow |
| 6,074,725 A | 6/2000 | Kennedy |
| 6,074,827 A | 6/2000 | Nelson et al. |
| D428,497 S | 7/2000 | Lapeus et al. |
| 6,086,740 A | 7/2000 | Kennedy |
| 6,096,509 A | 8/2000 | Okun et al. |
| 6,100,541 A | 8/2000 | Nagle et al. |
| 6,102,897 A | 8/2000 | Lang |
| 6,103,537 A | 8/2000 | Ullman et al. |
| 6,106,685 A | 8/2000 | McBride et al. |
| 6,110,343 A | 8/2000 | Ramsey et al. |
| 6,123,205 A | 9/2000 | Dumitrescu et al. |
| 6,123,798 A | 9/2000 | Gandhi et al. |
| 6,130,098 A | 10/2000 | Handique et al. |
| 6,132,580 A | 10/2000 | Mathies et al. |
| 6,132,684 A | 10/2000 | Marino |
| 6,133,436 A | 10/2000 | Koster et al. |
| D433,759 S | 11/2000 | Mathis et al. |
| 6,143,250 A | 11/2000 | Tajima |
| 6,149,787 A | 11/2000 | Chow et al. |
| 6,156,199 A | 12/2000 | Zuk, Jr. |
| 6,158,269 A | 12/2000 | Dorenkott et al. |
| 6,167,910 B1 | 1/2001 | Chow |
| 6,168,948 B1 | 1/2001 | Anderson et al. |
| 6,171,850 B1 | 1/2001 | Nagle et al. |
| 6,174,675 B1 | 1/2001 | Chow et al. |
| 6,180,950 B1 | 1/2001 | Olsen |
| D438,311 S | 2/2001 | Yamanishi et al. |
| D438,632 S | 3/2001 | Miller |
| D438,633 S | 3/2001 | Miller |
| D439,673 S | 3/2001 | Brophy et al. |
| 6,197,595 B1 | 3/2001 | Anderson et al. |
| 6,211,989 B1 | 4/2001 | Wulf et al. |
| 6,213,151 B1 | 4/2001 | Jacobson et al. |
| 6,221,600 B1 | 4/2001 | MacLeod et al. |
| 6,228,635 B1 * | 5/2001 | Armstrong et al. ........ 435/286.5 |
| 6,232,072 B1 | 5/2001 | Fisher |
| 6,235,175 B1 | 5/2001 | Dubrow et al. |
| 6,235,313 B1 | 5/2001 | Mathiowitz et al. |
| 6,235,471 B1 | 5/2001 | Knapp et al. |
| 6,236,456 B1 | 5/2001 | Giebeler et al. |
| 6,236,581 B1 | 5/2001 | Lines et al. |
| 6,238,626 B1 | 5/2001 | Higuchi et al. |
| 6,251,343 B1 | 6/2001 | Dubrow et al. |
| 6,254,826 B1 | 7/2001 | Acosta et al. |
| 6,259,635 B1 | 7/2001 | Torelli et al. |
| 6,261,431 B1 | 7/2001 | Mathies et al. |
| 6,267,858 B1 | 7/2001 | Parce et al. |
| D446,306 S | 8/2001 | Ochi et al. |
| 6,271,021 B1 | 8/2001 | Burns et al. |
| 6,274,089 B1 | 8/2001 | Chow et al. |
| 6,280,967 B1 | 8/2001 | Ransom et al. |
| 6,281,008 B1 | 8/2001 | Komai et al. |
| 6,284,113 B1 | 9/2001 | Bjornson et al. |
| 6,287,254 B1 | 9/2001 | Dodds |
| 6,287,774 B1 | 9/2001 | Kikiforov |
| 6,291,248 B1 | 9/2001 | Haj-Ahmad |
| 6,294,063 B1 | 9/2001 | Becker et al. |
| 6,302,134 B1 | 10/2001 | Kellogg et al. |
| 6,302,304 B1 | 10/2001 | Spencer |
| 6,303,343 B1 | 10/2001 | Kopf-sill |
| 6,306,273 B1 | 10/2001 | Wainright et al. |
| 6,306,590 B1 | 10/2001 | Mehta et al. |
| 6,319,469 B1 | 11/2001 | Mian et al. |
| 6,322,683 B1 | 11/2001 | Wolk et al. |
| 6,326,083 B1 | 12/2001 | Yang et al. |
| 6,326,147 B1 | 12/2001 | Oldham et al. |
| 6,326,211 B1 | 12/2001 | Anderson et al. |
| 6,334,980 B1 | 1/2002 | Hayes et al. |
| 6,337,435 B1 | 1/2002 | Chu et al. |
| 6,353,475 B1 | 3/2002 | Jensen et al. |
| 6,358,387 B1 | 3/2002 | Kopf-sill et al. |
| 6,366,924 B1 | 4/2002 | Parce |
| 6,368,871 B1 | 4/2002 | Christel et al. |
| 6,370,206 B1 | 4/2002 | Schenk |
| 6,375,185 B1 | 4/2002 | Lin |
| 6,375,901 B1 | 4/2002 | Robotti et al. |
| 6,379,884 B2 | 4/2002 | Wada et al. |
| 6,379,929 B1 | 4/2002 | Burns et al. |
| 6,379,974 B1 | 4/2002 | Parce et al. |
| 6,382,254 B1 | 5/2002 | Yang et al. |
| 6,391,541 B1 | 5/2002 | Petersen et al. |
| 6,391,623 B1 | 5/2002 | Besemer et al. |
| 6,395,161 B1 | 5/2002 | Schneider et al. |
| 6,398,956 B1 | 6/2002 | Coville et al. |
| 6,399,025 B1 | 6/2002 | Chow |
| 6,399,389 B1 | 6/2002 | Parce et al. |
| 6,399,952 B1 | 6/2002 | Majer et al. |
| 6,401,552 B1 | 6/2002 | Elkins |
| 6,403,338 B1 | 6/2002 | Knapp et al. |
| 6,408,878 B2 | 6/2002 | Unger et al. |
| 6,413,401 B1 | 7/2002 | Chow et al. |
| 6,416,642 B1 | 7/2002 | Alajoki et al. |
| 6,420,143 B1 | 7/2002 | Kopf-sill |
| 6,425,972 B1 | 7/2002 | Mcreynolds |
| D461,906 S | 8/2002 | Pham |
| 6,428,987 B2 | 8/2002 | Franzen |
| 6,430,512 B1 | 8/2002 | Gallagher |
| 6,432,366 B2 | 8/2002 | Ruediger et al. |
| 6,440,725 B1 | 8/2002 | Pourahmadi et al. |
| D463,031 S | 9/2002 | Slomski et al. |
| 6,444,461 B1 | 9/2002 | Knapp et al. |
| 6,447,661 B1 | 9/2002 | Chow et al. |
| 6,447,727 B1 | 9/2002 | Parce et al. |
| 6,448,064 B1 | 9/2002 | Vo-Dinh et al. |
| 6,453,928 B1 | 9/2002 | Kaplan et al. |
| 6,465,257 B1 | 10/2002 | Parce et al. |
| 6,468,761 B2 | 10/2002 | Yang et al. |
| 6,472,141 B2 | 10/2002 | Nikiforov |
| 6,475,364 B1 | 11/2002 | Dubrow et al. |
| D467,348 S | 12/2002 | McMichael et al. |
| D467,349 S | 12/2002 | Niedbala et al. |
| 6,488,897 B2 | 12/2002 | Dubrow et al. |
| 6,495,104 B1 | 12/2002 | Unno et al. |
| 6,498,497 B1 | 12/2002 | Chow et al. |
| 6,500,323 B1 | 12/2002 | Chow et al. |
| 6,500,390 B1 | 12/2002 | Boulton et al. |
| D468,437 S | 1/2003 | McMenamy et al. |
| 6,506,609 B1 | 1/2003 | Wada et al. |
| 6,509,193 B1 | 1/2003 | Tajima |
| 6,511,853 B1 | 1/2003 | Kopf-sill et al. |
| D470,595 S | 2/2003 | Crisanti et al. |
| 6,515,753 B2 | 2/2003 | Maher |
| 6,517,783 B2 | 2/2003 | Horner et al. |
| 6,520,197 B2 | 2/2003 | Deshmukh et al. |
| 6,521,188 B1 | 2/2003 | Webster |
| 6,524,456 B1 | 2/2003 | Ramsey et al. |
| 6,524,790 B1 | 2/2003 | Kopf-sill et al. |
| D472,324 S | 3/2003 | Rumore et al. |
| 6,534,295 B2 | 3/2003 | Tai et al. |
| 6,537,771 B1 | 3/2003 | Farinas et al. |
| 6,540,896 B1 | 4/2003 | Manz et al. |
| 6,544,734 B1 | 4/2003 | Briscoe et al. |
| 6,547,942 B1 | 4/2003 | Parce et al. |
| 6,555,389 B1 | 4/2003 | Ullman et al. |
| 6,556,923 B2 | 4/2003 | Gallagher et al. |
| D474,279 S | 5/2003 | Mayer et al. |
| D474,280 S | 5/2003 | Niedbala et al. |
| 6,558,916 B2 | 5/2003 | Veerapandian et al. |
| 6,558,945 B1 | 5/2003 | Kao |
| 6,569,607 B2 | 5/2003 | Mcreynolds |
| 6,572,830 B1 | 6/2003 | Burdon et al. |
| 6,575,188 B2 | 6/2003 | Parunak |
| 6,576,459 B2 | 6/2003 | Miles et al. |

(56) References Cited

U.S. PATENT DOCUMENTS

| | | |
|---|---|---|
| 6,579,453 B1 | 6/2003 | Bächler et al. |
| 6,589,729 B2 | 7/2003 | Chan et al. |
| 6,592,821 B1 | 7/2003 | Wada et al. |
| 6,597,450 B1 | 7/2003 | Andrews et al. |
| 6,602,474 B1 | 8/2003 | Tajima |
| 6,613,211 B1 | 9/2003 | Mccormick et al. |
| 6,613,512 B1 | 9/2003 | Kopf-sill et al. |
| 6,613,580 B1 | 9/2003 | Chow et al. |
| 6,613,581 B1 | 9/2003 | Wada et al. |
| 6,614,030 B2 | 9/2003 | Maher et al. |
| 6,620,625 B2 | 9/2003 | Wolk et al. |
| 6,623,860 B2 | 9/2003 | Hu et al. |
| 6,627,406 B1 | 9/2003 | Singh et al. |
| D480,814 S | 10/2003 | Lafferty et al. |
| 6,632,655 B1 | 10/2003 | Mehta et al. |
| 6,633,785 B1 | 10/2003 | Kasahara et al. |
| D482,796 S | 11/2003 | Oyama et al. |
| 6,649,358 B1 | 11/2003 | Parce et al. |
| 6,664,104 B2 | 12/2003 | Pourahmadi et al. |
| 6,669,831 B2 | 12/2003 | Chow et al. |
| 6,670,153 B2 | 12/2003 | Stern |
| D484,989 S | 1/2004 | Gebrian |
| 6,681,616 B2 | 1/2004 | Spaid et al. |
| 6,681,788 B2 | 1/2004 | Parce et al. |
| 6,685,813 B2 | 2/2004 | Williams et al. |
| 6,692,700 B2 | 2/2004 | Handique |
| 6,695,009 B2 | 2/2004 | Chien et al. |
| 6,706,519 B1 | 3/2004 | Kellogg et al. |
| 6,720,148 B1 | 4/2004 | Nikiforov |
| 6,730,206 B2 | 5/2004 | Ricco et al. |
| 6,733,645 B1 | 5/2004 | Chow |
| 6,734,401 B2 | 5/2004 | Bedingham et al. |
| 6,737,026 B1 | 5/2004 | Bergh et al. |
| 6,740,518 B1 | 5/2004 | Duong et al. |
| D491,272 S | 6/2004 | Alden et al. |
| D491,273 S | 6/2004 | Biegler et al. |
| D491,276 S | 6/2004 | Langille |
| 6,750,661 B2 | 6/2004 | Brooks et al. |
| 6,752,966 B1 | 6/2004 | Chazan |
| 6,756,019 B1 | 6/2004 | Dubrow et al. |
| 6,766,817 B2 | 7/2004 | da Silva |
| 6,773,567 B1 | 8/2004 | Wolk |
| 6,777,184 B2 | 8/2004 | Nikiforov et al. |
| 6,783,962 B1 | 8/2004 | Olander et al. |
| D495,805 S | 9/2004 | Lea et al. |
| 6,787,015 B2 | 9/2004 | Lackritz et al. |
| 6,787,016 B2 | 9/2004 | Tan et al. |
| 6,787,111 B2 | 9/2004 | Roach et al. |
| 6,790,328 B2 | 9/2004 | Jacobson et al. |
| 6,790,330 B2 | 9/2004 | Gascoyne et al. |
| 6,811,668 B1 | 11/2004 | Berndt et al. |
| 6,818,113 B2 | 11/2004 | Williams et al. |
| 6,819,027 B2 | 11/2004 | Saraf |
| 6,824,663 B1 | 11/2004 | Boone |
| D499,813 S | 12/2004 | Wu |
| D500,142 S | 12/2004 | Crisanti et al. |
| 6,827,831 B1 | 12/2004 | Chow et al. |
| 6,827,906 B1 | 12/2004 | Bjornson et al. |
| 6,838,156 B1 | 1/2005 | Neyer et al. |
| 6,838,680 B2 | 1/2005 | Maher et al. |
| 6,852,287 B2 | 2/2005 | Ganesan |
| 6,858,185 B1 | 2/2005 | Kopf-sill et al. |
| 6,859,698 B2 | 2/2005 | Schmeisser |
| 6,861,035 B2 | 3/2005 | Pham et al. |
| 6,878,540 B2 | 4/2005 | Pourahmadi et al. |
| 6,878,755 B2 | 4/2005 | Singh et al. |
| 6,884,628 B2 | 4/2005 | Hubbell et al. |
| 6,887,693 B2 | 5/2005 | McMillan et al. |
| 6,893,879 B2 | 5/2005 | Petersen et al. |
| 6,900,889 B2 | 5/2005 | Bjornson et al. |
| 6,905,583 B2 | 6/2005 | Wainright et al. |
| 6,905,612 B2 | 6/2005 | Dorian et al. |
| 6,906,797 B1 | 6/2005 | Kao et al. |
| 6,908,594 B1 | 6/2005 | Schaevitz et al. |
| 6,911,183 B1 | 6/2005 | Handique et al. |
| 6,914,137 B2 | 7/2005 | Baker |
| 6,915,679 B2 | 7/2005 | Chien et al. |
| 6,918,404 B2 | 7/2005 | da Silva |
| D508,999 S | 8/2005 | Fanning et al. |
| 6,939,451 B2 | 9/2005 | Zhao et al. |
| 6,942,771 B1 | 9/2005 | Kayyem |
| 6,958,392 B2 | 10/2005 | Fomovskaia et al. |
| D512,155 S | 11/2005 | Matsumoto |
| 6,964,747 B2 | 11/2005 | Banerjee et al. |
| 6,977,163 B1 | 12/2005 | Mehta |
| 6,984,516 B2 | 1/2006 | Briscoe et al. |
| D515,707 S | 2/2006 | Sinohara et al. |
| D516,221 S | 2/2006 | Wohlstadter et al. |
| 7,001,853 B1 | 2/2006 | Brown et al. |
| 7,004,184 B2 | 2/2006 | Handique et al. |
| D517,554 S | 3/2006 | Yanagisawa et al. |
| 7,010,391 B2 | 3/2006 | Handique et al. |
| 7,023,007 B2 | 4/2006 | Gallagher |
| 7,024,281 B1 | 4/2006 | Unno |
| 7,036,667 B2 | 5/2006 | Greenstein et al. |
| 7,037,416 B2 | 5/2006 | Parce et al. |
| 7,038,472 B1 | 5/2006 | Chien |
| 7,039,527 B2 | 5/2006 | Tripathi et al. |
| 7,040,144 B2 | 5/2006 | Spaid et al. |
| 7,049,558 B2 | 5/2006 | Baer et al. |
| D523,153 S | 6/2006 | Akashi et al. |
| 7,055,695 B2 | 6/2006 | Greenstein et al. |
| 7,060,171 B1 | 6/2006 | Nikiforov et al. |
| 7,066,586 B2 | 6/2006 | da Silva |
| 7,069,952 B1 | 7/2006 | Mcreynolds et al. |
| 7,099,778 B2 | 8/2006 | Chien |
| D528,215 S | 9/2006 | Malmsater |
| 7,101,467 B2 | 9/2006 | Spaid |
| 7,105,304 B1 | 9/2006 | Nikiforov et al. |
| D531,321 S | 10/2006 | Godfrey et al. |
| 7,118,910 B2 | 10/2006 | Unger et al. |
| 7,138,032 B2 | 11/2006 | Gandhi et al. |
| D534,280 S | 12/2006 | Gomm et al. |
| 7,148,043 B2 | 12/2006 | Kordunsky et al. |
| 7,150,814 B1 | 12/2006 | Parce et al. |
| 7,150,999 B1 | 12/2006 | Shuck |
| D535,403 S | 1/2007 | Isozaki et al. |
| 7,160,423 B2 | 1/2007 | Chien et al. |
| 7,161,356 B1 | 1/2007 | Chien |
| 7,169,277 B2 | 1/2007 | Ausserer et al. |
| 7,169,618 B2 | 1/2007 | Skould |
| D537,951 S | 3/2007 | Okamoto et al. |
| D538,436 S | 3/2007 | Patadia et al. |
| 7,192,557 B2 | 3/2007 | Wu et al. |
| 7,195,986 B1 | 3/2007 | Bousse et al. |
| 7,208,125 B1 | 4/2007 | Dong |
| 7,235,406 B1 | 6/2007 | Woudenberg et al. |
| 7,247,274 B1 | 7/2007 | Chow |
| D548,841 S | 8/2007 | Brownell et al. |
| D549,827 S | 8/2007 | Maeno et al. |
| 7,252,928 B1 | 8/2007 | Hafeman et al. |
| 7,270,786 B2 | 9/2007 | Parunak et al. |
| D554,069 S | 10/2007 | Bolotin et al. |
| D554,070 S | 10/2007 | Bolotin et al. |
| 7,276,330 B2 | 10/2007 | Chow et al. |
| D556,914 S | 12/2007 | Okamoto et al. |
| 7,303,727 B1 | 12/2007 | Dubrow et al. |
| D559,995 S | 1/2008 | Handique et al. |
| 7,323,140 B2 | 1/2008 | Handique et al. |
| 7,332,130 B2 | 2/2008 | Handique |
| 7,338,760 B2 | 3/2008 | Gong et al. |
| D566,291 S | 4/2008 | Parunak et al. |
| 7,351,377 B2 | 4/2008 | Chazan et al. |
| D569,526 S | 5/2008 | Duffy et al. |
| 7,374,949 B2 | 5/2008 | Kuriger |
| 7,390,460 B2 | 6/2008 | Osawa et al. |
| 7,419,784 B2 | 9/2008 | Dubrow et al. |
| 7,422,669 B2 | 9/2008 | Jacobson et al. |
| 7,440,684 B2 | 10/2008 | Spaid et al. |
| 7,476,313 B2 | 1/2009 | Siddiqi |
| 7,494,577 B2 | 2/2009 | Williams et al. |
| 7,494,770 B2 | 2/2009 | Wilding et al. |
| 7,514,046 B2 | 4/2009 | Kechagia et al. |
| 7,518,726 B2 | 4/2009 | Rulison et al. |

(56) References Cited

U.S. PATENT DOCUMENTS

| | | | |
|---|---|---|---|
| 7,521,186 B2 | 4/2009 | Burd Mehta | |
| 7,527,769 B2 | 5/2009 | Bunch et al. | |
| 7,553,671 B2 | 6/2009 | Sinclair et al. | |
| 7,595,197 B2 | 9/2009 | Brasseur | |
| 7,604,938 B2 | 10/2009 | Takahashi et al. | |
| 7,635,588 B2 | 12/2009 | King et al. | |
| 7,645,581 B2 | 1/2010 | Knapp et al. | |
| 7,670,559 B2 | 3/2010 | Chien et al. | |
| 7,674,431 B2 | 3/2010 | Ganesan | |
| 7,704,735 B2 | 4/2010 | Facer et al. | |
| 7,723,123 B1 | 5/2010 | Murphy et al. | |
| 7,727,371 B2 | 6/2010 | Kennedy et al. | |
| 7,727,477 B2 | 6/2010 | Boronkay et al. | |
| 7,744,817 B2 * | 6/2010 | Bui | 422/68.1 |
| D621,060 S | 8/2010 | Handique | |
| 7,867,776 B2 | 1/2011 | Kennedy et al. | |
| 7,892,819 B2 | 2/2011 | Wilding et al. | |
| D637,737 S | 5/2011 | Wilson et al. | |
| 7,998,708 B2 * | 8/2011 | Handique et al. | 435/91.2 |
| 8,088,616 B2 | 1/2012 | Handique | |
| 8,105,783 B2 | 1/2012 | Handique | |
| 8,133,671 B2 | 3/2012 | Williams et al. | |
| 8,182,763 B2 | 5/2012 | Duffy et al. | |
| D669,597 S | 10/2012 | Cavada et al. | |
| 8,287,820 B2 | 10/2012 | Williams et al. | |
| 8,323,584 B2 | 12/2012 | Ganesan | |
| 8,323,900 B2 | 12/2012 | Handique et al. | |
| 8,324,372 B2 | 12/2012 | Brahmasandra et al. | |
| 8,415,103 B2 | 4/2013 | Handique | |
| 8,420,015 B2 | 4/2013 | Ganesan et al. | |
| 8,440,149 B2 | 5/2013 | Handique | |
| 8,470,586 B2 | 6/2013 | Wu et al. | |
| 8,473,104 B2 | 6/2013 | Handique et al. | |
| D692,162 S | 10/2013 | Lentz et al. | |
| 2001/0012492 A1 | 8/2001 | Acosta et al. | |
| 2001/0021355 A1 | 9/2001 | Baugh et al. | |
| 2001/0023848 A1 | 9/2001 | Gjerde et al. | |
| 2001/0038450 A1 | 11/2001 | McCaffrey et al. | |
| 2001/0046702 A1 | 11/2001 | Schembri | |
| 2001/0055765 A1 | 12/2001 | O'Keefe et al. | |
| 2002/0001848 A1 | 1/2002 | Bedingham et al. | |
| 2002/0008053 A1 | 1/2002 | Hansen et al. | |
| 2002/0009015 A1 | 1/2002 | Laugharn, Jr. et al. | |
| 2002/0015667 A1 | 2/2002 | Chow | |
| 2002/0021983 A1 | 2/2002 | Comte et al. | |
| 2002/0037499 A1 | 3/2002 | Quake et al. | |
| 2002/0039783 A1 | 4/2002 | McMillan et al. | |
| 2002/0053399 A1 | 5/2002 | Soane et al. | |
| 2002/0054835 A1 | 5/2002 | Robotti et al. | |
| 2002/0055167 A1 | 5/2002 | Pourahmadi et al. | |
| 2002/0058332 A1 | 5/2002 | Quake et al. | |
| 2002/0060156 A1 | 5/2002 | Mathies et al. | |
| 2002/0068357 A1 | 6/2002 | Mathies et al. | |
| 2002/0141903 A1 | 10/2002 | Parunak et al. | |
| 2002/0142471 A1 | 10/2002 | Handique et al. | |
| 2002/0143297 A1 | 10/2002 | Francavilla et al. | |
| 2002/0143437 A1 | 10/2002 | Handique et al. | |
| 2002/0155477 A1 | 10/2002 | Ito | |
| 2002/0169518 A1 | 11/2002 | Luoma et al. | |
| 2002/0187557 A1 | 12/2002 | Hobbs et al. | |
| 2003/0019522 A1 | 1/2003 | Parunak | |
| 2003/0022392 A1 | 1/2003 | Hudak | |
| 2003/0049174 A1 | 3/2003 | Ganesan | |
| 2003/0049833 A1 | 3/2003 | Chen et al. | |
| 2003/0064507 A1 | 4/2003 | Gallagher et al. | |
| 2003/0070677 A1 | 4/2003 | Handique et al. | |
| 2003/0073106 A1 | 4/2003 | Johansen et al. | |
| 2003/0083686 A1 | 5/2003 | Freeman et al. | |
| 2003/0087300 A1 | 5/2003 | Knapp et al. | |
| 2003/0096310 A1 | 5/2003 | Hansen et al. | |
| 2003/0127327 A1 | 7/2003 | Kurnik | |
| 2003/0136679 A1 * | 7/2003 | Bohn et al. | 204/543 |
| 2003/0186295 A1 | 10/2003 | Colin et al. | |
| 2003/0190608 A1 | 10/2003 | Blackburn et al. | |
| 2003/0199081 A1 | 10/2003 | Wilding et al. | |
| 2003/0799081 | 10/2003 | Wilding et at | |
| 2003/0211517 A1 | 11/2003 | Carulli et al. | |
| 2004/0014238 A1 | 1/2004 | Krug et al. | |
| 2004/0018119 A1 | 1/2004 | Massaro | |
| 2004/0029258 A1 | 2/2004 | Heaney et al. | |
| 2004/0029260 A1 | 2/2004 | Hansen et al. | |
| 2004/0037739 A1 | 2/2004 | McNeely et al. | |
| 2004/0053290 A1 | 3/2004 | Terbrueggen et al. | |
| 2004/0063217 A1 | 4/2004 | Webster et al. | |
| 2004/0072278 A1 | 4/2004 | Chou et al. | |
| 2004/0072375 A1 | 4/2004 | Gjerde et al. | |
| 2004/0086427 A1 | 5/2004 | Childers et al. | |
| 2004/0086956 A1 | 5/2004 | Bachur | |
| 2004/0141887 A1 | 7/2004 | Mainquist et al. | |
| 2004/0151629 A1 | 8/2004 | Pease et al. | |
| 2004/0157220 A1 | 8/2004 | Kurnool et al. | |
| 2004/0161788 A1 | 8/2004 | Chen et al. | |
| 2004/0189311 A1 | 9/2004 | Glezer et al. | |
| 2004/0200909 A1 | 10/2004 | McMillan et al. | |
| 2004/0209331 A1 * | 10/2004 | Ririe | 435/91.2 |
| 2004/0209354 A1 | 10/2004 | Mathies et al. | |
| 2004/0219070 A1 | 11/2004 | Handique | |
| 2004/0235154 A1 | 11/2004 | Oh et al. | |
| 2004/0240097 A1 | 12/2004 | Evans | |
| 2005/0009174 A1 | 1/2005 | Nikiforov et al. | |
| 2005/0013737 A1 | 1/2005 | Chow et al. | |
| 2005/0041525 A1 * | 2/2005 | Pugia et al. | 366/341 |
| 2005/0042639 A1 | 2/2005 | Knapp et al. | |
| 2005/0048540 A1 | 3/2005 | Inami et al. | |
| 2005/0058574 A1 | 3/2005 | Bysouth et al. | |
| 2005/0084424 A1 | 4/2005 | Ganesan et al. | |
| 2005/0106066 A1 | 5/2005 | Saltsman et al. | |
| 2005/0121324 A1 | 6/2005 | Park et al. | |
| 2005/0129580 A1 | 6/2005 | Swinehart et al. | |
| 2005/0133370 A1 | 6/2005 | Park et al. | |
| 2005/0135655 A1 | 6/2005 | Kopf-sill et al. | |
| 2005/0152808 A1 | 7/2005 | Ganesan | |
| 2005/0170362 A1 | 8/2005 | Wada et al. | |
| 2005/0186585 A1 | 8/2005 | Juncosa et al. | |
| 2005/0202470 A1 | 9/2005 | Sundberg et al. | |
| 2005/0202504 A1 | 9/2005 | Anderson et al. | |
| 2005/0208676 A1 | 9/2005 | Kahatt | |
| 2005/0220675 A1 | 10/2005 | Reed et al. | |
| 2005/0227269 A1 | 10/2005 | Lloyd et al. | |
| 2005/0233370 A1 | 10/2005 | Ammann et al. | |
| 2005/0238545 A1 | 10/2005 | Parce et al. | |
| 2005/0272079 A1 | 12/2005 | Burns et al. | |
| 2006/0041058 A1 | 2/2006 | Yin et al. | |
| 2006/0057039 A1 | 3/2006 | Morse et al. | |
| 2006/0057629 A1 | 3/2006 | Kim | |
| 2006/0062696 A1 | 3/2006 | Chow et al. | |
| 2006/0094108 A1 * | 5/2006 | Yoder et al. | 435/287.2 |
| 2006/0113190 A1 | 6/2006 | Kurnik | |
| 2006/0133965 A1 | 6/2006 | Tajima et al. | |
| 2006/0134790 A1 | 6/2006 | Tanaka et al. | |
| 2006/0148063 A1 | 7/2006 | Fauzzi et al. | |
| 2006/0165558 A1 | 7/2006 | Witty et al. | |
| 2006/0165559 A1 | 7/2006 | Greenstein et al. | |
| 2006/0166233 A1 | 7/2006 | Wu et al. | |
| 2006/0177376 A1 | 8/2006 | Tomalia et al. | |
| 2006/0177855 A1 | 8/2006 | Utermohlen et al. | |
| 2006/0183216 A1 | 8/2006 | Handique | |
| 2006/0207944 A1 | 9/2006 | Siddiqi | |
| 2006/0210435 A1 | 9/2006 | Alavie et al. | |
| 2006/0246493 A1 | 11/2006 | Jensen et al. | |
| 2006/0246533 A1 | 11/2006 | Fathollahi et al. | |
| 2007/0004028 A1 | 1/2007 | Lair et al. | |
| 2007/0009386 A1 | 1/2007 | Padmanabhan et al. | |
| 2007/0020699 A1 | 1/2007 | Carpenter et al. | |
| 2007/0026421 A1 | 2/2007 | Sundberg et al. | |
| 2007/0042441 A1 | 2/2007 | Masters et al. | |
| 2007/0092901 A1 | 4/2007 | Ligler et al. | |
| 2007/0098600 A1 | 5/2007 | Kayyem et al. | |
| 2007/0099200 A1 | 5/2007 | Chow et al. | |
| 2007/0104617 A1 | 5/2007 | Coulling et al. | |
| 2007/0154895 A1 | 7/2007 | Spaid et al. | |
| 2007/0177147 A1 | 8/2007 | Parce | |
| 2007/0178607 A1 | 8/2007 | Prober et al. | |
| 2007/0184463 A1 | 8/2007 | Molho et al. | |

(56) References Cited

U.S. PATENT DOCUMENTS

| | | | |
|---|---|---|---|
| 2007/0184547 A1* | 8/2007 | Handique et al. | 435/288.5 |
| 2007/0196237 A1* | 8/2007 | Neuzil et al. | 422/67 |
| 2007/0196238 A1 | 8/2007 | Kennedy et al. | |
| 2007/0199821 A1 | 8/2007 | Chow | |
| 2007/0215554 A1 | 9/2007 | Kreuwel et al. | |
| 2007/0218459 A1 | 9/2007 | Miller et al. | |
| 2007/0231213 A1 | 10/2007 | Prabhu et al. | |
| 2007/0243626 A1 | 10/2007 | Windeyer et al. | |
| 2007/0261479 A1 | 11/2007 | Spaid et al. | |
| 2007/0269861 A1 | 11/2007 | Williams et al. | |
| 2007/0292941 A1 | 12/2007 | Handique et al. | |
| 2008/0000774 A1 | 1/2008 | Park et al. | |
| 2008/0017306 A1 | 1/2008 | Liu et al. | |
| 2008/0050804 A1 | 2/2008 | Handique et al. | |
| 2008/0056948 A1 | 3/2008 | Dale et al. | |
| 2008/0069729 A1 | 3/2008 | McNeely | |
| 2008/0075634 A1 | 3/2008 | Herchenbach et al. | |
| 2008/0090244 A1 | 4/2008 | Knapp et al. | |
| 2008/0095673 A1 | 4/2008 | Xu | |
| 2008/0118987 A1 | 5/2008 | Eastwood et al. | |
| 2008/0124723 A1 | 5/2008 | Dale et al. | |
| 2008/0149840 A1 | 6/2008 | Handique et al. | |
| 2008/0160601 A1 | 7/2008 | Handique | |
| 2008/0182301 A1 | 7/2008 | Handique et al. | |
| 2008/0192254 A1 | 8/2008 | Kim et al. | |
| 2008/0226502 A1 | 9/2008 | Jonsmann et al. | |
| 2009/0047713 A1 | 2/2009 | Handique | |
| 2009/0129978 A1 | 5/2009 | Wilson et al. | |
| 2009/0130719 A1 | 5/2009 | Handique | |
| 2009/0130745 A1 | 5/2009 | Williams et al. | |
| 2009/0131650 A1 | 5/2009 | Brahmasandra et al. | |
| 2009/0134069 A1 | 5/2009 | Handique | |
| 2009/0136385 A1 | 5/2009 | Handique et al. | |
| 2009/0136386 A1 | 5/2009 | Duffy et al. | |
| 2009/0155123 A1 | 6/2009 | Williams et al. | |
| 2009/0189089 A1 | 7/2009 | Bedingham et al. | |
| 2009/0221059 A1 | 9/2009 | Handique et al. | |
| 2010/0009351 A1 | 1/2010 | Brahmasandra et al. | |
| 2010/0173393 A1 | 7/2010 | Handique et al. | |
| 2011/0008825 A1 | 1/2011 | Ingber et al. | |
| 2011/0027151 A1 | 2/2011 | Handique et al. | |
| 2011/0158865 A1 | 6/2011 | Miller et al. | |
| 2011/0207140 A1 | 8/2011 | Handique et al. | |
| 2011/0210257 A9 | 9/2011 | Handique et al. | |
| 2012/0022695 A1 | 1/2012 | Handique et al. | |
| 2012/0085416 A1 | 4/2012 | Ganesan | |
| 2012/0122108 A1 | 5/2012 | Handique | |
| 2012/0160826 A1 | 6/2012 | Handique | |
| 2012/0171759 A1 | 7/2012 | Williams et al. | |
| 2012/0183454 A1 | 7/2012 | Handique | |
| 2012/0258463 A1 | 10/2012 | Duffy et al. | |
| 2013/0037564 A1 | 2/2013 | Williams et al. | |
| 2013/0071851 A1 | 3/2013 | Handique et al. | |
| 2013/0096292 A1 | 4/2013 | Brahmasandra et al. | |
| 2013/0101990 A1 | 4/2013 | Handique et al. | |
| 2013/0164832 A1 | 6/2013 | Ganesan et al. | |
| 2013/0217013 A1 | 8/2013 | Steel et al. | |
| 2013/0217102 A1 | 8/2013 | Ganesan et al. | |
| 2013/0251602 A1 | 9/2013 | Handique et al. | |
| 2013/0280131 A1 | 10/2013 | Handique et al. | |
| 2014/0030798 A1 | 1/2014 | Wu et al. | |
| 2014/0045186 A1 | 2/2014 | Gubatayao et al. | |

FOREIGN PATENT DOCUMENTS

| | | | |
|---|---|---|---|
| EP | 0766256 | | 4/1997 |
| EP | 1541237 | * | 12/2004 |
| EP | 2372367 A1 | | 10/2011 |
| FR | 2672301 | | 8/1992 |
| FR | 2795426 | | 12/2000 |
| JP | 58212921 A | | 12/1983 |
| JP | H07-290706 | | 11/1995 |
| JP | 2001-509437 | | 7/2001 |
| JP | 2001-527220 | | 12/2001 |
| JP | 2002-503331 | | 1/2002 |
| JP | 2002-215241 | | 7/2002 |
| JP | 2003-500674 | | 1/2003 |
| JP | 2003-299485 | | 10/2003 |
| JP | 2003-047840 | | 2/2004 |
| JP | 2005-514718 | | 5/2005 |
| JP | 2005-518825 | | 6/2005 |
| JP | 2005-192554 | | 7/2005 |
| JP | 2005-204661 | | 8/2005 |
| JP | 2005-525816 | | 9/2005 |
| JP | 2005-291954 A | | 10/2005 |
| JP | 2005-532043 | | 10/2005 |
| JP | 2005-323519 | | 11/2005 |
| JP | 2007-074960 | | 3/2007 |
| WO | WO 88/06633 | | 9/1988 |
| WO | WO 90/12350 | | 10/1990 |
| WO | WO 92/05443 | | 4/1992 |
| WO | WO 94/11103 | | 5/1994 |
| WO | WO 96/04547 | | 2/1996 |
| WO | WO 97/05492 | | 2/1997 |
| WO | WO 97/21090 | | 6/1997 |
| WO | WO 98/00231 | | 1/1998 |
| WO | WO 98/22625 | | 5/1998 |
| WO | WO 98/49548 | | 11/1998 |
| WO | WO 98/53311 | | 11/1998 |
| WO | WO 99/01688 | | 1/1999 |
| WO | WO 99/09042 | | 2/1999 |
| WO | WO 99/12016 | | 3/1999 |
| WO | WO 99/33559 | | 7/1999 |
| WO | WO 01/05510 | | 1/2001 |
| WO | WO 01/14931 | | 3/2001 |
| WO | WO 01/27614 | | 4/2001 |
| WO | WO 01/28684 | | 4/2001 |
| WO | WO 01/41931 | | 6/2001 |
| WO | WO 01/54813 | | 8/2001 |
| WO | WO 01/89681 | | 11/2001 |
| WO | WO 02/072264 | | 9/2002 |
| WO | WO 02/078845 | | 10/2002 |
| WO | WO 03/012325 | | 2/2003 |
| WO | WO 03/012406 | | 2/2003 |
| WO | WO 03/048295 | | 6/2003 |
| WO | WO 03/055605 | | 7/2003 |
| WO | WO 03/076661 | | 9/2003 |
| WO | WO 2004/007081 | | 1/2004 |
| WO | WO 2004/055522 | | 7/2004 |
| WO | WO 2004/074848 | | 9/2004 |
| WO | WO 2005/011867 | | 2/2005 |
| WO | WO 2005/108620 | | 11/2005 |
| WO | WO 2005/118867 | | 12/2005 |
| WO | WO 2006/032044 | | 3/2006 |
| WO | WO 2006/079082 | | 7/2006 |
| WO | WO 2006/119280 | | 11/2006 |
| WO | WO 2007/044917 | | 4/2007 |
| WO | WO 2007/050327 | | 5/2007 |
| WO | WO 2007/064117 | | 6/2007 |
| WO | WO 2008/030914 | | 3/2008 |
| WO | WO 2008/060604 | | 5/2008 |
| WO | WO 2009/012185 | | 1/2009 |
| WO | WO 2010/118541 | | 10/2010 |

OTHER PUBLICATIONS

Brahmasandra et al., On-chip DNA detection in microfabricated separation systems, SPIE Conference on Microfuidic Devices and Systems, 1998, vol. 3515, pp. 242-251, Santa Clara, CA.

Handique et al., 2001, Mathematical modeling of drop mixing in a split-type microchannel, J. Micromech Microeng, 11:548-554.

International Search Report and Written Opinion for PCT/US07/024022 dated Jan. 5, 2009.

Mascini et al., "DNA electrochemical biosensors", Fresenius J. Anal. Chem., 369: 15-22, (2001).

Nakagawa et al., Fabrication of amino silane-coated microchip for DNA extraction from whole blood, J of Biotechnology, Mar. 2, 2005, vol. 116, pp. 105-111.

Plambeck et al., "Electrochemical Studies of Antitumor Antibiotics", J. Electrochem Soc.: Electrochemical Science and Technology (1984), 131(11): 2556-2563.

Wang, "Survey and Summary, from DNA Biosensors to Gene Chips", Nucleic Acids Research, 28(16):3011-3016, (2000).

(56) References Cited

OTHER PUBLICATIONS

Goldmeyer et al., "Identification of *Staphylococcus aureus* and Determination of Methicillin Resistance Directly from Positive Blood Cultures by Isothermal Amplification and a Disposable Detection Device", J Clin Microbiol. (Apr. 2008) 46(4): 1534-1536.

Meyers, R.A., Molecular Biology and Biotechnology: A Comprehensive Desk Reference; VCH Publishers, Inc. New York, NY; (1995) pp. 418-419.

Bollet, C. et al., "A simple method for the isolation of chromosomal DNA from Gram positive or acid-fast bacteria", Nucleic Acids Research, vol. 19, No. 8 (1991), p. 1955.

Breadmore, M.C. et al., "Microchip-Based Purification of DNA from Biological Samples", Anal. Chem., vol. 75 (2003), pp. 1880-1886.

Brody, et al., Diffusion-Based Extraction in a Microfabricated Device, Sensors and Actuators Elsevier, 1997, vol. A58, No. 1, pp. 13-18.

Broyles, et al., "Sample Filtration Concentration, and Separation Integrated on Microfluidic Devices" Analytical Chemisty (American Chemical Society), vol. 75 No. 11: pp. 2761-2767, (Jun. 1, 2003).

Burns et al., "An Integrated Nanoliter DNA Analysis Device", Science 282:484-487 (1998).

Carlen et al., "Paraffin Actuated Surface Micromachined Valve," in IEEE MEMS 2000 Conference, p. 381-385, Miyazaki, Japan, Jan. 2000.

Chung, Y. et al., "Microfluidic chip for high efficiency DNA extraction", Miniaturisation for Chemistry, Biology & Bioengineering, vol. 4, No. 2 (Apr. 2004), pp. 141-147.

Handique K., et al., On-Chip Thermopneumatic Pressure for Discrete Drop Pumping, Analytical Chemistry, American Chemical Society, Apr. 15, 2001, vol. 73, No. 8, 1831-1838.

Handique, K. et al, "Microflidic flow control using selective hydrophobic patterning", SPIE, vol. 3224, pp. 185-194 (1997).

Handique, K. et al., "Nanoliter-volume discrete drop injection and pumping in microfabricated chemical analysis systems", Solid-State Sensor and Actuator Workshop (Hilton Head, South Carolina, Jun. 8-11, 1998) pp. 346-349.

Handique, K. et al., "Mathematical Modeling of Drop Mixing in a Slit-Type Micochannel", J. Micromech. Microeng., 11:548-554 (2001).

Handique, K. et al., "Nanoliter Liquid Metering in Microchannels Using Hydrophobic Patterns", Anal. Chem., 72:4100-4109 (2000).

He, et al., Microfabricated Filters for Microfludic Analytical Systems, Analytical Chemistry, American Chemical Society, 1999, vol. 71, No. 7, pp. 1464-1468.

Ibrahim, et al., Real-Time Microchip PCR for Detecting Single-Base Differences in Viral and Human DNA, Analytical Chemistry, American Chemical Society, 1998, vol. 70, No. 9, pp. 2013-2017.

Khandurina, et al., Microfabricated Porous Membrane Structure for Sample Concentraction and Electrophoretic Analysis, Analytical Chemistry American Chemical Society, 1999, vol. 71, No. 9, pp. 1815-1819.

Kopp, et al., Chemical Amplification: Continuous-Flow PCR on a Chip, www.sciencemag.org, 1998, vol. 280, pp. 1046-1048.

Kutter, et al., Solid Phase Extraction on Microfludic Devices, J. Microcolumn Separations, John Wiley & Sons, Inc., 2000, vol. 12, No. 2, pp. 93-97.

Lagally, et al., Single-Molecule DNA Amplification and Analysis in an Integrated Microfluidic Device, Analytical Chemistry, American Chemical Society, 2001, vol. 73, No. 3 pp. 565-570.

Livache, T. et al., "Polypyrrole DNA chip on a Silicon Device: Example of Hepatitis C Virus Genotyping", Analytical Biochemistry, vol. 255 (1998), pp. 188-194.

Northrup, et al., A Miniature Analytical Instrument for Nucleic Acids Based on Micromachined Silicon Reaction Chambers, Analytical Chemistry, American Chemical Society, 1998, vol. 70, No. 5, pp. 918-922.

Oleschuk, et al., Trapping of Bead-Based Reagents within Microfluidic Systems,: On-Chip Solid-Phase Extraction and Electrochromatography, Analytical Chemistry, American Chemical Society, 2000, vol. 72, No. 3, pp. 585-590.

Orchid BioSciences, Inc., www.orchid.com, Jul. 6, 2001.

Roche, et al. "Ectodermal commitment of insulin-producing cells derived from mouse embryonic stem cells" Faseb J (2005) 19: 1341-1343.

Ross, et al., Analysis of DNA Fragments from Conventional and Microfabricated PCR Devices Using Delayed Extraction MALDI-TOF Mass Spectrometry, Analytical Chemistry, American Chemical Society, 1998, vol. 70, No. 10, pp. 2067-2073.

Shoffner, M. A. et al., Chip PCR.I. Surface Passivation of Microfabricated Silicon-Glass Chips for PCR, Nucleic Acids Research, Oxford University Press, 1996, vol. 24, No. 2, 375-379.

Smith, K. et al., "Comparison of Commercial DNA Extraction Kits for Extraction of Bacterial Genomic DNA from Whole-Blood Samples", Journal of Clinical Microbiology, vol. 41, No. 6 (Jun. 2003), pp. 2440-2443.

Waters, et al., Microchip Device for Cell Lysis, Multiplex PCR Amplification, and Electrophoretic Sizing, Analytical Chemistry, American Chemical Society, 1998, vol. 70, No. 1, pp. 158-162.

Weigl, et al., Microfluidic Diffusion-Based Separation and Detection, www.sciencemag.org, 1999, vol. 283, pp. 346-347.

Yoza, Brandon et al., DNA extraction using bacterial magnetic particles modified with hyperbranched polyamidoamine dendrimer, Mar. 20, 2003, vol. 101, No. 3, 219-228.

Yoza, et al., "Fully Automated DNA Extraction fro Blood Using Magnetic Particles Modified with a Hyperbranched Polyamidomine Dendrimer", Journal of Bioscience and Bioengineering, 95(1):21-26, 2003.

\* cited by examiner

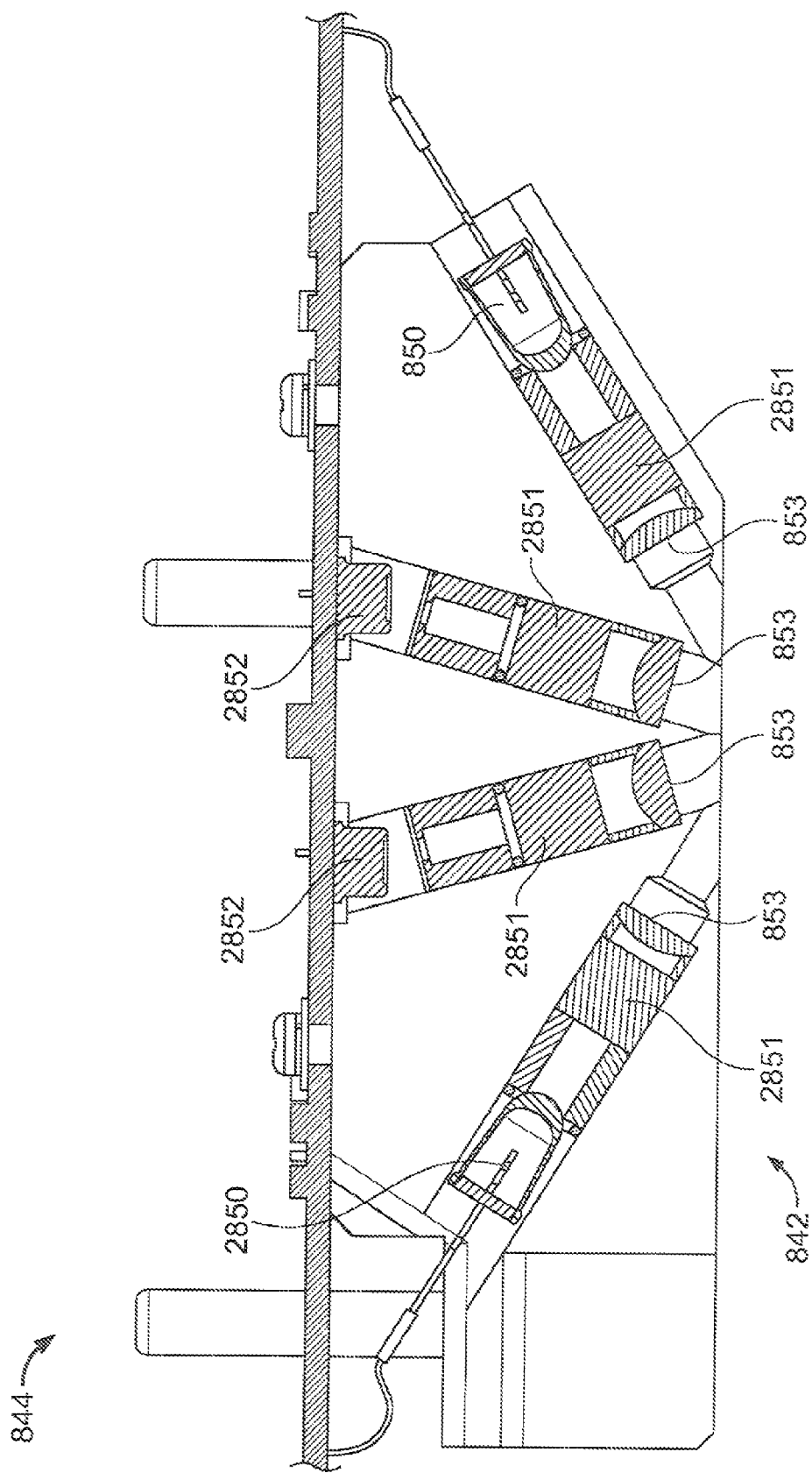

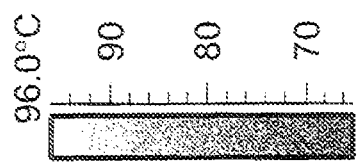
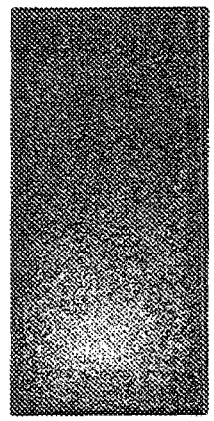
FIG. 8C-3
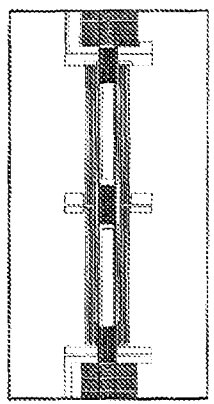
FIG. 8C-6
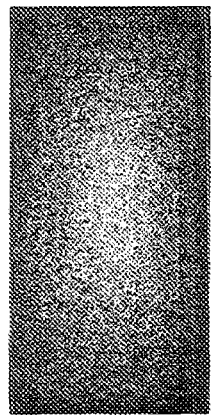
FIG. 8C-2
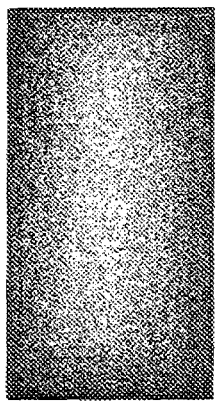
FIG. 8C-5
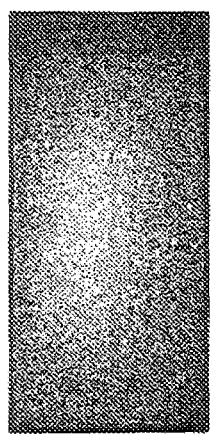
FIG. 8C-1
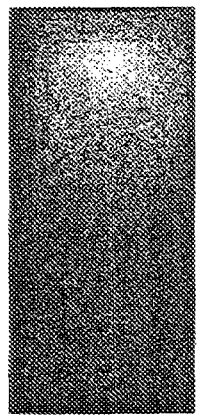
FIG. 8C-4

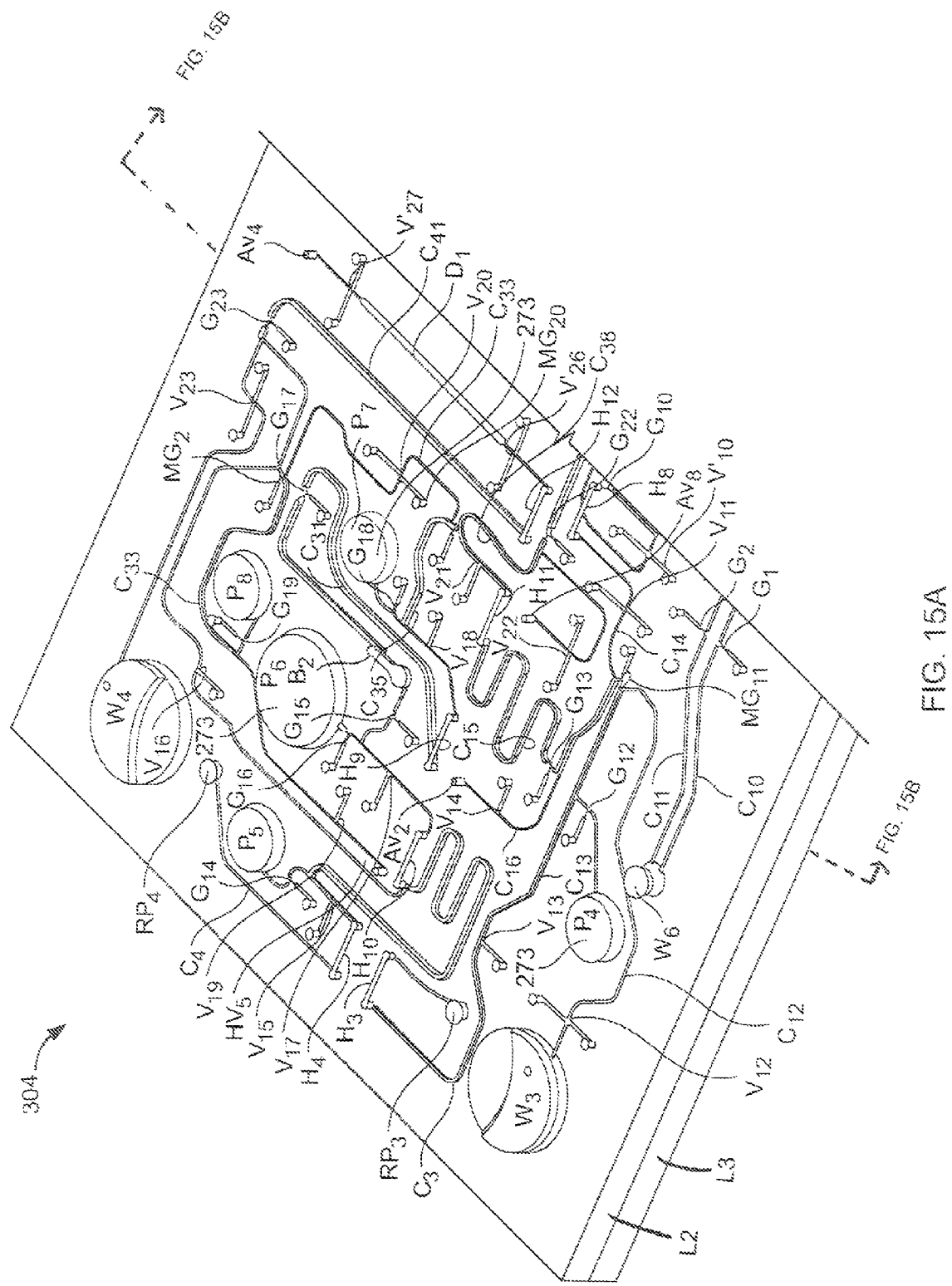

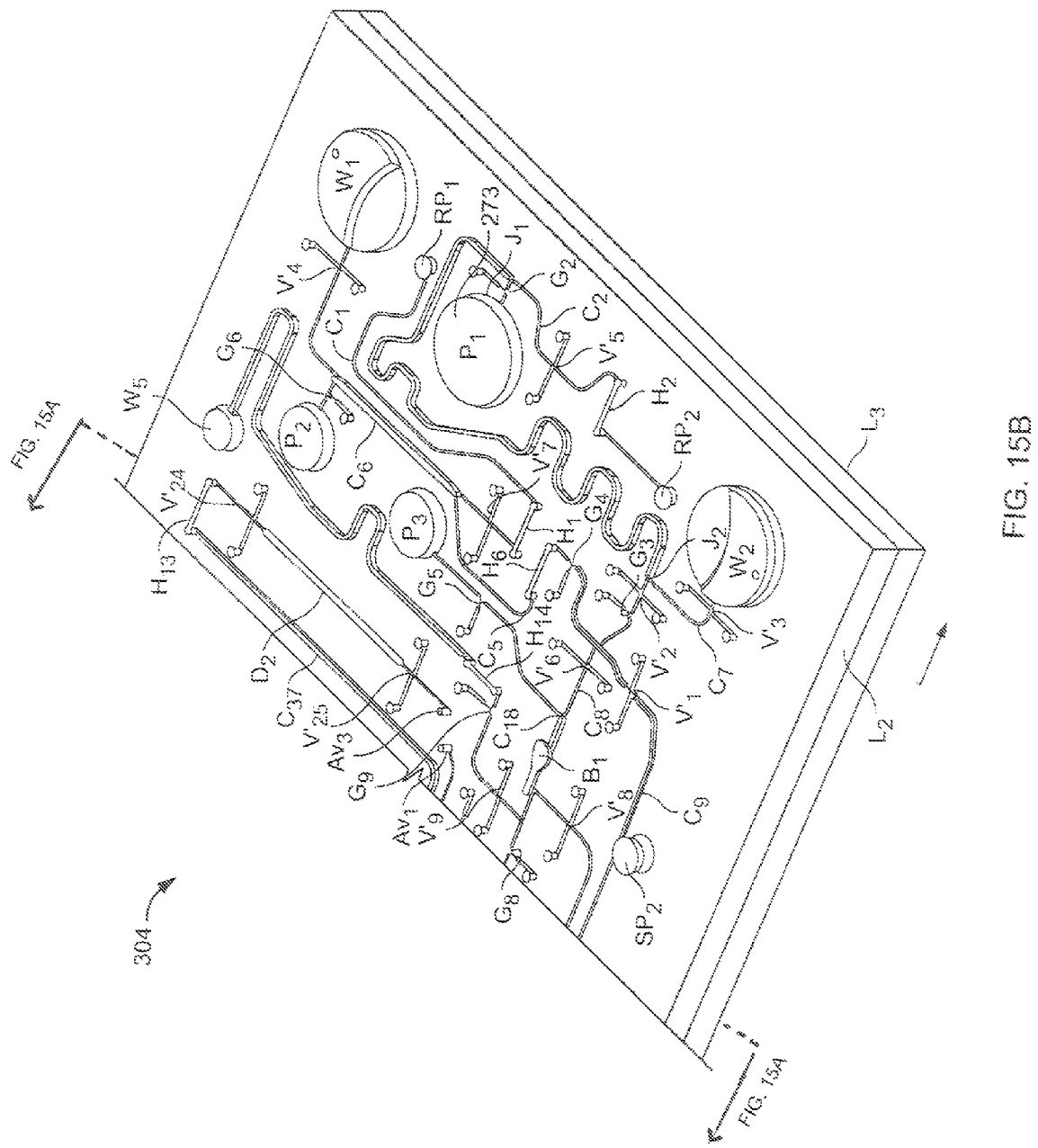

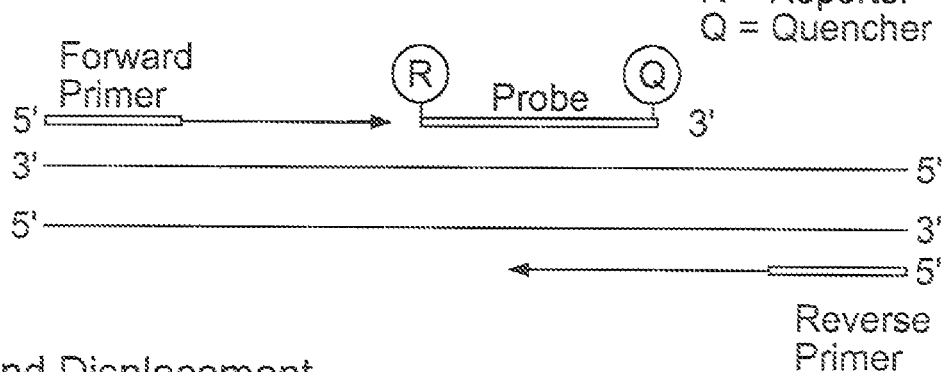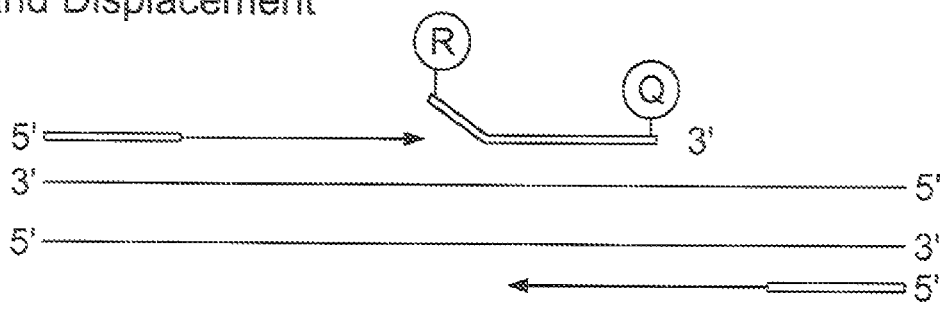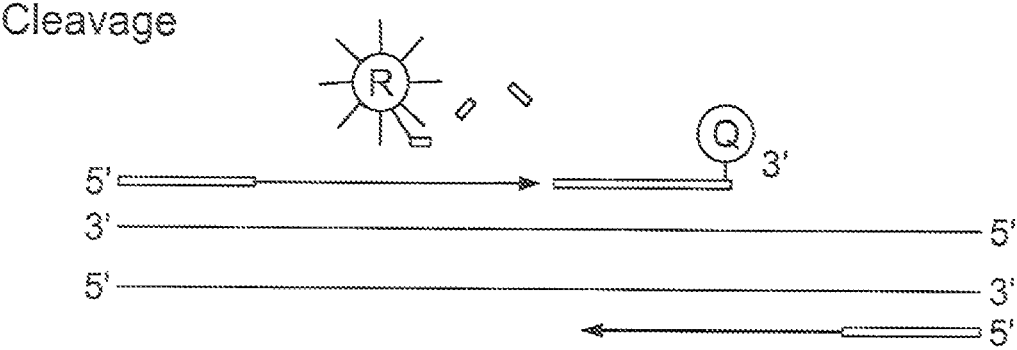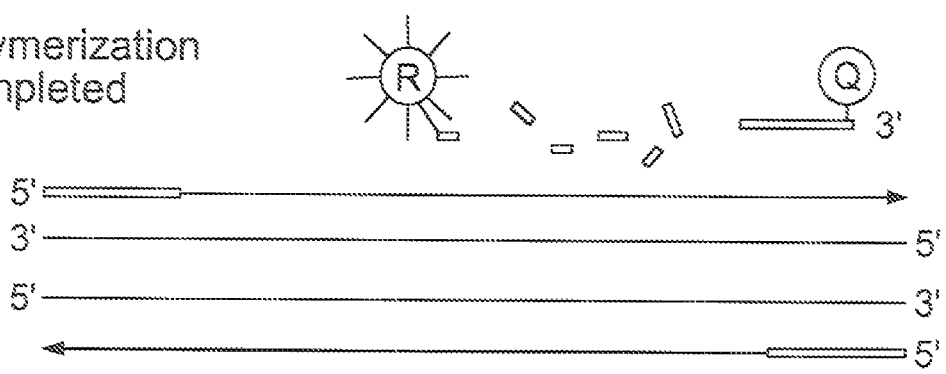
FIG. 44

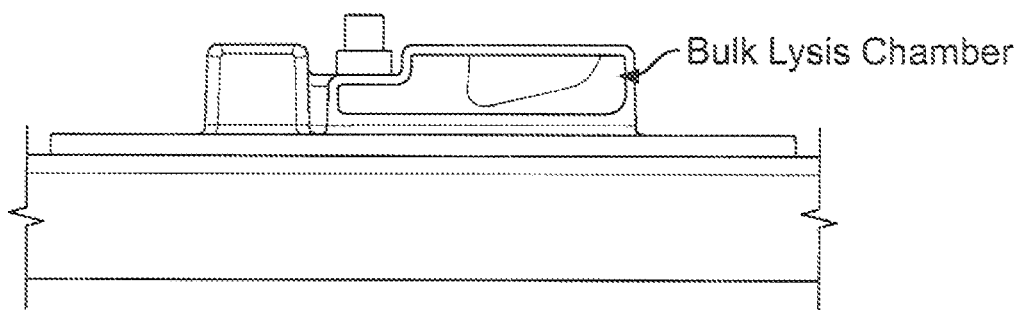
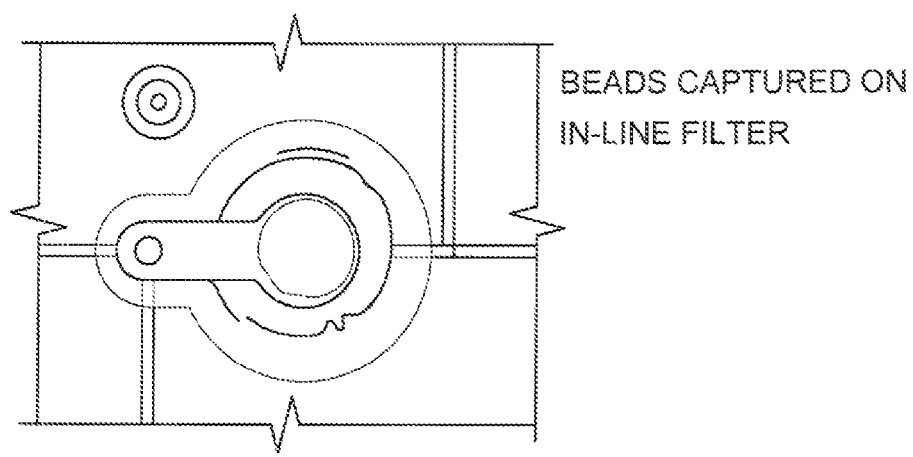
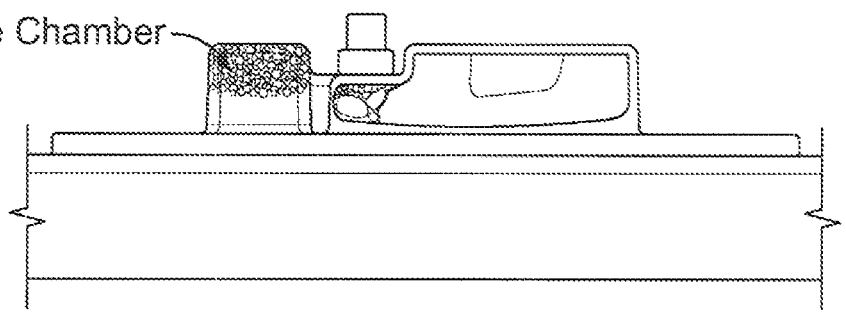
FIG. 49

Neutralization Mixing Channel

INTEGRATED SYSTEM FOR PROCESSING MICROFLUIDIC SAMPLES, AND METHOD OF USING THE SAME

RELATED APPLICATIONS

This application claims the benefit of priority under 35 U.S.C. §119(e) to U.S. provisional application Ser. No. 60/786,007, filed Mar. 24, 2006, and 60/859,284, filed Nov. 14, 2006, both of which are incorporated herein by reference in their entirety.

This application is also related to, and incorporates herein by reference the specifications of U.S. design application Ser. Nos. 29/257,028, 29/257,029, and 29/257,030, all of which filed on Mar. 27, 2006, and also U.S. patent application Ser. No. 11/580,267, filed Oct. 11, 2006, also incorporated herein by reference.

TECHNICAL FIELD

The technology described herein relates to an integrated apparatus for processing polynucleotide-containing samples and carrying out diagnostic tests on the same. More specifically, the technology relates to an apparatus for obtaining a diagnostic result on a biological sample using a microfluidic cartridge that receives the sample, in conjunction with a bench-top system. Methods of using the technology are also described herein.

BACKGROUND

The medical diagnostics industry is a critical element of today's healthcare infrastructure. At present, however, diagnostic analyses no matter how routine have become a bottleneck in patient care. There are several reasons for this. First, there are usually several steps in a diagnostic analysis between collecting the sample, and obtaining a diagnostic result, that require different levels of skill by operators, and different levels of complexity of equipment. For example, a biological sample, once extracted from a patient, must be put in a form suitable for a processing regime that typically involves using polymerase chain reaction (PCR) to amplify a nucleotide of interest. Once amplified, the presence of a nucleotide of interest in the sample needs to be determined unambiguously. Sample preparation is a process that is susceptible to automation but is also relatively routinely carried out in almost any location. By contrast, steps such as PCR and nucleotide detection have customarily only been within the compass of specially trained individuals having access to specialist equipment. Second, many diagnostic analyses can only be done with highly specialist equipment that is both expensive and only operable by trained clinicians. Such equipment is found in only a few locations—often just one in any given urban area. This means that most hospitals are required to send out samples to these locations for analysis, thereby incurring shipping costs and transportation delays, and possibly even sample loss, or mix-up. Third, some specialist equipment is typically not available 'on-demand' but instead runs in batches, thereby delaying the processing time for many samples because they must wait for a machine to fill up before they can be run.

The analysis of a biological sample to accomplish a particular diagnosis typically includes detecting one or more polynucleotides present in the sample. One example of detection is qualitative detection, which relates, for example, to the determination of the presence of the polynucleotide and/or the determination of information related to, for example, the type, size, presence or absence of mutations, and/or the sequence of the polynucleotide. Another example of detection is quantitative detection, which relates, for example, to the determination of the amount of polynucleotide present. Detection may therefore generally include both qualitative and quantitative aspects. Detecting polynucleotides qualitatively often involves establishing the presence of extremely small quantities in a sample. In order to improve sensitivity, therefore, the amount of polynucleotide in question is often amplified. For example, some detection methods include polynucleotide amplification by polymerase chain reaction (PCR) or a related amplification technique. Such techniques use a cocktail of ingredients, including one or more of an enzyme, a probe, and a labeling agent. Therefore, detection of polynucleotides can require use of a variety of different reagents, many of which require sensitive handling to maintain their integrity, both during use, and over time.

Understanding that sample flow breaks down into several key steps, it would be desirable to consider ways to automate as many of these as possible, and, desirably, to facilitate accomplishing as many as possible with a single machine that can be made available, on demand, to many users. There is therefore need for a method and apparatus of carrying out steps of sample preparation, PCR, and detection on biological samples in such a way that as few separate steps as possible are carried out.

The discussion of the background to the technology herein is included to explain the context of the technology. This is not to be taken as an admission that any of the material referred to was published, known, or part of the common general knowledge as at the priority date of any of the claims.

Throughout the description and claims of the specification the word "comprise" and variations thereof, such as "comprising" and "comprises", is not intended to exclude other additives, components, integers or steps.

SUMMARY

An apparatus, comprising: a receiving bay configured to receive an insertable microfluidic cartridge; at least one heat source thermally coupled to the cartridge and configured to apply heat to one or more selected regions of the cartridge at one or more selected times, in order to: create a micro-droplet of a polynucleotide-containing biological sample held on the cartridge; cause the micro-droplet to move between one or more positions on the microfluidic cartridge; lyse cells, where present in the biological sample, thereby releasing polynucleotides from the cells; prepare one or more of the polynucleotides for amplification; and amplify one or more of the polynucleotides; a detector configured to detect presence of the one or more amplified polynucleotides; and a processor coupled to the detector and the at least one heat source, wherein the processor is configured to control applying heat to the one or more selected regions of the microfluidic cartridge at one or more selected times.

The system herein further comprises an integrated system, comprising an apparatus and a complementary cartridge, wherein together the apparatus and cartridge process a sample that has been injected into the cartridge, and provide a diagnostic result on the sample.

The receiving bay of the apparatus can be configured to selectively receive the microfluidic cartridge, as further described herein and exemplified by the accompanying drawings. For example, the receiving bay and the microfluidic cartridge can be complementary in shape so that the microfluidic cartridge can be selectively received in, e.g., a single orientation. The microfluidic cartridge can have a registration member that fits into a complementary feature of the receiving bay. By selectively receiving the cartridge, the receiving bay can help a user to place the cartridge so that the apparatus can properly operate on the cartridge. The receiving bay can also be configured so that various components of the apparatus that can operate on the microfluidic cartridge (heat pumps, peltier coolers, heat-removing electronic elements, detectors, force members, and the like) can be positioned to properly operate on the microfluidic cartridge. For example, a contact heat source can be situated in the receiving bay such that it can be thermally coupled to one or more distinct locations of a microfluidic catridge that can be selectively received in the receiving bay.

The heat pump can be, for example, a heat source such as a resistor, a reversible heat pump such as a liquid-filled heat transfer circuit or a thermoelectric element, a radiative heat source such as a xenon lamp, and the like. The heat pump may be used not only to provide heat to the microfluidic elements but also to remove heat from microfluidic elements such as to reduce activity of certain reagents, freeze liquid in a microchannel to change its phase from liquid to solid, reduce the pressure of an air chamber to create a partial vacuum, etc.)

In various embodiments of the apparatus: the apparatus can further include a registration member that is complementary to the microfluidic cartridge, whereby the receiving bay receives the microfluidic cartridge in a single orientation; the apparatus can further include a sensor coupled to a processor, the sensor configured to sense whether the microfluidic cartridge can be selectively received.

The processor can be programmable to operate the detector to detect a polynucleotide or a probe thereof in a microfluidic cartridge located in the receiving bay.

The detector can be, for example, an optical detector. For example, the detector can include a light source that emits light in an absorption band of a fluorescent dye and a light detector that detects light in an emission band of the fluorescent dye, wherein the fluorescent dye corresponds to a fluorescent polynucleotide probe or a fragment thereof. For example, the optical detector can include a bandpass-filtered diode that selectively emits light in the absorption band of the fluorescent dye and a bandpass filtered photodiode that selectively detects light in the emission band of the fluorescent dye; or for example, the optical detector can be configured to independently detect a plurality of fluorescent dyes having different fluorescent emission spectra, wherein each fluorescent dye corresponds to a fluorescent polynucleotide probe or a fragment thereof; or for example, the optical detector can be configured to independently detect a plurality of fluorescent dyes at a plurality of different locations in the cartridge, wherein each fluorescent dye corresponds to a fluorescent polynucleotide probe or a fragment thereof.

The processor can be, for example, programmable to operate the at least one heat pump.

In various embodiments, the at least one heat pump can be a contact heat source selected from a resistive heater, a radiator, a fluidic heat exchanger and a Peltier device. The contact heat source can be configured at the receiving bay to be thermally coupled to a distinct location in a microfluidic cartridge received in the receiving bay, whereby the distinct location can be selectively heated. At least one additional contact heat source can be included, wherein the contact heat sources can be each configured at the receiving bay to be independently thermally coupled to a different distinct location in a microfluidic cartridge received in the receiving bay, whereby the distinct locations can be independently heated. The contact heat source can be configured to be in direct physical contact with a distinct location of a microfluidic cartridge received in the receiving bay. In various embodiments, each contact source heater can be configured to heat a distinct location having an average diameter in 2 dimensions from about 1 millimeter (mm) to about 15 mm (typically about 1 mm to about 10 mm), or a distinct location having a surface area of between about 1 $mm^2$ about 225 $mm^2$ (typically between about 1 $mm^2$ and about 100 $mm^2$, or in some embodiments between about 5 $mm^2$ and about 50 $mm^2$).

In various embodiments, the apparatus can include a compliant layer at the contact heat source, configured to thermally couple the contact heat source with at least a portion of a microfluidic cartridge received in the receiving bay. The compliant layer can have a thickness of between about 0.05 and about 2 millimeters, and a Shore hardness of between about 25 and about 100.

In various embodiments, at least one heat pump can be a radiative heat source configured to direct heat to a distinct location of a microfluidic cartridge received in the receiving bay.

In various embodiments, the one or more force members configured to apply force to at least a portion of a microfluidic cartridge received in the receiving bay.

In various embodiments, the one or more force members can be configured to apply force to thermally couple the at least one heat pump to at least a portion of the microfluidic cartridge. The one or more force members can be configured to operate a mechanical member at the microfluidic cartridge, the mechanical member selected from the group consisting of a pierceable reservoir, a valve or a pump.

In various embodiments, the one or more force members can be configured to apply force to a plurality of locations in the microfluidic cartridge. The force applied by the one or more force members can result in an average pressure at an interface between a portion of the receiving bay and a portion of the microfluidic cartridge of between about 5 kilopascals and about 50 kilopascals, for example, the average pressure can be at least about 14 kilopascals. At least one force member can be manually operated. At least one force member can be mechanically coupled to a lid at the receiving bay, whereby operation of the lid operates the force member.

In various embodiments, the apparatus can further include a lid at the receiving bay, the lid being operable to at least partially exclude ambient light from the receiving bay. The lid can be, for example, a sliding lid. The lid can include the optical detector. A major face of the lid at the optical detector or at the receiving bay can vary from planarity by less than about 100 micrometers, for example, less than about 25 micrometers. The lid can be configured to be removable from the apparatus. The lid can include a latching member.

In various embodiments, the apparatus can further include at least one input device coupled to the processor.

In various embodiments, the apparatus can further include a heating stage configured to be removable from the apparatus wherein at least one heat pump can be located in the heating stage.

In various embodiments, the cartridge can further include an analysis port. The analysis port can be configured to allow an external sample system to analyze a sample in the microfluidic cartridge; for example, the analysis port can be a hole or window in the apparatus which can accept an optical detection probe that can analyze a sample in situ in the microfluidic cartridge.

In some embodiments, the analysis port can be configured to direct a sample from the microfluidic cartridge to an external sample system; for example, the analysis port can include a conduit in fluid communication with the microfluidic cartridge that directs a liquid sample to a chromatography apparatus, an optical spectrometer, a mass spectrometer, or the like.

In some embodiments, the apparatus can include a receiving bay configured to receive a microfluidic cartridge in a single orientation; at least one radiative heat source thermally coupled to the receiving bay; at least two contact heat sources configured in the receiving bay to be thermally coupled to distinct locations, whereby the distinct locations can be selectively heated; one or more force members configured to apply force to at least a portion of the microfluidic cartridge received in the receiving bay, wherein at least one of the one or more force members can be configured to apply force to thermally couple the contact heat sources to the distinct locations, and at least one of the one or more force members can be configured to operate a mechanical member at the microfluidic cartridge, the mechanical member selected from the group consisting of a pierceable reservoir; a lid at the receiving bay, the lid being operable to at least partially exclude ambient light from the receiving bay, the lid comprising an optical detector configured to independently detect one or more fluorescent dyes, optionally having different fluorescent emission spectra, wherein each fluorescent dye corresponds to a fluorescent polynucleotide probe or a fragment thereof; at least one input device selected from the group consisting of a keyboard, a touch-sensitive surface, a microphone, and a mouse, at least one data storage medium selected from the group consisting of a hard disk drive, an optical disk drive, a communication interface selectede from the group consisting of: a serial connection, a parallel connection, a wireless network connection, and a wired network connection, a sample identifier selected from an optical character reader, a bar code reader, and a radio frequency tag reader; at least one output selected from a display, a printer, a speaker, and a processor coupled to the detector, the sensor, the heat sources, the input, and the output.

A microfluidic cartridge can include a microfluidic network and a retention member in fluid communication with the microfluidic network, the retention member being selective for at least one polynucleotide over at least one polymerase chain reaction inhibitor. In some embodiment, the microfluidic cartridge also includes a registration member.

In various embodiments of the microfluidic cartridge, the microfluidic cartridge can further include a sample inlet valve in fluid communication with the microfluidic network. The sample inlet valve can be configured to accept a sample at a pressure differential compared to ambient pressure of between about 20 kilopascals and 200 kilopascals, for example between about 70 kilopascals and 110 kilopascals.

In various embodiments, the microfluidic network can include a filter in fluid communication with the sample inlet valve, the filter being configured to separate at least one component from a sample mixture introduced at the sample inlet.

In various embodiments, the microfluidic network can include at least one thermally actuated pump in fluid communication with the microfluidic network. The thermally actuated pump can include a thermoexpansive material selected from a gas, a liquid vaporizable at a temperature between 25° C. and 100° C. at 1 atmosphere, and an expancel polymer.

In various embodiments, the microfluidic network can include at least one thermally actuated valve in fluid communication with the microfluidic network. The thermally actuated valve can include a material having a solid to liquid phase transition at a temperature between 25° C. and 100° C. at 1 atmosphere.

In various embodiments, the microfluidic network can include at least one sealed reservoir containing a reagent, a buffer or a solvent. The sealed reservoir can be, for example, a self-piercing blister pack configured to bring the reagent, the buffer or the solvent into fluid communication with the microfluidic network.

In various embodiments, the microfluidic network can include at least at least one hydrophobic vent.

In various embodiments, the microfluidic network can include at least one reservoir configured to receive and to contain waste such as fluids and/or particulate matter such as cellular debris.

In various embodiments, the retention member can include a polyalkylene imine or a polycationic polyamide, for example, polyethylene imine, poly-L-lysine or poly-D-lysine. The retention member can be in the form of one or more particles. The retention member can be removable from the microfluidic cartridge.

In various embodiments, the microfluidic network can include a lysis reagent. The lysis reagent can include one or more lyophilized pellets of surfactant, wherein the microfluidic network can be configured to contact the lyophilized pellet of surfactant with a liquid to create a lysis reagent solution. The microfluidic network can be configured to contact a sample with the lysis reagent to produce a lysed sample.

In various embodiments, the microfluidic network can be configured to couple heat from an external heat source to the sample to produce the lysed sample. For example, the microfluidic network can be configured to contact the retention member and the lysed sample to create a polynucleotide-loaded retention member.

In various embodiments, the microfluidic cartridge can further include a filter configured to separate the polynucleotide-loaded retention member from liquid.

In various embodiments, the microfluidic cartridge can further include a reservoir containing a wash buffer, wherein the microfluidic network can be configured to contact the polynucleotide-loaded retention member with the wash buffer, for example, the wash buffer can have a pH of at least about 10.

In various embodiments, the microfluidic cartridge can include a reservoir containing a release buffer, wherein the microfluidic cartridge can be configured to contact the polynucleotide-loaded retention member with the release buffer to create a released polynucleotide sample.

In various embodiments, the microfluidic network can be configured to couple heat from an external heat source to the polynucleotide-loaded retention member to create the released polynucleotide sample.

In various embodiments, the microfluidic cartridge can include a reservoir containing a neutralization buffer, wherein the microfluidic network can be configured to contact the released polynucleotide sample with the neutralization buffer to create a neutralized polynucleotide sample.

In various embodiments, the microfluidic cartridge can include a PCR reagent mixture comprising a polymerase enzyme and a plurality of nucleotides. The PCR reagent mixture can be in the form of one or more lyophilized pellets, and the microfluidic network can be configured to contact the PCR pellet with liquid to create a PCR reagent mixture solution.

In various embodiments, the microfluidic network can be configured to couple heat from an external heat source with the PCR reagent mixture and the neutralized polynucleotide sample under thermal cycling conditions suitable for creating PCR amplicons from the neutralized polynucleotide sample.

In various embodiments, the PCR reagent mixture can further include a positive control plasmid and a fluorogenic hybridization probe selective for at least a portion of the plasmid.

In various embodiments, the microfluidic cartridge can include a negative control polynucleotide, wherein the microfluidic network can be configured to independently contact each of the neutralized polynucleotide sample and the negative control polynucleotide with the PCR reagent mixture under thermal cycling conditions suitable for independently creating PCR amplicons of the neutralized polynucleotide sample and PCR amplicons of the negative control polynucleotide.

In various embodiments, the microfluidic cartridge can include at least one probe that can be selective for a polynucleotide sequence, wherein the microfluidic cartridge can be configured to contact the neutralized polynucleotide sample or a PCR amplicon thereof with the probe. The probe can be a fluorogenic hybridization probe. The fluorogenic hybridization probe can include a polynucleotide sequence coupled to a fluorescent reporter dye and a fluorescence quencher dye. The PCR reagent mixture can further include a positive control plasmid and a plasmid fluorogenic hybridization probe selective for at least a portion of the plasmid and the microfluidic cartridge can be configured to allow independent optical detection of the fluorogenic hybridization probe and the plasmid fluorogenic hybridization probe.

In various embodiments, the probe can be selective for a polynucleotide sequence that can be characteristic of an organism, for example any organism that employs deoxyribonucleic acid or ribonucleic acid polynucleotides. Thus, the probe can be selective for any organism. Suitable organisms include mammals (including humans), birds, reptiles, amphibians, fish, domesticated animals, farmed animals, wild animals, extinct organisms, bacteria, fungi, viruses, plants, and the like. The probe can also be selective for components of organisms that employ their own polynucleotides, for example mitochondria. In some embodiments, the probe can be selective for microorganisms, for example, organisms used in food production (for example, yeasts employed in fermented products, molds or bacteria employed in cheeses, and the like) or pathogens (e.g., of humans, domesticated or wild mammals, domesticated or wild birds, and the like). In some embodiments, the probe can be selective for organisms selected from the group consisting of gram positive bacteria, gram negative bacteria, yeast, fungi, protozoa, and viruses.

In various embodiments, the probe can be selective for a polynucleotide sequence that is characteristic of Group B *Streptococcus*.

In various embodiments, the microfluidic cartridge can be configured to allow optical detection of the fluorogenic hybridization probe.

In various embodiments, the microfluidic cartridge can further include a computer-readable label. For example, the label can include a bar code, a radio frequency tag or one or more computer-readable characters. The label can be formed of a mechanically compliant material. For example, the mechanically compliant material of the label can have a thickness of between about 0.05 and about 2 millimeters and a Shore hardness of between about 25 and about 100.

In various embodiments, the microfluidic cartridge can be further surrounded by a sealed pouch, during handling and storage, and prior to being inserted into the chamber. The microfluidic cartridge can be sealed in the pouch with an inert gas. The sealed pouch may also contain a packet of dessicant.

The microfluidic cartridge can bedisposable.

In various embodiments, the microfluidic cartridge can contain one or more sample lanes. For example, a sample lane can include a thermally actuated pump, a thermally actuated valve, a sample inlet valve, a filter, and at least one reservoir. The lanes can be independent of each other, or can be partially dependent, for example, the lanes can share one or more reagents such as the lysis reagent.

In some embodiments, the microfluidic cartridge can include a registration member; and a microfluidic network. The microfluidic network includes, in fluidic communication: at least one thermally actuated pump; at least one thermally actuated valve; a sample inlet valve configured to accept a sample at a pressure differential compared to ambient pressure of between about 70 kilopascals and 110 kilopascals; a retention member selective for at least one polynucleotide over at least one polymerase chain reaction inhibitor, the retention member being in the form of a plurality of particles formed of a polyalkylene imine or a polycationic polyamide; a filter configured to separate the polynucleotide-loaded retention member from liquid; a plurality of reservoirs, at least said one said reservoir being a sealed, self-piercing blister pack reservoir. The plurality of reservoirs can contain among them: a lysis reagent, the microfluidic network being configured to contact a sample introduced at the sample inlet with the lysis reagent and the retention member to create a polynucleotide-loaded retention member; a reservoir containing a w ash buffer, the microfluidic network being configured to contact the polynucleotide-loaded retention member with the wash buffer; a reservoir containing a release buffer, the microfluidic network being configured to contact the polynucleotide-loaded retention member with the release buffer to create a released polynucleotide sample; a neutralization buffer, the microfluidic network being configured to contact the released polynucleotide sample with the neutralization buffer to create a neutralized polynucleotide sample; a PCR reagent mixture comprising a polymerase enzyme, a positive control plasmid, a fluorogenic hybridization probe selective for at least a portion of the plasmid and a plurality of nucleotides; and at least one probe that can be selective for a polynucleotide sequence, wherein the microfluidic network can be configured to contact the neutralized polynucleotide sample or a PCR amplicon thereof with the probe. Further, the microfluidic network can be configured to couple heat from an external heat source with the PCR reagent mixture and the neutralized polynucleotide sample under thermal cycling conditions suitable for creating PCR amplicons from the neutralized polynucleotide sample.

In various embodiments, a polynucleotide analysis system can include both the the microfluidic cartridge and the apparatus, as further described herein.

In various embodiments, a polynucleotide sample kit can include a microfluidic cartridge comprising a microfluidic network and a retention member in fluid communication with the microfluidic network, the retention member being selective for at least one polynucleotide over at least one polymerase chain reaction inhibitor a sample container; and a liquid transfer member such as a syringe.

In various embodiments, the polynucleotide sample kit can further include instructions to employ the liquid transfer member to transfer a sample from the sample container to the microfluidic network.

In various embodiments, the polynucleotide sample kit can further include instructions to employ the liquid transfer member to direct a sample from the sample container, and a volume of air into the microfluidic network, the volume of air being between about 0.5 mL and about 5 mL.

In various embodiments, the polynucleotide sample kit can further include a filter, and, for example, instructions to employ the liquid transfer member to direct a sample from the sample container through the filter into the microfluidic network.

In various embodiments, the polynucleotide sample kit can further include at least one computer-readable label on the sample container. The label can include, for example, a bar code, a radio frequency tag or one or more computer-readable characters. The microfluidic cartridge can be sealed in a pouch with an inert gas.

In various embodiments, the polynucleotide sample kit can further include a sampling member; a transfer container; and instructions to contact the sampling member to a biological sample and to place the sampling member in the transfer container.

In various embodiments, the polynucleotide sample kit can further include a sample buffer, and, for example, instructions to contact the sampling member and the sample buffer.

In various embodiments, the polynucleotide sample kit can further include at least one probe that can be selective for a polynucleotide sequence, e.g., the polynucleotide sequence that is characteristic of a pathogen selected from the group consisting of gram positive bacteria, gram negative bacteria, yeast, fungi, protozoa, and viruses.

In some embodiments, the polynucleotide sample kit can include a microfluidic cartridge comprising a microfluidic network, a retention member in fluid communication with the microfluidic network, and a flurogenic probe, the retention member being selective for at least one polynucleotide over at least one polymerase chain reaction inhibitor, the flurogenic probe being selective for a polynucleotide sequence that can be characteristic of a pathogen selected from the group consisting of gram positive bacteria, gram negative bacteria, yeast, fungi, protozoa, and viruses; a sample container; a liquid transfer member; a sampling member; a transfer container; a sample buffer; and instructions. The instructions can include instructions to: employ the liquid transfer member to transfer a sample from the sample container to the microfluidic network; employ the liquid transfer member to direct a sample from the sample container and a volume of air into the microfluidic network, the volume of air being between about 0.5 mL and about 5 mL; employ the liquid transfer member to direct a sample from the sample container through a filter into the microfluidic network; and contact the sampling member to a biological sample and to place the sampling member in the transfer container.

A method for sampling a polynucleotide can include the steps of contacting the retention member at the microfluidic cartridge with a biological sample, the biological sample comprising at least one polynucleotide, thereby producing a polynucleotide-loaded retention member in the microfluidic cartridge; separating at least a portion of the biological sample from the polynucleotide-loaded retention member; and releasing at least a portion of a polynucleotide from the polynucleotide-loaded retention member, thereby creating a released polynucleotide sample.

In various embodiments, the method can further include one or more of the following steps: placing the microfluidic cartridge in the receiving bay of the apparatus; operating the force member in the apparatus to apply pressure at an interface between a portion of the receiving bay and a portion of the microfluidic cartridge (e.g., creating a pressure between about 5 kilopascals and about 50 kilopascals, or in some embodiments, at least about 14 kilopascals); employing the force member to apply force to a mechanical member in the microfluidic cartridge, the mechanical member selected from the group consisting of a pierceable reservoir, a valve or a pump, to release at least one reagent, buffer, or solvent from a reservoir in the microfluidic chip; and/or closing the lid to operate the force member, wherein the force member can be mechanically coupled to a lid at the receiving bay.

In some embodiments, the method can further include employing a sample identifier to read a label on the microfluidic cartridge or a label on the biological sample.

In some embodiments, the method can further include introducing a crude biological sample into the microfluidic cartridge and separating the biological sample from the crude biological sample in the microfluidic cartridge, e.g., using a filter in the cartridge, or the biological sample can be separated from a crude biological sample prior to introducing the biological sample into the microfluidic cartridge.

In some embodiments, the method can further include lysing the biological sample, for example, using heat, a lysis reagent, and the like. In some embodiments, wherein the microfluidic cartridge comprises one or more lyophilized pellets of lysis reagent, the method can further include reconstituting the lyophilized pellet of surfactant with liquid to create a lysis reagent solution.

In various embodiments, the method can further include one or more of the following: heating the biological sample in the microfluidic cartridge; pressurizing the biological sample in the microfluidic cartridge at a pressure differential compared to ambient pressure of between about 20 kilopascals and 200 kilopascals, or in some embodiments between about 70 kilopascals and 110 kilopascals.

In some embodiments, the portion of the biological sample separated from the polynucleotide-loaded retention member can include at least one polymerase chain reaction inhibitor selected from the group consisting of hemoglobin, peptides, faecal compounds, humic acids, mucousol compounds, DNA binding proteins, or a saccharide. In some embodiments, the method can further include separating the polynucleotide-loaded retention member from substantially all of the polymerase chain reaction inhibitors in the biological sample.

In various embodiments, the method can further include one or more of the following: directing a fluid in the microfluidic cartridge by operating a thermally actuated pump or a thermally actuated valve; contacting the polynucleotide-loaded retention member with a wash buffer; heating the polynucleotide-loaded retention member to a temperature of at least about 50° C. (in some embodiments, the temperature can be 100° C. or less); heating the polynucleotide-loaded retention member for less than about 10 minutes; contacting the polynucleotide-loaded retention member with a release buffer to create a released polynucleotide sample (for example, in some embodiments, the the release buffer can have a volume of less than about 50 microliters, the release buffer can include a detergent, and/or the release buffer can have a pH of at least about 10); and/or contacting the released polynucleotide sample with a neutralization buffer to create a neutralized polynucleotide sample.

In various embodiments, the method can further include one or more of the following: contacting the neutralized polynucleotide sample with a PCR reagent mixture comprising a polymerase enzyme and a plurality of nucleotides (in some embodiments, the PCR reagent mixture can further include a positive control plasmid and a fluorogenic hybridization probe selective for at least a portion of the plasmid); in some embodiments, the PCR reagent mixture can be in the form of one or more lyophilized pellets, and the method can further include reconstituting the PCR pellet with liquid to create a PCR reagent mixture solution; heating the PCR reagent mixture and the neutralized polynucleotide sample under thermal cycling conditions suitable for creating PCR amplicons from the neutralized polynucleotide sample; contacting the neutralized polynucleotide sample or a PCR amplicon thereof with at least one probe that can be selective for a polynucleotide sequence; independently contacting each of the neutralized polynucleotide sample and a negative control polynucleotide with the PCR reagent mixture under thermal cycling conditions suitable for independently creating PCR amplicons of the neutralized polynucleotide sample and PCR amplicons of the negative control polynucleotide; and/or contacting the neutralized polynucleotide sample or a PCR amplicon thereof and the negative control polynucleotide or a PCR amplicon thereof with at least one probe that is selective for a polynucleotide sequence.

In various embodiments, the method can further include one or more of the following: determining the presence of a polynucleotide sequence in the biological sample, the polynucleotide sequence corresponding to the probe, if the probe is detected in the neutralized polynucleotide sample or a PCR amplicon thereof; determining a contaminated result if the probe is detected in the negative control polynucleotide or a PCR amplicon thereof; and/or in some embodiments, wherein wherein the PCR reagent mixture further comprises a positive control plasmid and a plasmid probe selective for at least a portion of the plasmid, the method further including determining a PCR reaction has occurred if the plasmid probe is detected.

In various embodiments, the method does not comprise centrifugation of the polynucleotide-loaded retention member.

In some embodiments, the method for sampling a polynucleotide can include: placing a microfluidic cartridge in the receiving bay of an apparatus; operating a force member in the apparatus to apply pressure at an interface between a portion of the receiving bay and a portion of the microfluidic cartridge, the force operating to release at least one reagent, buffer, or solvent from a reservoir in the microfluidic cartridge; lysing a biological sample in the microfluidic cartridge to create a lysed biological sample; contacting a retention member at a microfluidic cartridge with the lysed biological sample, the biological sample comprising at least one polynucleotide, thereby producing a polynucleotide-loaded retention member in the microfluidic cartridge, wherein the retention member is in the form of a plurality of particles of a polyalkylene imine or a polycationic polyamide; contacting the polynucleotide-loaded retention member with a wash buffer; heating the polynucleotide-loaded retention member to a temperature of at least about 50° C. for less than about 10 minutes; contacting the polynucleotide-loaded retention member with a release buffer to create a released polynucleotide sample contacting the released polynucleotide sample with a neutralization buffer to create a neutralized polynucleotide sample; contacting the neutralized polynucleotide sample with a PCR reagent mixture under thermal cycling conditions suitable for creating PCR amplicons from the neutralized polynucleotide sample, the PCR reagent mixture comprising a polymerase enzyme, a positive control plasmid a fluorogenic hybridization probe selective for at least a portion of the plasmid, and a plurality of nucleotides, contacting the neutralized polynucleotide sample or a PCR amplicon thereof with at least one fluorogenic probe that can be selective for a polynucleotide sequence, wherein the probe can be selective for a polynucleotide sequence that can be characteristic of an organism selected from the group consisting of gram positive bacteria, gram negative bacteria, yeast, fungi, protozoa, and viruses; and detecting the fluorogenic probe and determining the presence of the organism for which the one fluorogenic probe can be selective.

In various embodiments, a computer program product includes computer readable instructions thereon for operating the apparatus.

In some embodiments, a computer program product includes computer readable instructions thereon for causing the system to create a released polynucleotide sample from a biological sample. The computer readable instructions can include instructions for contacting the retention member with the biological sample under conditions suitable for producing a polynucleotide-loaded retention member; separating at least a portion of the biological sample from the polynucleotide-loaded retention member; and releasing at least a portion of a polynucleotide from the polynucleotide-loaded retention member, thereby creating a released polynucleotide sample.

In various embodiments, the computer program product can include one or more instructions to cause the system to: output an indicator of the placement of the microfluidic cartridge in the receiving bay; read a sample label or a microfluidic cartridge label; output directions for a user to input a sample identifier; output directions for a user to load a sample transfer member with the biological sample; output directions for a user to apply a filter to the sample transfer member; output directions for a user to introduce the biological sample into the microfluidic cartridge; output directions for a user to cause the biological sample to contact a lysis reagent in the microfluidic cartridge; output directions for a user to place the microfluidic cartridge in the receiving bay; output directions for a user to operate a force member in the apparatus to apply pressure at an interface between a portion of the receiving bay and a portion of the microfluidic cartridge; output directions for a user to close the lid to operate the force member; and/or output directions for a user to pressurize the biological sample in the microfluidic cartridge by injecting the biological sample with a volume of air between about 0.5 mL and about 5 mL.

In various embodiments, the computer program product can include one or more instructions to cause the system to: lyse the biological sample; lyse the biological sample with a lysis reagent; reconstitute a lyophilized pellet of surfactant with liquid to create a lysis reagent solution; heat the biological sample; separate the polynucleotide-loaded retention member from at least a portion of the biological sample; separate the polynucleotide-loaded retention member from substantially all of the polymerase chain reaction inhibitors in the biological sample; direct a fluid in the microfluidic cartridge by operating a thermally actuated pump or a thermally actuated valve; contact the polynucleotide-loaded retention member with a wash buffer; heat the polynucleotide-loaded retention member to a temperature of at least about 50° C. (in some embodiments, the temperature can be about 100° C. or less); heat the polynucleotide-loaded retention member for less than about 10 minutes; contact the polynucleotide-loaded retention member with a release buffer to create a released polynucleotide sample; and/or contact the released polynucleotide sample with a neutralization buffer to create a neutralized polynucleotide sample.

In various embodiments, the computer program product can include one or more instructions to cause the system to: contact the neutralized polynucleotide sample with a PCR reagent mixture comprising a polymerase enzyme and a plurality of nucleotides; heat the PCR reagent mixture and the neutralized polynucleotide sample under thermal cycling conditions suitable for creating PCR amplicons from the neutralized polynucleotide sample; contact the neutralized polynucleotide sample or a PCR amplicon thereof with at least one probe that can be selective for a polynucleotide sequence; independently contact each of the neutralized polynucleotide sample and a negative control polynucleotide with the PCR reagent mixture under thermal cycling conditions suitable for independently creating PCR amplicons of the neutralized polynucleotide sample and PCR amplicons of the negative control polynucleotide; contact the neutralized polynucleotide sample or a PCR amplicon thereof and the negative control polynucleotide or a PCR amplicon thereof with at least one probe that can be selective for a polynucleotide sequence; output a determination of the presence of a polynucleotide sequence in the biological sample, the polynucleotide sequence corresponding to the probe, if the probe is detected in the neutralized polynucleotide sample or a PCR amplicon thereof; and/or output a determination of a contaminated result if the probe is detected in the negative control polynucleotide or a PCR amplicon thereof.

In various embodiments, the computer program product can include one or more instructions to cause the system to automatically conduct one or more of the steps of the method.

In various embodiments, wherein the microfluidic network comprises two or more sample lanes each including a thermally actuated pump, a thermally actuated valve, a sample inlet valve, a filter, and at least one reservoir, wherein the computer readable instructions can be configured to independently operate each said lane in the system.

In some embodiments, the computer program product includes computer readable instructions thereon for causing a system to create a released polynucleotide sample from a biological sample. The system can include a microfluidic cartridge comprising a microfluidic network and, a retention member in fluid communication with the microfluidic network, the retention member being selective for at least one polynucleotide over at least one polymerase chain reaction inhibitor; and an apparatus comprising a receiving bay configured to selectively receive the microfluidic cartridge; at least one heat pump configured to be thermally coupled to the microfluidic cartridge in the receiving bay; a detector; and a programmable processor coupled to the detector and the heat pump. The computer readable instructions can include instructions for: lysing a biological sample by contacting the biological sample with a lysis reagent and heating to produce a lysed sample; contacting the retention member with the biological sample and/or the lysed sample to produce a polynucleotide-loaded retention member; separating at least a portion of the biological sample from the polynucleotide-loaded retention member; contacting the polynucleotide-loaded retention member with a wash buffer; contacting the polynucleotide-loaded retention member with a release buffer and or heat to release at least a portion of a polynucleotide from the polynucleotide-loaded retention member, thereby creating a released polynucleotide sample; contacting the released polynucleotide sample with a neutralization buffer to create a neutralized polynucleotide sample; independently contacting each of the neutralized polynucleotide sample and a negative control polynucleotide with a PCR reagent mixture under thermal cycling conditions suitable for independently creating PCR amplicons, the PCR reagent mixture comprising a polymerase enzyme, a plurality of nucleotides, a positive control plasmid and a plasmid probe selective for at least a portion of the plasmid; determining a PCR reaction has occurred if the plasmid probe is detected; contacting the neutralized polynucleotide sample or a PCR amplicon thereof and the negative control polynucleotide or a PCR amplicon thereof with at least one probe that is selective for a polynucleotide sequence; determining the presence of a polynucleotide sequence in the biological sample, the polynucleotide sequence corresponding to the probe, if the probe is detected in the neutralized polynucleotide sample or a PCR amplicon thereof; and determining a contaminated result if the probe is detected in the negative control polynucleotide or a PCR amplicon thereof.

The details of one or more embodiments of the technology are set forth in the accompanying drawings and the description below. Other features, objects, and advantages of the technology will be apparent from the description and drawings, and from the claims. Like reference symbols in the various drawings indicate like elements.

DESCRIPTION OF DRAWINGS

FIG. 5 is a diagram of a fluorescent detection module.

FIGS. 8A-8C show a plan view of heater circuitry adjacent to a PCR reaction zone; and thermal images of heater circuitry in operation.

FIGS. 15A and 15B, taken together, illustrate a perspective view of a microfluidic network of the microfluidic cartridge of FIGS. 14A and 14B.

FIG. 44 is a schematic of an exemplary real-time PCR assay based on the TaqMan® assay.

FIG. 49 depicts DNA capture beads which can be employed.

DETAILED DESCRIPTION

A system, microfluidic cartridge, kit, methods, and computer program product, are now further described Analysis of biological samples often includes determining whether one or more polynucleotides (e.g., a DNA, RNA, mRNA, or rRNA) can be present in the sample. For example, one may analyze a sample to determine whether a polynucleotide indicative of the presence of a particular pathogen (such as a bacterium or a virus) can be present. The polynucleotide may be a sample of genomic DNA, or may be a sample of mitochondrial DNA. Typically, biological samples can be complex mixtures. For example, a sample may be provided as a blood sample, a tissue sample (e.g., a swab of, for example, nasal, buccal, anal, or vaginal tissue), a biopsy aspirate, a lysate, as fungi, or as bacteria. Polynucleotides to be determined may be contained within particles (e.g., cells (e.g., white blood cells and/or red blood cells), tissue fragments, bacteria (e.g., gram positive bacteria and/or gram negative bacteria), fungi, spores). One or more liquids (e.g., water, a buffer, blood, blood plasma, saliva, urine, spinal fluid, or organic solvent) can typically be part of the sample and/or can be added to the sample during a processing step.

Methods for analyzing biological samples include providing a biological sample (e.g., a swab), releasing polynucleotides from particles (e.g., cells such as bacteria) of the sample, amplifying one or more of the released polynucleotides (e.g., by polymerase chain reaction (PCR)), and determining the presence (or absence) of the amplified polynucleotide(s) (e.g., by fluorescence detection). Biological samples, however, typically include inhibitors (e.g., mucousal compounds, hemoglobin, faecal compounds, and DNA binding proteins) that can inhibit determining the presence of polynucleotides in the sample. For example, such inhibitors can reduce the amplification efficiency of polynucleotides by PCR and other enzymatic techniques for determining the presence of polynucleotides. If the concentration of inhibitors is not reduced relative to the polynucleotides to be determined, the analysis can produce false negative results. The methods and related systems herein for processing biological samples (e.g., samples having one or more polynucleotides to be determined) are typically able to reduce the concentration of inhibitors relative to the concentration of polynucleotides to be determined by methods further described herein.

Various aspects of a system and a microfluidic cartridge are described herein. Additional disclosures of various components thereof may be found in U.S. application Ser. No. 11/580,267, and in provisional application Ser. No. 60/859, 284, the specifications of which are hereby incorporated by reference.

System Overview

Figure 1:
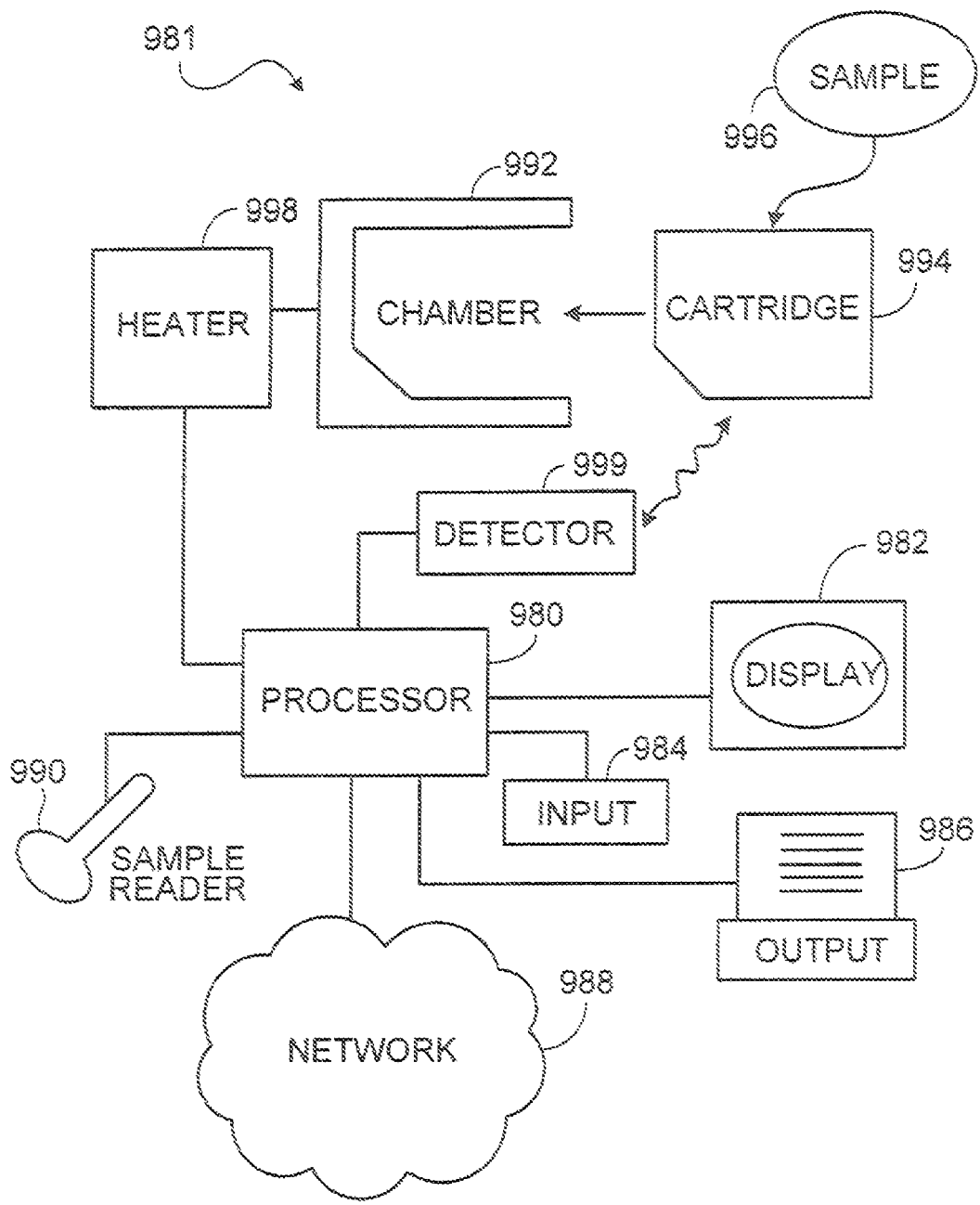
FIG. 1 shows a schematic overview of an apparatus described herein.

A schematic overview of a system 981 for carrying out analyses described herein is shown in FIG. 1. The geometric arrangement of the components of system 981 shown in FIG. 1 is exemplary and not intended to be limiting. A processor 980, such as a microprocessor, is configured to control functions of various components of the system as shown, and is thereby in communication with each such component. In particular, processor 980 is configured to receive data about a sample to be analyzed, e.g., from a sample reader 990, which may be a barcode reader, an optical character reader, or an RFID scanner (radio frequency tag reader). For example, the sample identifier can be a handheld bar code reader. Processor 980 is configured to accept user instructions from an input 984, where such instructions may include instructions to start analyzing the sample, and choices of operating conditions. Processor 980 is also configured to communicate with a display 982, so that, for example, results of analysis are transmitted to the display. Additionally, processor 980 may transmit one or more questions to be displayed on display 982 that prompt a user to provide input in response thereto. Thus, in certain embodiments, input 984 and display 982 are integrated with one another. Processor 980 is optionally further configured to transmit results of an analysis to an output device such as a printer, a visual display, or a speaker, or a combination thereof. Processor 980 is still further optionally connected via a communication interface such as a network interface to a computer network 988. The communication interface can be one or more interfaces selected from the group consisting of: a serial connection, a parallel connection, a wireless network connection and a wired network connection. Thereby, when the system is suitably addressed on the network, a remote user may access the processor and transmit instructions, input data, or retrieve data, such as may be stored in a memory (not shown) associated with the processor, or on some other computer-readable medium that is in communication with the processor.

Although not shown in FIG. 1, in various embodiments, input 984 can include one or more input devices selected from the group consisting of: a keyboard, a touch-sensitive surface, a microphone, a track-pad, a retinal scanner, and a mouse.

Additionally, in various embodiments, the apparatus can further comprise a data storage medium configured to receive data from one or more of the processor, an input device, and a communication interface, the data storage medium being one or more media selected from the group consisting of: a hard disk drive, an optical disk drive, a flash card, and a CD-Rom.

Processor 980 is further configured to control various aspects of sample diagnosis, as follows in overview, and as further described in detail herein. The system is configured to operate in conjunction with a complementary cartridge 994, such as a microfluidic cartridge. The cartridge is itself configured, as further described herein, to receive a biological sample 996 in a form suitable for work-up and diagnostic analysis. The cartridge is received by a receiving bay 992 in the system. The receiving bay is in communication with a heater 998 that itself is controlled by processor 980 in such a way that specific regions of the cartridge are heated at specific times during sample work-up and analysis. The processor is also configured to control a detector 999 that receives an indication of a diagnosis from the cartridge 994. The diagnosis can be transmitted to the output device 986 and/or the display 982, as described hereinabove.

A suitable processor 980 can be designed and manufactured according to, respectively, design principles and semiconductor processing methods known in the art.

The system shown in outline in FIG. 1, as with other exemplary embodiments described herein, is advtangaeous because it does not require locations within the system suitably configured for storage of reagents. Neither does the system, or other exemplary embodiments herein, require inlet or outlet ports that are configured to receive reagents from, e.g., externally stored containers such as bottles, canisters, or reservoirs. Therefore, the system in FIG. 1 is self-contained and operates in conjunction with a microfluidic cartridge, wherein the cartridge has locations within it dedicated to reagent storage.

The system of FIG. 1 may be configured to carry out operation in a single location, such as a laboratory setting, or may be portable so that it can accompany, e.g., a physician, or other healthcare professional, who may visit patients at different locations. The system is typically provided with a power-cord so that it can accept AC power from a mains supply or generator. An optional transformer (not shown) built into the system, or situated externally between a power socket and the system, transforms AC input power into a DC output for use by the system. The system may also be configured to operate by using one or more batteries and therefore is also typically equipped with a battery recharging system, and various warning devices that alert a user if battery power is becoming too low to reliably initiate or complete a diagnostic analysis.

The system of FIG. 1 may further be configured, in other embodiments, for multiplexed sample analysis. In one such configuration, multiple instances of a system, as outlined in FIG. 1, are operated in conjunction with one another to accept and to process multiple cartridges, where each cartridge has been loaded with a different sample. Each component shown in FIG. 1 may therefore be present as many times as there are samples, though the various components may be configured in a common housing.

In still another configuration, a system is configured to accept and to process multiple cartridges, but one or more components in FIG. 1 is common to multiple cartridges. For example, a single device may be configured with multiple cartridge receiving bays, but a common processor and user interface suitably configured to permit concurrent, consecutive, or simultaneous, control of the various cartridges. It is further possible that such an embodiment, also utilizes a single sample reader, and a single output device.

In still another configuration, a system as shown in FIG. 1 is configured to accept a single cartridge, but wherein the single cartridge is configured to process more than 1, for example, 2, 3, 4, 5, or 6, samples in parallel, and independently of one another. Exemplary technology for creating cartridges that can handle multiple samples is described elsewhere, e.g., in U.S. application Ser. No. 60/859,284, incorporated herein by reference.

It is further consistent with the present technology that a cartridge can be tagged, e.g., with a molecular bar-code indicative of the sample, to facilitate sample tracking, and to minimize risk of sample mix-up. Methods for such taggin are described elsewhere, e.g., in U.S. patent application publication Ser. No. 10/360,854, incorporated herein by reference.

Exemplary Systems

Figure 2A:
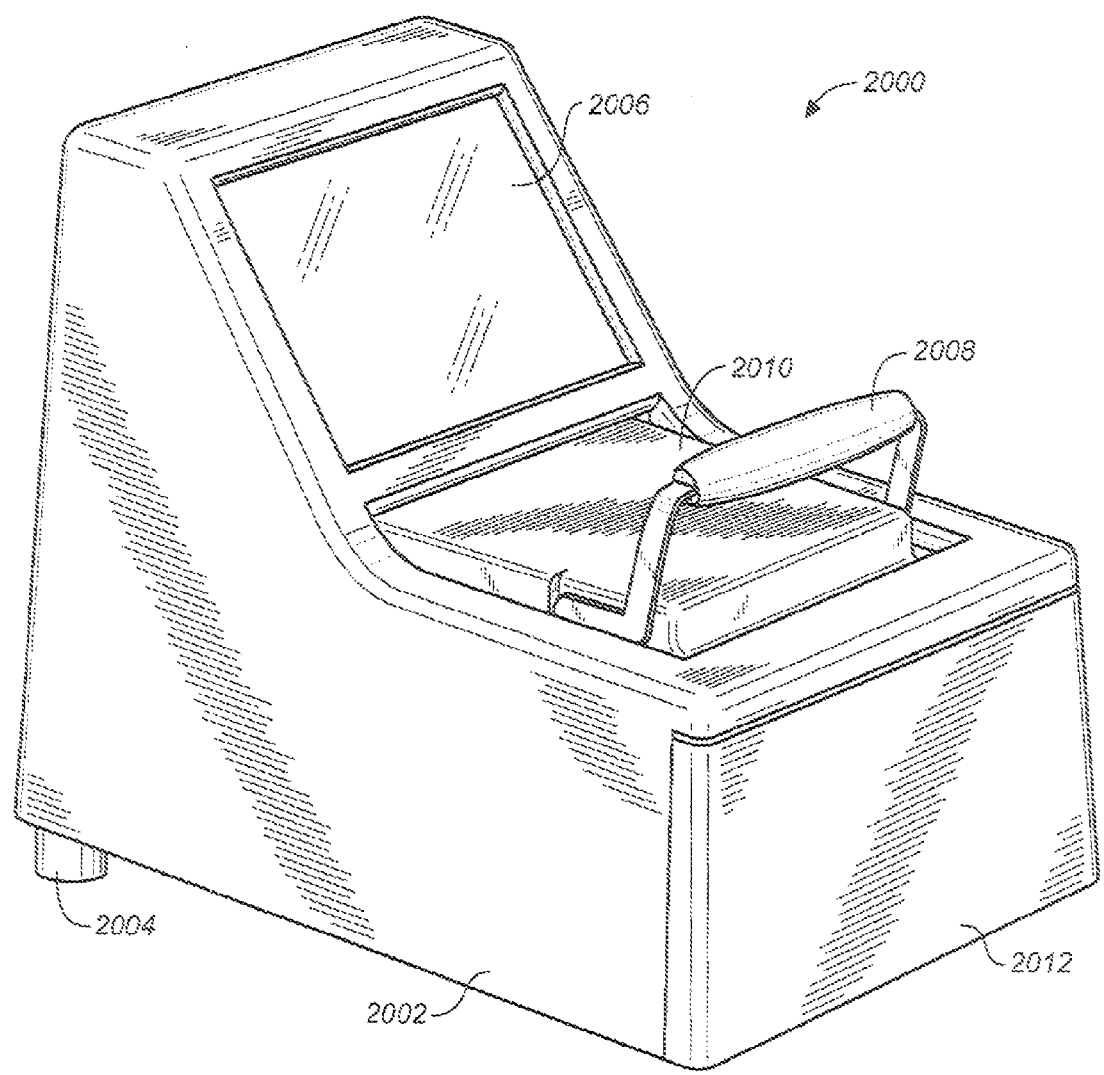
FIGS. 2A-2E show perspective views of an exemplary apparatus, in various configurations, as further described herein.

FIGS. 2A-2E show exterior perspective views of various configurations of an exemplary system, as further described herein. FIG. 2A shows a perspective view of a system 2000 for receiving microfluidic cartridge (not shown), and for causing and controlling various processing operations to be performed a sample introduced into the cartridge. The elements of system 2000 are not limited to those explicitly shown. For example, although not shown, system 2000 may be connected to a hand-held bar-code reader, as further described herein.

System 2000 comprises a housing 2002, which can be made of metal, or a hardened plastic. The form of the housing shown in FIG. 2A embodies stylistic as well as functional features. Other embodiments of the invention may appear somewhat differently, in their arrangement of the components, as well as their overall appearance, in terms of smoothness of lines, and of exterior finish, and texture. System 2000 further comprises one or more stabilizing members 2004. Shown in FIG. 2A is a stabilizing foot, of which several are normally present, located at various regions of the underside of system 2000 so as to provide balance and support. For example, there may be three, four, five, six, or eight such stabilizing feet. The feet may be moulded into and made of the same material as housing 2002, or may be made of one or more separate materials and attached to the underside of system 2000. For example, the feet may comprise a rubber that makes it hard for system 2000 to slip on a surface on which it is situated, and also protects the surface from scratches. The stabilizing member of members may take other forms than feet, for example, rails, runners, or one or more pads.

System 2000 further comprises a display 2006, which may be a liquid crystal display, such as active matrix, an OLED, or some other suitable form. It may present images and other information in color or in black and white. Display 2006 may also be a touch-sensitive display and therefore may be configured to accept input from a user in response to various displayed prompts. Display 2006 may have an anti-reflective coating on it to reduce glare and reflections from overhead lights in an laboratory setting. Display 2006 may also be illuminated from, e.g., a back-light, to facilitate easier viewing in a dark laboratory.

Figure 2B:
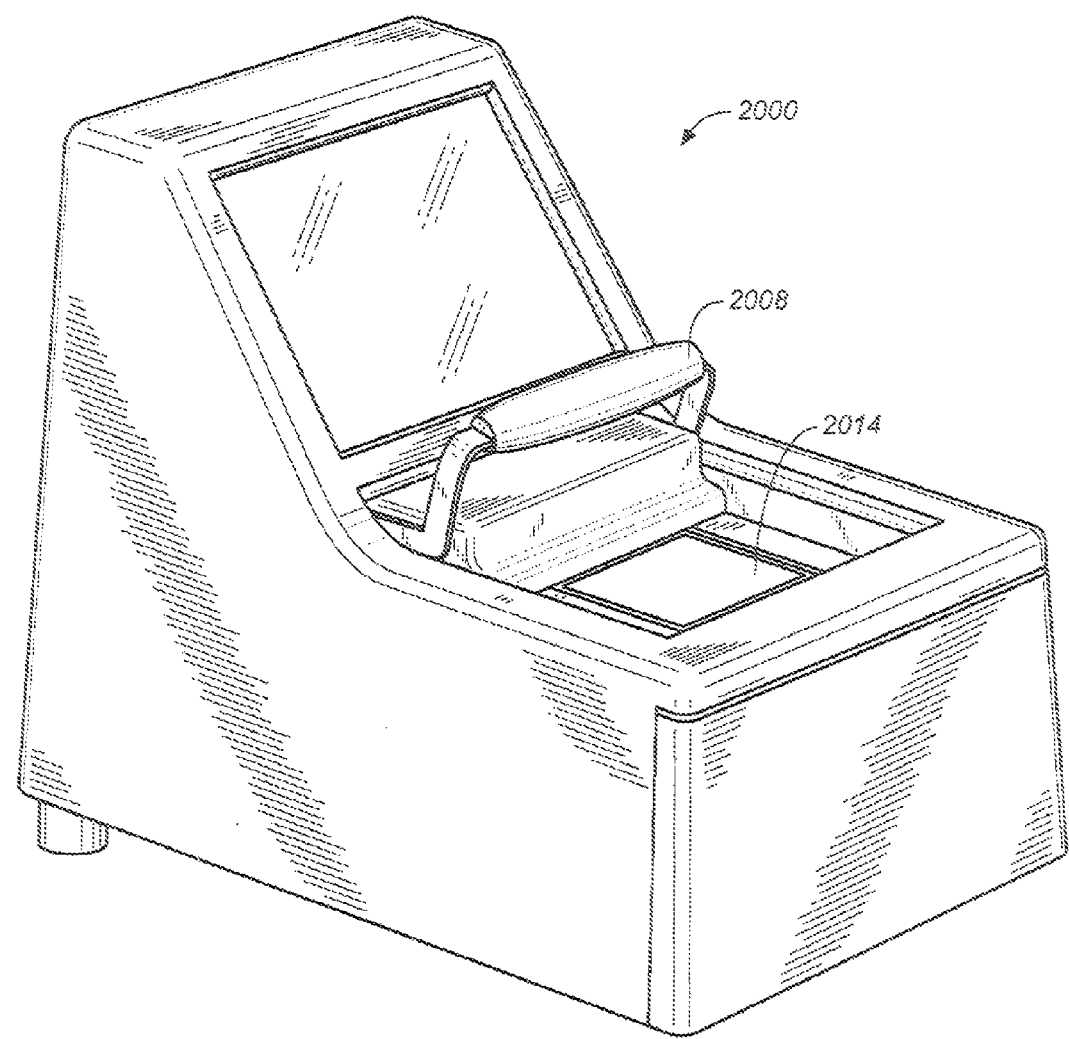

System 2000, as shown in FIG. 2A, also comprises a moveable lid 2010, having a handle 2008. The lid 2010 can slide back and forward. In FIG. 2A, the lid is in a forward position, whereby it is "closed". In FIG. 2B, the lid is shown in a back position, wherein the lid is "open" and reveals a receiving bay 2014 that is configured to receive a microfluidic cartridge. Of course, as one of ordinary skill in the art would appreciate, the technology described herein is not limited to a lid that slides, or one that slides back and forward. Side to side movement is also possible, as is a configuration where the lid is "open" when positioned forward in the device. It is also possible that the lid is a hinged lid, or one that is totally removable.

Figure 2C:
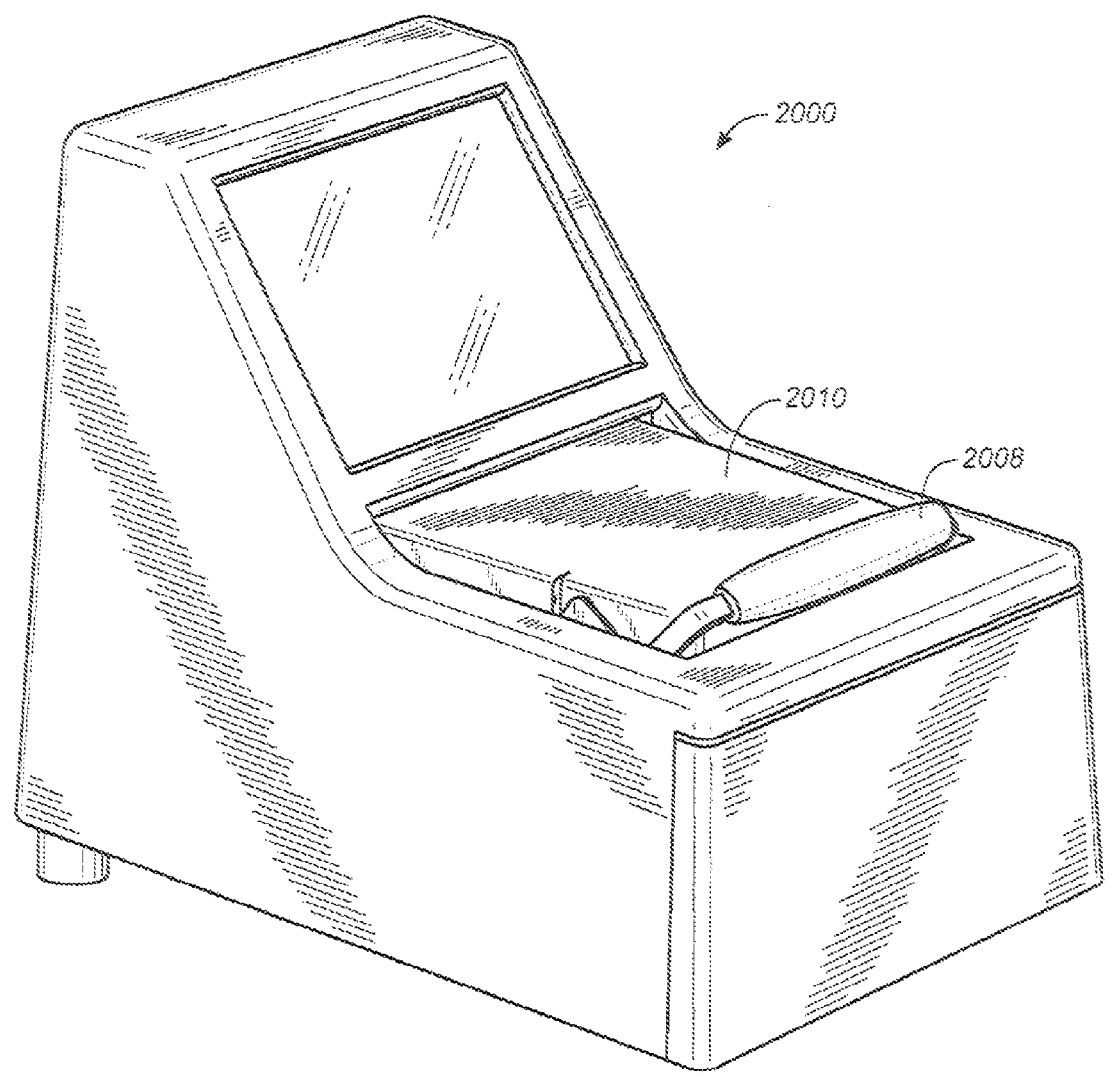

Handle 2008 performs a role of permitting a user to move lid 2010 form one position to another, and also performs a role of causing pressure to be forced down on the lid, when in a closed position, so that pressure can be applied to a cartridge in the receiving bay 2014. In FIG. 2C, handle 2008 is shown in a depressed position, wherein force is thereby applied to lid 2014, and thus pressure is applied to a cartridge received in the receiving bay beneath the lid.

In one embodiment, the handle and lid assembly are also fitted with a mechanical sensor that does not permit the handle to be depressed when there is no cartridge in the receiving bay. In another embodiment, the handle and lid assembly are fitted with a mechanical latch that does not permit the handle to be raised when an analysis is in progress.

Figure 2D:
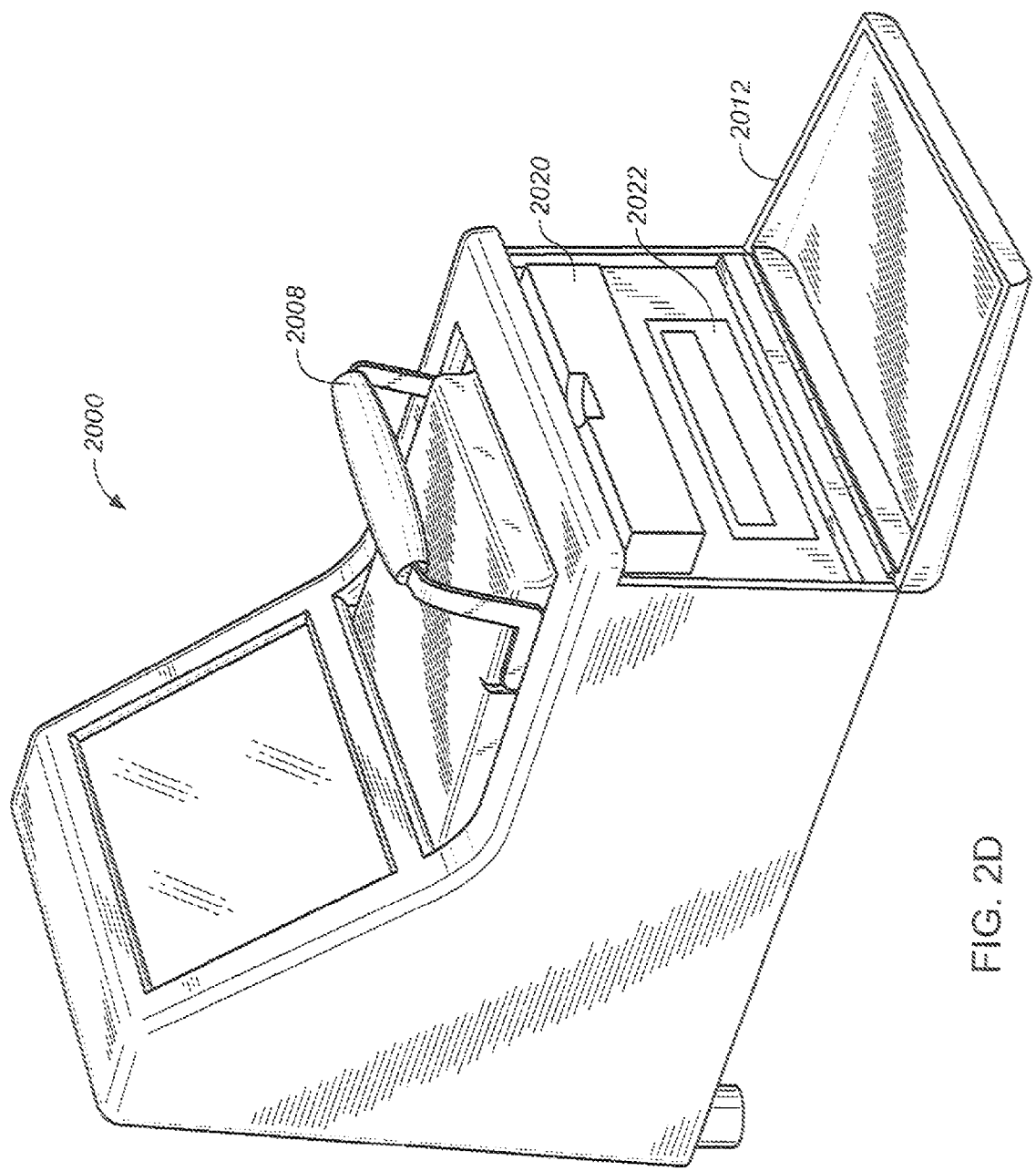

A further configuration of system 2000 is shown in FIG. 2D, wherein a door 2012 is in an open position. Door 2012 is shown in a closed position in FIGS. 2A-C. The door is an optional component that permits a user to access a heater module 2020, and also a computer-readable medium input tray 2022. System 2000 can function without a door that covers heater module 2020 and medium input 2022, but such a door has convenience attached to it. Although the door 2012 is shown hinged at the bottom, it may also be hinged at one of its sides, or at its upper edge. Door 2012 may alternatively be a removable cover, instead of being hinged. Door 2012, may also be situated at the rear, or side of system 2000 for example, if access to the heater module and/or computer readable medium input is desired on a different face of the system. It is also consistent with the system herein that the heater module, and the computer readable medium input are accessed by separate doors on the same or different sides of the device, and wherein such separate doors may be independently hinged or removable.

Heater module 2020 is preferably removable, and is further described hereinbelow.

Computer readable medium input 2022 may accept one or more of a variety of media. Shown in FIG. 2D is an exemplary form of input 2022, a CD-Rom tray for accepting a CD, DVD, or mini-CD, or mini-DVD, in any of the commonly used readable, read-writable, and writable formats. Also consistent with the description herein is an input that can accept another form of medium, such as a floppy disc, flash memory such as memory stick, compact flash, smart data-card, or secure-data card, a pen-drive, portable USB-drive, zip-disk, and others. Such an input can also be configured to accept several different forms of media. Such an input 2022 is in communication with a processor (as described in connection with FIG. 1, though not shown in FIGS. 2A-E), that can read data from a computer-readable medium when properly inserted into the input.

Figure 2E:
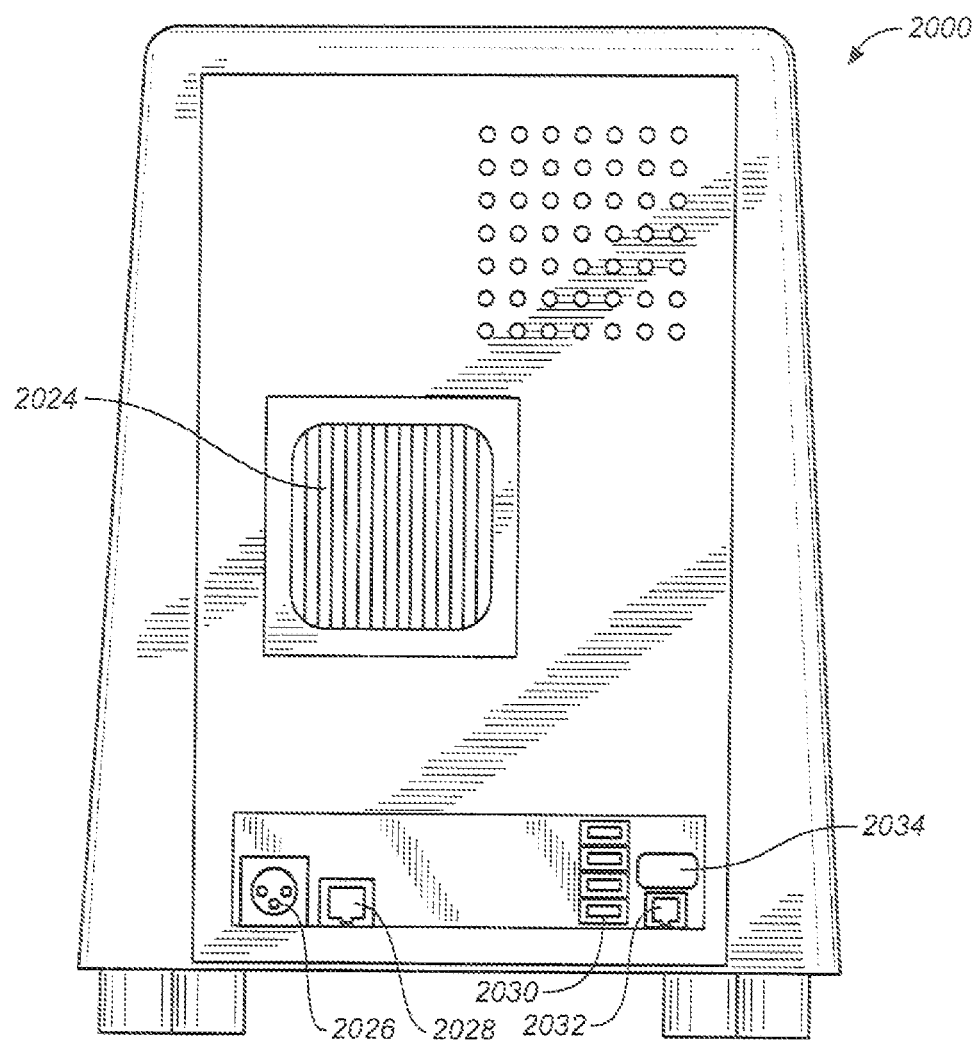

FIG. 2E shows a plan view of a rear of system 2000. Shown are an air vent 2024, or letting surplus heat escape during an analysis. Typically, on the inside of system 2000, and by air vent 2024 and not shown in FIG. 2E, is a fan. Other ports shown in FIG. 2E are as follows: a power socket 2026 for accepting a power cord that will connect system 2000 to a supply of electricity; an ethernet connection 2028 for linking system 2000 to a computer network such as a local area network; an phone-jack connection 2032 for linking system 2000 to a communication network such as a telephone network; one or more USB ports 2030, for connecting system 2000 to one or more peripheral devices such as a printer, or a computer hard drive; an infra-red port for communicating with, e.g., a remote controller (not shown), to permit a user to control the system without using a touch-screen interface. For example, a user could remotely issue scheduling commands to system 2000 to cause it to start an analysis at a specific time in the future.

Features shown on the rear of system 2000 may be arranged in any different manner, depending upon an internal configuration of various components. Additionally, features shown as being on the rear of system 2000, may be optionally presented on another face of system 2000, depending on design preference. Shown in FIG. 2E are exemplary connections. It would be understood that various other features, including inputs, outputs, sockets, and connections, may be present on the rear face of system 2000, though not shown, or on other faces of system 2000.

Figure 3:
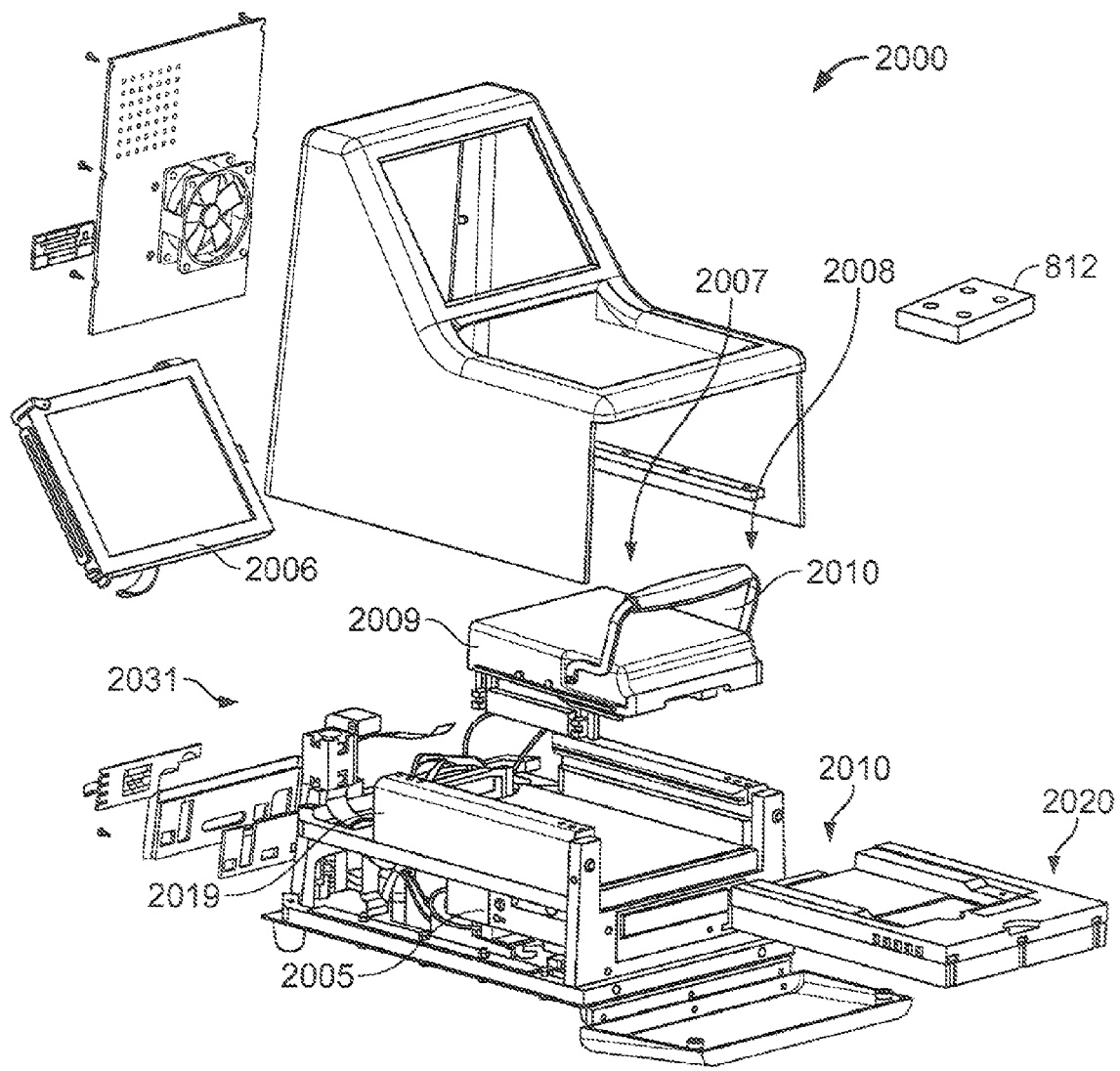
FIG. 3 is an exploded view of typical components of an apparatus.

An exploded view of an exemplary embodiment of the apparatus is shown in FIG. 3, particularly showing internal features of apparatus 2000. Apparatus 2000 can comprise a computer readable medium configured with hardware/firmware that can be employed to drive and monitor the operations on a cartridge used therewith, as well as software to interpret, communicate and store the results of a diagnostic test performed on a sample processed in the cartridge. Referring to FIG. 3, typical components of the apparatus 2000 are shown and include, for example, control electronics 2005, removable heater/sensor module 2020, detector 2009 such as a fluorescent detection module, display screen or optionally combined display and user interface 2006 (e.g., a medical grade touch sensitive liquid crystal display (LCD)). In some embodiments, lid 2010, detector 2009, and handle 2008 can be collectively referred to as slider module 2007. Additional components of apparatus 2000 may include one or more mechanical fixtures such as frame 2019 to hold the various modules (e.g., the heater/sensor module 2020, and/or the slider module 2007) in alignment, and for providing structural rigidity. Detector module 2009 can be placed in rails to facilitate opening and placement of cartridge 2060 in the apparatus 2000, and to facilitate alignment of the optics upon closing. Heater/sensor module 2020 can be also placed on rails for easy removal and insertion of the assembly.

Embodiments of apparatus 2000 also include software (e.g., for interfacing with users, conducting analysis and/or analyzing test results), firmware (e.g., for controlling the hardware during tests on the cartridge 812), and one or more peripheral communication interfaces shown collectively as 2031 for peripherals (e.g., communication ports such as USB/Serial/Ethernet to connect to storage such as compact disc or hard disk, to connect input devices such as a bar code reader and/or a keyboard, to connect to other computers or storage via a network, and the like).

Figure 4:
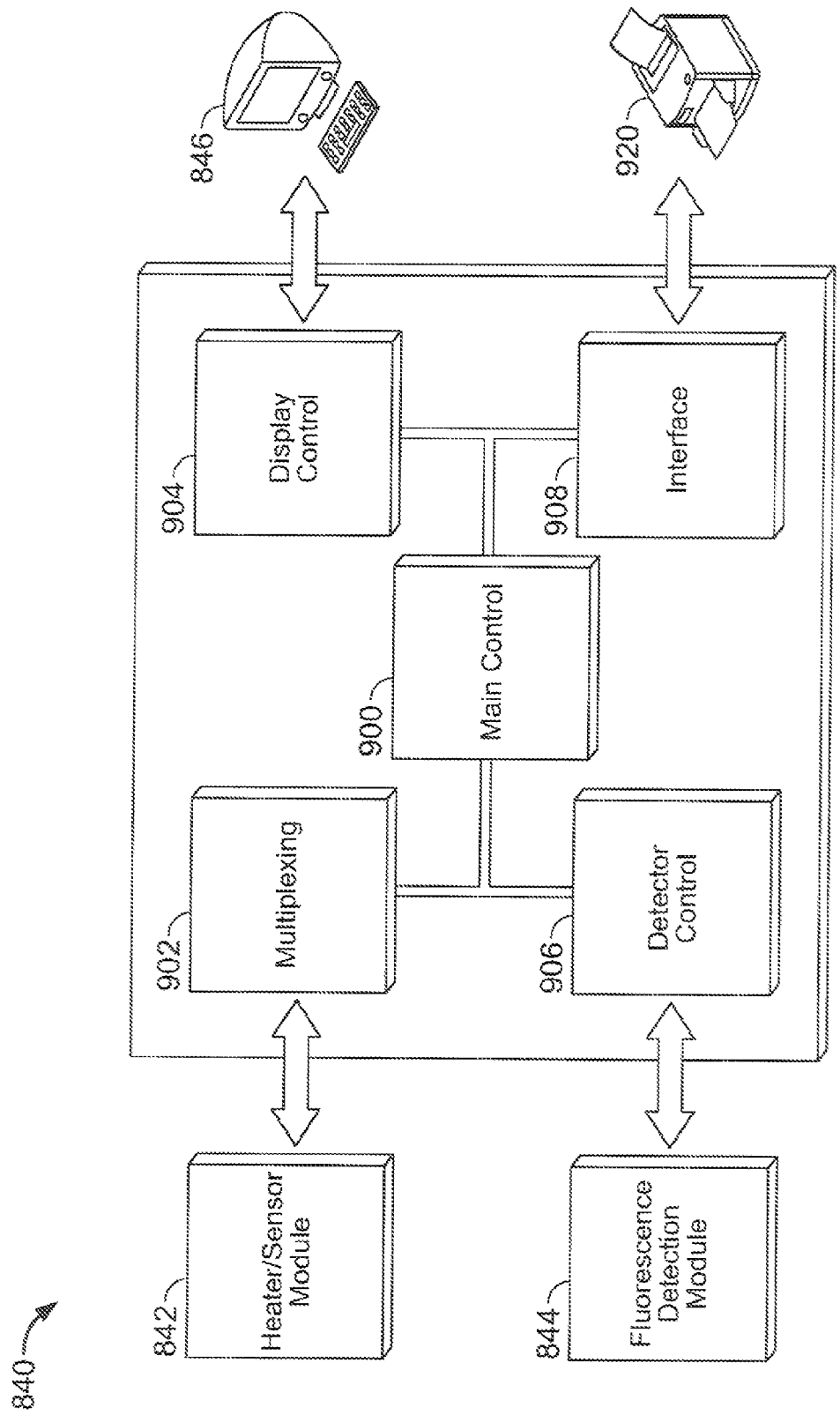
FIG. 4 is a block diagram of an apparatus.

Control electronics 840, shown schematically in the block diagram in FIG. 4, can include one or more functions in various embodiments, for example for, main control 900, multiplexing 902, display control 904, detector control 906, and the like. The main control function may serve as the hub of control electronics 840 in apparatus 2000 and can manage communication and control of the various electronic functions. The main control function can also support electrical and communications interface 908 with a user or an output device such as a printer 920, as well as optional diagnostic and safety functions. In conjunction with main control function 900, multiplexer function 902 can control sensor data 914 and output current 916 to help control heater/sensor module 2020. The display control function 904 can control output to and, if applicable, interpret input from touch screen LCD 846, which can thereby provide a graphical interface to the user in certain embodiments. The detector function 906 can be implemented in control electronics 840 using typical control and processing circuitry to collect, digitize, filter, and/or transmit the data from a detector 2009 such as one or more fluorescence detection modules.

In various embodiments, fluorescent detection module 2009 can be a miniaturized, highly sensitive fluorescence detection system which can, for example, be capable of real-time analysis of a fluorescent signal emanating from a suitably positioned microfluidic cartridge, as shown in FIG. 5. Detection module 2009 can employ one or more light sources 2850 (e.g., light emitting diodes (LED's)), one or more detectors 2852 (e.g., photodiodes), and one or more filters 2851 and/or lenses 2853. In some embodiments, detection module 2009 can contain multiple (e.g., six) detection elements, where each element can detect one or more fluorescent probes.

Figure 6A:
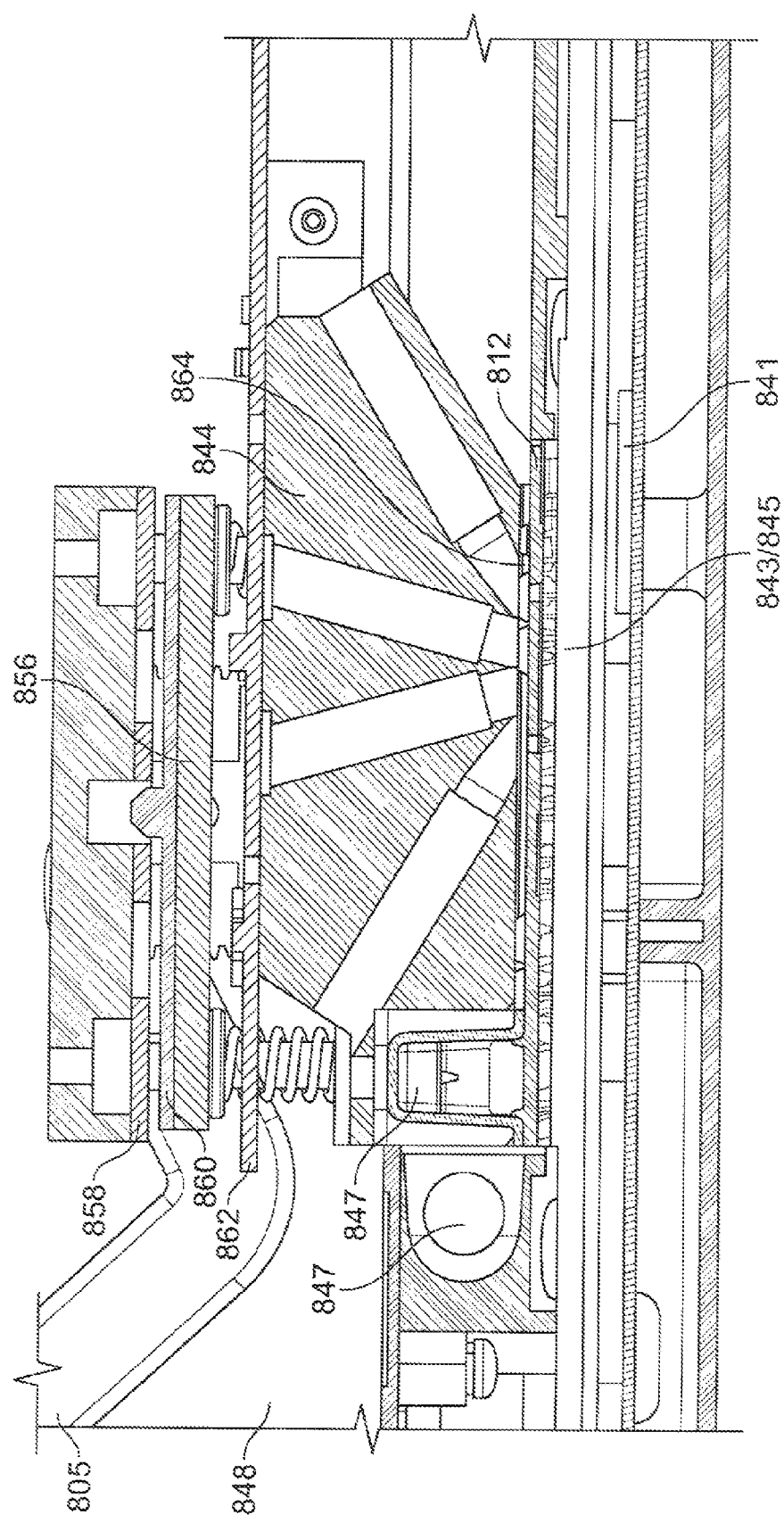
FIGS. 6A and 6B depict the location, in various embodiments, of a microfluidic cartridge after installation into an apparatus.
Figure 6B:
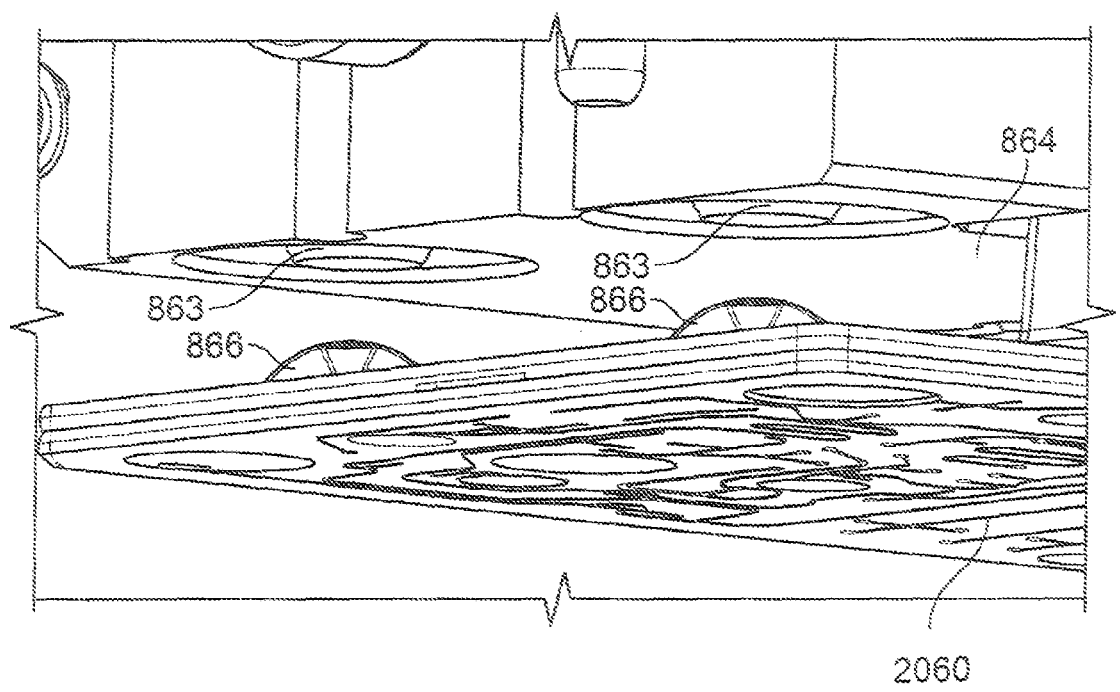

In various embodiments, slider module 2007 of the apparatus 2000 can house the detection module 2009 (e.g., optical detection system) as well as mechanical assembly/optics jig 856 to press down on microfluidic cartridge 2020 when the handle 2008 of the slider module 2007 is pressed down. FIGS. 6A and 6B depict the location, in various embodiments, of the microfluidic cartridge 2060 after insertion into the apparatus 2000. Optics jig 856 can be suspended from the case of slider module 2007 at one or more (e.g., 4) points. Upon closing slider module 2007 and turning handle 2008 of the apparatus 2000 down, one or more mechanical actuators 858 (e.g., four cams) can push down plate 860 against one or more (e.g., 4) springs 862. Upon compression, springs 862 can deliver force on detector module 2009. A bottom surface 864 of detector module 2009 can be made flat (e.g., within 250 microns, typically within 100 microns, more typically within 25 microns), and surface 864 can press upon cartridge 2060, which can have a compliant layer 868 (e.g., Shore hardness approximately 50-70) with a thickness from 0.1-2.5 mm at no compression, typically about 1.5 mm thick at no compression. Consequently, compression of cartridge 2060, in combination with flat surface 864, can make the pressure, and thus the thermal contact, more or less uniform over microfluidic cartridge 2060. One or more springs 862 in slider module 2007 can deliver a force (e.g., from 5-500 N, typically about 200-250 N) to generate a pressure (e.g., 2 psi) over the bottom of microfluidic cartridge 2060. FIG. 6B also shows that, when the slider module 2007 can be closed, mechanical features 863 of the slider module 2007 can press down on self-pierceable reservoirs 866 of the microfluidic cartridge 2060, causing the reservoir contents (e.g., DI water, PCR reagents) be released.

Removable Heater Module

Figure 7:
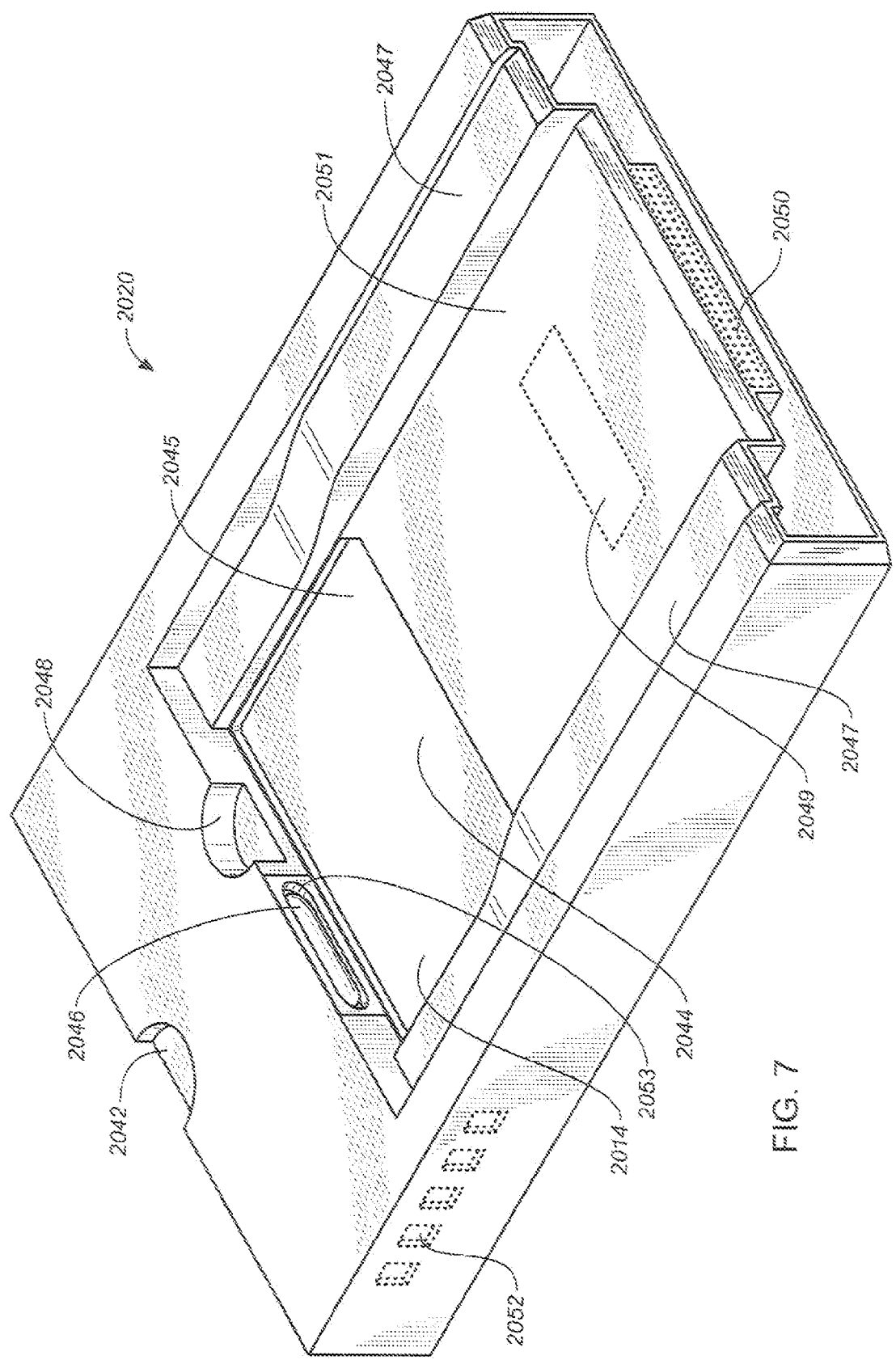
FIG. 7 shows a perspective view of a removable heater module, as further described herein.

An exemplary removable heater module 2020 is shown in FIG. 7. The module is configured to deliver localized heat to various selected regions of a cartridge received in the receiving bay 2014. Shown in FIG. 7 is a heater module having a recessed surface 2044 that provides a platform for supporting a cartridge when in receiving bay 2014. In one embodiment, the cartridge rests directly on surface 2044. Surface 2044 is shown as recessed, in FIG. 7, but need not be so.

Area 2044 is configured to accept a microfluidic cartridge in a single orientation. Therefore area 2044 can be equipped with a registration member such as a mechanical key that prevents a user from placing a cartridge into receiving bay 2014 in the wrong configuration. Shown in FIG. 7 as an exemplary mechanical key 2045 is a diagonally cutout corner of area 2044 into which a complementarily cutout corner of a microfluidic cartridge fits (see, e.g., FIG. 9). Other registration members are consistent with the apparatus described herein: for example, a feature engineered on one or more edges of a cartridge including but not limited to: several, such as two or more, cut-out corners, one or more notches cut into one or more edges of cartridge of FIG. 9; or one or more protrusions fabricated into one or more edges of cartridge of FIG. 9. Alternative registration members include one or more lugs or bumps engineered into an underside of a cartridge, complementary to one or more recessed sockets or holes in surface 2044. Alternative registration members include one or more recessed sockets or holes engineered into an underside of a cartridge, complementary to one or more lugs or bumps on surface 2044. In general, the pattern of features is such that the cartridge possesses at least one element of asymmetry so that it can only be inserted in a single orientation into the receiving bay.

Also shown in FIG. 7 is a hand-grasp 2042 that facilitates removal and insertion of the heater module by a user. Cutaway 2048 permits a user to easily remove a cartridge from receiving bay 2014 after a processing run where, e.g., a user's thumb of finger when grabbing the top of the cartridge, is afforded comfort space by cutaway 2048. Both cutaways 2042 and 2048 are shown as semicircular recesses in the embodiment of FIG. 7, but it would be understood that they are not so limited in shape. Thus, rectangular, square, triangular, oval, and other shaped recesses are also consistent with a heater module as described herein.

In the embodiment of FIG. 7, which is designed to be compatible with the system of FIGS. 2A-E, the front of the heater module is at the left of the figure. At the rear of heater module 2020 is an electrical connection 2050, such as an RS-232 connection, that permits electrical signals to be directed to heaters located at specific regions of area 2044 during sample processing and analysis, as further described herein. Thus, underneath area 2044 and not shown in FIG. 7 can be an array of heat sources, such as resistive heaters, that are configured to align with specified locations of a microfluidic cartridge properly inserted into the receiving bay. Surface 2044 is able to be cleaned periodically to ensure that any liquid spills that may occur during sample handling do not cause any short circuiting.

Other non-essential features of heater module 2020 are as follows. One or more air vents 2052 can be situated on one or more sides (such as front, rear, or flanking) or faces (such as top or bottom) of heater module 2020, to permit excess heat to escape, when heaters underneath receiving bay 2014, are in operation. The configuration of air vents in FIG. 7 is exemplary and it would be understood that other numbers and shapes thereof are consistent with routine fabrication and use of a heater module. For example, although 5 square air vents are shown, other numbers such as 1, 2, 3, 4, 6, 8, or 10 air vents are possible, arranged on one side, or spread over two or more sides and/or faces of the heater module. In further embodiments, air vents may be circular, rectangular, oval, triangular, polygonal, and having curved or squared vertices, or still other shapes, including irregular shapes.

Heater module 2020 may further comprise one or more guiding members 2047 that facilitate inserting the heater module into an apparatus as further described herein for an embodiment in which heater module 2020 is removable by a user. Heater module is advantageously removable because it permits system 2000 to be easily reconfigured for a different type of analysis, such as employing a different cartridge with a different registration member and/or microfluidic network, in conjunction with the same or a different sequence of processing operations. In other embodiments, heater module 2020 is designed to be fixed and only removable, e.g., for cleaning, replacement, or maintenance, by the manufacturer or an authorized maintenance agent, and not routinely by the user. Guiding members may perform one or more roles of ensuring that the heater module is aligned correctly in the apparatus, and ensuring that the heater module makes a tight fit and does not significantly move during processing and analysis of a sample, or during transport of the apparatus. Guiding members shown in the embodiment of FIG. 7 are on either side of receiving bay 2044 and stretch along a substantial fraction of he length of module 2020. Other guiding members are consistent with use herein, and include but are not limited to other numbers of guiding members such as 1, 3, 4, 5, 6, or 8, and other positions thereof, including positioned in area 2051 of module 2020. Guiding members 2047 are shown having a non-constant thickness along their lengths. It is consistent herein that other guiding members may have essentially constant thickness along their lengths.

Adjacent receiving bay 2014 is a non-contact heating element 2046, such as lamp, set into a recessed area 2053. Recessed area 2053 may also be configured with a reflector, or a reflective coating, so that as much as thermal and optical energy from non-contact heating element 2046 as possible is directed outwards towards receiving bay 2014. Element 2046 is a heat lamp in certain embodiments. Element 2046 is configured to receive electrical energy and thereby heat up from the effects of electrical resistance. Element 2046 provides a way of heating a raised region of a cartridge received in receiving bay 2014. The raised region of the cartridge (see, e.g., FIG. 9) may contain a lysis chamber, and application of heat from non-contact heating element 2046 can have the effect of lysing cells within the lysis chamber.

Also shown in FIG. 7 is an optional region of fluorescent material, such as optically fluorescent material, 2049 on area 2051 of heater module 2020. The region of fluorescent material is configured to be detected by a detection system further described herein. The region 2049 is used for verifying the state of optics in the detection system prior to sample processing and analysis and therefore acts as a control, or a standard. For example, in one embodiment a lid of the apparatus (see, e.g., FIG. 2A) when in an open position permits ambient light to reach region 2049 and thereby cause the fluorescent material to emit a characteristic frequency or spectrum of light that can be measured by the detector for, e.g., standardization or calibration purposes. In another embodiment, instead of relying on ambient light to cause the fluorescent material to fluoresce, light source from the detection system itself, such as one or more LED's, is used. The region 2049 is therefore positioned to align with a position of a detector. Region 2049 is shown as rectangular, but may be configured in other shapes such as square, circular, elliptical, triangular, polygonal, and having curved or squared vertices. It is also to be understood that the region 2049 may be situated at other places on the heater module 2020, according to convenience and in order to be complementary to the detection system deployed.

Heater module 2020 also comprises an array of heaters, situated beneath area 2044 and not shown in FIG. 7. As further described herein, such heaters may be resistive heaters, configured to heat specifically and at specific times, according to electrical signals received.

In particular and not shown in FIG. 7, heater/sensor module 2020 can include, for example, a multiplexing function 902 in a discrete multiplexing circuit board (MUX board), one or more heaters (e.g., a microheater), one or more temperature sensors (optionally combined together as a single heater/sensor unit with one or more respective microheaters, e.g., as photolithographically fabricated on fused silica substrates), and a non-contact heating element 2046. The micro-heaters and non-contact heating element can provide thermal energy that can actuate various microfluidic components on a suitably positioned microfluidic cartridge. A sensor (e.g., as a resistive temperature detector (RTD)) can enable real time monitoring of the micro-heaters and the non-contact heater(s) 2046, for example through a feedback based mechanism to allow for control of the temperature. One or more microheaters can be aligned with corresponding microfluidic components (e.g., valves, pumps, gates, reaction chambers) to be heated on a suitably positioned microfluidic cartridge. A microheater can be designed to be slightly bigger than the corresponding microfluidic component(s) on the microfluidic cartridge so that even though the cartridge may be slightly misaligned, such as off-centered, from the heater, the individual components can be heated effectively.

Non-contact heater 2046 can also serve as a radiation heat source to heat one section of a suitably positioned microfluidic cartridge. For example, a 20 W Xenon lamp may be used as the non-contact heating element 2046. In various embodiments, heater/sensor module 2020 can be specific to particular cartridge designs and can be easily replaceable through the front panel of the apparatus 800. Heater/sensor module 2020 can be configured to permit cleaning of heating surface 2044 with common cleaning agents (e.g., a 10% bleach solution).

Figure 8A:
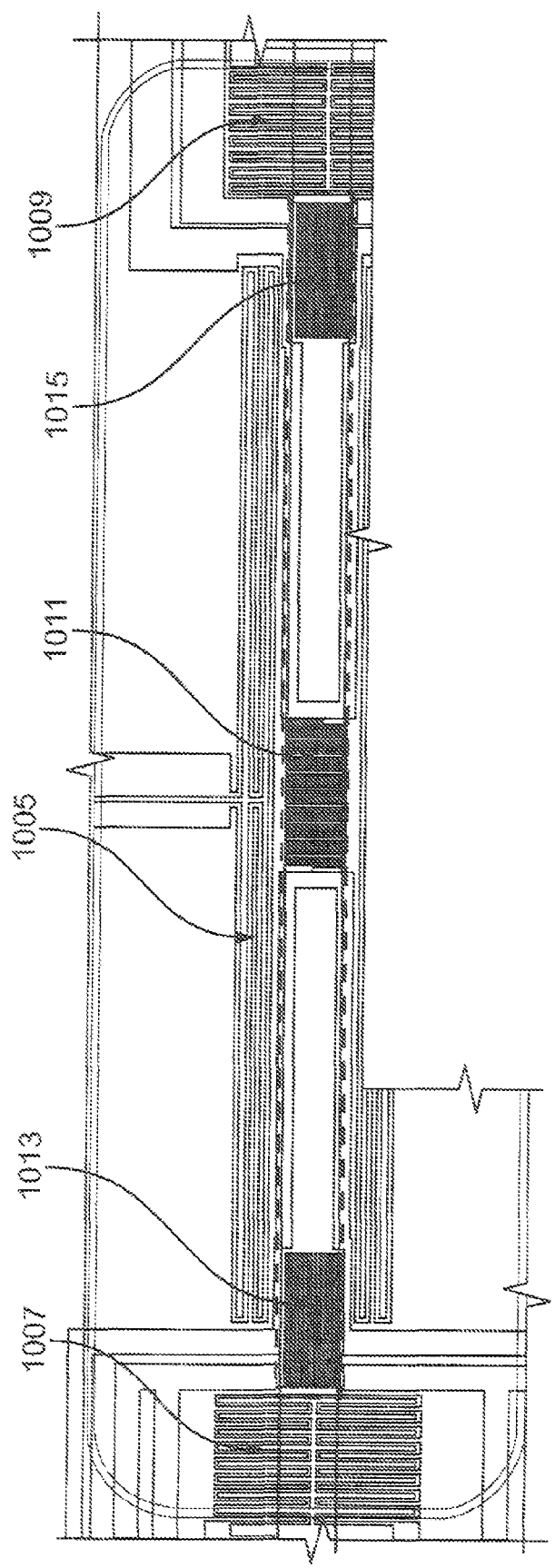
Figure 8B:
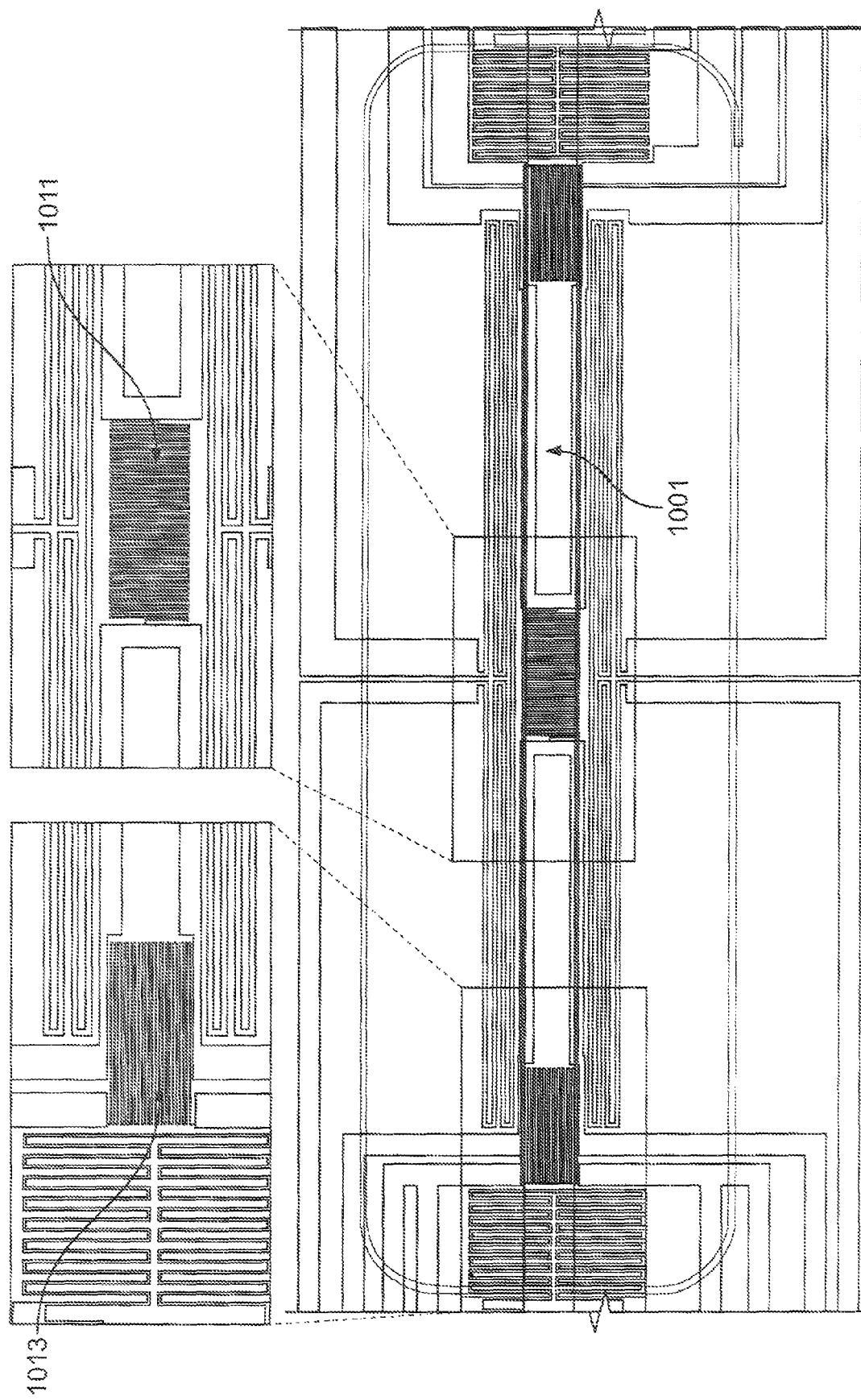

Referring to FIGS. 8A and 8B, an exemplary set of heaters configured to heat, cyclically, PCR reaction zone 1001 is shown. It is to be understood that heater configurations to actuate other regions of a microfluidic cartridge such as other gates, valves, and actuators, may be designed and deployed according to similar principles to those governing the heaters shown in FIGS. 8A and 8B. An exemplary PCR reaction zone 1001, typically a chamber or channel having a volume ~1.6 µl, is configured with a long side and a short side, each with an associated heating element. A PCR reaction zone may also be referred to as a PCR reactor, herein. The apparatus therefore preferably includes four heaters disposed along the sides of, and configured to heat, a given PCR reaction zone, as shown in the exemplary embodiment of FIG. 8A: long top heater 1005, long bottom heater 1003, short left heater 1007, and short right heater 1009. The small gap between long top heater 1005 and long bottom heater 1003 results in a negligible temperature gradient (less than 1° C. across the width of the PCR channel at any point along the length of the PCR reaction zone) and therefore an effectively uniform temperature throughout the PCR reaction zone. The heaters on the short edges of the PCR reactor provide heat to counteract the gradient created by the two long heaters from the center of the reactor to the edge of the reactor.

It would be understood by one of ordinary skill in the art that still other configurations of one or more heater(s) situated about a PCR reaction zone are consistent with the methods and apparatus described herein. For example, a 'long' side of the reaction zone can be configured to be heated by two or more heaters. Specific orientations and configurations of heaters are used to create uniform zones of heating even on substrates having poor thermal conductivity because the poor thermal conductivity of glass, or quartz, or fused silica substrates is utilized to help in the independent operation of various microfluidic components such as valves and independent operation of the various PCR lanes. It would be further understood by one of ordinary skill in the art, that the principles underlying the configuration of heaters around a PCR reaction zone are similarly applicable to the arrangement of heaters adjacent to other components of the microfluidic cartridge, such as actuators, valves, and gates.

In certain embodiments, each heater has an associated temperature sensor. In the embodiment of FIG. 8A, a single temperature sensor 1011 is used for both long heaters. A temperature sensor 1013 for short left heater, and a temperature sensor 1015 for short right heater are also shown. The temperature sensor in the middle of the reactor is used to provide feedback and control the amount of power supplied to the two long heaters, whereas each of the short heaters has a dedicated temperature sensor placed adjacent to it in order to control it. Temperature sensors are preferably configured to transmit information about temperature in their vicinity to the processor at such times as the heaters are not receiving current that causes them to heat. This can be achieved with appropriate control of current cycles.

In order to reduce the number of sensor or heater elements required to control a PCR heater, we may use the heaters to sense as well as heat, and thereby obviate the need to have a separate dedicated sensor for each heater. In another embodiment, each of the four heaters may be designed to have an appropriate wattage, and connect the four heaters in series or in parallel to reduce the number of electronically-controllable elements from 4 to just 1, thereby reducing the burden on the associated electronic circuitry.

FIG. 8B shows expanded views of heaters and temperature sensors used in conjunction with a PCR reaction zone of FIG. 8A. Temperature sensors 1001 and 1013 are designed to have a room temperature resistance of approximately 200-300 ohms. This value of resistance is determined by controlling the thickness of the metal layer deposited (e.g., a sandwich of 400 Å TiW/3,000 Å Au/400 Å TiW), and etching the winding metal line to have a width of approximately 10-25 µm and 20-40 mm length. The use of metal in this layer gives it a temperature coefficient of resistivity of the order of 0.5-20° C./ohms, preferably in the range of 1.5-3° C./ohms. Measuring the resistance at higher temperatures enables determination of the exact temperature of the location of these sensors.

The configuration for uniform heating, shown in FIG. 8A for a single PCR reaction zone, can also be applied to a multi-lane PCR cartridge in which multiple independent PCR reactions occur.

Each heater can be independently controlled by a processor and/or control circuitry used in conjunction with the apparatus described herein. FIG. 8C shows thermal images, from the top surface of a microfluidic cartridge when heated by heaters configured as in FIGS. 8A and 8B, when each heater in turn is activated, as follows: (A): Long Top only; (B) Long Bottom only; (C) Short Left only; (D) Short Right only; and (E) All Four Heaters on. Panel (F) shows a view of the reaction zone and heaters on the same scale as the other image panels in FIG. 8C. Also shown in the figure is a temperature bar.

Microfluidic Cartridge

Figure 9:
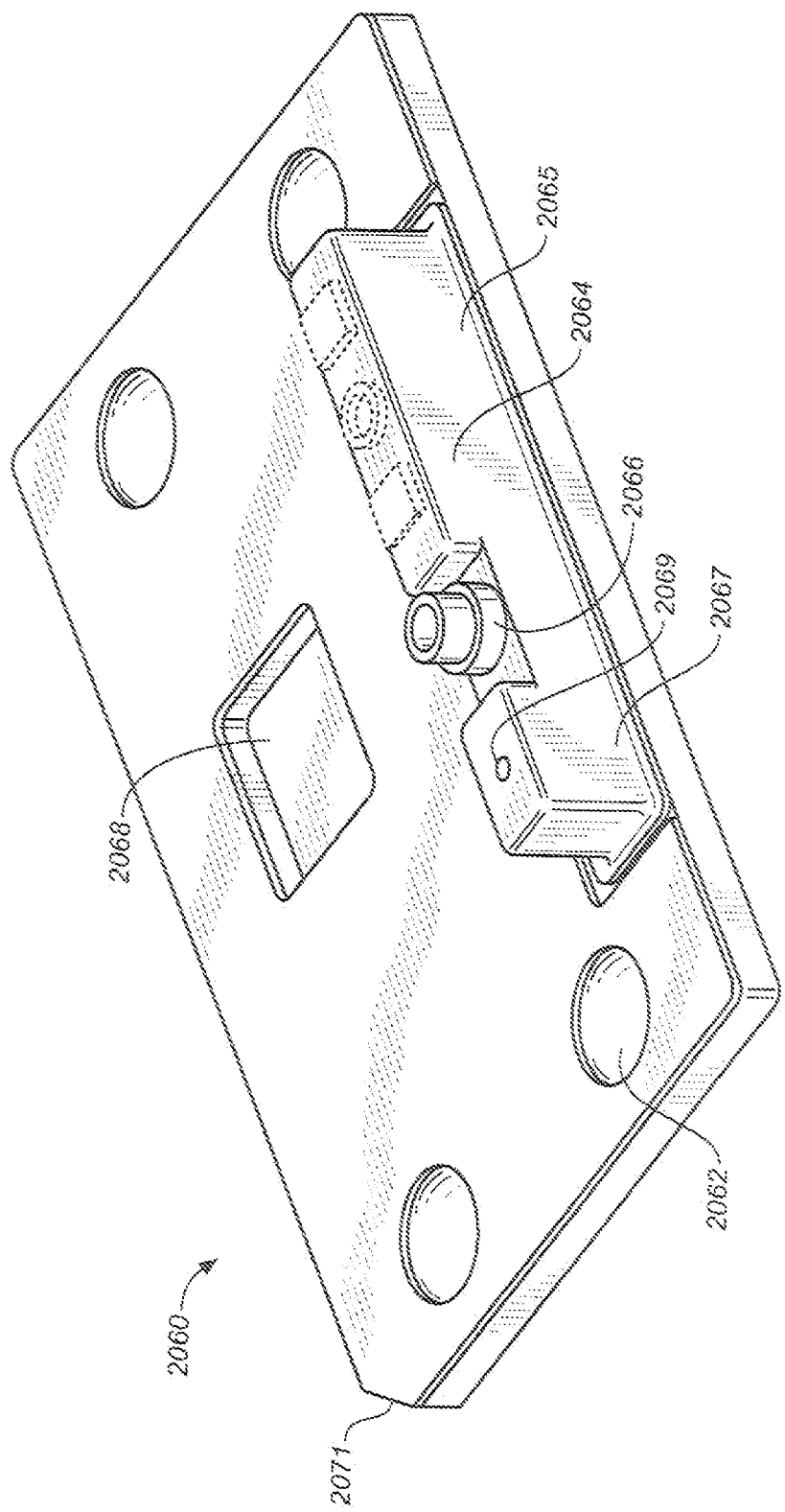
FIG. 9 shows a perspective view of a microfluidic cartridge, as further described herein.

FIG. 9 shows a perspective view of an exterior of an exemplary microfluidic cartridge 2060 for use in conjunction with the system described herein. Present in cartridge 2060 is at least one reagent package 2062. Four such reagent packages are shown, though other numbers of such packages, such as but not limited to one, two, three, five, six, eight, ten, and twelve, are possible, depending upon application. Cartridge 2060 further comprises a tower 2064 that contains reagents, and is fitted with an inlet 2066, such as a luer, through which a portion of a biological sample can be introduced. Tower 2064 can also comprise one or more chambers such as a bulk lysis chamber 2065 and a waste chamber 2067. Waste chamber 2067 may have a vent 2069 for releasing gases such as air.

Other than tower 2064, cartridge 2060 is substantially planar such that it can be easily handled by an operator and can be easily matched to a complementary receiving bay of an apparatus such as shown in FIG. 1.

Cartridge 2060 further comprises a port 2068 through which a detector can receive a signal directly or indirectly from one or more polynucleotides in the sample, during processing or amplification, in order to provide a user with a diagnostic result on the sample.

Cartridge 2060 can further comprise a registration member such as a mechanical key, complementary to a corresponding registration member in the receiving bay. Shown in FIG. 9 is an exemplary registration member 2071, a corner cut-out from the cartridge.

The integrated system, as described herein, comprises an apparatus configured to receive a microfluidic cartridge, and a microfluidic cartridge. It is consistent with the system described herein that a number of different configurations of microfluidic cartridge, and purposes thereof, are compatible with suitably configured apparati. Thus, for example, although benefits are described wherein a single cartridge is capable of accepting a collected biological sample, working up the sample, including lysing cells to liberate and collect polynucleotides contained therein, applying pre-amplification preparatory steps to the polynucleotides, amplifying the polynucleotides, and causing the amplified polynucleotides to be detected, it is also consistent with the descriptions herein that other microfluidic cartridges can be used. Such other cartridges can be configured to carry out fewer, such as one or more, of the aforementioned steps, and, correspondingly the apparatus for use therewith is configured to cause fewer such steps to be effectuated. It is to be understood therefore, that when presenting various exemplary configurations of microfluidic cartridge herein, the various components thereof can be used interchangeably (e.g., an exemplary valve described in connection with one cartridge can also be used in a network described in connection with another cartridge) both without modification, and with suitable adjustments or modifications of geometry or size, as appropriate.

Aspects of Microfluidic Cartridges

Accordingly, the technology herein also comprises a microfluidic cartridge having attributes, as follows. Thus the technology includes a microfluidic cartridge that is configured to process one or more polynucleotides, e.g., to concentrate the polynucleotide(s) and/or to separate the polynucleotide(s) from inhibitor compounds, (e.g., hemoglobin, peptides, faecal compounds, humic acids, mucousol compounds, DNA binding proteins, or a saccharide) that might inhibit detection and/or amplification of the polynucleotides.

The microfluidic cartridge can be configured to contact the polynucleotides and a relatively immobilized compound that preferentially associates with (e.g., retains) the polynucleotides as opposed to inhibitors. An exemplary compound is a poly-cationic polyamide (e.g., poly-L-lysine and/or poly-D-lysine), or polyethyleneimine (PEI), which may be bound to a surface (e.g., surfaces of one or more particles). The compound retains the polynucleotides so that the polynucleotides and inhibitors may be separated, such as by washing the surface to which the compound and associated polynucleotides are bound. Upon separation, the association between the polynucleotide and compound may be disrupted to release (e.g., separate) the polynucleotides from the compound and surface.

In some embodiments, the surface (e.g., surfaces of one or more particles) can be modified with a poly-cationic substance such as a polyamide or PEI, which may be covalently bound to the surface. The poly-cationic polyamide may include at least one of poly-L-lysine and poly-D-lysine. In some embodiments, the poly-cationic polyamide (e.g., the at least one of the poly-L-lysine and the poly-D-lysine) has an average molecular weight of at least about 7500 Da. The poly-cationic polyamide (e.g., the at least one of the poly-L-lysine and the poly-D-lysine) may have an average molecular weight of less than about 35,000 Da (e.g., an average molecular weight of less than about 30,000 Da (e.g., an average molecular weight of about 25,000 Da)). The poly-cationic polyamide (e.g., the at least one of the poly-L-lysine and the poly-D-lysine) may have a median molecular weight of at least about 15,000 Da. The poly-cationic polyamide (e.g., the at least one of the poly-L-lysine and the poly-D-lysine) may have a median molecular weight of less than about 25,000 Da (e.g., a median molecular weight of less than about 20,000 Da (e.g., a median molecular weight of about 20,000 Da). If the polycationic material is PEI, its molecular weight is preferably in the range 600-800 Daltons.

In other embodiments, the microfluidic cartridge includes a surface having a polycationic polyamide or PEI bound thereto and a sample introduction passage in communication with the surface for contacting the surface with a fluidic sample.

In some embodiments, the apparatus includes a heat source configured to heat an aqueous liquid in contact with the surface to at least about 65° C.

In some embodiments, the cartridge includes a reservoir of liquid having a pH of at least about 10 (e.g., about 10.5 or more). The cartridge can be configured to contact the surface with the liquid (e.g., by actuating a pressure source to move the liquid).

Another aspect of the microfluidic cartridge relates to a retention member, e.g., a plurality of particles such as beads, comprising bound PEI, or poly-lysine, e.g., poly-L-lysine, and related methods and systems. An exemplary method for processing a sample includes contacting a retention member with a mixture that includes providing a mixture including a liquid and an amount of polynucleotide. The retention member may be configured to preferentially retain polynucleotides as compared to polymerase chain reaction inhibitors. Substantially all of the liquid in the mixture can be removed from the retention member. The polynucleotides can be released from the retention member. The polynucleotide may have a size of less than about 7.5 Mbp.

The liquid may be a first liquid, and removing substantially all of the liquid from the retention member may include contacting the retention member with a second liquid.

Contacting the retention member with a second liquid can include actuating a thermally actuated pressure source to apply a pressure to the second liquid. Contacting the retention member with a second liquid can include opening a thermally actuated valve to place the second liquid in fluid communication with the retention member.

The second liquid may have a volume of less than about 50 microliters, and may include a detergent (e.g., SDS).

The retention member may include a surface having a compound configured to bind polynucleotides preferentially to polymerase chain reaction inhibitors (such inhibitors including, for example, hemoglobin, peptides, faecal compounds, humic acids, mucousol compounds, DNA binding proteins, or a saccharide).

The surface may include a poly-lysine (e.g., poly-L-lysine and/or poly-D-lysine) or PEI.

Releasing polynucleotidges from the retention member may include heating the retention member to a temperature of at least about 50° C. (e.g., at about 65° C.). The temperature may be insufficient to boil the liquid in the presence of the retention member during heating. The temperature may be 100° C. or less (e.g., less than 100° C., about 97° C. or less). The temperature may be maintained for less than about 10 minutes (e.g., for less than about 5 minutes, for less than about 3 minutes). The releasing may be performed without centrifugation of the retention member.

In certain embodiments, PCR inhibitors can be rapidly removed from clinical samples to create a PCR-ready sample. Methods herein therefore may comprise the preparation of a polynucleotide-containing sample that can be substantially free of inhibitors. Such samples may be prepared from, e.g., crude lysates resulting from thermal, chemical, ultrasonic, mechanical, electrostatic, and other lysing techniques. The samples may be prepared without centrifugation. The samples may be prepared using other microfluidic devices or on a larger scale.

The retention member may be used to prepare polynucleotide samples for further processing, such as amplification by polymerase chain reaction. In certain embodiments, more than 90% of a polynucleotide present in a sample may be bound to the retention member, released, and recovered.

In certain embodiments, a polynucleotide may be bound to the retention member, released, and recovered, in less than about 10 minutes (e.g., less than about 7½ minutes, less than about 5 minutes, or less than about 3 minutes).

A polynucleotide may be bound to a retention member, released, and recovered without subjecting the polynucleotide, retention member, and/or inhibitors to centrifugation.

the polynucleotides and inhibitors generally excludes subjecting the polynucleotides, inhibitors, processing region, and/or retention member to sedimentation (e.g., centrifugation).

In various embodiments, the microfluidic cartridge can include a PCR reagent mixture comprising a polymerase enzyme and a plurality of nucleotides. The PCR reagent mixture can be in the form of one or more lyophilized pellets, and the microfluidic network can be configured to contact the PCR pellet with liquid to create a PCR reagent mixture solution.

In various embodiments, the microfluidic cartridge can be configured to couple heat from an external heat source with the PCR reagent mixture and the neutralized polynucleotide sample under thermal cycling conditions suitable for creating PCR amplicons from the neutralized polynucleotide sample.

In various embodiments, the PCR reagent mixture can further include a positive control plasmid and a fluorogenic hybridization probe selective for at least a portion of the plasmid.

In various embodiments, the microfluidic cartridge can include a negative control polynucleotide, wherein the microfluidic network can be configured to independently contact each of the neutralized polynucleotide sample and the negative control polynucleotide with the PCR reagent mixture under thermal cycling conditions suitable for independently creating PCR amplicons of the neutralized polynucleotide sample and PCR amplicons of the negative control polynucleotide.

In various embodiments, the microfluidic cartridge can include at least one probe that can be selective for a polynucleotide sequence, wherein the microfluidic cartridge can be configured to contact the neutralized polynucleotide sample or a PCR amplicon thereof with the probe. The probe can be a fluorogenic hybridization probe. The fluorogenic hybridization probe can include a polynucleotide sequence coupled to a fluorescent reporter dye and a fluorescence quencher dye. The PCR reagent mixture can further include a positive control plasmid and a plasmid fluorogenic hybridization probe selective for at least a portion of the plasmid and the microfluidic cartridge can be configured to allow independent optical detection of the fluorogenic hybridization probe and the plasmid fluorogenic hybridization probe.

In various embodiments, the probe can be selective for a polynucleotide sequence that can be characteristic of an organism, for example any organism that employs deoxyribonucleic acid or ribonucleic acid polynucleotides. Thus, the probe can be selective for any organism. Suitable organisms include mammals (including humans), birds, reptiles, amphibians, fish, domesticated animals, farmed animals, wild animals, extinct organisms, bacteria, fungi, viruses, plants, and the like. The probe can also be selective for components of organisms that employ their own polynucleotides, for example mitochondria. In some embodiments, the probe can be selective for microorganisms, for example, organisms used in food production (for example, yeasts employed in fermented products, molds or bacteria employed in cheeses, and the like) or pathogens (e.g., of humans, domesticated or wild mammals, domesticated or wild birds, and the like). In some embodiments, the probe can be selective for organisms selected from the group consisting of gram positive bacteria, gram negative bacteria, yeast, fungi, protozoa, and viruses.

In various embodiments, the probe can be selective for a polynucleotide sequence that can be characteristic of an organism selected from the group consisting of *Staphylococcus* spp., e.g., *S. epidermidis, S. aureus*, Methicillin-resistant *Staphylococcus aureus* (MRSA), Vancomycin-resistant *Staphylococcus; Streptococcus* (e.g. α, β, or γ-hemolytic, Group A, B, C, D or G) such as *S. pyogenes, S. agalactiae; E. faecalis, E. durans*, and *E. faecium* (formerly *S. faecalis, S. durans, S. faecium*); nonenterococcal group D *streptococci*, e.g., *S. bovis* and *S. equines; Streptococci viridans*, e.g., *S. mutans, S. sanguis, S. salivarius, S. mitior, A. milleri, S. constellatus, S. intermedius*, and *S. anginosus; S. iniae; S. pneumoniae; Neisseria*, e.g., *N. meningitides, N. gonorrhoeae, saprophytic Neisseria* sp; *Erysipelothrix*, e.g., *E. rhusiopathiae; Listeria* spp., e.g., *L. monocytogenes*, rarely *L. ivanovii* and *L. seeligeri; Bacillus*, e.g., *B. anthracis, B. cereus, B. subtilis, B. subtilus niger, B. thuringiensis; Nocardia asteroids; Legionella*, e.g., *L. pneumonophilia, Pneumocystis*, e.g., *P. carinii; Enterobacteriaceae* such as *Salmonella, Shigella, Escherichia* (e.g., *E. coli, E. coliO157:H7); Klebsiella, Enterobacter, Serratia, Proteus, Morganella, Providencia, Yersinia*, and the like, e.g., *Salmonella*, e.g., *S. typhi S. paratyphi* A, B (*S. schottmuelleri*), and C (*S. hirschfeldii*), *S. dublin S. choleraesuis, S. enteritidis, S. typhimurium, S. heidelberg, S. newport, S. infantis, S. agona, S. montevideo*, and *S. saint-paul; Shigella*, e.g., subgroups: A, B, C, and D, such as *S. flexneri, S. sonnei, S. boydii, S. dysenteriae; Proteus (P. mirabilis, P. vulgaris*, and *P. myxofaciens), Morganella (M. morganii); Providencia (P. rettgeri, P. alcalifaciens*, and *P. stuartii); Yersinia*, e.g., *Y. pestis, Y. enterocolitica; Haemophilus*, e.g., *H. influenzae, H. parainfluenzae H. aphrophilus, H. ducreyi; Brucella*, e.g., *B. abortus, B. melitensis, B. suis, B. canis; Francisella*, e.g., *F. tularensis; Pseudomonas*, e.g., *P. aeruginosa, P. paucimobilis, P. putida, P. fluorescens, P. acidovorans, Burkholderia (Pseudomonas) pseudomallei, Burkholderia mallei, Burkholderia cepacia* and *Stenotrophomonas maltophilia; Campylobacter*, e.g., *C. fetus fetus, C. jejuni, C. pylori (Helicobacter pylori); Vibrio*, e.g., *V. cholerae, V. parahaemolyticus, V. mimicus, V. alginolyticus, V. hollisae, V. vulnificus*, and the nonagglutinable vibrios; *Clostridia*, e.g., *C. perfringens, C. tetani, C. difficile, C. botulinum; Actinomyces*, e.g., *A. israelii; Bacteroides*, e.g., *B. fragilis, B. thetaiotaomicron, B. distasonis, B. vulgatus, B. ovatus, B. caccae*, and *B. merdae; Prevotella*, e.g., *P. melaninogenica;* genus *Fusobacterium; Treponema*, e.g. *T. pallidum subspecies endemicum, T. pallidum subspecies pertenue, T. carateum*, and *T. pallidum subspecies pallidum*; genus *Borrelia*, e.g., *B. burgdorferi;* genus *Leptospira; Streptobacillus*, e.g., *S. moniliformis; Spirillum*, e.g., *S. minus; Mycobacterium*, e.g., *M. tuberculosis, M. bovis, M. africanum, M. avium M. intracellulare, M. kansasii, M. xenopi, M. marinum, M. ulcerans*, the *M. fortuitum* complex (*M. fortuitum* and *M. chelonei), M. leprae, M. asiaticum, M. chelonei* subsp. *abscessus, M. fallax, M. fortuitum, M. malmoense, M. shimoidei, M. simiae, M. szulgai, M. xenopi; Mycoplasma*, e.g., *M. hominis, M. orale, M. salivarium, M. fermentans, M. pneumoniae, M. bovis, M. tuberculosis, M. avium, M. leprae; Mycoplasma*, e.g., *M. genitalium; Ureaplasma*, e.g., *U. urealyticum; Trichomonas*, e.g., *T. vaginalis; Cryptococcus*, e.g., *C. neoformans; Histoplasma*, e.g., *H.*

*capsulatum; Candida*, e.g., *C. albicans; Aspergillus* sp; *Coccidioides*, e.g., *C. immitis; Blastomyces*, e.g. *B. dermatitidis; Paracoccidioides*, e.g., *P. brasiliensis; Penicillium*, e.g., *P. mameffei; Sporothrix*, e.g., *S. schenckii; Rhizopus, Rhizomucor, Absidia*, and *Basidiobolus*; diseases caused by *Bipolaris, Cladophialophora, Cladosporium, Drechslera, Exophiala, Fonsecaea, Phialophora, Xylohypha, Ochroconis, Rhinocladiella, Scolecobasidium*, and *Wangiella; Trichosporon*, e.g., *T. beigelii; Blastoschizomyces*, e.g., *B. capitatus; Plasmodium*, e.g., *P. falciparum, P. vivax, P. ovale*, and *P. malariae; Babesia* sp; *protozoa* of the genus *Trypanosoma*, e.g., *T. cruzi; Leishmania*, e.g., *L. donovani, L. major L. tropica, L. mexicana, L. braziliensis, L. viannia braziliensis; Toxoplasma*, e.g., *T. gondii*; Amoebas of the genera *Naegleria* or *Acanthamoeba; Entamoeba histolytica; Giardia lamblia*; genus *Cryptosporidium*, e.g., *C. parvum; Isospora belli; Cyclospora cayetanensis; Ascaris lumbricoides; Trichuris trichiura; Ancylostoma duodenale* or *Necator americanus; Strongyloides stercoralis Toxocara*, e.g., *T. canis, T. cati; Baylisascaris*, e.g., *B. procyonis; Trichinella*, e.g., *T. spiralis; Dracunculus*, e.g., *D. medinensis*; genus *Filarioidea; Wuchereria bancrofti; Brugia*, e.g., *B. malayi*, or *B. timori; Onchocerca volvulus; Loa loa; Dirofilaria immitis*; genus *Schistosoma*, e.g., *S. japonicum, S. mansoni, S. mekongi, S. intercalatum, S. haematobium; Paragonimus*, e.g., *P. Westermani, P. Skriabini; Clonorchis sinensis; Fasciola hepatica; Opisthorchis* sp; *Fasciolopsis buski; Diphyllobothrium latum; Taenia*, e.g., *T. saginata, T. solium; Echinococcus*, e.g., *E. granulosus, E. multilocularis; Picornaviruses*, rhinoviruses echoviruses, coxsackieviruses, influenza virus; paramyxoviruses, e.g., types 1, 2, 3, and 4; adnoviruses; Herpesviruses, e.g., HSV-1 and HSV-2; varicella-zoster virus; human T-lymphotrophic virus (type I and type II); Arboviruses and Arenaviruses; Togaviridae, Flaviviridae, Bunyaviridae, Reoviridae; Flavivirus; Hantavirus; Viral encephalitis (alphaviruses e.g., Venezuelan equine encephalitis, eastern equine encephalitis, western equine encephalitis); Viral hemorrhagic fevers (filoviruses, e.g., Ebola, Marburg, and arenaviruses, e.g., Lassa, Machupo); Smallpox (variola); retroviruses e.g., human immunodeficiency viruses 1 and 2; human papillomavirus (HPV) types 6, 11, 16, 18, 31, 33, and 35.

In various embodiments, the probe can be selective for a polynucleotide sequence that can be characteristic of an organism selected from the group consisting of *Pseudomonas aeruginosa, Proteus mirabilis, Klebsiella oxytoca, Klebsiella pneumoniae, Escherichia coli, Acinetobacter Baumannii, Serratia marcescens, Enterobacter aerogenes, Enterococcus faecium*, vancomycin-resistant enterococcus (VRE), *Staphylococcus aureus*, methecillin-resistant *Staphylococcus aureus* (MRSA), *Streptococcus viridans, Listeria monocytogenes, Enterococcus* spp., *Streptococcus* Group B, *Streptococcus* Group C, *Streptococcus* Group G, *Streptococcus* Group F, *Enterococcus faecalis, Streptococcus pneumoniae, Staphylococcus epidermidis, Gardenerella vaginalis, Micrococcus* sps., *Haemophilus influenzae, Neisseria gonorrhoeee, Moraxella catarrahlis, Salmonella* sps., *Chlamydia trachomatis, Peptostreptococcus productus, Peptostreptococcus anaerobius, Lactobacillus fermentum, Eubacterium lentum, Candida glabrata, Candida albicans, Chlamydia* spp., *Camplobacter* spp., *Salmonella* spp., smallpox (variola major), Yersina Pestis, Herpes Simplex Virus I (HSV I), and Herpes Simplex Virus II (HSV II).

In various embodiments, the probe can be selective for a polynucleotide sequence that is characteristic of Group B *Streptococcus*.

The technology herein also comprises a microfluidic cartridge having a component for inhibiting motion of fluid. The component comprises a channel, a first mass of a thermally responsive substance (TRS) disposed on a first side of the channel, a second mass of a TRS disposed on a second side of the channel opposite the first side of the channel, a gas pressure source associated with the first mass of the TRS. Actuation of the gas pressure source drives the first mass of the TRS into the second mass of the TRS and obstructs the channel.

The microfluidic cartridge can include a second gas pressure source associated with the second mass of the TRS. Actuation of the second gas pressure source drives the second mass of TRS into the first mass of TRS. At least one (e.g., both) of the first and second masses of TRS may be a wax.

Another aspect of the microfluidic cartridge includes a component for obstructing a channel of a microfluidic cartridge. A mass of a TRS can be heated and driven across the channel (e.g., by gas pressure) into a second mass of TRS. The second mass of TRS may also be driven (e.g., by gas pressure) toward the first mass of TRS.

Another aspect of the microfluidic cartridge is an actuator. The actuator includes a channel, a chamber connected to the channel, at least one reservoir of encapsulated liquid disposed in the chamber, and a gas surrounding the reservoir within the chamber. Heating the chamber expands the reservoir of encapsulated liquid and pressurizes the gas. Typically the liquid has a boiling point of about 90° C. or less. The liquid may be a hydrocarbon having about 10 carbon atoms or fewer. The liquid may be encapsulated by a polymer.

An actuator may include multiple reservoirs of encapsulated liquid disposed in the chamber. The multiple reservoirs may be dispersed within a solid (e.g., a wax). The multiple reservoirs may be disposed within a flexible enclosure (e.g., a flexible sack).

Another aspect of the microfluidic cartridge includes pressurizing a gas within a chamber of the device to create a gas pressure sufficient to move a liquid within a channel of the microfluidic device. Pressurizing the gas typically expands at least one reservoir of encapsulated liquid disposed within the chamber. Expanding the at least one reservoir can include heating the chamber. Pressurizing the gas can include expanding multiple reservoirs of encapsulated liquid.

Another aspect of a microfluidic cartridge for use herein includes combining (e.g., mixing) first and second liquid volumes. The device includes a mass of a temperature responsive substance (TRS) that separates first and second channels of the device. The device can be configured to move a first liquid along the first channel so that a portion (e.g., a medial portion) of the first liquid can be adjacent the TRS, and to move a second liquid along the second channel so that a portion (e.g., a medial portion) of second liquid can be adjacent the TRS. A heat source can be actuated to move the TRS (e.g., by melting, dispersing, fragmenting). The medial portions of the first and second liquids typically combine without being separated by a gas interface. Typically, only a subset of the first liquid and a subset of the second liquid can be combined. The liquids mix upon being moved along a mixing channel. The liquids when combined should be moved at least two droplet lengths to get good mixing by interlayering and transverse diffusion (perpendicular to the length of the microchannel) without having to rely on longitudinal diffusion alone for mixing (see, also, e.g., "Mathematical modeling of drop mixing in a slit-type microchannel", K Handique, et al., *J. Micromech. Microeng.*, 11 548-554, (2001), incorporated herein by reference). By moving the combined drop by a drop length, the liquid in the middle of the receding drop is caused to move to the front of the leading drop and then towards the channel wall. At the receding end of the drop, liquid moves from the wall towards the center of the drop. This motion of the drop results in interlayering between the two liquids. Further interlayering can be achieved by repeating the method additional times, such as over further drop lengths.

The microfluidic cartridge further includes a lyophilized reagent particle. In some embodiments, the lyophilized particles include multiple smaller particles each having a plurality of ligands that preferentially associate with polynucleotides as compared to PCR inhibitors. The lyophilized particles can also (or alternatively) include lysing reagents (e.g., enzymes) configured to lyse cells to release polynucleotides. The lyophilized particles can also (or alternatively) include enzymes (e.g., proteases) that degrade proteins.

Cells can be lysed by combining a solution of the cells, e.g., in a microfluidic droplet, with the lyophilized particles thereby reconstituting the particles. The reconstituted lysing reagents lyse the cells. The polynucleotides associate with ligands of the smaller particles. During lysis, the solution may be heated (e.g., radiatively using a lamp such as a heat lamp, or by a contact heat source.

In some embodiments, lyophilized particles include reagents (e.g., primers, control plasmids, polymerase enzymes) for performing PCR.

Another aspect of the microfluidic cartridge includes a liquid reservoir capable of holding a liquid (e.g., a solvent, a buffer, a reagent, or combination thereof). In general, the reservoir can have one or more of the following features, as further described in international application publication no. WO2006/079082.

The reservoir can include a wall that can be manipulated (e.g., pressed or depressed) to decrease a volume within the reservoir. For example, the reservoir can include a piercing member (e.g., a needle-like or otherwise pointed or sharp member) that ruptures another portion of the reservoir (e.g., a portion of the wall) to release liquid. The piercing member can be internal to the reservoir such that the piercing member ruptures the wall from an inner surface of the reservoir (e.g., wall) outwards.

In general, the wall resists passage of liquid or vapor therethrough. In some embodiments, the wall lacks stretchiness. The wall may be flexible. The wall may be, e.g., a metallic layer, e.g., a foil layer, a polymer, or a laminate including a combination thereof. The wall may be formed by vacuum formation (e.g., applying a vacuum and heat to a layer of material to draw the layer against a molding surface). The molding surface may be concave such that the wall can be provided with a generally convex surface.

Exemplary liquids held by the reservoir include water and aqueous solutions including one or more salts (e.g., magnesium chloride, sodium chloride, Tris buffer, or combination thereof). The reservoir can retain the liquid (e.g., without substantial evaporation thereof) for a period of time (e.g., at least 6 months or at least a year). In some embodiments, less than 10% (e.g., less than about 5%) by weight of the liquid evaporates over a year.

The piercing member may be an integral part of a wall of the reservoir. For example, the reservoir can include a wall having an internal projection, which may be in contact with liquid in the reservoir. The reservoir also includes a second wall opposite the piercing member. During actuation, the piercing member can be driven through the second wall (e.g., from the inside out) to release liquid.

In some embodiments, a maximum amount of liquid retained by a reservoir can be less than about 1 ml. For example, a reservoir may hold about 500 microliters or less (e.g., 300 microliters or less). Generally, a reservoir holds at least about 25 microliters (e.g., at least about 50 microliters). The reservoir can introduce within about 10% of the intended amount of liquid (e.g., 50±5 µl).

The reservoir can deliver a predetermined amount of liquid that can be substantially air-free (e.g., substantially gas-free). Upon introduction of the liquid, the substantially air and/or gas free liquid produces few or no bubbles large enough to obstruct movement of the liquid within the microfluidic device. Use of a piercing member internal to the reservoir can enhance an ability of the reservoir to deliver substantially air and/or gas free liquids.

In some embodiments, the reservoir can be actuated to release liquid by pressing (e.g., by one's finger or thumb or by mechanical pressure actuation). The pressure may be applied directly to a wall of the reservoir or to a plunger having a piercing member. In various embodiments, minimal pressure can be required to actuate the reservoir. An automated system can be used to actuate (e.g., press upon) a plurality of reservoirs simultaneously or in sequence.

Actuation of the reservoir may include driving a piercing member through a wall of the reservoir. In some embodiments, the reservoir does not include a piercing member. Instead, internal pressure generated within the reservoir ruptures a wall of the reservoir allowing liquid to enter the microfluidic device.

Upon actuating a reservoir to introduce liquid into the microfluidic device, liquid generally does not withdraw back into the reservoir. For example, upon actuation, the volume of the reservoir may decrease to some minimum but generally does not increase so as to withdraw liquid back into the reservoir. For example, the reservoir may stay collapsed upon actuation. In such embodiments, the flexible wall may be flexible but lack hysteresis, elasticity, or stretchiness. Alternatively or in combination, the reservoir may draw in air from a vent without withdrawing any of the liquid.

The reservoir preserves the reactivity and composition of reagents therein (e.g., the chemicals within the reservoir may exhibit little or no change in reactivity over 6 months or a year).

The flexible wall of the reservoir can limit or prevent leaching of chemicals therethrough. The reservoir can be assembled independently of a microfluidic cartridge and then secured to the microfluidic cartridge.

Exemplary Microfluidic Cartridge for Processing Polynucleotides

Figure 10:
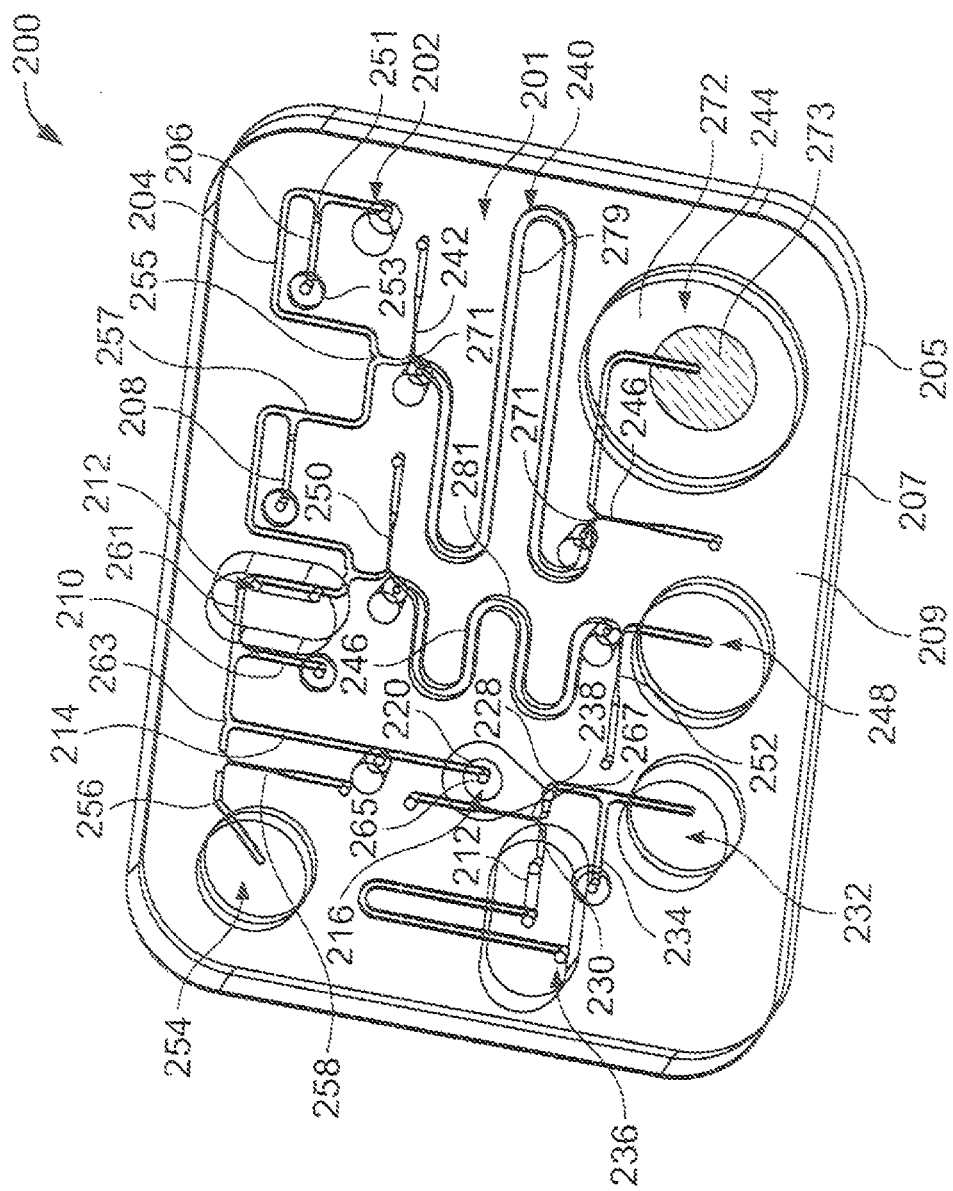
FIG. 10 is a perspective view of a microfluidic device.

Referring to FIG. 10, a portion of an exemplary microfluidic cartridge 200 suitable for use with the system described herein includes first, second, and third layers 205, 207, and 209 that define a microfluidic network 201 having various components configured to process a sample that includes one or more polynucleotides to be detected. Cartridge 200 typically processes the sample by, among other aspects, increasing the concentration of a polynucleotide to be determined and/or by reducing the concentration of inhibitors relative to the concentration of polynucleotide to be determined. The various features of cartridge 200 may be incorporated wholesale, or with suitable modification, into alternative configurations of cartridge that carry out polynucleotide processing in conjunction with various other operations.

Fabrication of Cartridge

Microfluidic cartridge 200 can be fabricated as desired. Typically, layers 205, 207, and 209 can be formed of a polymeric material. Components of network 201 can typically be formed by molding (e.g., by injection molding) layers 207, 209. Layer 205 can typically be a flexible polymeric material (e.g., a laminate) that can be secured (e.g., adhesively and/or thermally) to layer 207 to seal components of network 201.

Layers 207 and 209 may be secured to one another using adhesive. Other methods of cartridge fabrication suitable for application herein can be found described in U.S. provisional patent application Ser. No. 60/859,284, filed Nov. 14, 2006, and incorporated herein by reference in its entirety.

Microfluidic Network

An exemplary arrangement of components of network 201 is as follows, as further described in U.S. Patent Application Publication No. 2006/0166233, incorporated herein by reference.

Network 201 includes an inlet 202 by which sample material can be introduced to the network and an output 236 by which a processed sample can be removed (e.g., expelled by or extracted from) network 201. A channel 204 extends between inlet 202 and a junction 255. A valve 206 can be positioned along channel 204. A reservoir channel 240 extends between junction 255 and an actuator 244. Gates 242 and 246 can be positioned along channel 240. A channel 257 extends between junction 255 and a junction 259. A valve 208 can be positioned along channel 257. A reservoir channel 246 extends between junction 259 and an actuator 248. Gates 250 and 252 can be positioned along channel 246. A channel 261 extends between junction 259 and a junction 263. A valve 210 and a hydrophobic vent 212 can be positioned along channel 261. A channel 256 extends between junction 263 and an actuator 254. A gate 258 can be positioned along channel 256.

A channel 214 extends between junction 263 and a processing chamber 220, which has an inlet 265 and an outlet 267. A channel 228 extends between processing chamber outlet 267 and a waste reservoir 232. A valve 234 can be positioned along channel 228. A channel 230 extends between processing chamber outlet 267 and output 236.

Particular components of microfluidic network 201 are further described as follows.

Processing Chamber

Figure 11:
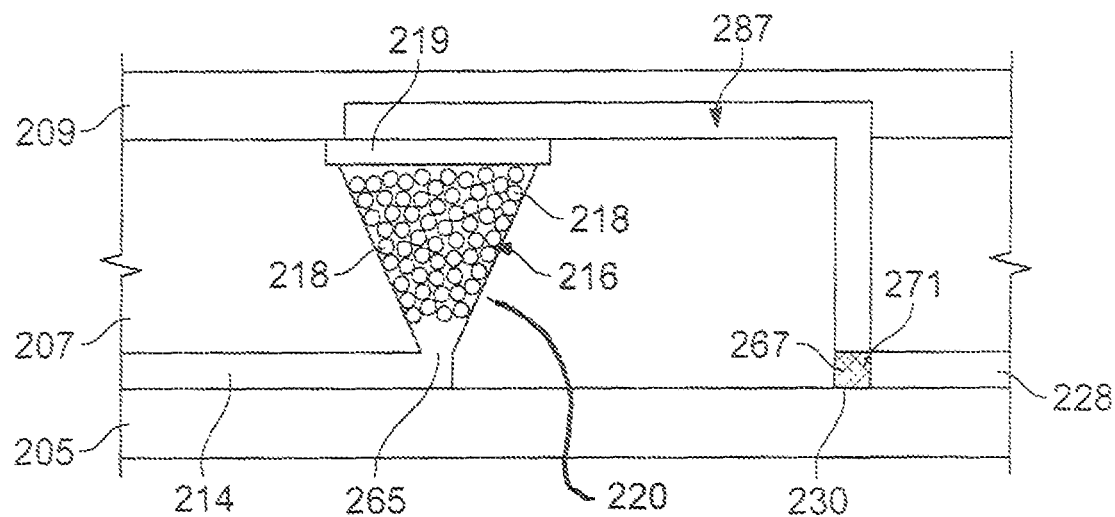
FIG. 11 is a cross-sectional view of a processing region for retaining polynucleotides and/or separating polynucleotides from inhibitors.

Referring also to FIG. 11, processing chamber 220 includes a plurality of particles (e.g., beads, microspheres) 218 configured to retain polynucleotides of the sample under a first set of conditions (e.g., a first temperature and/or first pH) and to release the polynucleotides under a second set of conditions (e.g., a second, higher temperature and/or a second, more basic pH). Typically, the polynucleotides can be retained preferentially as compared to inhibitors that may be present in the sample. Particles 218 can be configured as a retention member 216 (e.g., a column) through which sample material (e.g., polynucleotides) must pass when moving between the inlet 265 and outlet 267 of processing region 220.

A filter 219 prevents particles 218 from passing downstream of processing region 220. A channel 287 connects filter 219 with outlet 267. Filter 219 has a surface area within processing region 220 that can be larger than the cross-sectional area of inlet 265. For example, in some embodiments, the ratio of the surface area of filter 219 within processing chamber 220 to the cross-sectional area of inlet 265 (which cross-sectional area is typically about the same as the cross-sectional area of channel 214) can be at least about 5 (e.g., at least about 10, at least about 20, at least about 30). In some embodiments, the surface area of filter 219 within processing region 220 can be at least about 1 mm$^2$ (e.g., at least about 2 mm$^2$, at least about 3 mm$^2$). In some embodiments, the cross-sectional area of inlet 265 and/or channel 214 can be about 0.25 mm$^2$ or less (e.g. about 0.2 mm$^2$ or less, about 0.15 mm$^2$ or less, about 0.1 mm$^2$ or less). The larger surface area presented by filter 219 to material flowing through processing chamber 220 helps prevent clogging of the processing region while avoiding significant increases in the void volume (described hereinbelow) of the processing region.

Particles 218 can be modified with at least one ligand that retains polynucleotides (e.g., preferentially as compared to inhibitors). Typically, the ligands retain polynucleotides from liquids having a pH about 9.5 or less (e.g., about 9.0 or less, about 8.75 or less, about 8.5 or less). As a sample solution moves through processing chamber 220, polynucleotides can be retained while the liquid and other solution components (e.g., inhibitors) can be less retained (e.g., not retained) and exit the processing region. In general, the ligands release polynucleotides when the pH can be about 10 or greater (e.g., about 10.5 or greater, about 11.0 or greater). Consequently, polynucleotides can be released from the ligand modified particles into the surrounding liquid.

Exemplary ligands on particles 218 include, for example, polyamides (e.g., polycationic polyamides such as poly-L-lysine, poly-D-lysine, poly-DL-omithine) and PEI. Other ligands include, for example, intercalators, poly-intercalators, minor groove binders polyamines (e.g., spermidine), homopolymers and copolymers comprising a plurality of amino acids, and combinations thereof. In some embodiments, the ligands have an average molecular weight of at least about 5,000 Da (e.g., at least about 7,500 Da, of at least about 15,000 Da). In some embodiments, the ligands have an average molecular weight of about 50,000 Da or less (e.g., about 35,000, or less, about 27,500 Da or less). In some embodiments, the ligand can be a polylysine ligand attached to the particle surface by an amide bond.

In certain embodiments, the ligands on the particles 218 can be resistant to enzymatic degradation, such as degradation by protease enzymes (e.g., mixtures of endo- and exo-proteases such as pronase) that cleave peptide bonds. Exemplary protease resistant ligands include, for example, poly-D-lysine and other ligands that can be enantiomers of ligands susceptible to enzymatic attack.

Particles 218 can typically be formed of a material to which the ligands can be associated. Exemplary materials from which particles 218 can be formed include polymeric materials that can be modified to attach a ligand. Typical polymeric materials provide or can be modified to provide carboxylic groups and/or amino groups available to attach ligands. Exemplary polymeric materials include, for example, polystyrene, latex polymers (e.g., polycarboxylate coated latex), polyacrylamide, polyethylene oxide, and derivatives thereof. Polymeric materials that can used to form particles 218 are described in U.S. Pat. No. 6,235,313 to Mathiowitz et al., which patent is incorporated herein by reference. Other materials include glass, silica, agarose, and amino-propyl-tri-ethoxy-silane (APES) modified materials.

Exemplary particles that can be modified with suitable ligands include carboxylate particles (e.g., carboxylate modified magnetic beads (Sera-Mag Magnetic Carboxylate modified beads, Part #3008050250, Seradyn) and Polybead carboxylate modified microspheres available from Polyscience, catalog no. 09850). In some embodiments, the ligands include poly-D-lysine and the beads comprise a polymer (e.g., polycarboxylate coated latex). In other embodiments, the ligands include PEI.

In general, the ratio of mass of particles to the mass of polynucleotides retained by the particles can be no more than about 25 or more (e.g., no more than about 20, no more than about 10). For example, in some embodiments, about 1 gram of particles retains about 100 milligrams of polynucleotides.

Typically, the total volume of processing chamber 220 (including particles 218) between inlet 265 and filter 219 can be about 15 microliters or less (e.g., about 10 microliters or less, about 5 microliters or less, about 2.5 microliters or less, about 2 microliters or less). In an exemplary embodiment, the total volume of processing region 220 can be about 2.3 microliters. In some embodiments, particles 218 occupy at least about 10 percent (e.g., at least about 15 percent) of the total volume of processing region 220. In some embodiments, particles 218 occupy about 75 percent or less (e.g., about 50 percent or less, about 35 percent or less) of the total volume of processing chamber 220.

In some embodiments, the volume of processing chamber 220 that can be free to be occupied by liquid (e.g., the void volume of processing chamber 220 including interstices between particles 218) can be about equal to the total volume minus the volume occupied by the particles. Typically, the void volume of processing region 220 can be about 10 microliters or less (e.g., about 7.5 microliters or less, about 5 microliters or less, about 2.5 microliters or less, about 2 microliters or less). In some embodiments, the void volume can be about 50 nanoliters or more (e.g., about 100 nanoliters or more, about 250 nanoliters or more). For example, in an exemplary embodiment, the total volume of processing chamber 220 can be about 2.3 microliters, the volume occupied by particles can be about 0.3 microliters, and the volume free to be occupied by liquid (void volume) can be about 2 microliters.

Particles 218 typically have an average diameter of about 20 microns or less (e.g., about 15 microns or less, about 10 microns or less). In some embodiments, particles 218 have an average diameter of at least about 4 microns (e.g., at least about 6 microns, at least about 8 microns).

In some embodiments, a volume of channel 287 between filter 219 and outlet 267 can be substantially smaller than the void volume of processing chamber 220. For example, in some embodiments, the volume of channel 287 between filter 219 and outlet 267 can be about 35% or less (e.g., about 25% or less, about 20% or less) of the void volume. In an exemplary embodiment, the volume of channel 287 between filter 219 and outlet 267 can be about 500 nanoliters.

The particle density can typically be at least about $10^8$ particles per milliliter (e.g., about $10^9$ particles per milliliter). For example, a processing region with a total volume of about 1 microliter may include about $10^3$ beads.

Filter 219 typically has pores with a diameter smaller than the diameter of particles 218. In an exemplary embodiment, filter 219 has pores having an average width of about 8 microns, where particles 218 have an average diameter of about 10 microns.

In some embodiments, at least some (e.g., all) of the particles can be magnetic. In alternative embodiments, few (e.g., none) of the particles are magnetic.

In some embodiments, at least some (e.g., all) the particles can be solid. In some embodiments, at least some (e.g., all) the particles can be porous (e.g., the particles may have channels extending at least partially within them).

Further components that may be found in microfluidic network 201 are as follows. Channels Channels of microfluidic network 201 typically have at least one sub-millimeter cross-sectional dimension. For example, channels of network 201 may have a width and/or a depth of about 1 mm or less (e.g., about 750 microns or less, about 500 microns, or less, about 250 microns or less).

Valves

A valve can be a component that has a normally open state allowing material to pass along a channel from a position on one side of the valve (e.g., upstream of the valve) to a position on the other side of the valve (e.g., downstream of the valve). Upon actuation, the valve transitions to a closed state that prevents material from passing along the channel from one side of the valve to the other. For example, in FIG. 10, valve 206 includes a mass 251 of a thermally responsive substance (TRS) that can be relatively immobile at a first temperature and more mobile at a second temperature (e.g., a phase transition material (PTM) of a known melting point, typically about 60° C., or about 75° C., or about 90° C., such as a paraffin wax, solder, etc.). A chamber 253 can be in gaseous communication with mass 251. Upon heating gas (e.g., air) in chamber 253 and heating mass 251 of TRS to the second temperature, gas pressure within chamber 253 moves mass 251 into channel 204 obstructing material from passing therealong. Other valves of network 201 have a similar structure and operate in a similar fashion as valve 206.

A mass of TRS can be an essentially solid mass or an agglomeration of smaller particles that cooperate to obstruct the passage. Examples of TRS's include a eutectic alloy (e.g., a solder), wax (e.g., an olefin), polymers, plastics, and combinations thereof. The first and second temperatures can be insufficiently high to damage materials, such as polymer layers of cartridge 200. Generally, the second temperature can be less than about 90° C. and the first temperature can be less than the second temperature (e.g., about 70° C. or less).

A gate can be a component that can have a closed state that does not allow material to pass along a channel from a position on one side of the gate to another side of the gate, and an open state that does allow material to pass along a channel from a position on one side of the gate to another side of the gate. Actuation of an open gate can transition the gate to a closed state in which material is not permitted to pass from one side of the gate (e.g., upstream of the gate) to the other side of the gate (e.g., downstream of the gate). Upon actuation, a closed gate can transition to an open state in which material is permitted to pass from one side of the gate (e.g., upstream of the gate) to the other side of the gate (e.g., downstream of the gate). For example, gate 242 in FIG. 10 includes a mass 271 of TRS positioned to obstruct passage of material between junction 255 and channel 240. Upon heating mass 271 to a second temperature, the mass changes state (e.g., by melting, by dispersing, by fragmenting, and/or dissolving) to permit passage of material between junction 255 and channel 240.

Figure 12A:
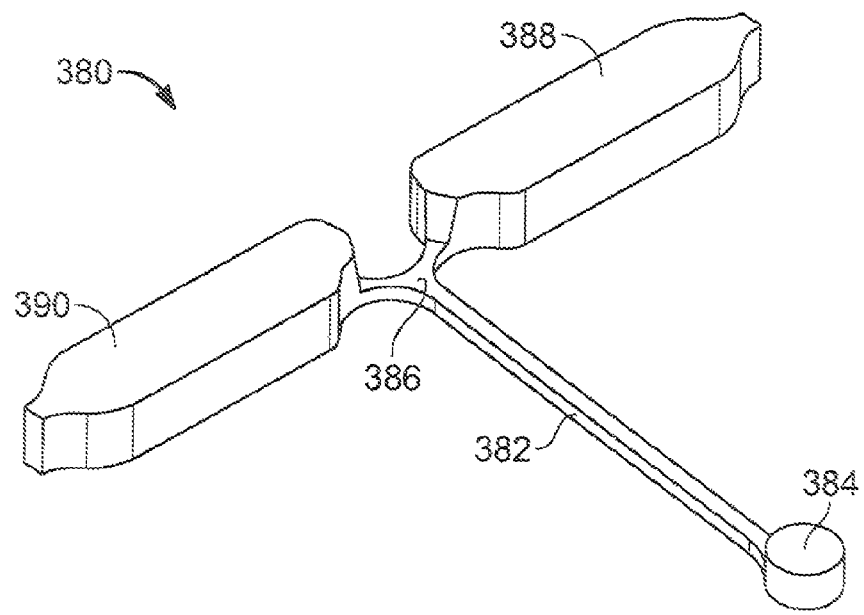
FIG. 12A is a perspective view of a gate.

In various embodiments, a microfluidic network 201 can include a narrow gate 380 as shown in FIG. 12A where a gate loading channel 382 used for loading wax from a wax loading hole 384 to a gate junction 386 can be narrower (e.g., approximately 150 μm wide and 100 microns deep). An upstream channel 388 as well as a downstream channel 390 of the gate junction 386 can be made wide (e.g., ~500 μm) and deep (e.g., ~500 μm) to help ensure the wax stops at the gate junction 386. The amount of gate material melted and moved out of the gate junction 386 may be minimized for optimal gate 380 opening. As an off-cartridge heater may be used to melt the thermally responsive substance in gate 380, a misalignment of the heater could cause the wax in the gate loading channel 382 to be melted as well. Therefore, narrowing the dimension of the loading channel may increase reliability of gate opening. In the case of excessive amounts of wax melted at the gate junction 386 and gate loading channel 382, the increased cross-sectional area of the downstream channel 390 adjacent to the gate junction 386 can prevent wax from clogging the downstream channel 390 during gate 380 opening. The dimensions of the upstream channel 388 at the gate junction 386 can be made similar to the downstream channel 390 to ensure correct wax loading during gate fabrication.

Figure 12B:
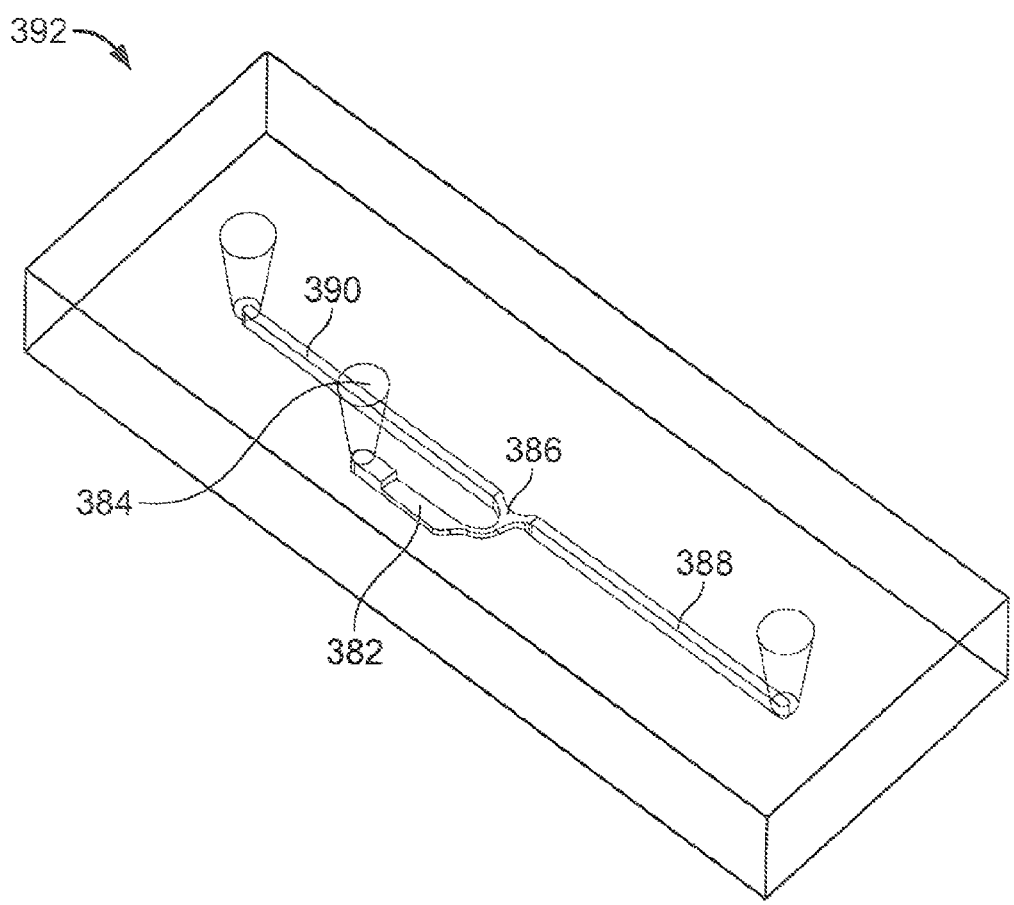
FIG. 12B is a perspective view of a bent gate.

In various embodiments, the gate can be configured to minimize the effective area or footprint of the gate within the network, such as bent gate 392 as shown in FIG. 12B. Minimizing the effective area or footprint of the gate within the network can increase the density of a given microfluidic network and can thereby reduce the cost per part, provide for a more compact network, minimize network channel length or volume, or the like. Still other configurations are possible, though not explicitly shown in the drawings, according to specific layouts of microfluidic network.

In the microfluidic cartridge of FIG. 10, the portion of channel 240 between gates 242 and 246 forms a fluid reservoir 279 configured to hold a liquid (e.g., water, an organic liquid, or combination thereof). During storage, gates 242 and 246 limit (e.g., prevent) evaporation of liquid within the fluid reservoir. During operation of cartridge 200, the liquid of reservoir 279 can typically be used as a wash liquid to remove inhibitors from processing region 220 while leaving polynucleotides associated with particles 218 (FIG. 11). Typically, the wash liquid can be a solution having one or more additional components (e.g., a buffer, chelator, surfactant, a detergent, a base, an acid, or a combination thereof). Exemplary solutions include, for example, a solution of 10-50 mM Tris at pH 8.0, 0.5-2 mM EDTA, and 0.5%-2% SDS, a solution of 10-50 mM Tris at pH 8.0, 0.5 to 2 mM EDTA, and 0.5%-2% Triton X-100.

The portion of channel 247 between gates 250 and 252 form a fluid reservoir 281 configured like reservoir 279 to hold a liquid (e.g., a solution) with limited or no evaporation. During operation of cartridge 200, the liquid of reservoir 281 can typically be used as a release liquid into which polynucleotides that had been retained by particles 218 can be released. An exemplary release liquid can be a hydroxide solution (e.g., a NaOH solution) having a concentration of, for example, between about 2 mM hydroxide (e.g., about 2 mM NaOH) and about 500 mM hydroxide (e.g., about 500 mM NaOH). In some embodiments, liquid in reservoir 281 can be a hydroxide solution having a concentration of about 25 mM or less (e.g., a hydroxide concentration of about 15 mM).

Reservoirs 279, 281 typically each independently hold at least about 0.375 microliters of liquid (e.g., at least about 0.750 microliters, at least about 1.25 microliters, at least about 2.5 microliters). In some embodiments, reservoirs 279, 281 each independently hold about 7.5 microliters or less of liquid (e.g., about 5 microliters or less, about 4 microliters or less, about 3 microliters or less).

Actuators

An actuator can be a component that provides a gas pressure that can move material (e.g., sample material and/or reagent material) between one location in a network e.g., network 201, and another location. For example, referring to FIG. 13, actuator 244 includes a chamber 272 having a mass 273 of thermally expansive material (TEM) therein. When heated, the TEM expands decreasing the free volume within chamber 272 and pressurizing the gas (e.g., air) surrounding mass 273 within chamber 272. Typically, gates such as gates 246 and 242 in network 201 can be actuated with actuator 244. Consequently, the pressurized gas drives liquid in fluid reservoir 279 towards junction 255. In some embodiments, actuator 244 can generate a pressure differential of more than about 3 psi (e.g., at least about 4 psi, at least about 5 psi) between the actuator and junction 255.

Figure 13:
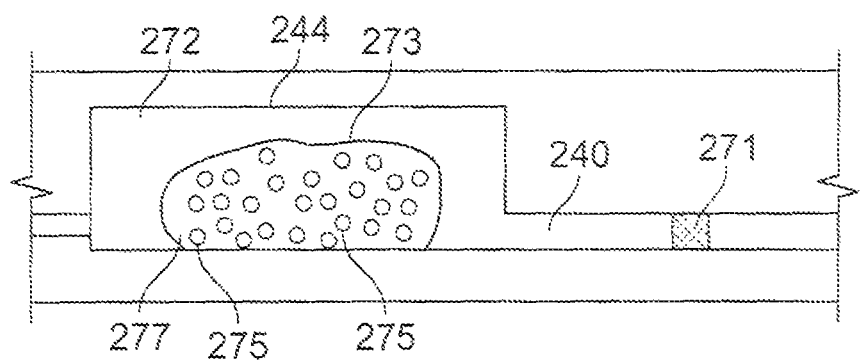
FIG. 13 is a cross-sectional view of an actuator.

In one embodiment, shown in FIG. 13, the TEM includes a plurality of sealed liquid reservoirs (e.g., spheres) 275 dispersed within a carrier 277. Typically, the liquid can be a high vapor pressure liquid (e.g., isobutane and/or isopentane) sealed within a casing (e.g., a polymeric casing formed of monomers such as vinylidene chloride, acrylonitrile and methylmethacrylate). Carrier 277 has properties (e.g., flexibility and/or an ability to soften (e.g., melt) at higher temperatures) that permit expansion of the reservoirs 275 without allowing the reservoirs to pass along channel 240. In some embodiments, carrier 277 can be a wax (e.g., an olefin) or a polymer with a suitable glass transition temperature. Typically, the reservoirs make up at least about 25 weight percent (e.g., at least about 35 weight percent, at least about 50 weight percent) of the TEM. In some embodiments, the reservoirs make up about 75 weight percent or less (e.g., about 65 weight percent or less, about 50 weight percent or less) of the TEM. Suitable sealed liquid reservoirs can be obtained from Expancel (available from Akzo Nobel).

When the TEM can be heated (e.g., to a temperature of at least about 50° C. (e.g., to at least about 75° C., or at least about 90° C.)), the liquid vaporizes and increases the volume of each sealed reservoir and of mass 273. Carrier 277 softens allowing mass 273 to expand. Typically, the TEM can be heated to a temperature of less than about 150° C. (e.g., about 125° C. or less, about 110° C. or less, about 100° C. or less) during actuation. In some embodiments, the volume of the TEM expands by at least about 5 times (e.g., at least about 10 times, at least about 20 times, at least about 30 times).

Vents

A hydrophobic vent (e.g., vent 212) can be a structure that permits gas to exit a channel while limiting (e.g., preventing) liquid from exiting the channel. Typically, hydrophobic vents include a layer of porous hydrophobic material (e.g., a porous filter such as a porous hydrophobic membrane from Osmonics) that defines a wall of the channel. As described hereinbelow, hydrophobic vents can be used to position a microdroplet of sample at a desired location within network 201.

The hydrophobic vents of the present technology are preferably constructed so that the amount of air that escapes through them can be maximized while minimizing the volume of the channel below the vent surface. Accordingly, it is preferable that the vent can be constructed so as to have a hydrophobic membrane of large surface area and a shallow cross section of the microchannel below the vent surface.

Hydrophobic vents typically have a length of at least about 2.5 mm (e.g., at least about 5 mm, at least about 7.5 mm) along a channel. The length of the hydrophobic vent can typically be at least about 5 times (e.g., at least about 10 times, at least about 20 times) larger than a depth of the channel within the hydrophobic vent. For example, in some embodiments, the channel depth within the hydrophobic vent can be about 300 microns or less (e.g., about 250 microns or less, about 200 microns or less, about 150 microns or less).

The depth of the channel within the hydrophobic vent can typically be about 75% or less (e.g., about 65% or less, about 60% or less) of the depth of the channel upstream and downstream of the hydrophobic vent. For example, in some embodiments the channel depth within the hydrophobic vent can be about 150 microns and the channel depth upstream and downstream of the hydrophobic vent can be about 250 microns.

A width of the channel within the hydrophobic vent can typically be at least about 25% wider (e.g., at least about 50% wider) than a width of the channel upstream from the vent and downstream from the vent. For example, in an exemplary embodiment, the width of the channel within the hydrophobic vent can be about 400 microns and the width of the channel upstream and downstream from the vent can be about 250 microns.

In use, cartridge 200 can typically be thermally associated with an array of heat sources configured to operate various components (e.g., valves, gates, actuators, and processing region 220) of the cartridge. In some embodiments, the heat sources can be controlled by a processor in a system such as that further described herein, which operates to receive and to monitor the cartridge during use. The processor (e.g., a microprocessor) is configured to actuate the heat sources individually and at different times, according to a desired protocol. Processors configured to operate microfluidic cartridges, suitable for use or for modification for use herein, are described in U.S. application Ser. No. 09/819,105, filed Mar. 28, 2001 (now U.S. Pat. No. 7,010,391), which patent is incorporated herein by reference. In other embodiments, the heat sources can be integral with the cartridge itself.

Cartridge 200 may be operated as follows. Valves of network 201 can be fabricated in an open state. Gates of network 201 can be fabricated in a closed state. A fluid sample, such as a biological sample as further described herein, comprising polynucleotides can be introduced to network 201 via inlet 202. For example, sample can be introduced with a syringe having a Luer fitting. The syringe provides pressure to initially move the sample within network 201. Sample passes along channels 204, 257, 261, and 214 to inlet 265 of processing region 220. The sample passes through processing region 220, exits via outlet 267, and passes along channel 228 to waste chamber 232. When the trailing edge (e.g., the upstream liquid-gas interface) of the sample reaches hydrophobic vent 212, pressure provided by the introduction device (e.g., the syringe) can be released from network 201 stopping further motion of the sample.

Typically, the amount of sample introduced can be about 500 microliters or less (e.g., about 250 microliters or less, about 100 microliters or less, about 50 microliters or less, about 25 microliters or less, about 10 microliters or less). In some embodiments, the amount of sample can be about 2 microliters or less (e.g., about 0.5 microliters or less).

Polynucleotides entering processing region 220 pass through interstices between the particles 218. Polynucleotides of the sample contact retention member 216 and can be preferentially retained as compared to liquid of the sample, and certain other sample components (e.g., inhibitors). Typically, retention member 220 retains at least about 50% of polynucleotides (e.g., at least about 75%, at least about 85%, at least about 90%) of the polynucleotides present in the sample that entered processing region 220. Liquid of the sample and inhibitors present in the sample exit the processing region 220 via outlet 267 and enter waste chamber 232. Processing region 220 can typically be at a temperature of about 50° C. or less (e.g., 30° C. or less) during introduction of the sample.

Processing continues by washing retention member 216 with liquid of reservoir 279 to separate remaining inhibitors from polynucleotides retained by retention member 216. To wash retention member 216, valve 206 can be closed and gates 242, 246 of first reservoir 240 can be opened. Actuator 244 can be actuated to move wash liquid within reservoir 279 along channels 257, 261, and 214, through processing region 220, and into waste reservoir 232. The wash liquid moves sample that may have remained within channels 204, 257, 261, and 214 through the processing region and into waste chamber 232. Once the trailing edge of the wash liquid reaches vent 212, the gas pressure generated by actuator 244 can be vented and further motion of the liquid can be stopped.

The volume of wash liquid moved by actuator 244 through processing region 220 can typically be at least about 2 times the void volume of processing region 220 (e.g., at least about 3 times the void volume) and can be about 10 times the void volume or less (e.g., about 5 times the void volume or less). Processing region can typically be at a temperature of about 50° C. or less (e.g., 30° C. or less) during washing. Exemplary wash fluids include liquids described with respect to reservoirs 279 and 281, herein.

Processing continues by releasing polynucleotides from retention member 216. Typically, wash liquid from reservoir 279 can be replaced with release liquid (e.g., an hydroxide solution) from reservoir 281 before releasing the polynucleotides. Valve 208 can be closed and gates 250, 252 can be opened. Actuator 248 can be actuated, thereby moving release liquid within reservoir 281 along channels 261, 214 and into processing region 220 and in contact with retention member 216. When the trailing edge of release liquid from reservoir 281 reaches hydrophobic vent 212, pressure generated by actuator 248 can be vented stopping the further motion of the liquid. The volume of liquid moved by actuator 248 through processing region 220 can typically be at least about equal to the void volume of the processing region 220 (e.g., at least about 2 times the void volume) and can be about 10 times the void volume or less (e.g., about 5 times the void volume or less).

Once retention member 216 with retained polynucleotides has been contacted with liquid from reservoir 281, a releasing step can typically be performed. Typically, the releasing includes heating release liquid present within processing region 216. Generally, the liquid can be heated to a temperature insufficient to boil liquid in the presence of the retention member. In some embodiments, the temperature can be 100° C. or less (e.g., less than 100° C., about 97° C. or less). In some embodiments, the temperature can be about 65° C. or more (e.g., about 75° C. or more, about 80° C. or more, about 90° C. or more). In some embodiments, the temperature is maintained for about 1 minute or more (e.g., about 2 minutes or more, about 5 minutes or more, about 10 minutes or more). In some embodiments, the temperature can be maintained for about 30 minutes (e.g., about 15 minutes or less, about 10 minutes or less, about 5 minutes or less). In an exemplary embodiment, processing region 220 can be heated to between about 65 and 90° C. (e.g., to about 70° C.) for between about 1 and 7 minutes (e.g., for about 2 minutes). Such temperatures and times vary according to the sample and can be chosen accordingly by one of ordinary skill in the art.

The polynucleotides can be released into the liquid present in the processing region 220 (e.g., the polynucleotides can typically be released into an amount of release liquid having a volume about the same as the void volume of the processing region 220). Typically, the polynucleotides can be released into about 10 microliters or less (e.g., about 5 microliters or less, about 2.5 microliters or less) of liquid.

In certain embodiments, the ratio of the volume of original sample moved through the processing region 220 to the volume of liquid into which the polynucleotides can be released can be at least about 10 (e.g., at least about 50, at least about 100, at least about 250, at least about 500, at least about 1000). In some embodiments, polynucleotides from a sample having a volume of about 2 ml can be retained within the processing region, and released into about 4 microliters or less (e.g., about 3 microliters or less, about 2 microliters or less, about 1 microliter or less) of liquid.

The liquid into which the polynucleotides can be released typically includes at least about 50% (e.g., at least about 75%, at least about 85%, at least about 90%) of the polynucleotides present in the sample that entered processing region 220. The concentration of polynucleotides present in the release liquid may be higher than in the original sample because the volume of release liquid can typically be less than the volume of the original liquid sample moved through the processing region. For example the concentration of polynucleotides in the release liquid may be at least about 10 times greater (e.g., at least about 25 times greater, at least about 100 times greater) than the concentration of polynucleotides in the sample introduced to cartridge 200. The concentration of inhibitors present in the liquid into which the polynucleotides can be released can generally be less than concentration of inhibitors in the original fluid sample by an amount sufficient to increase the amplification efficiency for the polynucleotides.

The time interval between introducing the polynucleotide containing sample to processing region 220 and releasing the polynucleotides into the release liquid can typically be about 15 minutes or less (e.g., about 10 minutes or less, about 5 minutes or less).

Liquid including the released polynucleotides may be removed from the processing region 220 as follows. Valves 210 and 234 can be closed. Gates 238 and 258 can be opened. Actuator 254 can be actuated to generate pressure that moves liquid and polynucleotides from processing region 220, into channel 230, and toward outlet 236. The liquid with polynucleotides can be removed using, for example, a syringe or automated sampling device. Depending upon the liquid in contact with retention member 216 during polynucleotide release, the solution with released polynucleotide may be neutralized with an amount of buffer (e.g., an equal volume of 25-50 mM Tris-HCl buffer pH 8.0).

While releasing the polynucleotides has been described as including a heating step, the polynucleotides may be released without heating. For example, in some embodiments, the liquid of reservoir 281 has an ionic strength, pH, surfactant concentration, composition, or combination thereof that releases the polynucleotides from the retention member at ambient temperature, without need for additional heating.

While the polynucleotides have been described as being released into a single volume of liquid present within processing region 220, other configurations can be used. For example, polynucleotides may be released with the concomitant (stepwise or continuous) introduction of fluid into and/or through processing region 220. In such embodiments, the polynucleotides may be released into liquid having a volume of about 10 times or less (e.g., about 7.5 times or less, about 5 times or less, about 2.5 times or less, about 2 times or less) than the void volume of the processing region 220.

While reservoirs 279, 281 have been described as holding liquids between first and second gates, other configurations can be used. For example, liquid for each reservoir may be held within a pouch (e.g., a blister pack, as further described herein) isolated from network 201 by a generally impermeable membrane. The pouch can be configured so that a user can rupture the membrane driving liquid into reservoirs 279, 281 where actuators 244, 248 can move the liquid during use.

While processing regions have been described as having microliter scale dimensions, other dimensions can be used. For example, processing regions with surfaces (e.g., particles) configured to preferentially retain polynucleotides as opposed to inhibitors may have large volumes (e.g., many tens of microliters or more, at least about 1 milliliter or more). In some embodiments, the processing region has a bench-top scale.

While processing region 220 has been described as having a retention member formed of multiple surface-modified particles, other configurations can be used. For example, in some embodiments, processing region 220 includes a retention member configured as a porous member (e.g., a filter, a porous membrane, or a gel matrix) having multiple openings (e.g., pores and/or channels) through which polynucleotides pass. Surfaces of the porous member can be modified to preferentially retain polynucleotides. Filter membranes available from, for example, Osmonics, can be formed of polymers that may be surface-modified and used to retain polynucleotides within processing region 220. In some embodiments, processing region 220 includes a retention member configured as a plurality of surfaces (e.g., walls or baffles) through which a sample passes. The walls or baffles can be modified to preferentially retain polynucleotides.

While processing region 220 has been described as a component of a microfluidic network, other configurations can be used. For example, in some embodiments, the retention member can be removed from a processing region for processing elsewhere. For example, the retention member may be contacted with a mixture comprising polynucleotides and inhibitors in one location and then moved to another location at which the polynucleotides can be removed from the retention member.

While reservoirs 275 have been shown as dispersed within a carrier, other configurations may be used. For example, reservoirs 275 can be encased within a flexible enclosure (e.g., a membrane, for example, an enclosure such as a sack). In some embodiments, reservoirs can be loose within chamber 272. In such embodiments, actuator 244 may include a porous member having pores too small to permit passage of reservoirs 275 but large enough to permit gas to exit chamber 272.

Exemplary Microfluidic Cartridge having a Lysing Chamber

Further microfluidic cartridge with various components are described in U.S. provisional application No. 60/553,553 filed Mar. 17, 2004 by Parunak, et al., and patent application publication no. 2005-0084424, which applications are incorporated herein by reference.

Figure 14A:
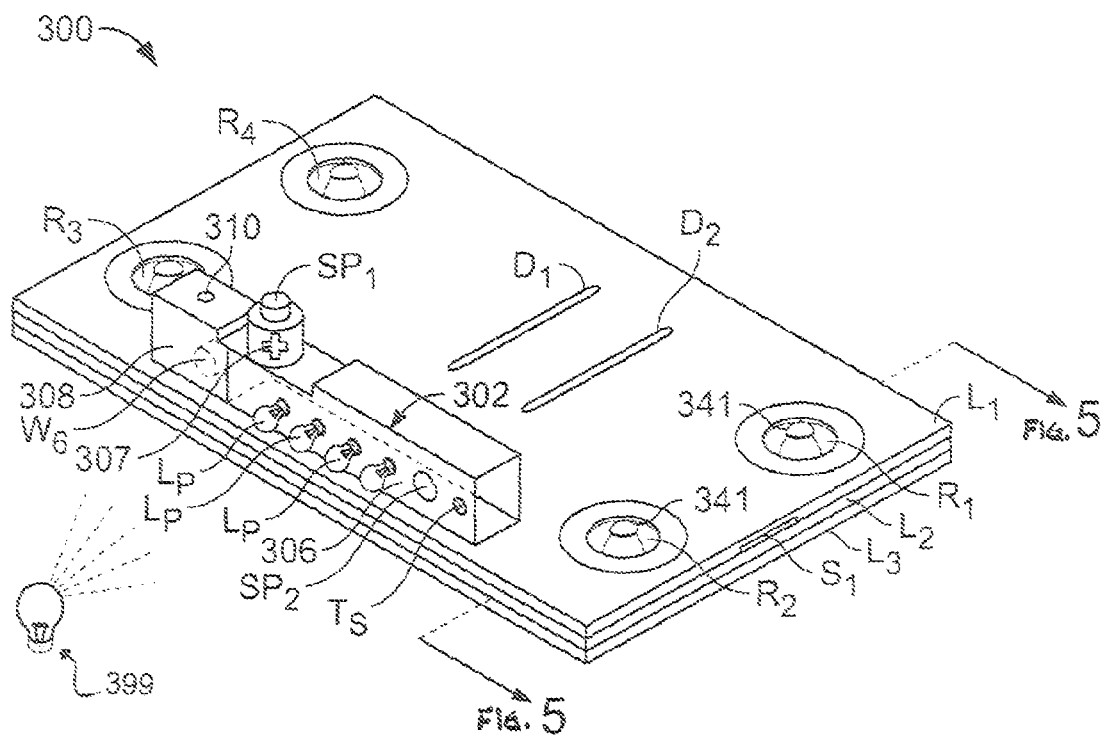
FIG. 14A is a perspective view of a microfluidic cartridge.

While microfluidic cartridges have been described that are configured to receive polynucleotides already released from cells, microfluidic cartridges for use herein can also be configured to release polynucleotides from cells (e.g., by lysing the cells). For example, referring to FIGS. 14A, 14B, 15A, and 15B, a microfluidic cartridge 300 includes a sample lysing chamber 302 in which cells can be lysed to release polynucleotides therein. Microfluidic cartridge 300 further includes substrate layers L1-L3, a microfluidic network 304 (only portions of which are seen in FIG. 14A), and liquid reagent reservoirs R1-R4. Liquid reagent reservoirs R1-R4 hold liquid reagents (e.g., for processing sample material) and can be connected to network 304 by reagent ports RP1-RP4. Microfluidic cartridge 300 can therefore be a self-contained environment that comprises all reagents and materials necessary to perform steps of work-up, cell-lysis, polynucleotide isolation, pre-amplification processing, amplification, and detection of a sample. In some embodiments, a sample is introduced having one or more of the required reagents mixed therewith; in which case the remaining reagents are stored on the cartridge. Reagents and other materials may be stored on cartridge 300 in liquid reagent reservoirs R1-R4, microfluidic channels or chambers in a microfluidic network, and/or in a lysing chamber 302.

Network 304 can be substantially defined between layers L2 and L3 but extends in part between all three layers L1-L3. Microfluidic network 304 includes various microfluidic components as further described herein, including channels Ci, valves Vi, double valves V'i, gates Gi, mixing gates MGi, vents Hi, gas actuators (e.g., pumps) Pi, a first processing region B1, a second processing region B2, detection zones Di, air vents AVi, and waste zones Wi.

FIGS. 15A, 15B, show two complementary halves of an exemplary microfluidic network 304. It would be understood by one of ordinary skill in the art, that the division of the network into two separate halves is arbitrary, and purely for ease of illustration. The arrangement of components shown in FIGS. 15A, 15B is exemplary; it would be understood by one of ordinary skill in the art that other such arrangements, such as different geometric arrangements of the same components, or different arrangements of different components may be constructed by one of ordinary skill in the art, to accomplish the steps described herein.

Figure 16:
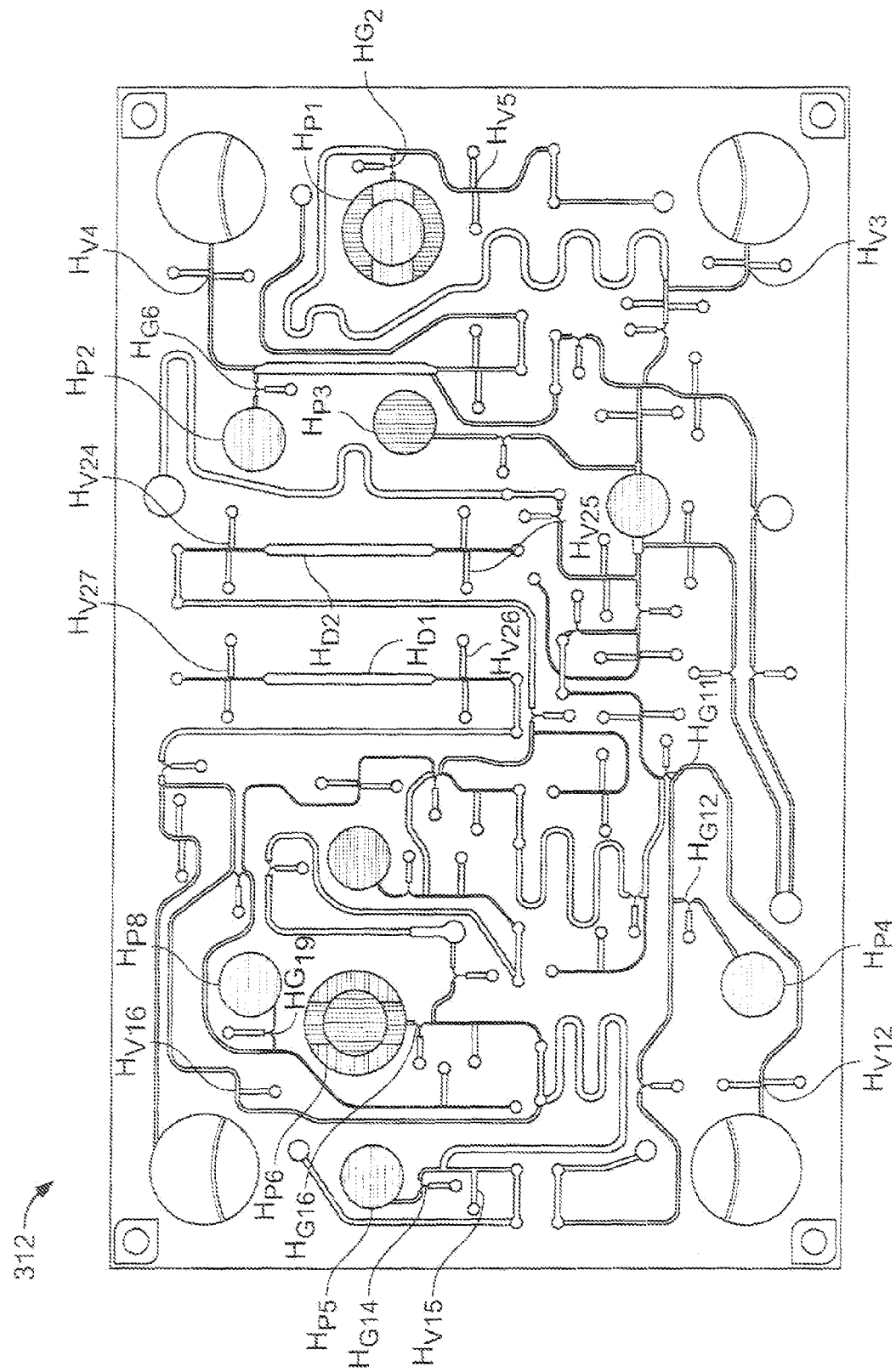
FIG. 16 illustrates an array of heat sources for operating components of the microfluidic cartridge of FIGS. 14A and 14B.

Components of network 304 can typically be thermally actuated. As seen in FIG. 16, an exemplary heat source network 312 includes heat sources (e.g., resistive heat sources) having locations that correspond to various thermally actuated components of microfluidic network 304. For example, the locations of heat sources HPi correspond to the locations of actuators Pi, the locations of heat sources HGi correspond to locations of gates Gi and mixing gates MGi, the locations of heat sources HVi correspond to the locations of valves Vi and double valves V'i, and the locations of heat sources HDi correspond to the locations of processing chambers Di, all of network 304. In use, the components of cartridge 300 can be disposed in thermal contact with corresponding heat sources of network 312, which can typically be operated using a processor as described above for cartridge 200. Heat source network 312 can be integral with or separate from cartridge 300 as described for cartridge 200. For example, heat source network 312 can be integrated into a heater module 2020, such as beneath the receiving bay 2014 in a manner that it aligns with a network of a cartridge disposed therein.

Further components of exemplary microfluidic cartridge 300 are as follows.

Air Vents

Air vents AVi can allow gas (e.g., air) displaced by the movement of liquids within network 304 to be vented so that pressure buildup does not inhibit desired movement of the liquids. For example, air vent AV2 permits liquid to move along channel C14 and into channel C16 by venting gas downstream of the liquid through vent AV2.

Valves

Valves Vi can have a normally open state allowing material to pass along a channel from a position on one side of the valve (e.g., upstream of the valve) to a position on the other side of the valve (e.g., downstream of the valve). The valves Vi can have a similar structure to valves of microfluidic cartridge 200, as further described herein.

Figure 17:
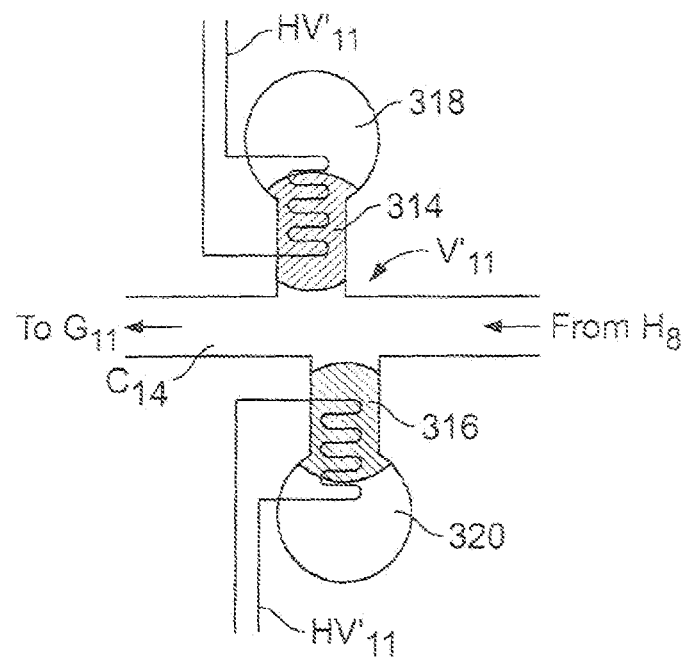
FIG. 17 and 18 illustrate a valve in the open and closed states respectively.
Figure 18:
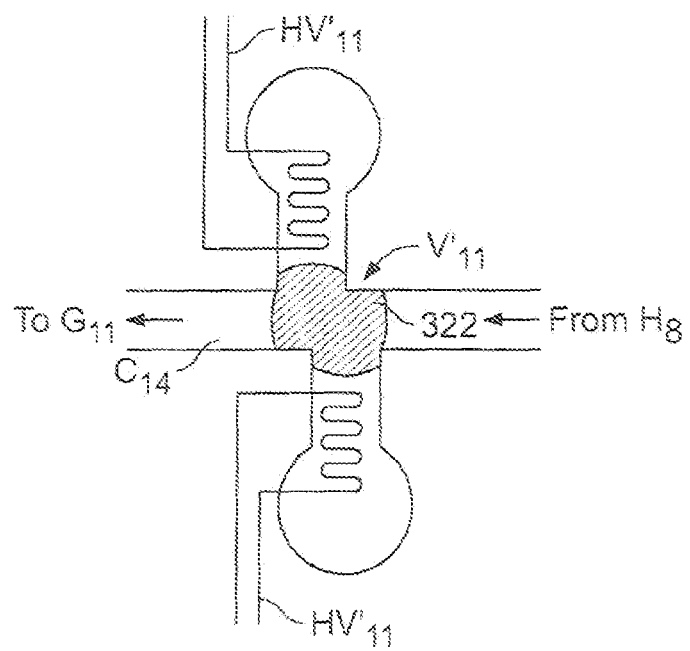

As seen in FIGS. 17 and 18, double valves V'i can also have a normally open state allowing material to pass along a channel from a position on one side of the valve (e.g., upstream of the valve) to a position on the other side of the valve (e.g., downstream of the valve). Taking double valve V11' of FIGS. 17 and 18 as an example, double valves Vi' include first and second masses 314, 316 of a TRS (e.g., a eutectic alloy or wax) spaced apart from one another on either side of a channel (e.g., channel C14). Typically, the TRS masses 314, 316 can be offset from one another (e.g., by a distance of about 50% of a width of the TRS masses or less). Material moving through the open valve passes between the first and second TRS masses 314, 316. Each TRS mass 314, 316 can be associated with a respective chamber 318, 320, which typically includes a gas (e.g., air).

The TRS masses 314, 316 and chambers 318, 320 of double valve Vi' can be in thermal contact with a corresponding heat source HV11' of heat source network 312. Actuating heat source HV11' causes TRS masses 314, 316 to transition to a more mobile second state (e.g., a partially melted state) and increases the pressure of gas within chambers 318, 320. The gas pressure drives TRS masses 314, 316 across channel C11 and closes valve HV11' (FIG. 18). Typically, masses 314, 316 at least partially combine to form a mass 322 that obstructs channel C11.

Returning to FIGS. 15A, 15B, gates Gi can have a normally closed state that does not allow material to pass along a channel from a position on one side of the gate to another side of the gate. Gates Gi can have a similar structure as described for gates of cartridge 200.

As seen in FIGS. 19A-19D for an exemplary portion of a microfluidic network, mixing gates MGi can allow two volumes of liquid to be combined (e.g., mixed) within network 304. Mixing gates MGi are described further below.

Actuators

Actuators Pi can provide a gas pressure to move material (e.g., sample material and/or reagent material) between one location of network 304 and another location. Actuators Pi can be similar in form to actuators of cartridge 200. For example, each actuator Pi includes a chamber with a mass 273 of TEM that can be heated to pressurize gas within the chamber. Each actuator Pi includes a corresponding gate Gi (e.g., gate G2 of actuator P1) that prevents liquid from entering the chamber of the actuator. The gate can typically be actuated (e.g., opened) to allow pressure created in the chamber of the actuator to enter the microfluidic network.

Waste Chambers

Waste chambers Wi can receive waste (e.g., overflow) liquid resulting from the manipulation (e.g., movement and/or mixing) of liquids within network 304. Typically, each waste chamber Wi has an associated air vent that allows gas displaced by liquid entering the chamber to be vented.

Processing Regions

First processing region B1 of network 304 can be a component that allows polynucleotides to be concentrated and/or separated from inhibitors of a sample. Processing region B1 can be configured and operated as processing region 220 of cartridge 200. In some embodiments, first processing region B1 includes a retention member (e.g., multiple particles (e.g., microspheres or beads), a porous member, multiple walls) having at least one surface modified with one or more ligands as described for processing region 220. For example, the ligand can include one or more polyamides (e.g., poly-cationic polyamides such as poly-L-lysine, poly-D-lysine, poly-DL-ornithine), or polyethyleneimine. In some embodiments, particles of the retention member can be disposed in lysing chamber 302 and can be moved into processing region B1 along with sample material.

Second processing region B2 can be a component that allows material (e.g., sample material) to be combined with compounds (e.g., reagents) for determining the presence of one or more polynucleotides. In some embodiments, the compounds include one or more PCR reagents (e.g., primers, control plasmids, and polymerase enzymes).

Lyophilized Particles

In some embodiments, the compounds for determining the presence of one or more polynucleotides can be stored within a processing region such as B2 as one or more lyophilized particles (e.g., pellets). The particles generally have a room temperature (e.g., about 20° C.) shelf-life of at least about 6 months (e.g., at least about 12 months). Liquid entering the second processing region B2 dissolves (e.g., reconstitutes) the lyophilized compounds.

Typically, the lyophilized particle(s) of processing region B2 have an average volume of about 5 microliters or less (e.g., about 4 microliters or less, about 3 microliters or less, about 2 microliters or less). In some embodiments, the lyophilized particle(s) of processing region B2 have an average diameter of about 4 mm or less (e.g., about 3 mm or less, about 2 mm or less) In an exemplary embodiment the lyophilized particle(s) have an average volume of about 2 microliters and an average diameter of about 1.35 mm. In other embodiments, the lyophilized particles may have a diameter of about 5 mm or less (e.g., about 2.5 mm or less, about 1.75 mm or less).

Lyophilized particles for determining the presence of one or more polynucleotides typically include multiple compounds. In some embodiments, the lyophilized particles include one or more compounds used in a reaction for determining the presence of a polynucleotide and/or for increasing the concentration of the polynucleotide. For example, lyophilized particles can include one or more enzymes for amplifying a polynucleotide, as by PCR.

Exemplary lyophilized particles include exemplary reagents for the amplification of polynucleotides associated with group B *streptococcus* (GBS) bacteria. In some embodiments, the lyophilized particles include one or more of a cryoprotectant, one or more salts, one or more primers (e.g., GBS Primer F and/or GBS Primer R), one or more probes (e.g., GBS Probe-FAM), one or more internal control plasmids, one or more specificity controls (e.g., Streptococcus pneumoniae DNA as a control for PCR of GBS), one or more PCR reagents (e.g., dNTPs and/or dUTPs), one or more blocking or bulking agents (e.g., non-specific proteins (e.g., bovine serum albumin (BSA), RNAseA, or gelatin), and a polymerase (e.g., glycerol-free Taq Polymerase). Of course, other components (e.g., other primers and/or specificity controls) can be used for amplification of other polynucleotides.

Cryoprotectants generally help increase the stability of the lyophilized particles and help prevent damage to other compounds of the particles (e.g., by preventing denaturation of enzymes during preparation and/or storage of the particles). In some embodiments, the cryoprotectant includes one or more sugars (e.g., one or more disaccharides (e.g., trehalose, melizitose, raffinose)) and/or one or more poly-alcohols (e.g., mannitol, sorbitol).

Lyophilized particles can be prepared as desired. A method for making lyophilized particles includes forming a solution of reagents of the particle and a cryoprotectant (e.g., a sugar or poly-alcohol). Typically, compounds of the lyophilized particles can be combined with a solvent (e.g., water) to make a solution, which can be then placed (e.g., dropwise, in discrete aliquots (e.g., drops) such as by pipette) onto a chilled hydrophobic surface (e.g., a diamond film or a polytetrafluorethylene surface). In general, the temperature of the surface can be reduced to near the temperature of liquid nitrogen (e.g., about −150° F. or less, about −200° F. or less, about −275° F. or less), such as by use of a cooling bath of a cryogenic agent directly underneath. The solution can be dispensed without contacting the cryogenic agent. The solution freezes as discrete particles. The frozen particles can be subjected to a vacuum, typically while still frozen, for a pressure and time sufficient to remove the solvent (e.g., by sublimation) from the pellets. Such methods are further described in international patent application publication no. WO 2006/119280, incorporated herein by reference.

In general, the concentrations of the compounds in the solution from which the particles are made can be higher than when reconstituted in the microfluidic cartridge. Typically, the ratio of the solution concentration to the reconstituted concentration can be at least about 3 (e.g., at least about 4.5). In some embodiments, the ratio can be about 6.

An exemplary solution for preparing lyophilized pellets for use in the amplification of polynucleotides indicative of the presence of GBS can be made by combining a cryoprotecant (e.g., 120 mg of trehalose as dry powder), a buffer solution (e.g., 48 microliters of a solution of 1M Tris at pH 8.4, 2.5M KCl, and 200 mM $MgCl_2$), a first primer (e.g., 1.92 microliters of 500 micromolar GBS Primer F (Invitrogen)), a second primer (e.g., 1.92 microliters of 500 micromolar GBS Primer R (Invitrogen)), a probe (e.g., 1.92 microliters of 250 micromolar GBS Probe-FAM (IDT/Biosearch Technologies)), a control probe (e.g., 1.92 microliters of 250 micromolar Cal Orange 560 (Biosearch Technologies)), a template plasmid (e.g., 0.6 microliters of a solution of $10^5$ copies plasmid per microliter), a specificity control (e.g., 1.2 microliters of a solution of 10 nanograms per microliter (e.g., about 5,000,000 copies per microliter) *streptococcus pneumoniae* DNA (ATCC)), PCR reagents (e.g., 4.8 microliters of a 100 millimolar solution of dNTPs (Epicenter) and 4 microliters of a 20 millimolar solution of dUTPs (Epicenter)), a bulking agent (e.g., 24 microliters of a 50 milligram per milliliter solution of BSA (Invitrogen)), a polymerase (e.g., 60 microliters of a 5 U per microliter solution of glycerol-free Taq Polymerase (Invitrogen/Eppendorf)) and a solvent (e.g., water) to make about 400 microliters of solution. About 200 aliquots of about 2 microliters each of this solution can be frozen and desolvated as described above to make 200 pellets. When reconstituted, the 200 particles make a PCR reagent solution having a total volume of about 2.4 milliliters.

Reagent Reservoirs

As seen in FIG. 14, reagent reservoirs Ri can be configured to hold liquid reagents (e.g., water, buffer solution, hydroxide solution) separated from network 304 until ready for use. Reservoirs R1 include an enclosure 329 that defines a sealed space 330 for holding liquids. Each space 330 can be separated from reagent port RPi and network 304 by a lower wall 333 of enclosure 329. A capping material 341 (e.g., a laminate, adhesive, or polymer layer) may overlie an upper wall of the enclosure.

A portion of enclosure 329 can be formed as an actuation mechanism (e.g., a piercing member 331) oriented toward the lower wall 333 of each enclosure. When cartridge 300 can be used, reagent reservoirs Ri can be actuated by depressing piercing member 331 to puncture wall 333. Piercing member 331 can be depressed by a user (e.g., with a thumb) or by the operating system used to operate cartridge 300.

Wall 333 can typically be formed of a material having a low vapor transmission rate (e.g., Aclar, a metallized (e.g. aluminum) laminate, a plastic, or a foil laminate) that can be ruptured or pierced. Reservoir 330 holds an amount of liquid suited for cartridge 300. For example, the reservoir may hold up to about 200 microliters. The piercing member 331 may account for a portion (e.g., up to about 25%) of that volume. The material of the laminate inside the blister that may touch corrosive reagent such as basic sodium hydroxide should not corrode even after six to twelve months of exposure.

In general, reservoirs Ri can be formed and filled as desired. For example, the upper wall of the enclosure can be sealed to the lower wall 333 (e.g., by adhesive and/or thermal sealing). Liquid can be introduced into the reservoir by, for example, an opening at the lower end of the piercing member 331. After filling, the opening can be sealed (e.g., by heat sealing through the localized application of heat or by the application of a sealing material (e.g., capping material 341)).

When wall 333 can be punctured, fluid from the reservoir enters network 333. For example, as seen in FIGS. 14 and 15, liquid from reservoir R2 enters network 304 by port RP2 and travels along a channel C2. Gate G3 prevents the liquid from passing along channel C8. Excess liquid passes along channel C7 and into waste chamber W2. When the trailing edge of liquid from reservoir R2 passes hydrophobic vent H2, pressure created within the reservoir can be vented stopping further motion of the liquid. Consequently, network 304 receives an aliquot of liquid reagent having a volume defined by the volume of channel C2 between a junction J1 and a junction J2. When actuator P1 can be actuated, this aliquot of reagent can be moved further within network 304. Reagent reservoirs R1, R3, and R4 can be associated with corresponding channels, hydrophobic vents, and actuators.

In the configuration shown, reagent reservoir R1 typically holds a release liquid (e.g., a hydroxide solution as described above for cartridge 200) for releasing polynucleotides retained within processing region B1. Reagent reservoir R2 typically holds a wash liquid (e.g., a buffer solution as described above for cartridge 200) for removing un-retained compounds (e.g., inhibitors) from processing region B1 prior to releasing the polynucleotides. Reagent reservoir R3 typically holds a neutralization buffer (e.g., 25-50 mM Tris-HCl buffer at pH 8.0). Reagent reservoir R4 typically holds deionized water.

While reservoirs have been shown as having a piercing member formed of a wall of the reservoir, other configurations are possible. For example, in some embodiments, the reservoir includes a needle-like piercing member that extends through an upper wall of the reservoir into the sealed space toward a lower wall of the reservoir. The upper wall of the reservoir may be sealed at the needle-like piercing member (e.g., with an adhesive, an epoxy). In use, the upper wall can be depressed driving the piercing member through the lower wall forcing liquid in the sealed space to enter a microfluidic network.

While reservoirs have been described as including an actuation mechanism (e.g., a piercing member), other configurations are possible. For example, in some embodiments, a lower wall of the sealed space of the reservoir includes a weakened portion that overlies an opening to a microfluidic network. The lower wall material (e.g., laminate, polymer film, or foil) that overlies the opening can be thick enough to prevent loss of the liquid within the sealed space but thin enough to rupture upon the application of pressure to the liquid therein. Typically, the material overlying the opening can be thinner than the adjacent material. Alternatively, or in addition, the weakened material can be formed by leaving this material relatively unsupported as compared to the surrounding material of the lower wall.

Figure 20A:
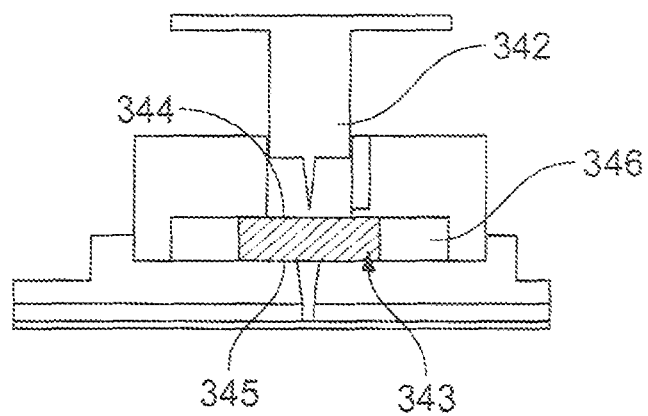
FIGS. 20A-20C illustrate a reservoir with actuation mechanism.

While reservoirs have been described as having a sealed spaced formed in part by a wall of the sealed space, other configurations are possible. For example, referring to FIG. 20A, a reservoir includes a plunger-like actuation mechanism (e.g., a piercing member 342) and a gasket-like sealed space 343 having upper and lower layers 344, 345 respectively (e.g., upper and lower laminate layers). Liquid can be sealed between the upper and lower layers. The sealed space can be surrounded by a supporting structure 346 (e.g., a toroidal gasket) that supports the sealed space at its upper and lower peripheral surfaces.

Figure 20B:
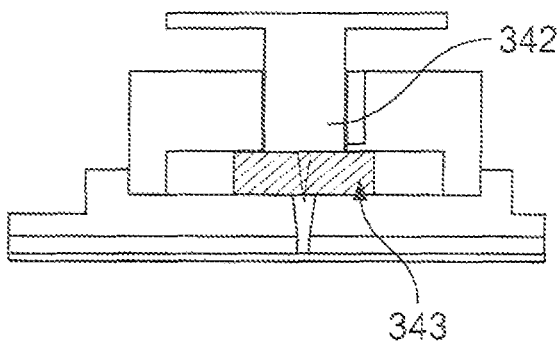

Referring to FIG. 20B, piercing member 342 is shown as being depressed until the piercing member 342 has pierced both the upper and lower layers bringing the liquid into communication with the microfluidic network. A vent 346 adjacent the plunger allows gas trapped between the piercing member and the upper layer of the sealed space to escape without being forced into the microfluidic network.

Figure 20C:
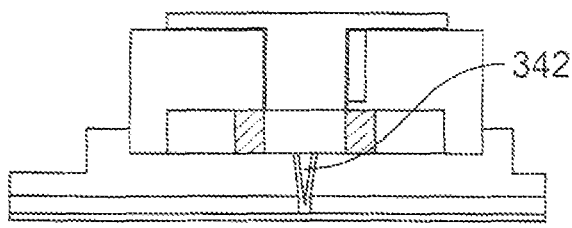

Referring to FIG. 20C, piercing member 342 is shown as fully actuated. A portion of the piercing member has displaced a corresponding volume of liquid from the sealed space and introduced the predetermined volume of liquid into the microfluidic cartridge.

Figure 21A:
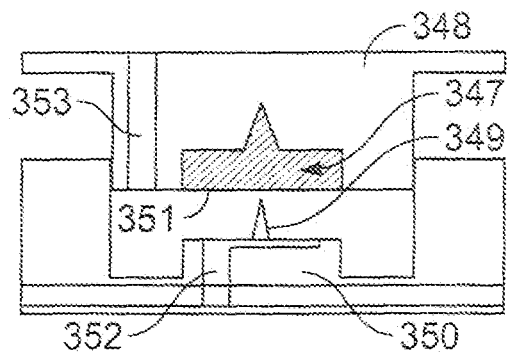
FIGS. 21A-21C illustrate a reservoir with actuation mechanism.

While the reservoirs have been described as having a sealed space that may be stationary with respect to a piercing member, other configurations are possible. For example, FIG. 21A illustrates a reservoir having a sealed space 347 that can be secured with (e.g., integral with) respect to an actuation mechanism having a movable member 348 (e.g., a plunger) and a piercing member 349 supported by a piercing member support 350 that can be stationary with respect to the sealed space. Typically, the sealed space can be defined by a cavity within the movable member and a lower wall 351 that seals liquid within the sealed space. Piercing member can be configured to rupture the lower wall when the movable member can be depressed. Piercing member support has a shape generally complementary to the cavity of the movable member. Piercing member support includes a channel 352 connected to a microfluidic network to allow fluid released from the enclosed space to enter the microfluidic network.

Figure 21B:
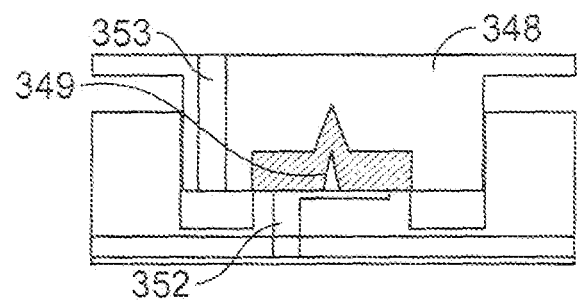
Figure 21C:
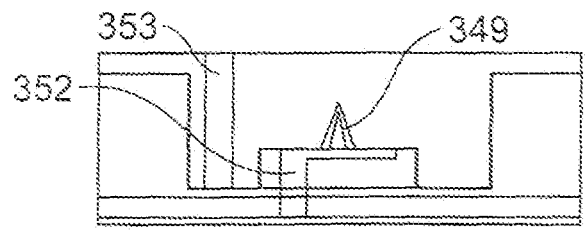

Referring to FIG. 21B, the movable member has been depressed so that the piercing member has just ruptured the lower layer of the sealed space. Referring to FIG. 21C, the reservoir has been fully depressed onto the piercing member and piercing member support. The volume of fluid displaced from the reservoir generally corresponds to the volume of the piercing member support that enters the enclosed space. A channel 353 allows air displaced by the moveable member to exit.

Figure 22:
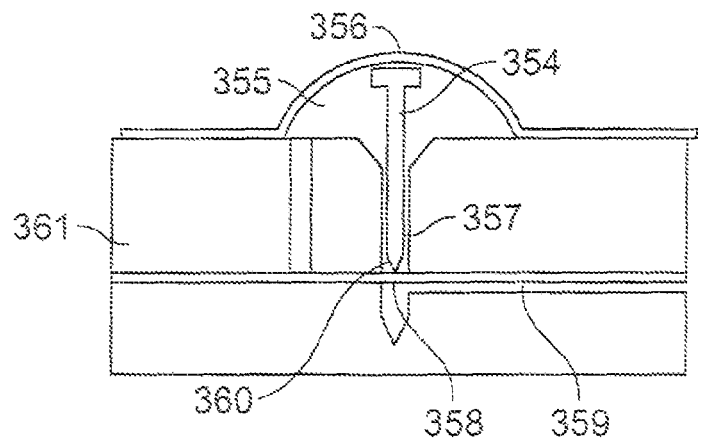
FIG. 22 illustrates a reservoir with actuation mechanism.

While reservoirs have been described as having a piercing member that can be secured with respect to some portion of the reservoir, other configurations are possible. For example, referring to FIG. 22, a reservoir includes an actuation mechanism 354 (e.g., a piercing member such as a needle-like piercing member) that can be unsecured with respect to the reservoir. A sealed space 355 of the reservoir can be defined by an upper wall 356 and includes a channel 357 extending through a portion of a substrate 361 in which a microfluidic network can be defined. A lower wall 358 of the sealed space separates the sealed space from a channel 359 of the microfluidic network. The piercing member occupies the channel 357 of the sealed space so that the piercing tip 360 of the piercing member rests against the lower wall 358. Depressing the upper wall 356 of the reservoir drives the piercing member 354 through the lower wall and forces liquid within the sealed space into the microfluidic network.

Figure 23A:
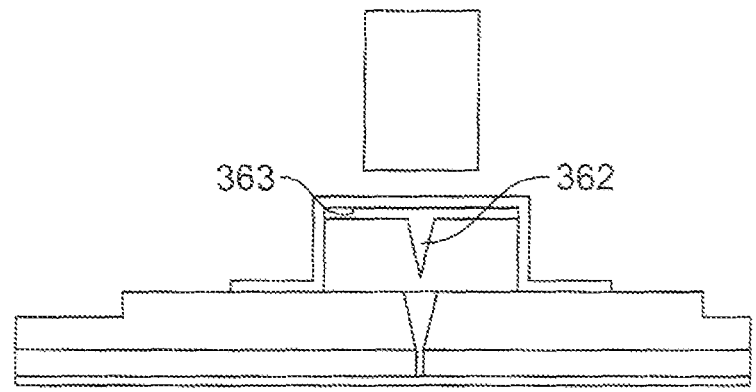
FIGS. 23A-23B illustrate a reservoir with actuation mechanism.
Figure 23B:
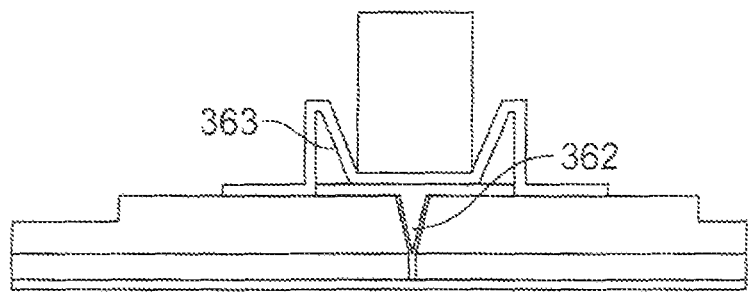

As another example, FIGS. 23A and 23B illustrate a reservoir including an actuation mechanism (e.g., a piercing member) that can initially be secured to an interior of an upper wall of the reservoir but separates at least partially from the upper wall upon actuation of the reservoir.

Figure 24A:
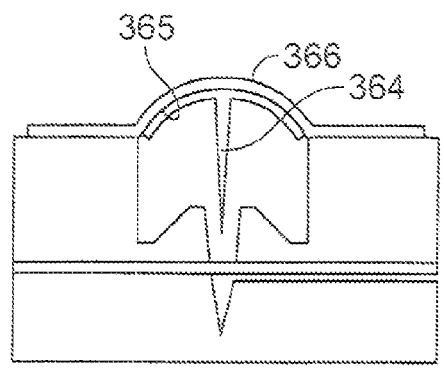
FIGS. 24A-24B illustrate a reservoir with actuation mechanism.
Figure 24B:
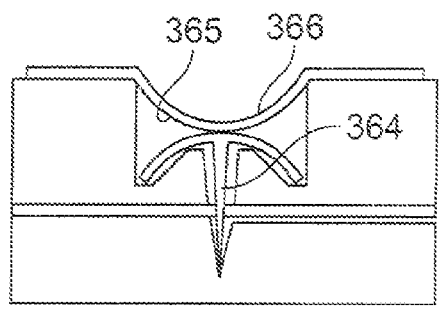

As yet another example, FIGS. 24A and 24B illustrate a reservoir including a piercing member 364 that can initially be secured to an interior 365 of an upper wall 366 of the reservoir but substantially separates (e.g., completely separates) from the upper wall upon actuation of the reservoir.

Figure 25:
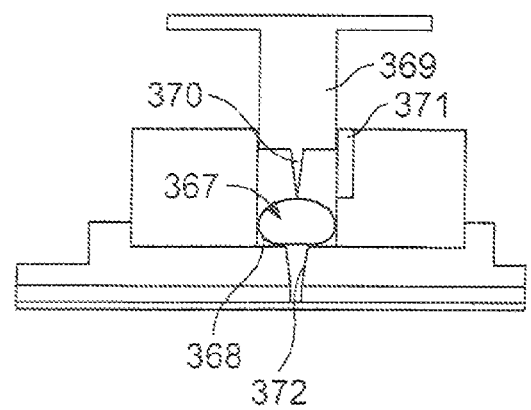
FIG. 25 illustrates a reservoir with actuation mechanism.

While reservoirs have been described as having an enclosed space that can be fixed or otherwise integral with a portion of the reservoir, other configurations are possible. For example, referring to FIG. 25, a reservoir includes a capsule-like enclosed space 367 defined by an outer wall 368. The outer wall can generally be formed of a material having a low vapor transmission rate. Reservoir also includes an actuation mechanism having a moveable member 369 with a piercing member 370 that pierces the enclosed space to release liquid therein. The liquid passes along a channel 372 leading to a microfluidic network. A channel 371 allows gas (e.g., air) otherwise trapped by the movable member to exit.

Figure 26:
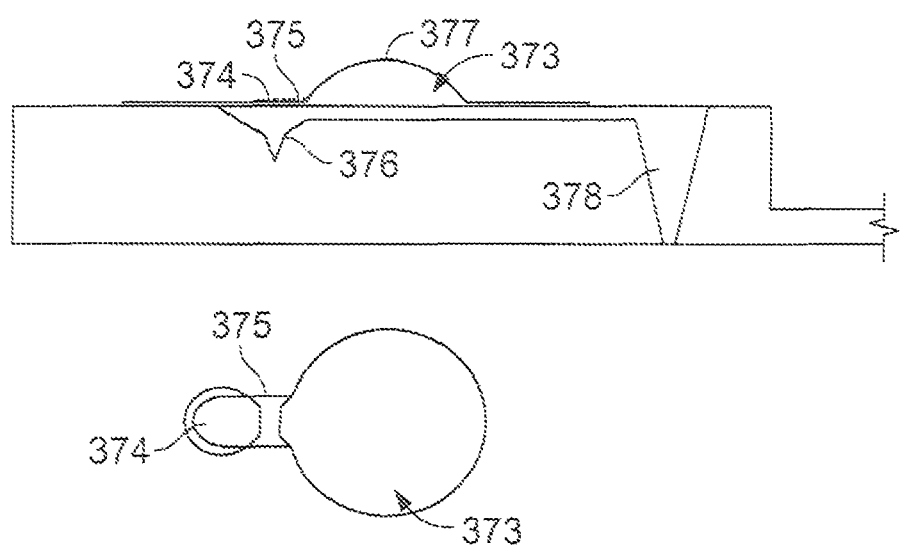
FIG. 26 illustrates a reservoir with actuation mechanism.

While reservoirs have been described as generally overlying an inlet to a microfluidic network, other configurations are possible. For example, referring to FIG. 26, a reservoir includes an enclosed space 373 in which liquid can be stored and a connecting portion 374 connected to an inlet 376 of a microfluidic network. The enclosed space 373 and connecting portion 374 can be separated by a rupturable seal 375 (e.g., a weak seal). In general, the rupturable seal 375 prevents liquid or vapor from exiting the enclosed space. However, upon the application of pressure to the liquid (e.g., by depressing a wall 377 of the enclosed space), the rupturable seal 375 ruptures allowing the liquid to pass through the weak seal to the connecting portion and into the microfluidic network 378.

Figure 27A:
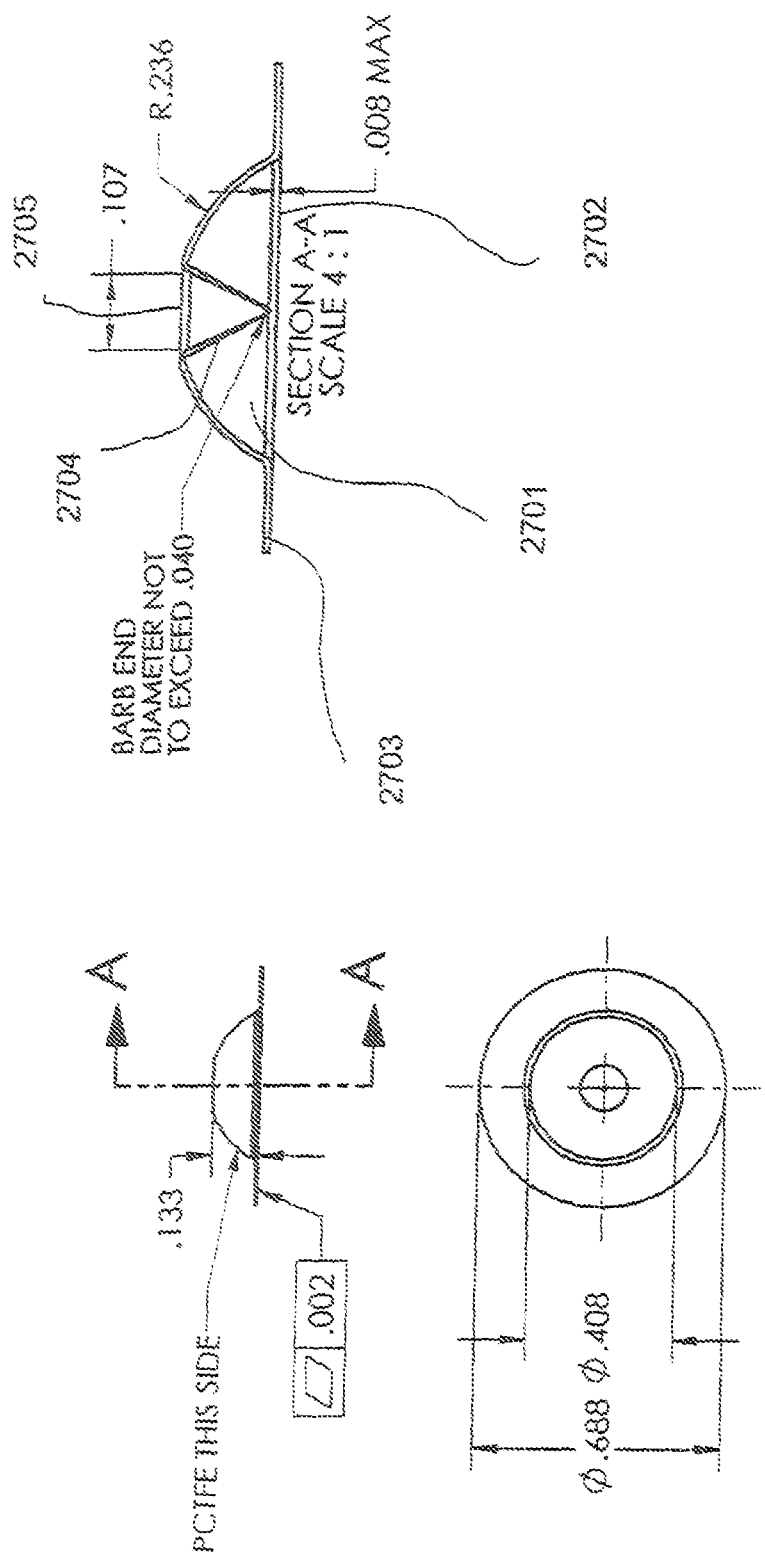
FIGS. 27A and 27B illustrate embodiments of a reagent pack with a piercing member.

A still further embodiment of a reservoir with a piercing member is shown in FIG. 27A, which shows a reservoir 2701 having an outer shell 2703 and a piercing element 2704 that can both be made of the same piece of material. Such a combined shell and piercing element can be formed from many processes known to one of ordinary skill in the art. Especially preferred processes can be vacuum thermo-forming and injection moulding. Piercing element 2704 can generally be conical in shape, with the apex adjacent to a membrane 2702; its apex preferably does not exceed 0.040". The piercing element will puncture membrane 2702 and release liquid from reservoir 2701 when the outer shell can be depressed. Representative dimensions are shown on FIG. 27A. The reservoir may be constructed so that the upper surface can be level, with a flat protective piece 2705 covering the base of the conical shape of piercing element 2704.

Figure 27B:
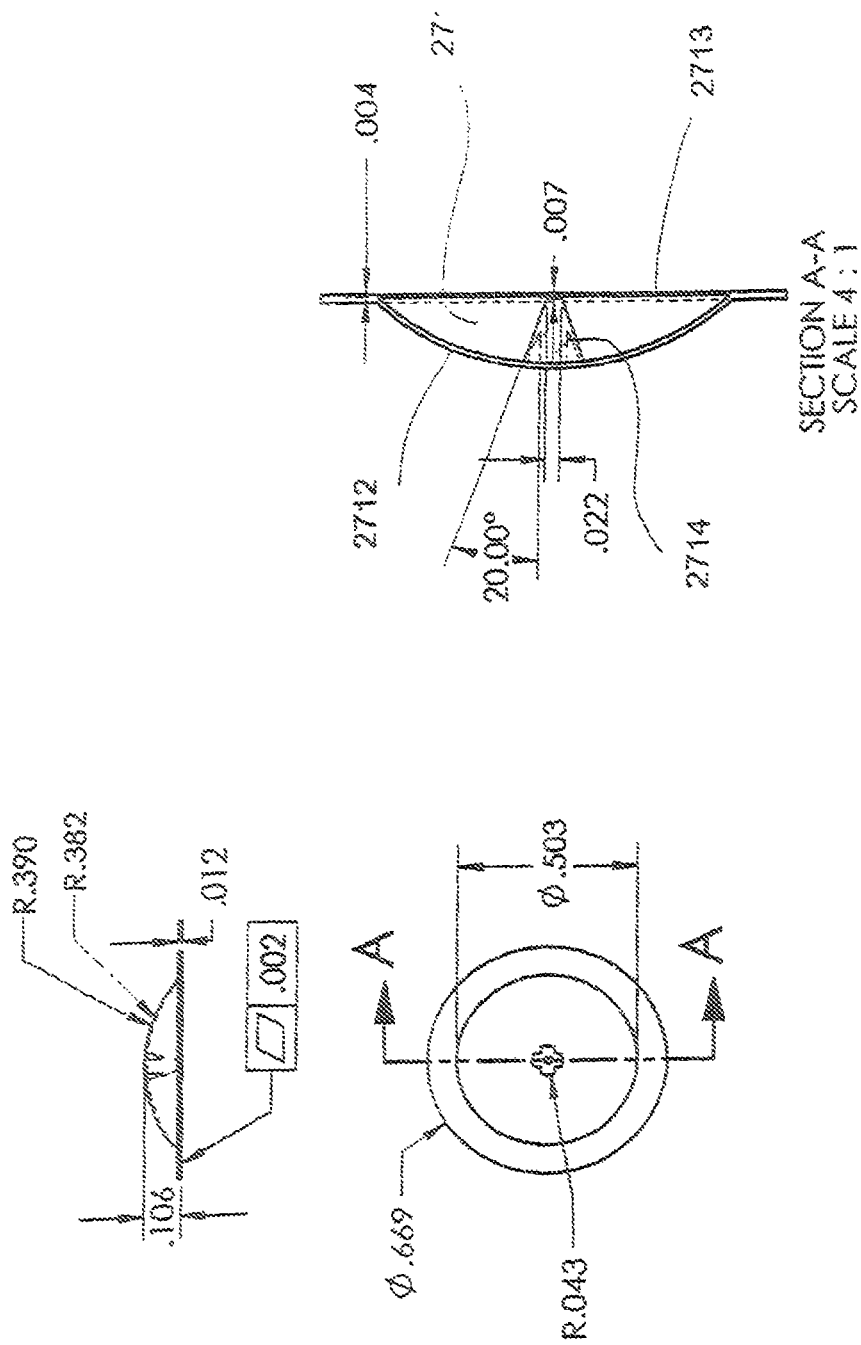

Yet another embodiment of a reservoir with a piercing member is shown in FIG. 27B, showing a reservoir 2711 having a single-piece outer shell 2712 and piercing element 2714. Such a combined shell and piercing element can be formed from many processes known to one of ordinary skill in the art. Especially preferred processes can be vacuum thermo-forming and injection moulding. Piercing element 2714 can be frustoconical in shape, with its narrower side adjacent to membrane 2713. Alternatively, piercing element 2714 can comprise several separate piercing elements, arranged within a conical space. Preferably there can be four such piercing elements where multiple elements can be present.

It is to be understood that the dimensions of the reservoir, piercing element, shell and moulding shown in FIGS. 27A and 27B as decimal quantities in inches are exemplary. In particular, the dimensions can be such that the shell does not collapse under its own weight and is typically not so as strong to prohibit depression of the piercing member when required during operation of the cartridge.

Furthermore, the materials of the various embodiments can also be chosen so that the cartridge has a shelf-life of about a year. By this it is meant that the thickness of the various materials can be such that they resist loss, through means such as diffusion, of 10% of the liquid volume contained therein over a desired shelf-life period.

Preferably the volume of the reservoir can be around 150 µl before a shell is depressed. Upon depression of a shell, the volume can preferably be deformed to around half its original volume.

It is to be noted that completely filling the blister pack with a liquid reagent—with no remaining space for an air bubble results in a blister that requires application of significantly greater force than is preferable. Accordingly, the blister(s) are typically filled to about 80-95% of their volume, thereby reserving about 5-20%, typically 10-15% of the volume for air. Thus, in one embodiment, a blister that has a total volume of 200 µl is filled with 170 µl of liquid.

Lysing Chamber

Figure 14B:
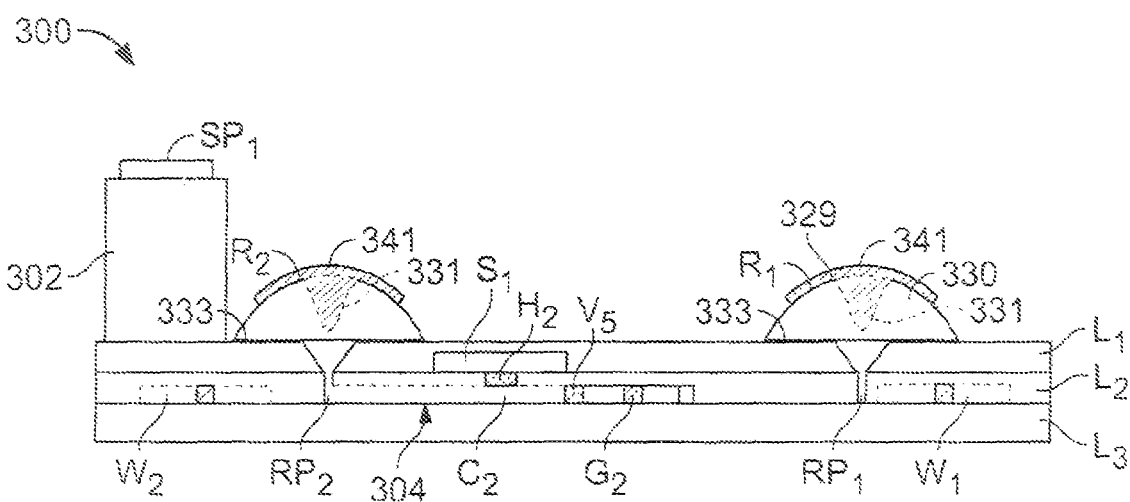
FIG. 14B is a side cross-sectional view of the microfluidic cartridge of FIGS. 14A and 14B.

Exemplary lysing chamber 302, as shown in FIGS. 14A and 14B, is shown in a tower configuration, protruding from a plane of microfluidic cartridge 300. Lysing chamber 302 can be divided into a primary lysing chamber 306 and a waste chamber 308. In one embodiment, primary and waste chambers 306, 308 are separated from one another so that material cannot pass from one of the chambers into the other chamber without passing through at least a portion of network 304. Primary lysing chamber 306 includes a sample input port SP1 for introducing sample to chamber 306, a sample output port SP2 connecting chamber 306 to network 304, and lyophilized reagent LP that interact with sample material within chamber 306 as described herein. Port SP2 is shown in FIG. 14A as being in the bottom of chamber 302. FIG. 15B shows a position of SP2 in relation to the rest of microfluidic network 304. Input port SP1 includes a one way valve that permits material (e.g., sample material and gas) to enter chamber 306 but limits (e.g., prevents) material from exiting chamber 308 by port SP1. Typically, port SP1 includes a fitting (e.g., a Luer fitting) configured to mate with a sample input device (e.g., a syringe) to form a gas-tight seal. Primary chamber 306 typically has a volume of about 5 milliliters or less (e.g., about 4 milliliters or less). Prior to use, primary chamber 306 can typically be filled with a gas (e.g., air).

Waste chamber 308 includes a waste portion W6 by which liquid can enter chamber 308 from network 304 and a vent 310 by which gas displaced by liquid entering chamber 308 can exit.

Lysing Reagent Particles

Lyophilized reagent particles LP of lysing chamber 302 include one or more compounds (e.g., reagents) configured to release polynucleotides from cells (e.g., by lysing the cells). For example, particles LP can include one or more enzymes configured to reduce (e.g., denature) proteins (e.g., proteinases, proteases (e.g., pronase), trypsin, proteinase K, phage lytic enzymes (e.g., PlyGBS)), lysozymes (e.g., a modified lysozyme such as ReadyLyse), cell specific enzymes (e.g., mutanolysin for lysing group B *streptococci*)).

In some embodiments, particles LP alternatively or additionally include components for retaining polynucleotides as compared to inhibitors. For example, particles LP can include multiple particles 218 surface modified with ligands as described above for processing chamber of cartridge 200. Particles LP can include enzymes that reduce polynucleotides that might compete with a polynucleotide to be determined for binding sites on the surface modified particles. For example, to reduce RNA that might compete with DNA to be determined, particles LP may include an enzyme such as an RNAase (e.g., RNAseA ISC BioExpress (Amresco)).

In an exemplary embodiment, particles LP include a cryoprotectant, particles modified with ligands configured to retain polynucleotides as compared to inhibitors, and one or more enzymes.

Typically, particles LP have an average volume of about 35 microliters or less (e.g., about 27.5 microliters or less, about 25 microliters or less, about 20 microliters or less). In some embodiments, the particles LP have an average diameter of about 8 mm or less (e.g., about 5 mm or less, about 4 mm or less) In an exemplary embodiment the lyophilized particle(s) have an average volume of about 20 microliters and an average diameter of about 3.5 mm.

Particles LP can be prepared as desired. Typically, the particles can be prepared using a cryoprotectant and chilled hydrophobic surface as described hereinabove for other reagent particles. For example, a solution for preparing particles LP can be prepared by combining a cryoprotectant (e.g., 6 grams of trehalose), a plurality of particles modified with ligands (e.g., about 2 milliliters of a suspension of carboxylate modified particles with poly-D-lysine ligands), a protease (e.g., 400 milligrams of pronase), an RNAase (e.g., 30 milligrams of RNAseA (activity of 120 U per milligram), an enzyme that digests peptidoglycan (e.g., ReadyLyse (e.g., 160 microliters of a 30,000 U per microliter solution of ReadyLyse)), a cell specific enzyme (e.g., mutanolysin (e.g., 200 microliters of a 50 U per microliter solution of mutanolysin), and a solvent (e.g., water) to make about 20 milliliters. About 1,000 aliquots of about 20 microliters each of this solution can be frozen and desolvated as described above to make 1,000 pellets. When reconstituted, the pellets can typically be used to make a total of about 200 milliliters of solution.

Exemplary Operation of Microfluidic Cartridge

In use, various components of cartridge 300 can be operated as follows. Valves Vi and Vi' of network 304 can be configured in the open state. Gates Gi and mixing gates MGi of network 304 can be configured in the closed state. Reagent ports R1-R4 can be depressed, e.g., by application of mechanical force, to introduce liquid reagents into network 304, as described hereinabove. A sample can be introduced to lysing chamber 302 via port SP1 and combined with lyophilized particles LP within primary lysing chamber 306. Typically, the sample includes a combination of particles (e.g., cells) and a buffer solution. For example, an exemplary sample includes about 2 parts whole blood to 3 about parts buffer solution (e.g., a solution of 20 mM Tris at pH 8.0, 1 mM EDTA, and 1% SDS). Another exemplary sample includes group B streptococci and a buffer solution (e.g., a solution of 20 mM Tris at pH 8.0, 1 mM EDTA, and 1% Triton X-100).

In general, the volume of sample introduced can be smaller than the total volume of primary lysing chamber 306. For example, the volume of sample may be about 50% or less (e.g., about 35% or less, about 30% or less) of the total volume of chamber 306. A typical sample has a volume of about 3 milliliters or less (e.g., about 1.5 milliliters or less). A volume of gas (e.g., air) can generally be introduced to primary chamber 306 along with the sample. Typically, the volume of gas introduced can be about 50% or less (e.g., about 35% or less, about 30% or less) of the total volume of chamber 306. The volume of sample and gas combine to pressurize the gas already present within chamber 306. Valve 307 of port SP1 prevents gas from exiting chamber 306. Because gates G3, G4, G8, and G10 can be in the closed state, the pressurized sample can be prevented from entering network 304 via port SP2.

The sample dissolves particles LP in chamber 306. Reconstituted lysing reagents (e.g., ReadyLyse, mutanolysin) begin to lyse cells of the sample releasing polynucleotides. Other reagents (e.g., protease enzymes such as pronase) begin to reduce or denature inhibitors (e.g., proteins) within the sample. Polynucleotides from the sample begin to associate with (e.g., bind to) ligands of particles 218 released from particles LP. Typically, the sample within chamber 306 can be heated (e.g., to at least about 50° C., to at least about 60° C.) for a period of time (e.g., for about 15 minutes or less, about 10 minutes or less, about 7 minutes or less) while lysing occurs. In some embodiments, optical energy can be used at least in part to heat contents of lysing chamber 306. For example, the operating system used to operate cartridge 300 can include a light source 399 (e.g., a lamp primarily emitting light in the infrared) disposed in thermal and/or optical contact with chamber 306. Such a light source can be that shown in connection with heater module 2020, FIG. 7, reference numeral 2046. Chamber 306 includes a temperature sensor TS used to monitor the temperature of the sample within chamber 306. The lamp output can be increased or decreased based on the temperature determined with sensor TS.

Continuing with the operation of cartridge 300, G2 can be actuated (e.g., opened) providing a path between port SP2 of primary lysing chamber 306 and port W6 of lysing waste chamber 308. The path extends along channel C9, channel C8, through processing region B1, and channel C11. Pressure within chamber 306 drives the lysed sample material (containing lysate, polynucleotides bound to particles 218, and other sample components) along the pathway. Particles 218 (with polynucleotides) can be retained within processing region B1 (e.g., by a filter) while the liquid and other components of the sample flow into waste chamber 308. After a period of time (e.g., between about 2 and about 5 minutes), the pressure in lysing chamber 306 can be vented by opening gate G1 to create a second pathway between ports SP2 and W6. Double valves V1' and V8' can be closed to isolate lysing chamber 302 from network 304.

Operation of cartridge 300 continues by actuating pump P1 and opening gates G2, G3 and G9. Pump P1 drives wash liquid in channel C2 downstream of junction J1 through processing region B1 and into waste chamber W5. The wash liquid removes inhibitors and other compounds not retained by particles 218 from processing region B1. When the trailing edge of the wash liquid (e.g., the upstream interface) passes hydrophobic vent H14, the pressure from actuator P1 vents from network 304, stopping further motion of the liquid. Double valves V2' and V9' can be closed.

Operation continues by actuating pump P2 and opening gates G6, G4 and G8 to move release liquid from reagent reservoir R1 into processing region B1 and into contact with particles 218. Air vent AV1 vents pressure ahead of the moving release liquid. Hydrophobic vent H6 vents pressure behind the trailing edge of the release liquid stopping further motion of the release liquid. Double valves V6' and V10' can be closed.

Operation continues by heating processing region B1 (e.g., by heating particles 218) to release the polynucleotides from particles 218. The particles can be heated as described above for cartridge 200. Typically, the release liquid includes about 15 mM hydroxide (e.g., NaOH solution) and the particles can be heated to about 70° C. for about 2 minutes to release the polynucleotides from the particles 218.

Operation continues by actuating pump P3 and opening gates G5 and G10 to move release liquid from process region B1 downstream. Air vent AV2 vents gas pressure downstream of the release liquid allowing the liquid to move into channel C16. Hydrophobic vent H8 vents pressure from upstream of the release liquid stopping further movement. Double valve V11' and valve V14 can be closed.

Figure 19A:
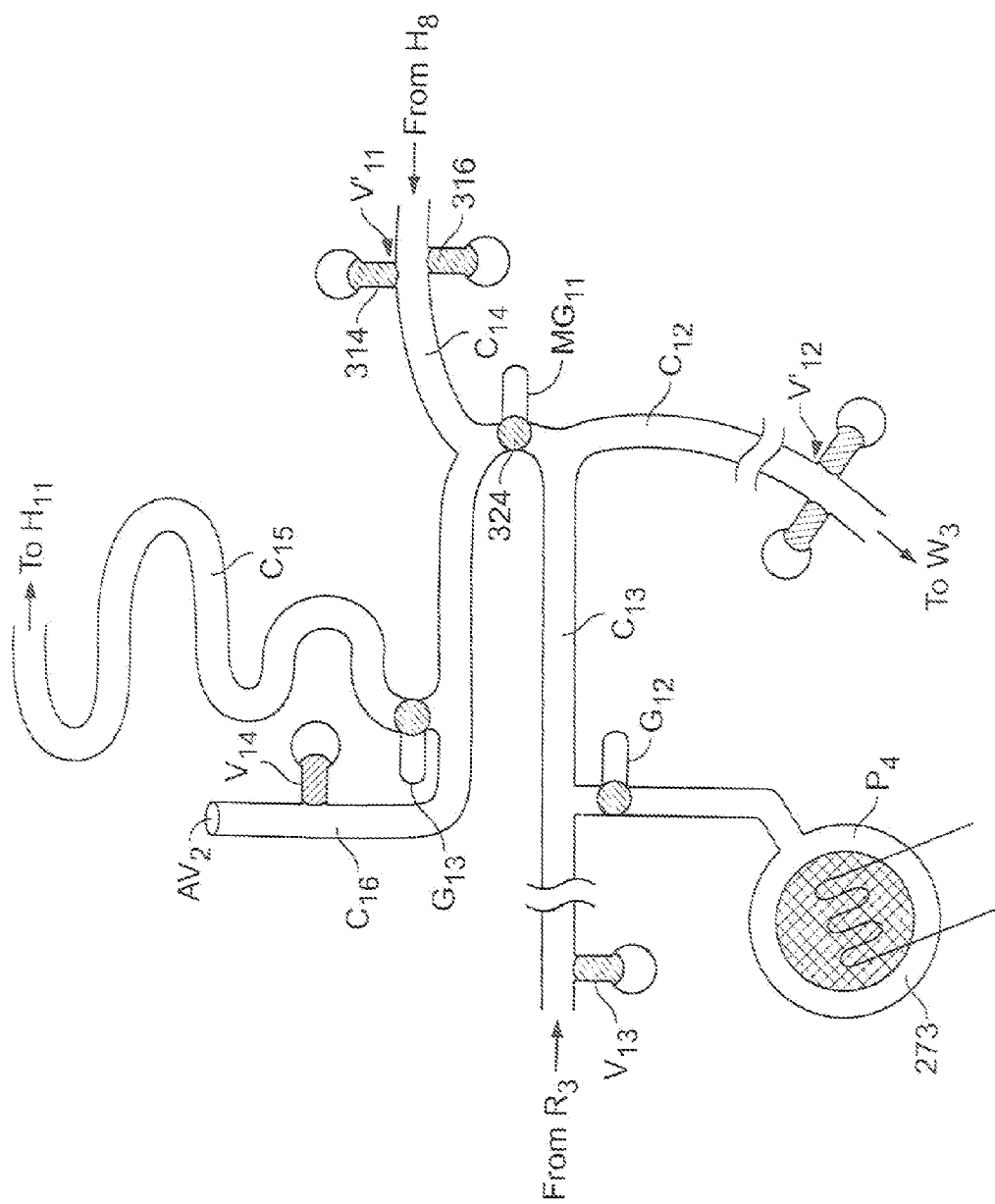
FIG. 19A-19D illustrate a mixing gate of the microfluidic network of FIGS. 6A and 6B and adjacent regions of the network.
Figure 19B:
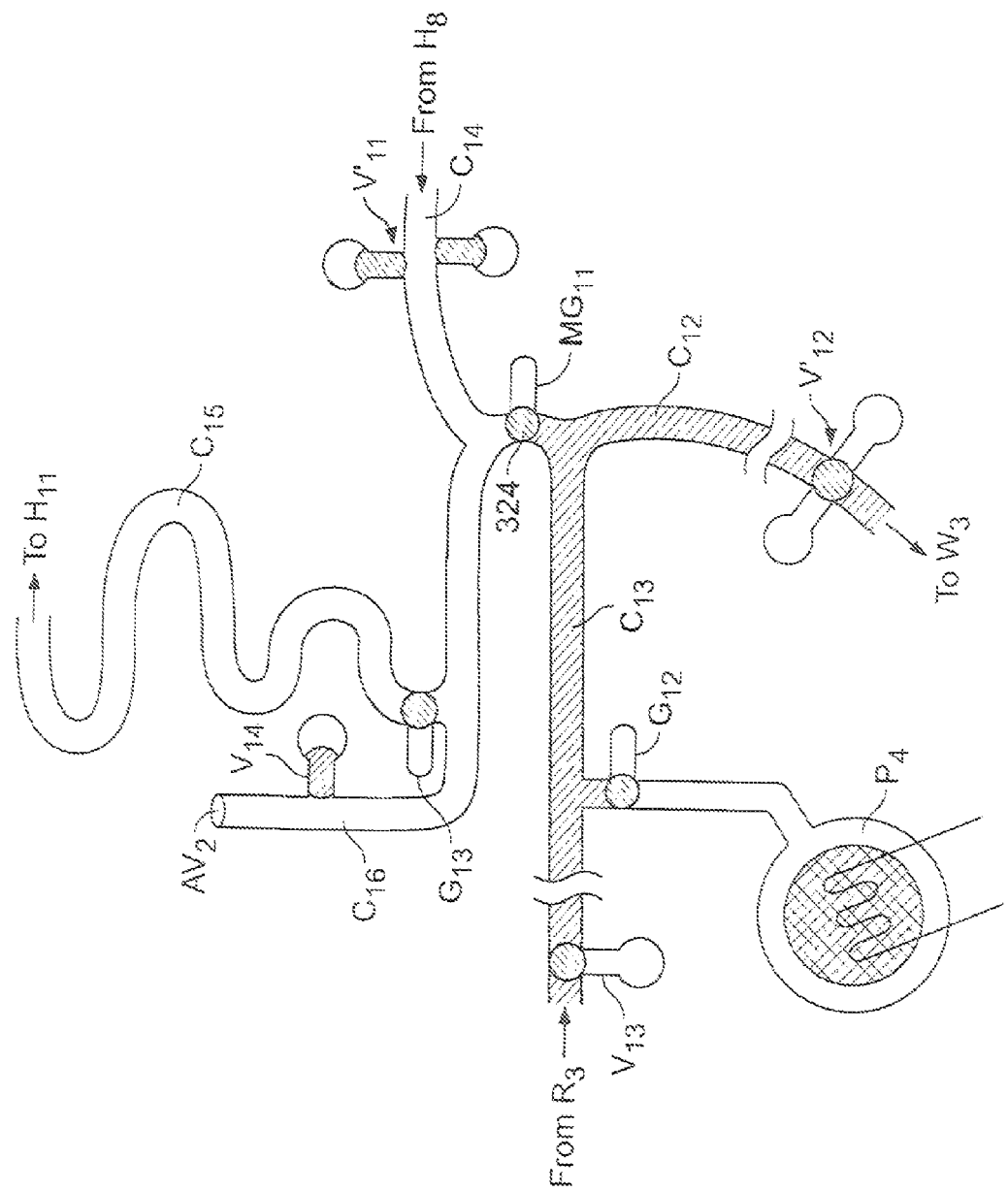

Referring to FIGS. 19A-19D, mixing gate MG11 can be used to mix a portion of release liquid including polynucleotides released from particles 218 and neutralization buffer from reagent reservoir R3. FIG. 19A shows the mixing gate MG11 region prior to depressing reagent reservoir R3 to introduce the neutralization buffer into network 304. FIG. 19B shows the mixing gate MG11 region, after the neutralization buffer has been introduced into channels C13 and C12. Double valve V13' can be closed to isolate network 304 from reagent reservoir R3. Double valve V12' can be closed to isolate network 304 from waste chamber W3. The neutralization buffer contacts one side of a mass 324 of TRS of gate MG11.

Figure 19C:
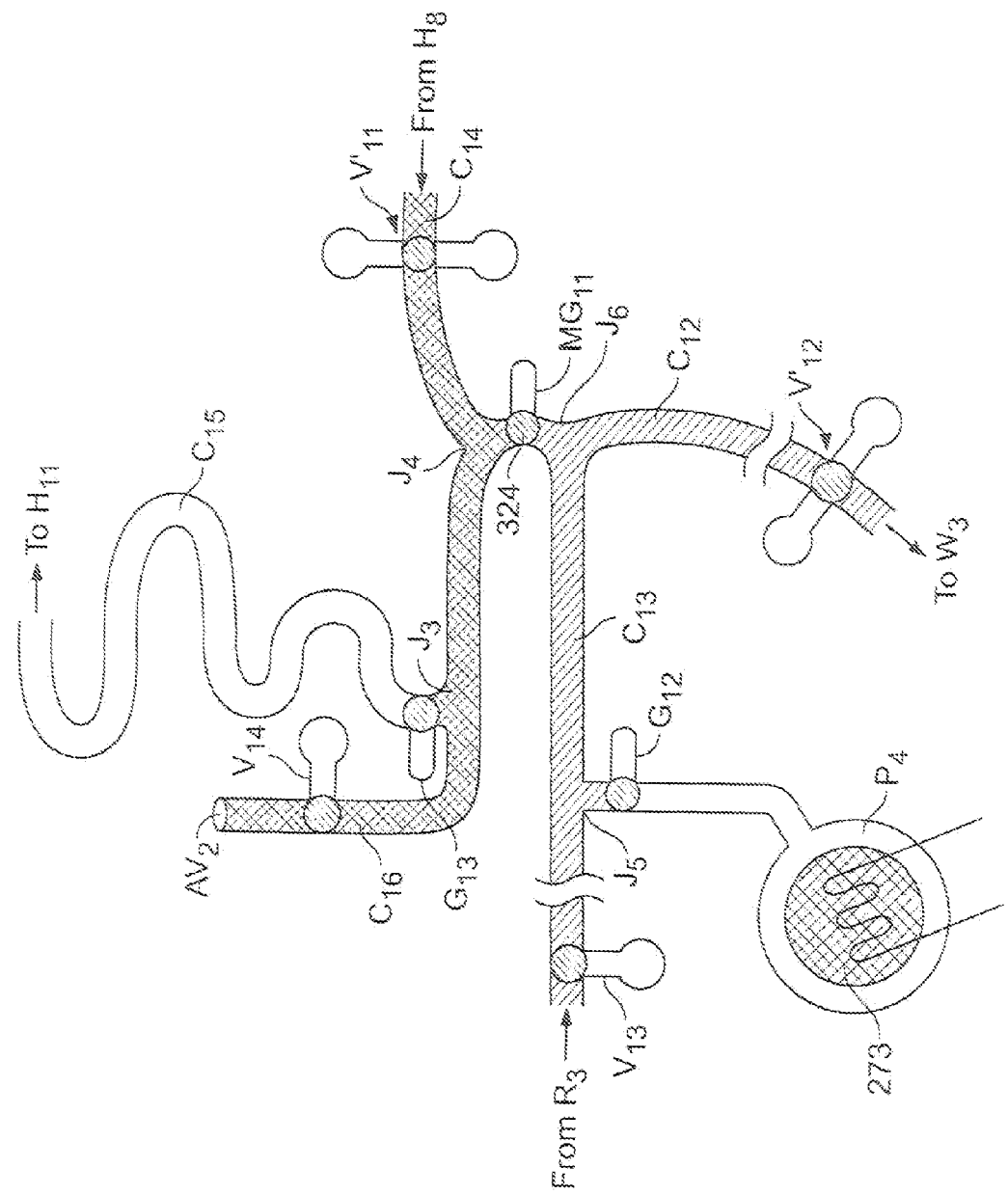

FIG. 19C shows the mixing gate MG11 region after release liquid has been moved into channel C16. The dimensions of microfluidic network 304 (e.g., the channel dimensions and the position of hydrophobic vent H8) can be configured so that the portion of release liquid positioned between junctions J3 and J4 of channels C16 and C14 corresponds approximately to the volume of liquid in contact with particles 218 during the release step. In some embodiments, the volume of liquid positioned between junctions J3 and J4 can be less than about 5 microliters (e.g., about 4 microliters or less, about 2.5 microliters or less). In an exemplary embodiment, the volume of release liquid between junctions J3 and J4 can be about 1.75 microliters. Typically, the liquid between junctions J3 and J4 includes at least about 50% of polynucleotides (at least about 75%, at least about 85%, at least about 90%) of the polynucleotides present in the sample that entered processing region B1. Valve V14 can be closed to isolate network 304 from air vent AV2.

Figure 19D:
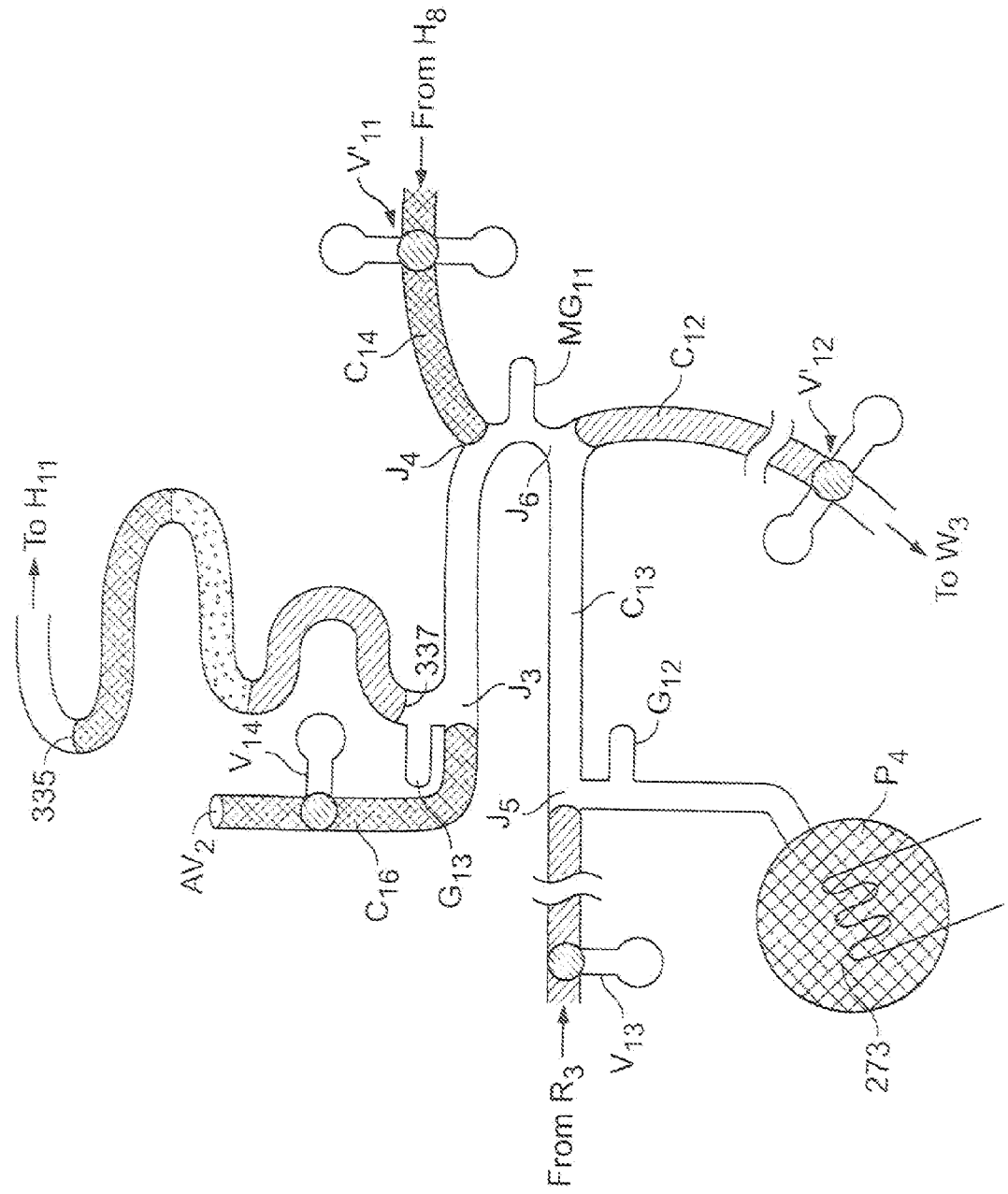

Before actuating mixing gate MG11, the release liquid at junction J4 and the neutralization buffer at a junction J6 between channels C13 and C12 can be separated by mass 324 of TRS (e.g., the liquids are not typically spaced apart by a volume of gas). To combine the release liquid and neutralization buffer, pump P4 and gates G12, G13, and MG11 can be actuated. Pump P4 drives the volume of neutralization liquid between junctions J5 and J6 and the volume of release liquid between junctions J4 and J3 into mixing channel C15 (FIG. 19D). Mass 324 of TRS typically disperses and/or melts allowing the two liquids to combine. The combined liquids include a downstream interface 335 (formed by junction J3) and an upstream interface (formed by junction J5). The presence of these interfaces allows more efficient mixing (e.g., recirculation of the combined liquid) than if the interfaces were not present. As seen in FIG. 19D, mixing typically begins near the interface between the two liquids. Mixing channel C15 can typically be at least about as long (e.g., at least about twice as long) as a total length of the combined liquids within the channel.

The volume of neutralization buffer combined with the release liquid can be determined by the channel dimensions between junction J5 and J6. Typically, the volume of combined neutralization liquid can be about the same as the volume of combined release liquid. In some embodiments, the volume of liquid positioned between junctions J5 and J6 can be less than about 5 microliters (e.g., about 4 microliters or less, about 2.5 microliters or less). In an exemplary embodiment the volume of release liquid between junctions J5 and J6 can be about 2.25 microliters (e.g., the total volume of release liquid and neutralization buffer can be about 4 microliters).

Returning to FIGS. 15A, 15B, the combined release liquid and neutralization buffer move along mixing channel C15 and into channel C32 (vented downstream by air vent AV8). Motion continues until the upstream interface of the combined liquids passes hydrophobic vent H11, which vents pressure from actuator P4 stopping further motion of the combined liquids.

Continuing with operation of cartridge 300, actuator P5 and gates G14, G15 and G17 can be actuated to dissolve the lyophilized PCR particle present in second processing region B2 in water from reagent reservoir R4. Hydrophobic vent H10 vents pressure from actuator P5 upstream of the water stopping further motion. Dissolution of a PCR-reagent pellet typically occurs in about 2 minutes or less (e.g., in about 1 minute or less). Valve V17 can be closed.

Continuing with operation of cartridge 300, actuator P6 and gate G16 can be actuated to drive the dissolved compounds of the lyophilized particle from processing region B2 into channel C31, where the dissolved reagents mix to form a homogenous dissolved lyophilized particle solution. Actuator P6 moves the solution into channels C35 and C33 (vented downstream by air vent AV5). Hydrophobic vent H9 vents pressure generated by actuator P6 upstream of the solution stopping further motion. Valves V18, V19, V20', and V22' can be closed.

Continuing with operation of cartridge 300, actuator P7 and gates G18, MG20 and G22 can be actuated to combine (e.g., mix) a portion of neutralized release liquid in channel 32 between gate MG20 and gate G22 and a portion of the dissolved lyophilized particle solution in channel C35 between gate G18 and MG20. The combined liquids travel along a mixing channel C37 and into detection region D2. An air vent AV3 vents gas pressure downstream of the combined liquids. When the upstream interface of the combined liquids passes hydrophobic vent H13, the pressure from actuator P7 can be vented and the combined liquids can be positioned within detection region D2.

Actuator P8 and gates MG2, G23, and G19 can be actuated to combine a portion of water from reagent reservoir R4 between MG2 and gate G23 with a second portion of the dissolved lyophilized particle solution in channel C33 between gate G19 and MG2. The combined liquids travel along a mixing channel C41 and into detection region D1. An air vent AV4 vents gas pressure downstream of the combined liquids. When the upstream interface of the combined liquids passes hydrophobic vent H12, the pressure from actuator P8 can be vented and the combined liquids can be positioned within detection region D1.

Continuing with operation of cartridge 300, double valves V26' and V27' can be closed to isolate detection region D1 from network 304 and double valves V24' and V25' can be closed to isolate detection region D2 from network 304. The contents of each detection region (neutralized release liquid with sample polynucleotides in detection region D2 with PCR reagents from dissolved lyophilized particle solution and deionized water with PCR reagents from dissolved lyophilized particle solution in detection region D1) can be subjected to heating and cooling steps to amplify polynucleotides (if present in detection region D2). The double valves of each detection region prevent evaporation of the detection region contents during heating. The amplified polynucleotides can typically be detected using fluorescence detection. Thus, typically above one or both of detection regions D1, D2, is a window (as in, e.g., FIG. 9) that permits detection of fluorescence from a fluorescent substance in reaction mixture when a detector is situated above the window.

While cartridges for carrying out various stages of processing samples have been shown and described herein as having a generally planar configuration, other configurations can be used and are consistent with an integrated system as described herein. For example, a cartridge having a generally tube-like or vial-like configuration is described in U.S. patent application publication no. 2006-0166233, incorporated herein by reference.

EXAMPLES

The following Examples are illustrative and are not intended to be limiting.

Example 1

Apparatus for Polynucleotide Processing

This non-limiting example describes various exemplary embodiments of an apparatus, system, microfluidic cartridge, kit, methods, and computer program product, as shown in FIGS. 28-40.

Figure 28:
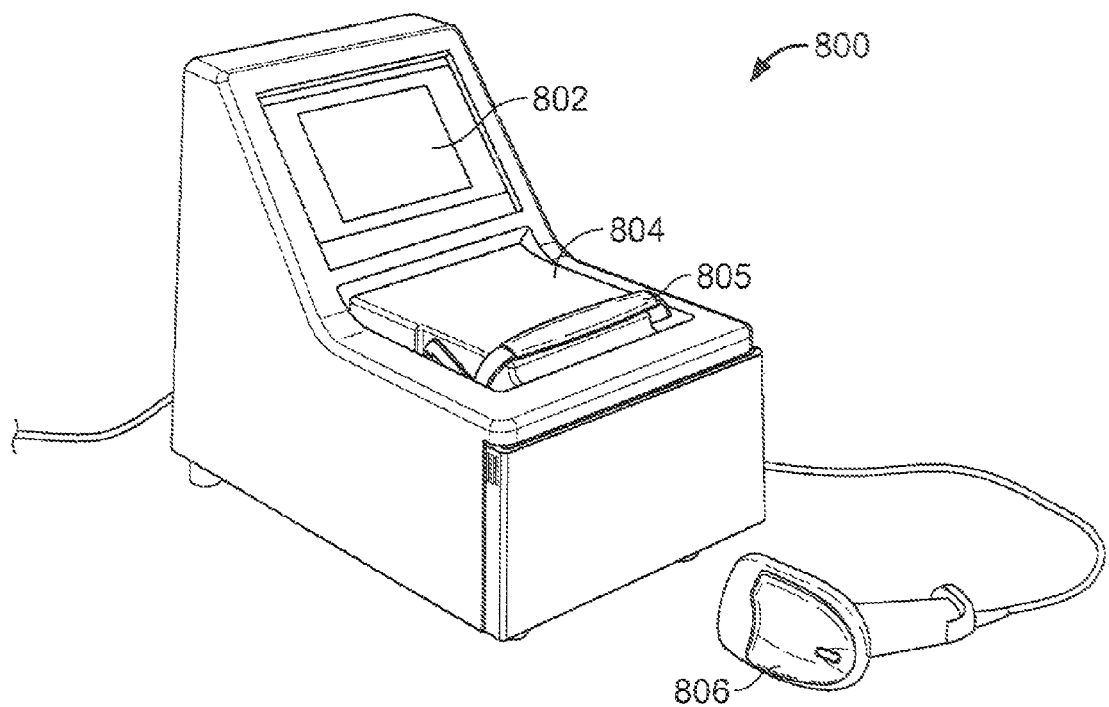
FIG. 28 depicts an apparatus that can operate as a small bench-top, real time polynucleotide analysis system.
Figure 36:
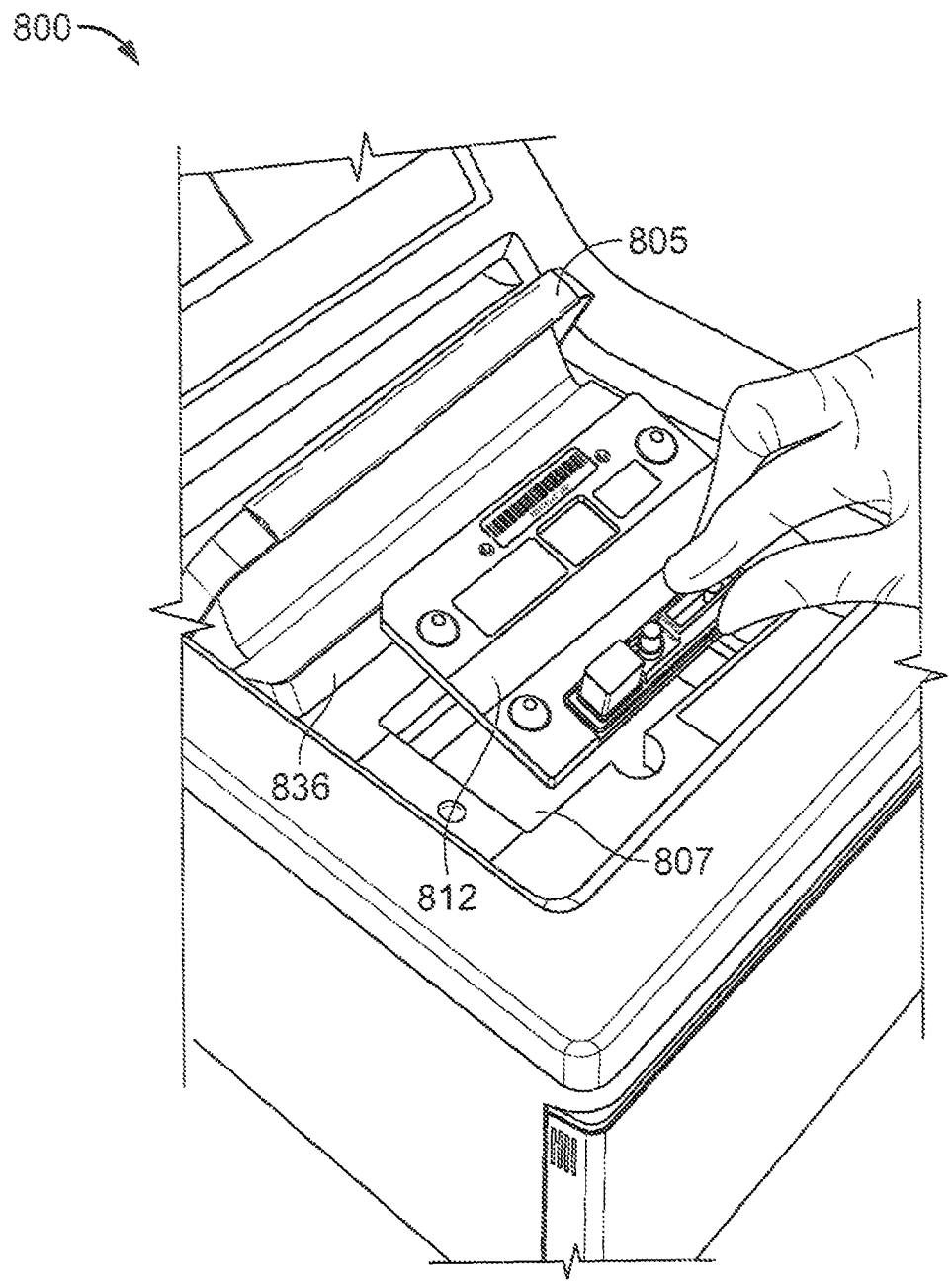
FIG. 36 depicts the placement of a microfluidic cartridge in a receiving bay of an apparatus.

For example, FIG. 28 is a diagram of an apparatus 800 that can operate as a small bench-top, real time, polynucleotide analysis system. Such a system can perform a variety of tests on polynucleotides, for example, testing samples from patients for signatures of one or more infectious diseases. The apparatus can function, for example, as a real time polynucleotide analysis system for use in the clinical diagnostic market to assist clinical personnel in testing and treating patients before they leave the medical environment. Apparatus 800 can include, for example, a housing having a display output 802, a lid 804 having a handle 805, and a bar code reader 806. Referring to FIGS. 28 and 36, apparatus 800 can also include a receiving bay 807, which can be covered by lid 804. In various embodiments, apparatus 800 can be portable, for example, apparatus 800 can weigh about 10 kg and can have dimensions of approximately 25 cm wide by 40 cm deep by 33 cm high.

Figure 29:
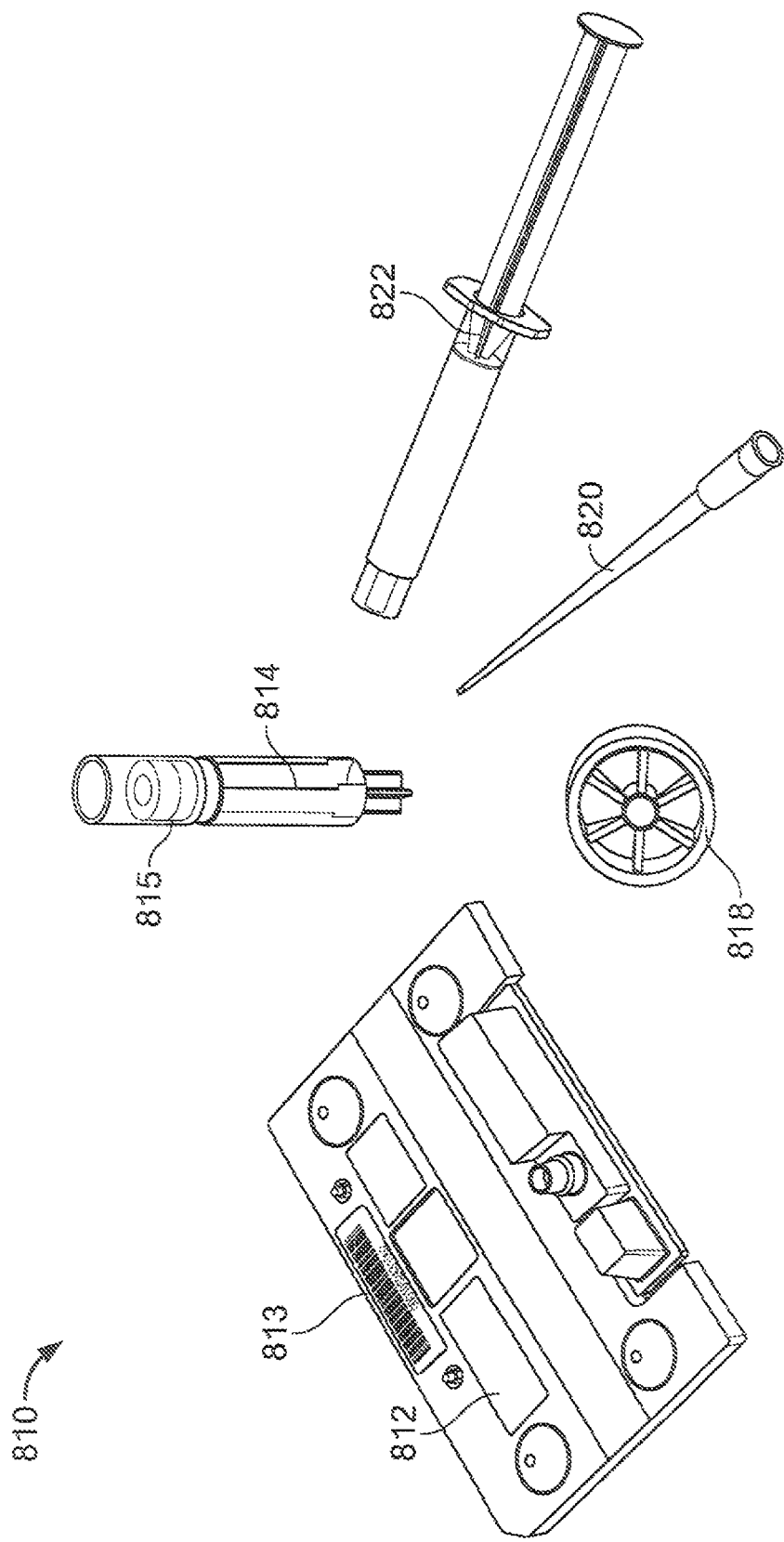
FIG. 29 depicts a sample kit that can be used with an apparatus.
Figure 30:
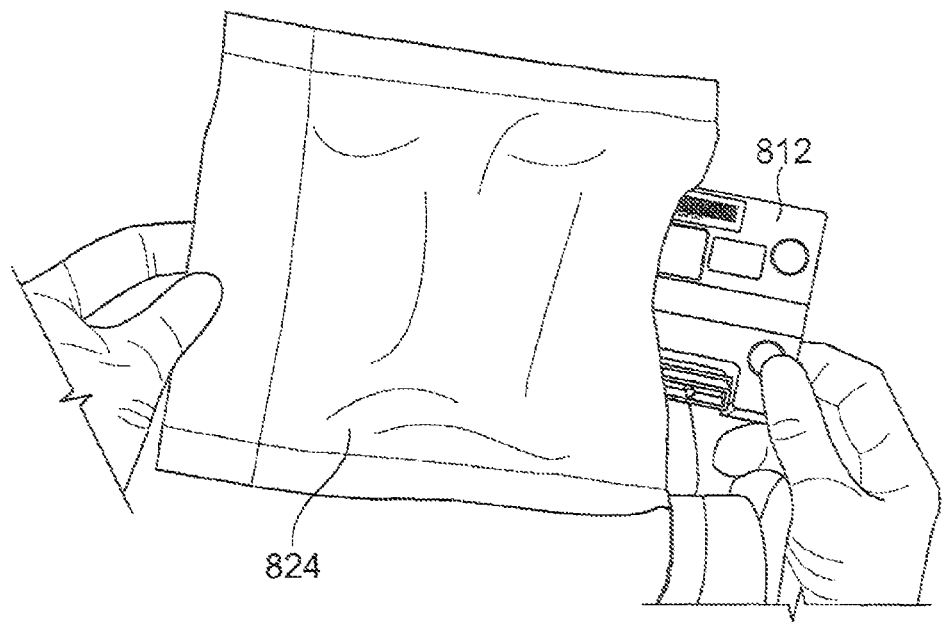
FIG. 30 depicts a pouch for components of a sample kit.

Apparatus 800 can be used with a sample kit 810, shown in FIG. 29. The sample kit 810 can include, for example, a microfluidic cartridge 812 with an optional label 813 (e.g., a barcode label), a sample container 814 with an optional label 815 (e.g., a barcode label), an optional filter 818, an optional pipette tip 820, and an optional syringe 822. Referring to FIG. 30, one or more components of the sample kit 810 (e.g., microfluidic cartridge 812) can be packaged, e.g., in a sealed pouch 824 which can optionally be hermetically sealed with an inert gas such as argon or nitrogen.

Figure 31:
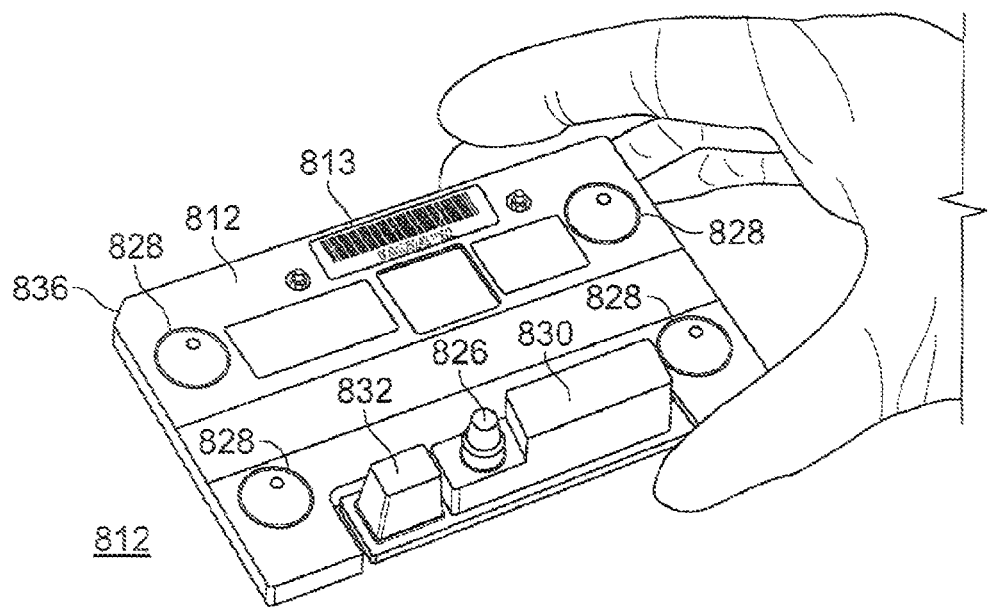
FIG. 31 depicts an exemplary microfluidic cartridge.

Microfluidic cartridge 812, as depicted in FIG. 31, can include a sample inlet 826, a plurality of self-pierceable reservoirs 828, a lysis reservoir 830, a waste reservoir 832, an optional label 813 (e.g., a bar code), and a registration member 836 (e.g., a beveled corner). Referring to FIGS. 31 and 36, registration member 836 can fit a complementary registration member feature 809 of receiving bay 807 in apparatus 800, which can be used to facilitate orientation of cartridge 812 when inserted in the apparatus 800. In some examples, microfluidic cartridge 812 can be designed to be slightly smaller (e.g., 50-300 microns, typically 200-300 microns) than well 807 in heater/sensor module 842 to facilitate placement and removal of microfluidic cartridge 812.

Figure 32:
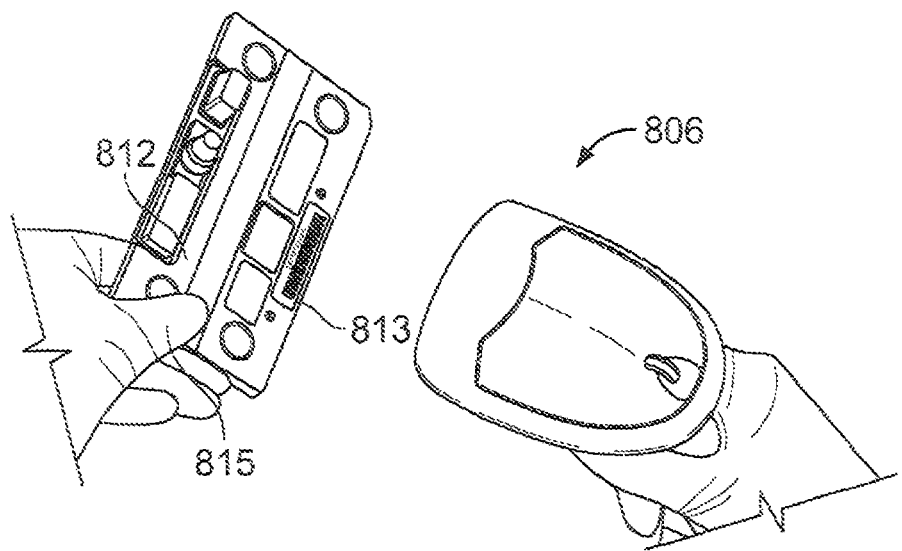
FIG. 32 depicts the use of a bar code reader to a read bar code on a microfluidic cartridge.
Figure 33:
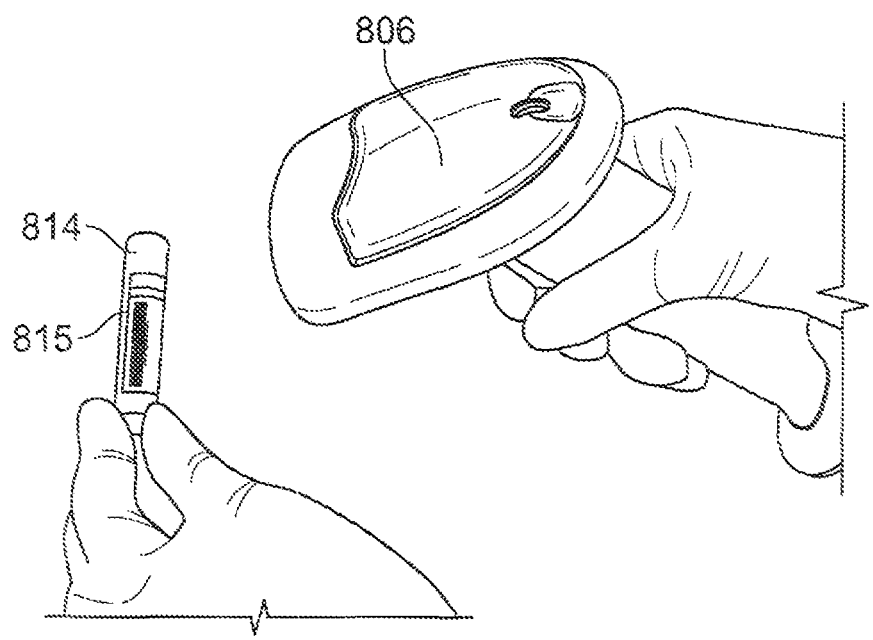
FIG. 33 depicts the use of a bar code reader a to read a bar code on a sample container.

Referring to FIGS. 32 & 33, the labels, e.g., bar codes 813 and 815, on the microfluidic cartridge 812 and/or sample container 814 can be recorded by apparatus 800, typically before performing a test, e.g., by entering a label code manually or by using a bar code reader 806.

Figure 34:
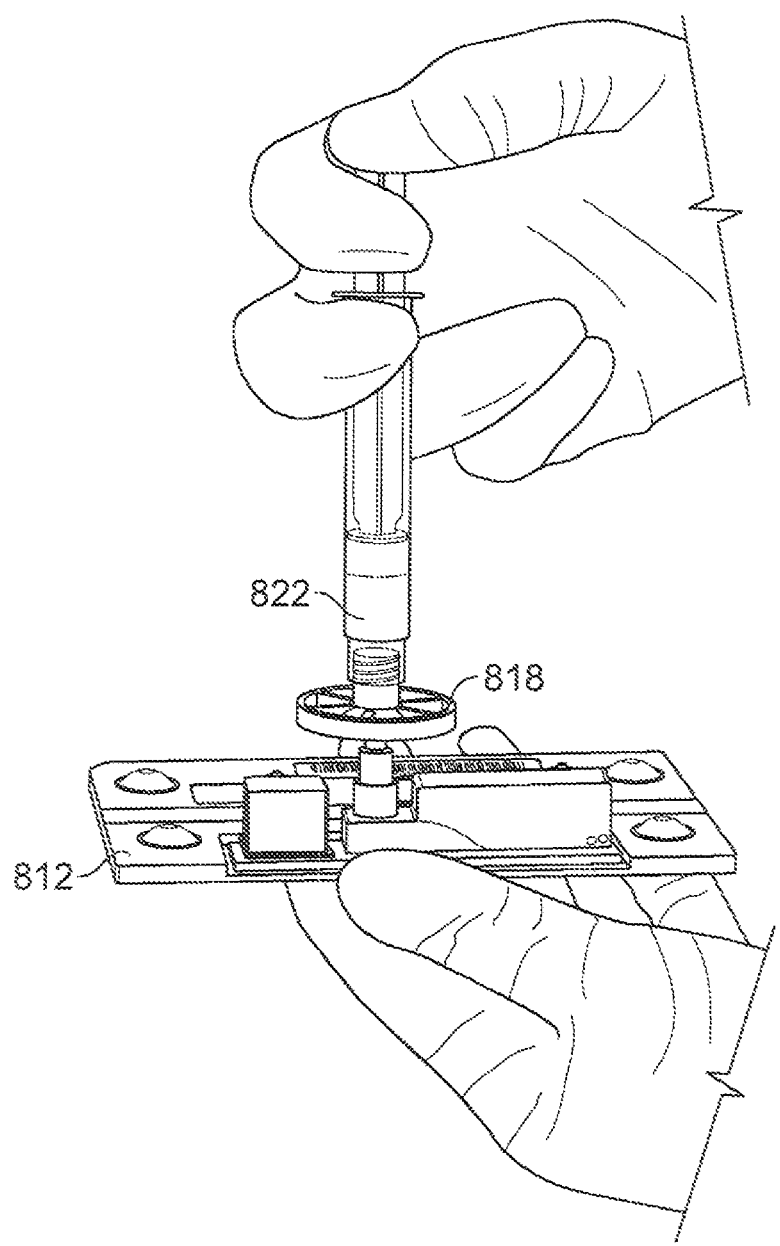
FIG. 34 depicts attachment of a filter to a lysis reservoir of a microfluidic cartridge via a sample inlet, whereby the contents of syringe may be injected into microfluidic cartridge through a filter.
Figure 35:
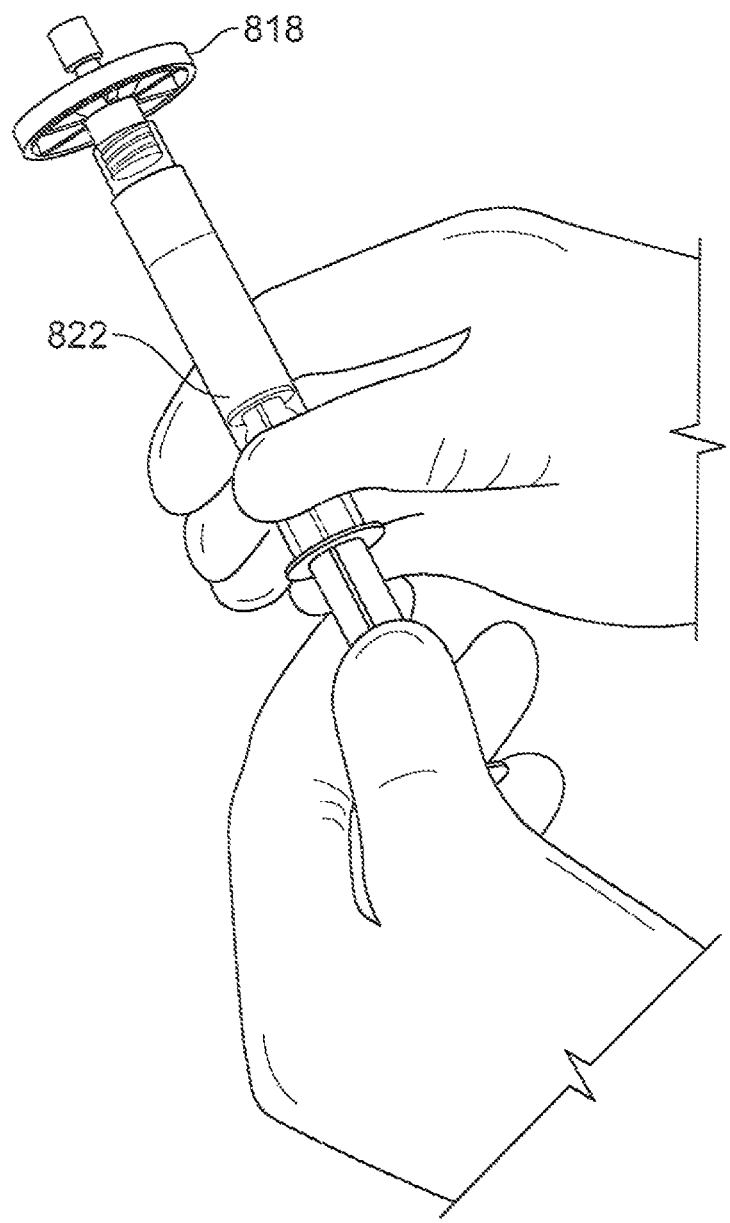
FIG. 35 depicts the addition of air to syringe in order to pressurize microfluidic cartridge.

In preparation for testing a sample, pipette tip 820 from kit 810 may be attached to the syringe 822, and a sample may be drawn from sample container 814 into syringe 822. Referring to FIG. 34, filter 818 can then be attached to lysis reservoir 830 of microfluidic cartridge 812 via sample inlet 826 (e.g., using a luer lock with a duckbill valve at sample inlet 826) and the contents (e.g., a sample/air mixture) of syringe 822 may be injected into microfluidic cartridge 812 through filter 818. Additional air (e.g., 1-3 mL) can be drawn into syringe 822 (as shown in FIG. 35) so that microfluidic cartridge 812 can be pressurized (e.g., 5-50 pounds per square inch (psi) with respect to ambient pressure, typically between 5-25 psi, more typically between 10-15 psi, with respect to ambient pressure). Microfluidic cartridge 812 can contain buffers, reagents, and the like, e.g., in lysis reservoir 830 in the form of liquids, solids, lyophilized reagent pellets, and the like. Microfluidic cartridge 812 can be agitated to mix the injected sample with the buffers, reagents, etc.

Referring to FIG. 35, microfluidic cartridge 812 can be pressurized using syringe 822 and filter 818 with added air. Microfluidic cartridge 812 can be placed in receiving bay 807 of apparatus 800, as shown in FIG. 36, and can be seated in a single orientation in receiving bay 807 of apparatus 800 due to the interaction between registration member 836 on microfluidic cartridge 812 and complementary registration member 809 in receiving bay 807.

Figure 37:
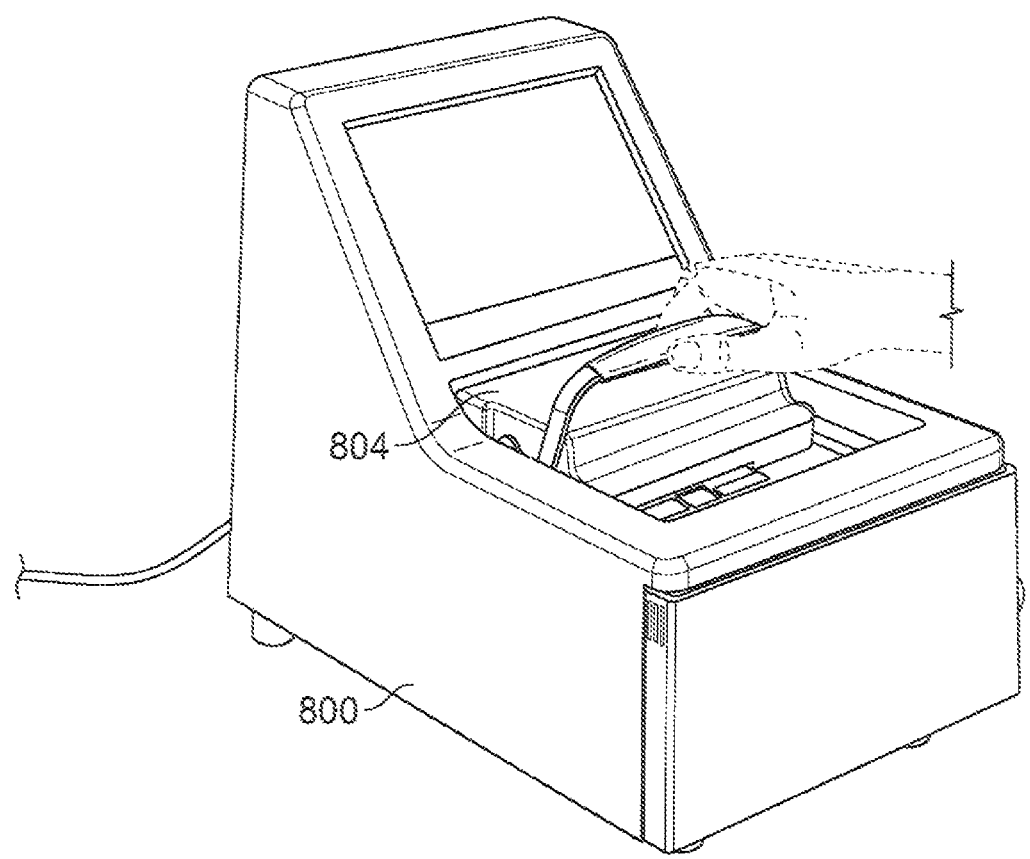
FIGS. 37 and 38 depict the closure of a lid of an apparatus.
Figure 38:
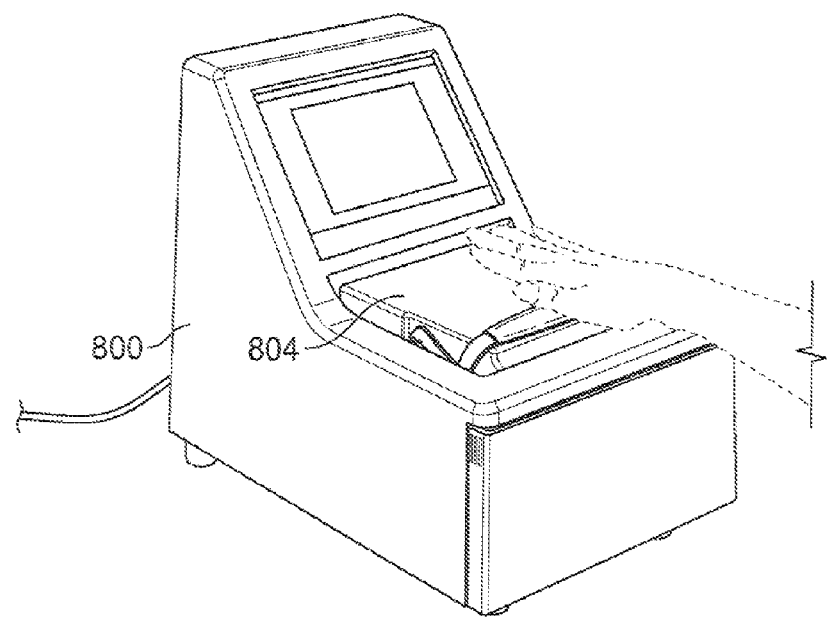
Figure 39:
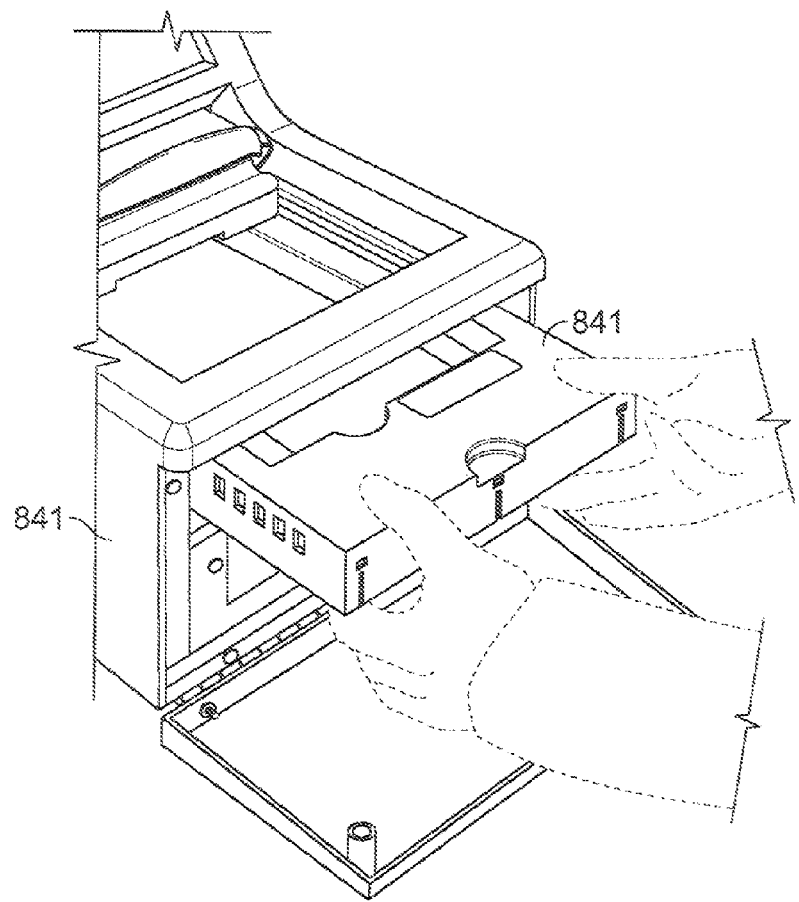
FIGS. 39 & 40 depict the removal of a heating/sensor module from an apparatus.
Figure 40:
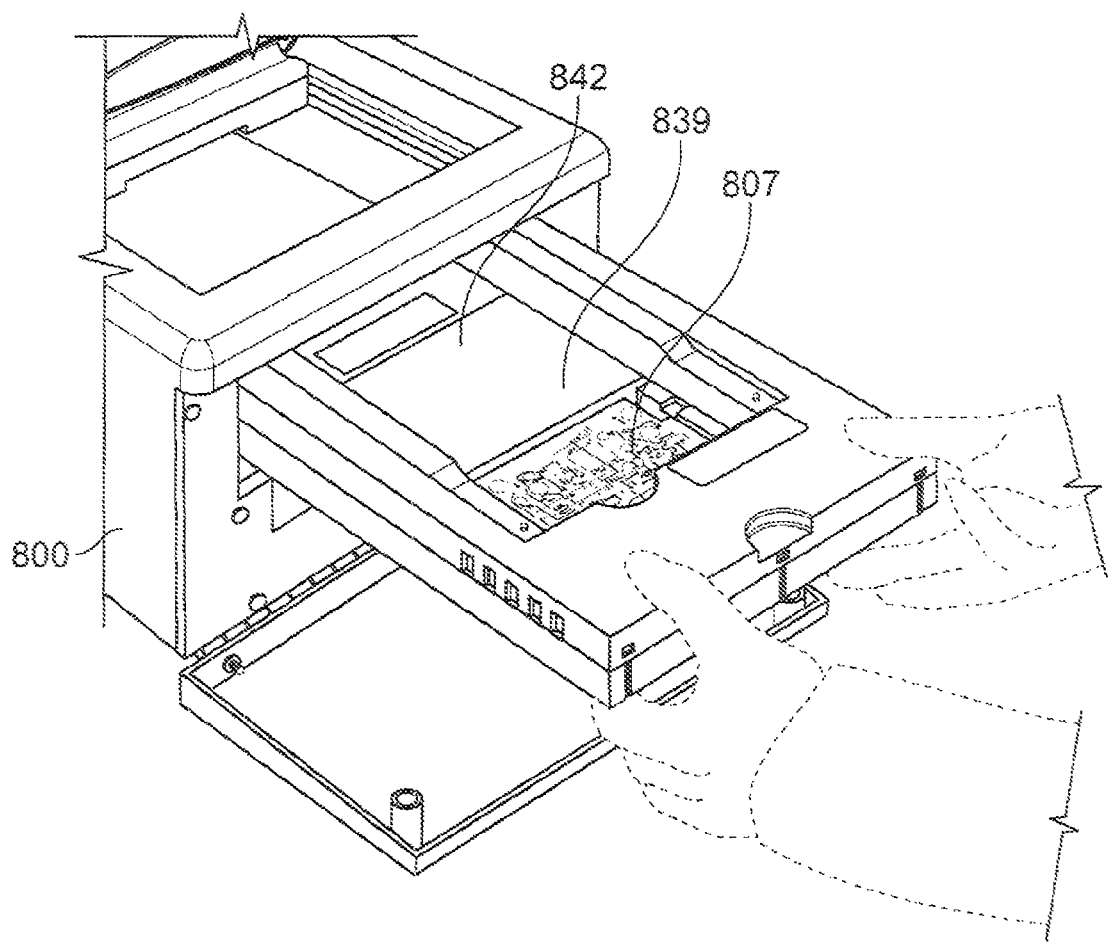

As shown in FIGS. 37 and 38, closure of lid 804 of apparatus 800 can serve to block ambient light from the sample bay. Additionally, closure of lid 804 can place an optical detector contained in lid 804 into position with respect to microfluidic cartridge 812. Also, lid 804 of the apparatus can be closed to apply pressure to microfluidic cartridge 812 to ensure thermal contact in well 807 with heating/sensor module 842. Referring to FIGS. 39 & 40, heating/sensor module 842 of apparatus 800 can be removable for cleaning, maintenance, or for replacement with a custom heating stage for a particular microfluidic cartridge 812.

Example 2

Apparatus for Polynucleotide Processing

This non-limiting example describes various embodiments of an apparatus, system, microfluidic cartridge, kit, methods, and computer program product, in particular, various aspects of using apparatus 800 as described in Example 1 relating to exemplary aspects of the method and the computer program product.

Referring to FIGS. 28-40, apparatus 800 may include or be configured with a computer program product in the form of control software. The software can provide apparatus with a "READY MODE" (e.g., standby mode) when not being used for analysis where the apparatus 800 can be plugged in and can await user input. An operator may slide open the lid 804 using the handle 805 to its full open position. The software and apparatus 800 may be configured to indicate on display output 802 that lid 804 is open and apparatus 800 is ready. The software and apparatus 800 may be configured to to perform a hardware and/or software self test. The software and apparatus 800 may be configured to request entry of a user ID and password screen, for example, to allow a user to log in by using a touch screen interface (e.g., by touching keys of an emulated keyboard on the display output 802), by scanning in a bar code representing the user, such as found on an ID badge, with bar code reader 806, and the like.

A user may then remove the microfluidic cartridge 812 and the sample container 814 from the sealed pouch 824. The software and apparatus 800 may be configured to request that the bar code 813 on the microfluidic cartridge 812 and/or the bar code 815 on the sample container 814 be scanned in using the bar code reader 806, as in FIGS. 32 and 33, before performing any test. The software and apparatus 800 may be configured to perform qualifying tests based on the bar codes (e.g., to determine whether microfluidic cartridge 812 and sample container 814 came from the same sealed pouch 824, whether kit 810 has passed an expiration date, whether kit 810 can be configured to be used with a particular analysis sequence to be conducted by the software and apparatus 800 and the like) before performing nucleic acid tests. The display output 802 may then advance to a screen requiring an input, such as a patient identifier. Apparatus 800 may also allow the patient information to be entered by scanning a bar code (e.g., on a medical ID bracelet assigned to the patient) using the bar code reader 806. Display output 802 can provide information to the user regarding, for example, results of a test that was previously run, selection options for tests to be run, and the like. Examples of information that may be provided include, but are not limited to: a test determination (e.g., positive/negative result), an internal control result (e.g., positive and/or negative), and/or patient results. In this example, the user may also be prompted to allow the apparatus 800 to perform additional tasks with the test data, such as recording or outputting the data to a printer, storage device, or to a computer, and the like.

Various embodiments of the software and apparatus 800 may be configured to allow a user to perform one or more optional functions (e.g., adjustments to apparatus 800 or the software) including, but not limited to: modifying user settings, modifying logout settings, setting the system clock, modifying display settings, modifying QC requirements, setting report preferences, configuring an attached printer, configuring a network connection, sending data via a network connection, selecting or adapting data analysis protocols, or the like.

Figure 41A:
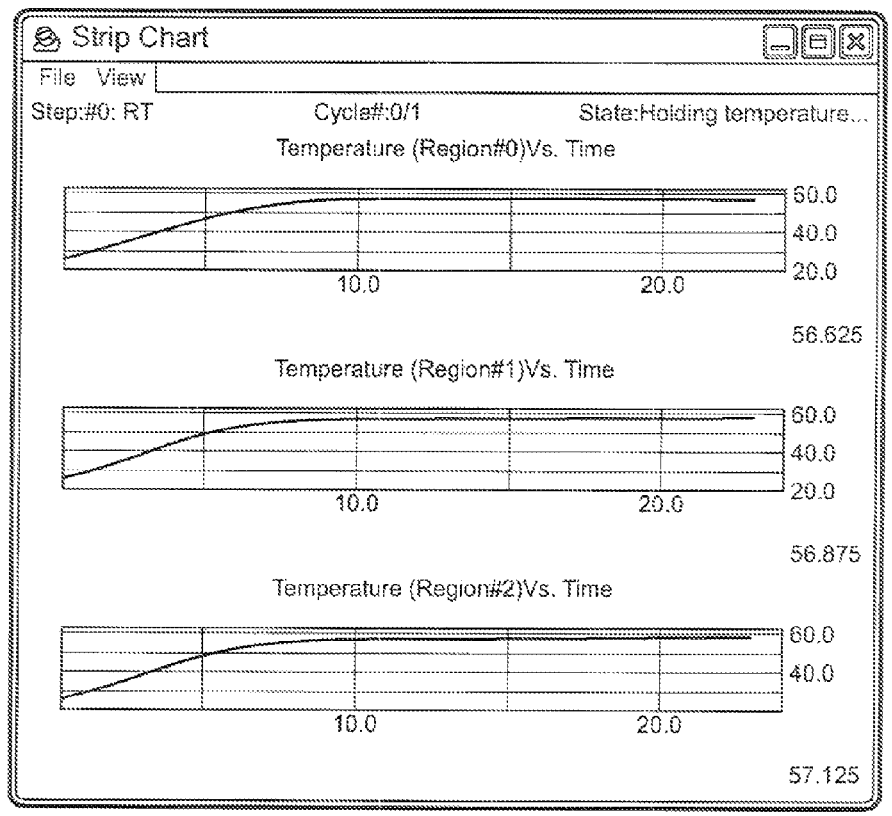
FIG. 41A is a graph of real time heat sensor data from an apparatus.
Figure 41B:
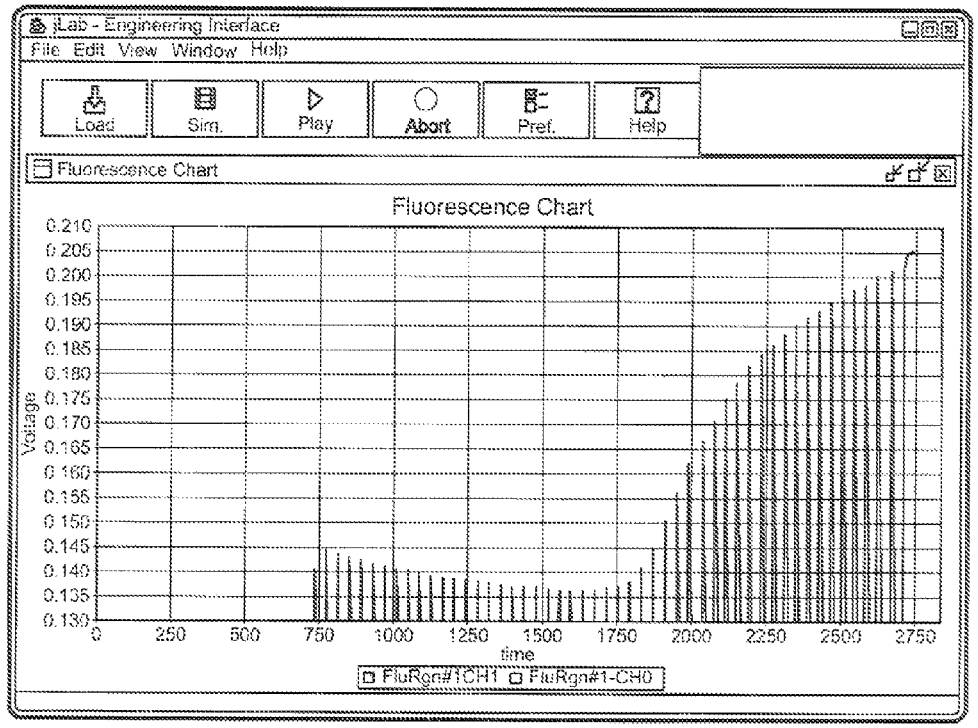
FIG. 41B is a graph of real time optical detector data from an apparatus.

In various embodiments, the software can include a user interface and device firmware. The user interface software can allow for aspects of interaction with the user including, but not limited to, entering patient/sample information, monitoring test progress, error warnings, printing test results, uploading of results to databases, updating software, and the like. The device firmware can operate apparatus 800 during the analytical tests and can have a generic portion that can be test independent and a portion specific to the test being performed. The test specific portion ("protocol") can specify the microfluidic operations and their order to accomplish the test. FIG. 41A shows a screen capture from an exemplary interface displaying real time heat sensor data. FIG. 41B shows a screen captures from an exemplary interface displaying real time optical detector data.

Example 3

Apparatus for Polynucleotide Processing

Figure 42:
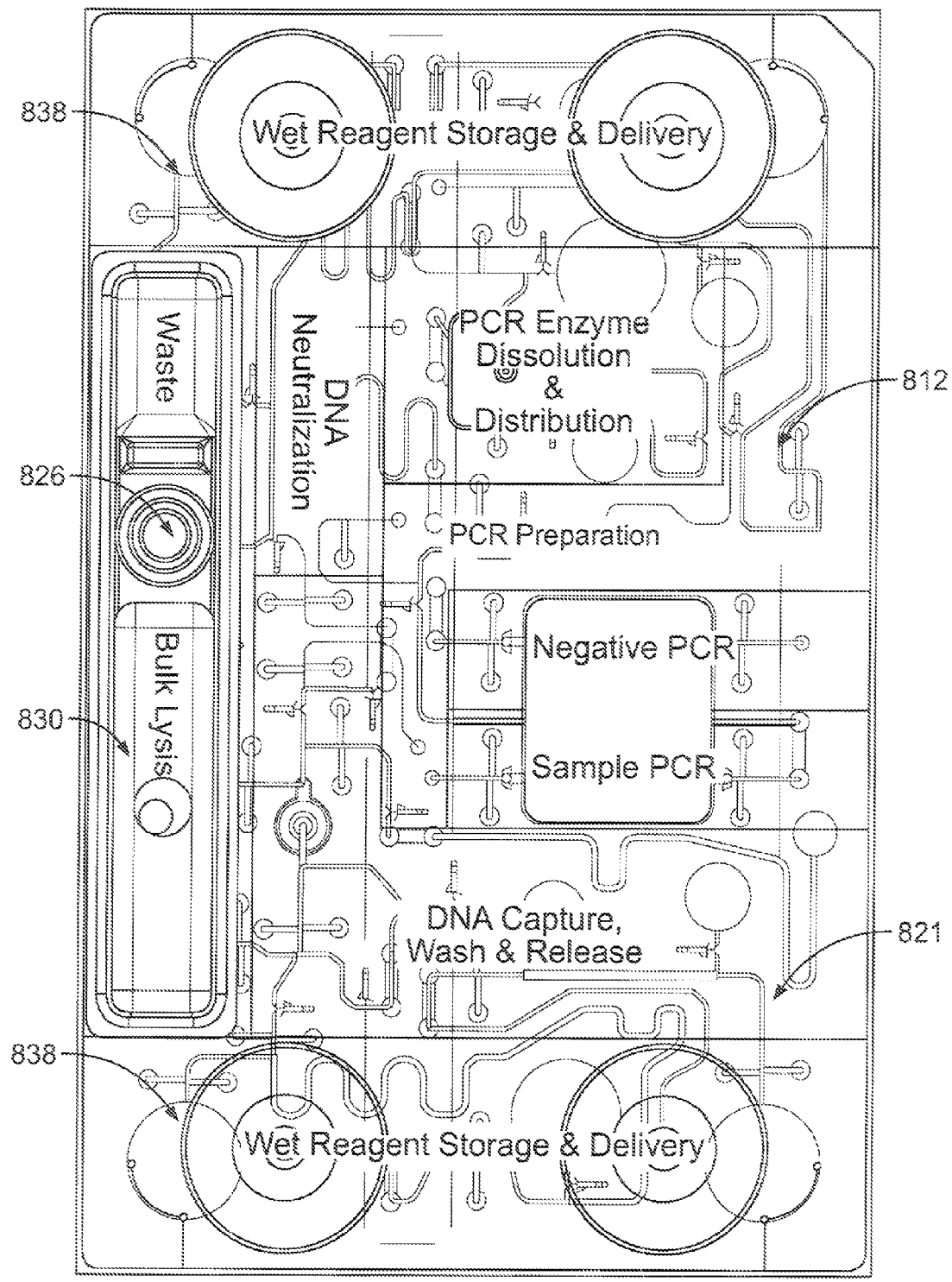
FIG. 42 is a schematic representation of various exemplary chambers and/or subunits in an exemplary microfluidic cartridge.

This non-limiting example describes various embodiments of the claimed apparatus, system, microfluidic cartridge, kit, methods, and computer program product. In one embodiment, the apparatus 800, shown in FIG. 28, may be a self-contained, real-time PCR device based on microfluidic technology for rapid and accurate diagnosis of pathogens (e.g., Group B *Streptococcus* (GBS) colonization in prenatal women). In an exemplary embodiment, when the microfluidic cartridge 812 (FIG. 31) can be installed, the apparatus 800 may actuate on-cartridge operations, detect & analyze the products of a PCR amplification and/or display the results on a graphical user interface. The microfluidic cartridge 812 may include a plurality of chambers and/or subunits, for performing a variety of tasks, with limited or no intervention by the user. FIG. 42 is a schematic representation of the various chambers and/or subunits in an exemplary microfluidic cartridge 812. Microfluidic cartridge 812 can accept unprocessed clinical samples (e.g., vaginal/rectal swab dipped in transport buffer in the case of GBS) via the sample inlet 826, which may be a luer-style injection port. Clinical swab samples containing human and bacterial cells and debris can be routinely collected in 2 ml of transport buffer. However, small volumes (e.g., on the order of a few microliters) can be easily processed on microfluidic devices. The incorporation of an interface between macro and micro operations can allow the adaptation of microfluidic technology for clinical diagnosis. Upon injection of a sample, the cartridge may be placed in the apparatus 800 and further operations; for example, sample preparation, reagent metering/mixing, and PCR amplification/detection may be performed in an automated and hands-free manner.

Figure 43:
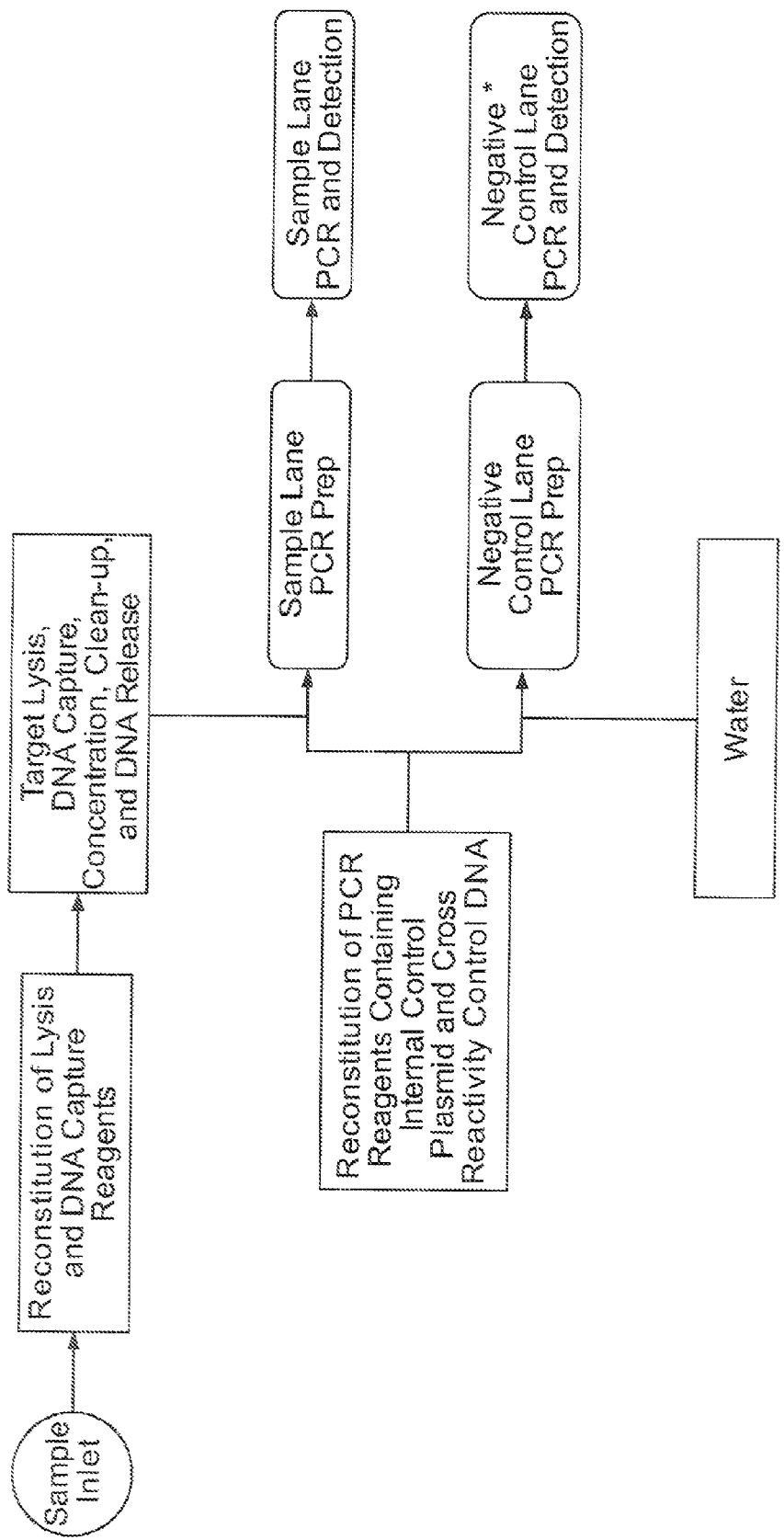
FIG. 43 is a schematic representation of the steps relating to PCR and detection that can be performed in an exemplary microfluidic cartridge.

FIG. 43 is a schematic representation of the steps relating to PCR and detection that can be performed in an exemplary microfluidic cartridge 812. In various embodiments, the steps to process samples for PCR based detection & diagnosis of pathogens (e.g., GBS from vaginal/rectal swabs) may include: lysis to release DNA (e.g., lysis of GBS cells to release polynucleotides), capture and concentration of DNA, and minimization of inhibitors and competitors to clean-up the DNA for PCR compatibility. Inhibitors present in clinical samples can increase the risk of a false negative result for PCR based diagnostic tests unless their influence can be mitigated through sample clean-up.

Cell lysis can be achieved by methods known to the art, for example, heat and/or chemical activation. In some embodiments, after a 1.0±0.2 mL sample can be injected into the lysis reservoir 830 via the sample inlet 826, the apparatus 800 may cause the sample to be mixed with lysis reagents from the wet reagent storage 838 and heated (e.g., for 7 minutes) in the lysis reservoir 830. Using this protocol, greater than 90% lysis efficiency has been achieved for GBS and other bacterial cells. The lysis reagents may also incorporate a cationic polyamide modified polycarbonate—polystyrene latex bead based DNA affinity matrix (e.g., retention member 821) to capture the negatively charged DNA which may be released during the lytic process. The affinity beads can bind to negatively charged DNA with very high affinity while potential PCR inhibitors can either fail to bind or can be removed during subsequent wash steps.

In one exemplary embodiment, the apparatus 800 may also automate the capture and cleaning of DNA from crude sample lysate (e.g., GBS sample lysate) to generate "PCR-ready" DNA. The contents of the lysis reservoir 830 (e.g., 1.0±0.2 mL sample and reagents) may be transferred to the DNA processing chamber 840. Affinity beads with bound DNA from the input sample can be trapped using an in-line bead column (e.g., a filter with specific pore size) and an on-cartridge pump can be used to wash the affinity beads to remove non-specifically bound moieties as well as soluble inhibitors by performing a buffer exchange. The bound DNA may be released by known methods, for example, by heating the affinity beads (e.g., to 80° C.) and/or by using a release buffer. The intact DNA can be recovered with this single step release in very small volume (3-4 µl) thereby achieving a significant concentration of the original target DNA. Other methods known to the art can be employed by the system to achieve cell lysis and DNA capture, wash, and release.

In the example described here, the basis for the real-time PCR assay used is the TaqMan® assay, the schematic operation of as depicted in FIG. 44. However, other assay techniques known to the art may be used (e.g., SYBR-Green I fluorescence). The TaqMan® PCR reaction exploits the 5' nuclease activity of certain DNA Polymerases to cleave a TaqMan® probe during PCR. The TaqMan® probe contains a reporter dye at the 5'-end of the probe and a quencher dye at the 3'-end of the probe. During the reaction, cleavage of the probe can separate the reporter dye and the quencher dye, which may result in increased fluorescence of the reporter. Accumulation of PCR products can be detected directly by monitoring the increase in fluorescence of the reporter dye. When the probe is intact, the proximity of the reporter dye to the quencher dye can result in suppression of the reporter (Fluorescence emission can be by Forster-type energy transfer). During PCR, if the target of interest can be present, the probe can anneal between the forward and reverse primer sites. The DNA Polymerase typically can cleave the probe between the reporter and the quencher if the probe hybridizes to the target. The probe fragments can then be displaced from the target, and polymerization of the strand can continue. The 3'-end of the probe can be blocked to prevent extension of the probe during PCR.

This process can typically occur, for example, in every thermal cycle and should not interfere with the exponential accumulation of product. The increase in fluorescence signal can typically be detected if the target sequence can be complementary to the probe and can be amplified during PCR. TaqMan® assay can offer a two-fold stringency (the primer typically binds and the probe typically binds to the target sequence) and hence detection of any nonspecific amplification can be reduced or eliminated.

Real-time PCR primers and probe sets for GBS (Streptococcus agalactiae) have been designed & tested using clinical samples. The PCR reagents may include a pair of hybridization primers specific to the portion of the cfb gene between positions 328 and 451 encoding the CAMP factor (Christie, Atkins and Munch-Petersen, see, e.g., *Boll Ist Sieroter Milan*, (1955 July-August); 34 (7-8):441-52). The CAMP factor is a diffusible extracellular protein and is produced by the majority of GBS. The gene encoding CAMP factor, cfb gene (GenBank access number: X72754), can be present in GBS isolate and has been used for the development of a PCR based identification of GBS (Danbing K., et al., (2000), *Clinical Chemistry*, 46, 324-331). Further, a specific TaqMan® style fluorogenic probe has also been designed & tested, in one example, to recognize the sequence amplified between the primers allowing real-time detection by using fluorescence measurements.

Figure 45:
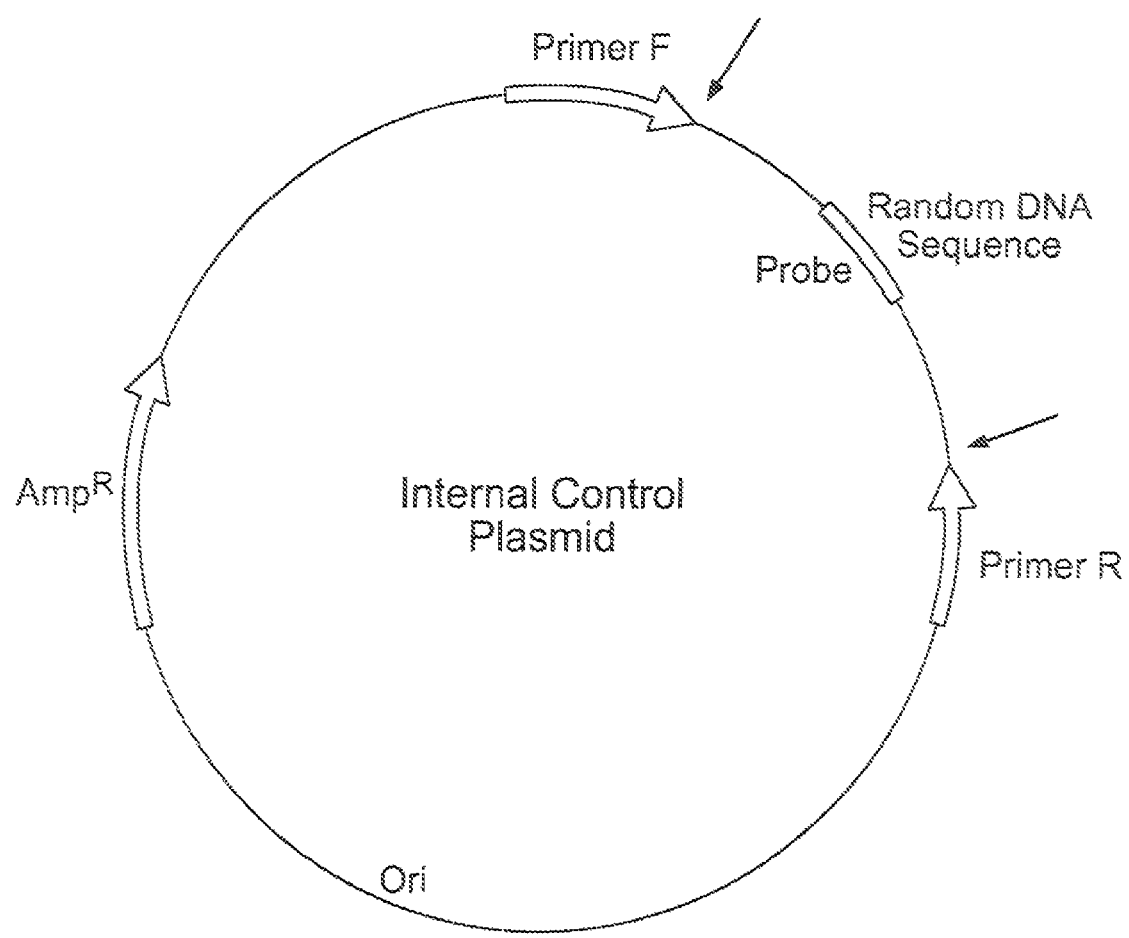
FIG. 45 is a schematic of positive internal control plasmids which can be employed.

In order to evaluate the DNA clean-up process and monitor the performance of our primers at run-time, positive internal control plasmids (e.g., as depicted in FIG. 45) can be employed. In various embodiments, the specific GBS primers have been employed to construct internal control plasmids as follows. A piece of random DNA sequence flanked by the specific PCR primers was generated by oligonucleotide synthesis. Any possible homology between this sequence and other DNA sequences especially *Strep. agalactiae* DNA, available in Genbank was checked carefully. A fluorogenic TaqMan® style probe was designed to recognize the amplicons generated from this sequence and a fluorophore (Cal Orange 560 or analog) different from the one used for GBS target sequence DNA (FAM or analog) was used for simultaneous dual color fluorescent detection. In certain embodiments, the amount of the internal control plasmid to be included in the PCR reaction was optimized to permit amplification of the internal control product without significant detrimental effect on the GBS specific amplification. In some examples, the specificity of the probes for internal controls was also tested and optimized by PCR using the DNA purified from the pathogens included in the cross reactivity testing list specified previously and GBS DNA.

In an exemplary embodiment, a robust system for carrying out rapid thermo-cycling using a microfluidic volume was designed, developed, and implemented in a microfluidic format. The microfluidic volumes that can be accommodated range from about 0.01 µl to about 10 µl, wherein the principal limitation on the lower limit is sensitivity of detection. Exemplary volumes are in the range 0.5-4.5 µl. Still other exemplary volumes are 2 µl. FIGS. 41A and 41B show screen shots of an exemplary apparatus 800 output (e.g., as seen on the touch sensitive LCD 846). FIG. 41A shows a microfluidic PCR module undergoing rapid thermo-cycling and FIG. 41B shows a real-time PCR assay. This data can be available to the user of apparatus 800 or can be hidden. In this case, the GBS cartridges were also designed to accommodate two PCR chambers to allow for incorporating an on-board negative control with each sample run to improve the fidelity of the result. In some examples, the chemistry has been optimized and a compatible detection system developed to enable two-color multiplex PCR thereby facilitating the use of internal positive controls to check for efficiency of sample prep and proper performance of the associated instrumentation. Due to very small thermal masses and efficient feedback-control based algorithms, it can be possible to perform ultra-fast thermo-cycling such that a typical 50-cycle PCR can be completed in approximately 20 minutes. Heat required for thermo-cycling can be provided by the heater/sensor module 842 and real-time multiplexed detection can be carried out by the optics module (e.g., the fluorescent detection module 844).

In various embodiments, any number (e.g., 0, 1, 2, or all) of the reagents for performing the PCR can be incorporated on the cartridge in a lyophilized format. At the time of use, the lyophilized PCR reagents can be reconstituted using, for example, deionized water, which may be stored on the microfluidic cartridge 812 in a blister format (e.g., in a self-pierceable reservoir 828). The reconstituted PCR reagents can be aliquoted into, e.g., two parts. In various embodiments, PCR ready DNA (output of the sample preparation module) can be mixed one aliquot and sent to the first PCR channel for real-time PCR (sample PCR). DI water containing non-target DNA can be mixed with the second aliquot of the PCR reagents and can be sent to the other PCR chamber (Negative PCR) to serve as the negative control.

Example 4

Apparatus for Polynucleotide Processing

In various embodiments, a microfluidic system (e.g., microfluidic cartridge 812) can include components such as micropumps for moving/mixing liquid drops, microreactors for performing thermally initiated biochemical reactions, and microvalves or microgates to enable control of the liquid pumping operations as well as to isolate regions of the cartridge such as the PCR chambers during thermocycling.

Figure 46:
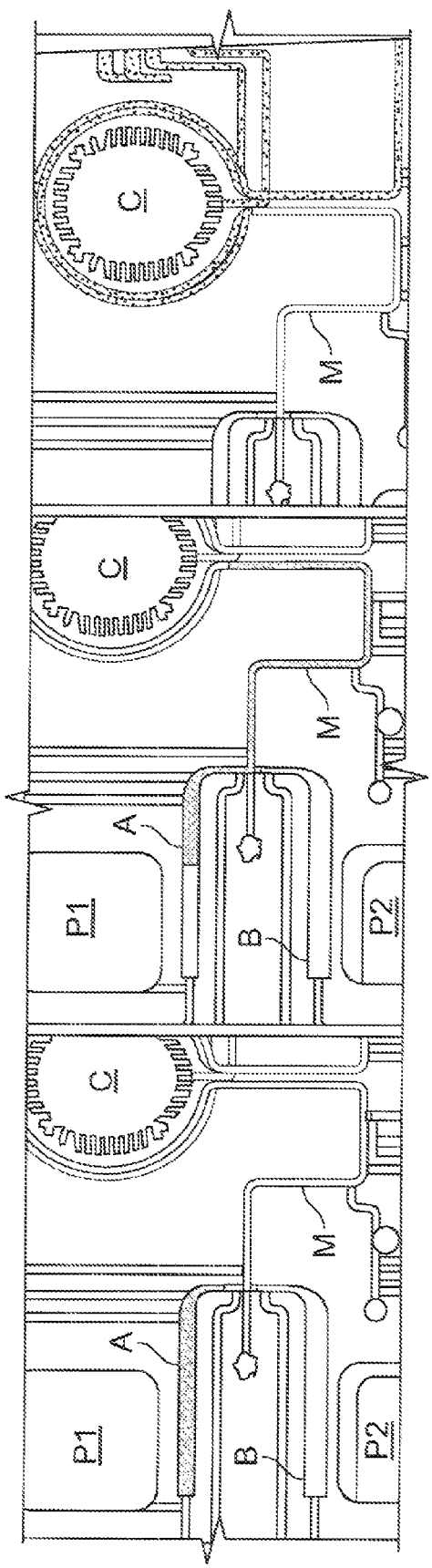
FIG. 46 depicts the mixing of two fluids ("A"—blue and "B"—orange).

In some embodiments, a liquid drop handling system can be used to produce liquid-sample injection and motion based on thermally actuated pumps (e.g. thermo-pneumatic pumping) that may be operated electronically without the use of mechanical valves. For example, by heating air trapped inside chambers that can be connected to the main channel, significant air pressure can be generated for thermo-pneumatic pumping. Increasing the temperature of the air can cause the pressure inside the chamber to rise until the pressure can be high enough to split off a drop (meter an aliquot) and move it to the desired location. This technique can be implemented as an on-cartridge actuation mechanism and may use, for example, molded chambers, channels and heaters. Typically, this can avoid mechanical moving parts and can facilitate fabrication. FIG. 46 shows photos of a demonstration showing the mixing of two fluids ("A"—blue and "B"—orange) using the drop-handling system described above. Pressure pumps P1 and P2 can be activated in a precisely controlled manner which can force the liquids to move as alternating rolling discrete drops along channel M, where they can mix, and finally be positioned into chamber C, where the PCR can take place.

In some embodiments, thermally expansive materials such as gas, readily vaporizable liquid (e.g., vaporizable between 25° C. and 100° C. at 1 atmosphere), and/or a thermally-expanding polymer (e.g., Expancel) may be introduced in thermally actuated pumps (e.g., thermopneumatic air chambers), which may minimize the size of the pumps to generate differential pressures greater than 5 psi. These materials can expand, e.g., by over 100% when a threshold temperature can be reached, causing it to partially or completely fill up the thermopneumatic chamber causing further compression of the air.

Figure 47A:
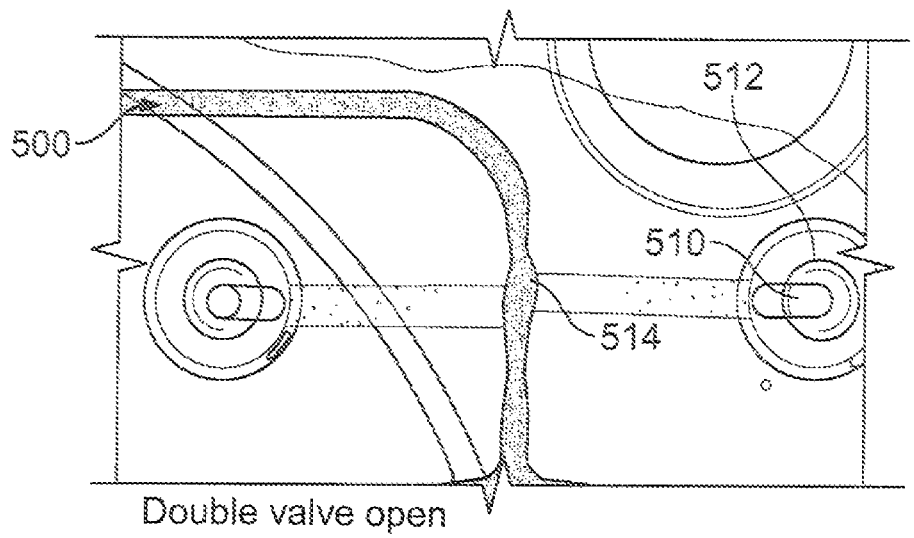
FIGS. 47A and 47B depict a thermally actuated pump 500 based on a phase transition material (PTM) 510, in a closed (FIG. 47A) and open (FIG. 47B) configurations.
Figure 47B:
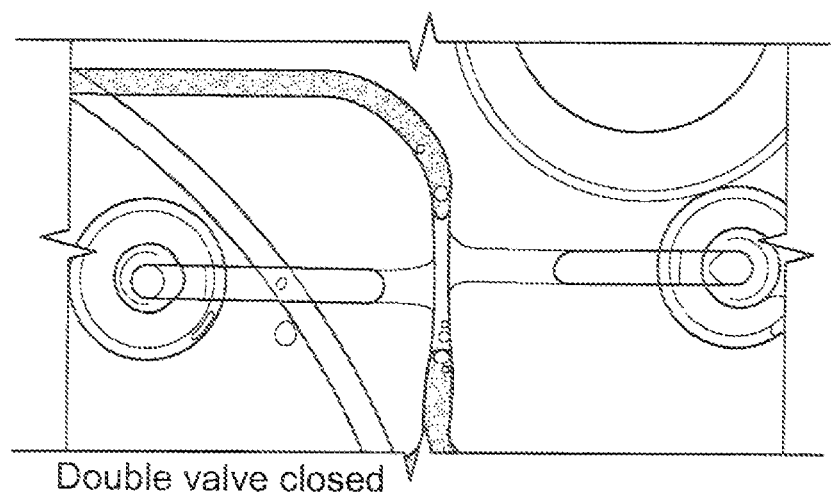

For example, FIGS. 47A and 47B depict a thermally actuated pump 500 based on a phase transition material (PTM)

Figure 47C:
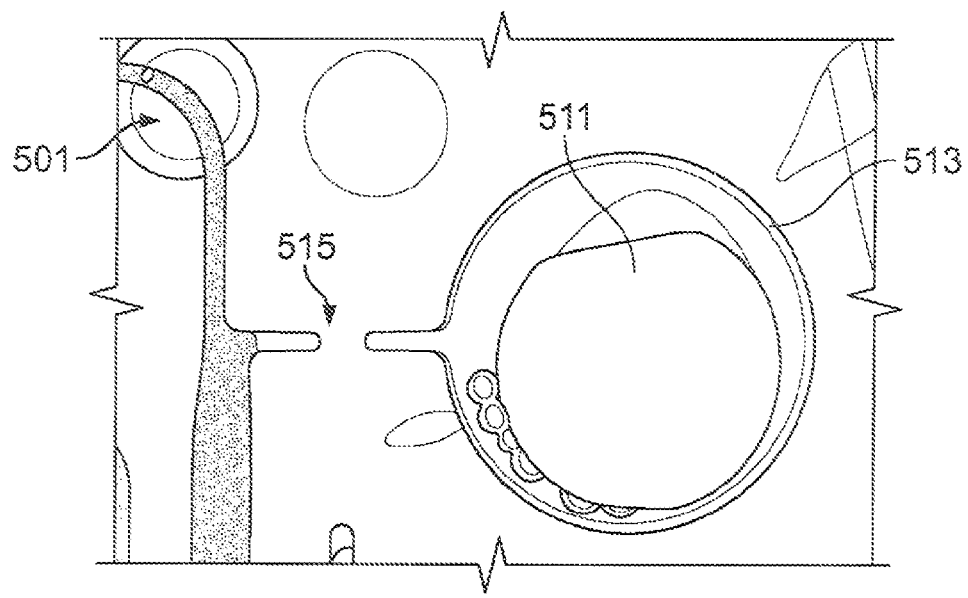
FIGS. 47C and 47D show another example of a pump 501 with expancel polymer 511 in chamber 513 which can be actuated to operate gat 515.
Figure 47D:
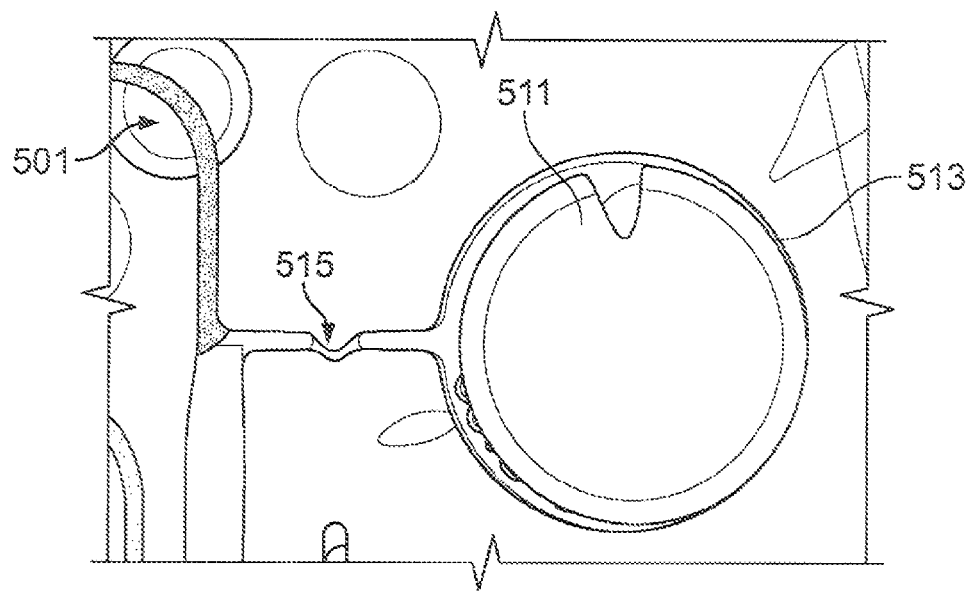

510 (a PTM of a known melting point (e.g., 60 C./75 C./90° C.) such as a paraffin wax, solder, Expancel, or the like), in a closed (FIG. 47A) and open (FIG. 47B) configurations. The PTM 510 can be constrained to a specific location. The specific location can be a sealed chamber 512 with the PTM 510 (typically about 50-100 µl) deposited on a laminate. Upon heating the pump to a temperature above 120° C., the PTM 510 irreversibly expands (up to 40 times its original size), compressing the air within the chamber 512, displacing the air from the chamber, and causing the adjacent gate 514 to open. FIGS. 47C and 47D show another example of a pump 501 with expancel polymer 511 in chamber 513 which can be actuated to operate gat 515.

An exemplary clinical sample input into the mirofluidic cartridge 812 can have a volume of approximately 1 milliliter. After enzymatic/thermal lysis of the cells, the released DNA can be bound to affinity-microbeads. These microbeads can be, for example, on the order of 10 microns in size. In various embodiments, a total amount of beads in the range of a few million can be used per microfluidic cartridge 812 for DNA concentration. In some cases, a minimum pressure of 10 psi (e.g., 10 psi, 11 psi, or 15 psi) may be used to concentrate the beads against an inline-filter area of a few square millimeters (pore size of 8 microns) in a few minutes (e.g. 3 minutes). This pressure can be generated, for example, by injecting extra air (e.g., 1-3 mL) into the bulk lysis chamber of the microfluidic cartridge 812. In some embodiments, a one-way duckbill valve at the luer inlet can be used to minimize or prevent air pressure from escaping through the inlet.

Reagents which can be employed for sample preparation and PCR reactions can be pumped into the microfluidic network by depressing the reagent blister domes by the slider of the instrument during use of the instrument.

In exemplary embodiments, the enzymes typically employed for cell lysis, DNA capture, and for performing real-time PCR can be lyophilized into pellets and stored at different locations of the cartridge. The contact of air can be minimized by storing the pellets in the microfluidic cartridge 812, for example, in a nitrogen purged chamber or a in a channel structure sealed on either ends of the microchannel by thermal gates. Buffers typically employed for sample preparation, reagent hydration and PCR can be stored in hermetically sealed reagent blisters (e.g., the self-pierceable reservoirs 828). Materials used for making the reagent blister can have high moisture vapor barrier and can minimize the loss of liquid during storage of the cartridge over a year. Waste generated from the clinical sample as well as the various wash buffers can be stored on-board the cartridge in chambers and microchannels (e.g., the waste reservoir 832, which can typically be leak-resistant).

Example 5

Aspects of Real-Time PCR

Figure 48:
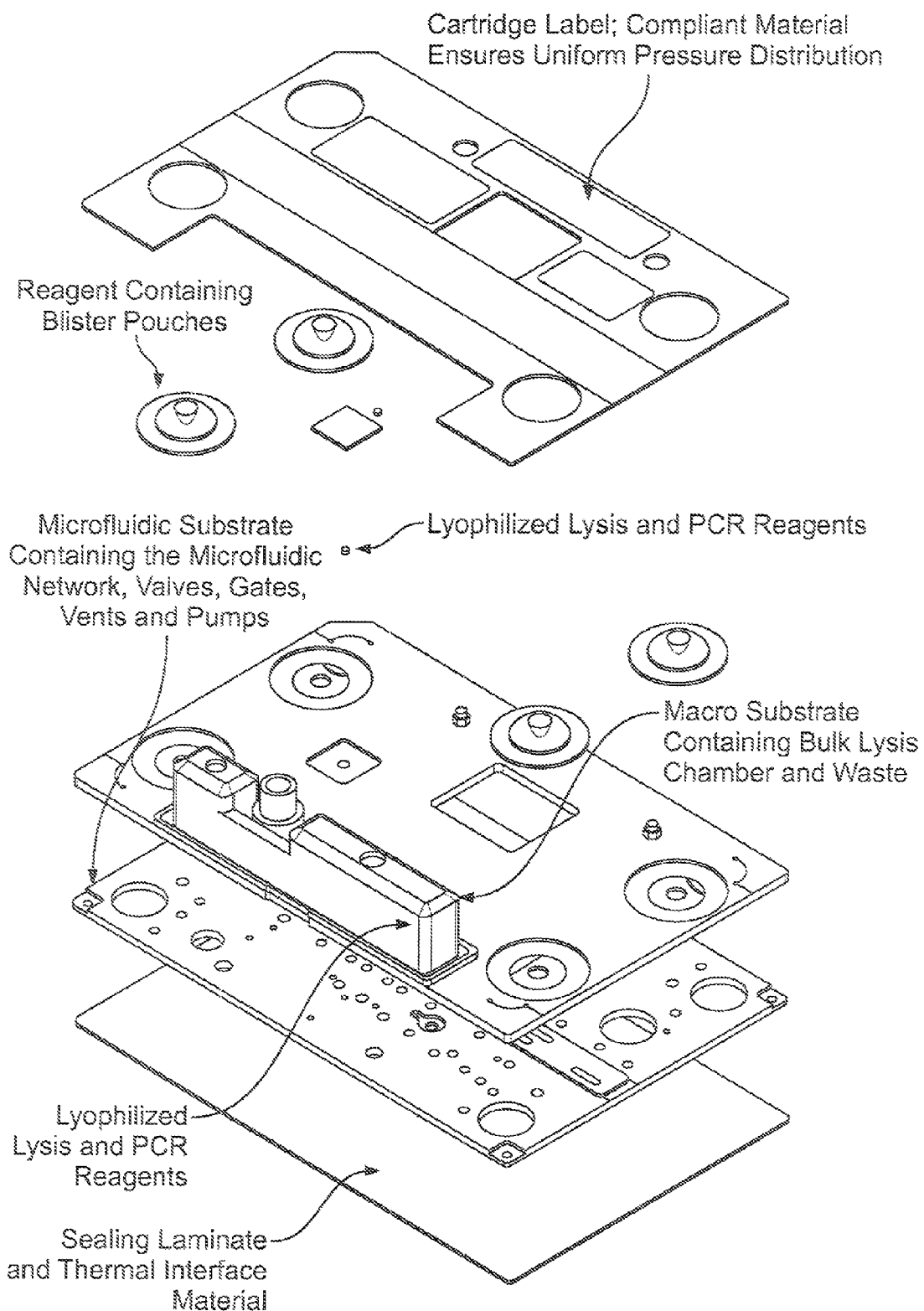
FIG. 48 depicts components of an integrated single, microfluidic technology based, disposable cartridge.

A plurality of steps that can be used for the accurate, real-time PCR based diagnosis of pathogens (e.g., Group B *Streptococcus* (GBS) colonization in prenatal women) was integrated into a single, microfluidic technology based, disposable cartridge, as shown in FIG. 48. Exemplary steps which can be performed in a "sample in; result out" style operation on such a cartridge include: bulk lysis; DNA capture, wash, and release; and PCR preparation and execution. In various embodiments of this cartridge, the sample and reagents can be contained on-board the microfluidic cartridge 812 (as shown in FIG. 31) and there typically is no need for manual interaction with the operation except, for example, during the act of injecting the sample into the device. Strategically positioned hydrophobic vents can be included to remove trapped air formed during processing and reagents typically employed for the assay can be packaged as lyophilized beads in the cartridge. Liquids required for reconstitution can be stored in blister pouches that release at the time of use.

In various embodiments, samples (e.g., GBS samples) can be introduced through the sample inlet 826, which may have a luer fitting for accommodating a syringe. A pre-filter (e.g., attached to the syringe) can be used to remove at least a portion of crude impurities from the sample and, in some embodiments, the sample (e.g., 1 mL) can be lysed in the lysis chamber using heat and/or lytic enzymes. Enzymes such as pronase, protienaseK, and RNAaseA can be used (e.g., during the lysis step) to remove the inhibitory proteinaceous matter and competing RNA molecules. Referring to FIG. 49, DNA capture beads can also be included in the master mix. The lysed liquid sample (e.g., containing the GBS and/or other DNA bound to affinity beads) can be backflowed into the microfluidic cartridge from the lysis chamber outlet. In some examples, the affinity beads with captured DNA can be retained by an in-line filter while the unwanted debris and the excess liquid may be sent to the waste chamber. In such embodiments, the beads used may be non-magnetic, or magnetic, and the filter is selected to discriminate particles by size. In other embodiments, the beads are magnetic, and are concentrated at a particular location of the microfluidic cartridge, such as a chamber or a channel, by applying a magnetic field configured to concentrate lines of flux at the location in question. The magnet employed may be an electromagnet, such as controlled by the processor to switch on and off at specified times during sample analysis. The magnet may alternatively be a permanent magnet, such as one that is moved into and out of place when required.

In some embodiments, the waste chamber is equipped with an anti-foaming agent, such as simeticone. Vigorous bubble formation can occur in the waste chamber because liquid enters it at high speed and, upon mixing with air in the waste chamber, foams. It is undesirable if the foam overflows from the waste chamber. Presence of a de-foaming agent can mitigate this phenomenon. The defoaming agent can be present in powder, tablet, pellet, or particle form.

In some embodiments, the beads can be subject to washing to remove unbound and non-specifically bound matter and the cleaned DNA can be released into a small volume (~3 µl) compartment and concentrated (e.g., by a factor of about 300). In various embodiments, the concentrated DNA can then be mixed with the appropriate PCR reagents and/or be sent to a PCR channel for real-time PCR. An Internal Control plasmid (along with its cognate Probe) may also be included in the first PCR channel, which can act as a positive control. In a second PCR channel (if present), DI water containing non-target DNA and the internal control can be mixed along with the PCR reagents, to act as a negative control.

A user may introduce a sample in the bulk lysis sample through luer-duckbill valve (e.g., the sample inlet 826), shake gently to dissolve lysis reagent pellets, and introduce an excess amount of air (e.g., 0.25-0.75 ml) into the lysis chamber to over-pressurize the lysis chamber. The absolute pressure (P) generated in the lysis chamber having a chamber volume, $V_{chamber}$, is related to the amount of liquid sample injected, $V_{sample}$, and the volume of extra air injected, $V_{extra\ air}$, by the formula:

$$P = \frac{P_{atm}(V_{Chamber} - V_{sample})}{(V_{Chamber} + V_{sample} + V_{extraAir})}$$

The microfluidic cartridge 812 then may be placed in the apparatus 800 and the slider module 848 closed. On closing, the slider module 848 may press reagent blisters (e.g., self-piercing reservoirs 828), causing them to burst and release reagents (e.g., wash buffer, release buffer, neutralization buffer and water) into the channels with reagents.

Figure 50A:
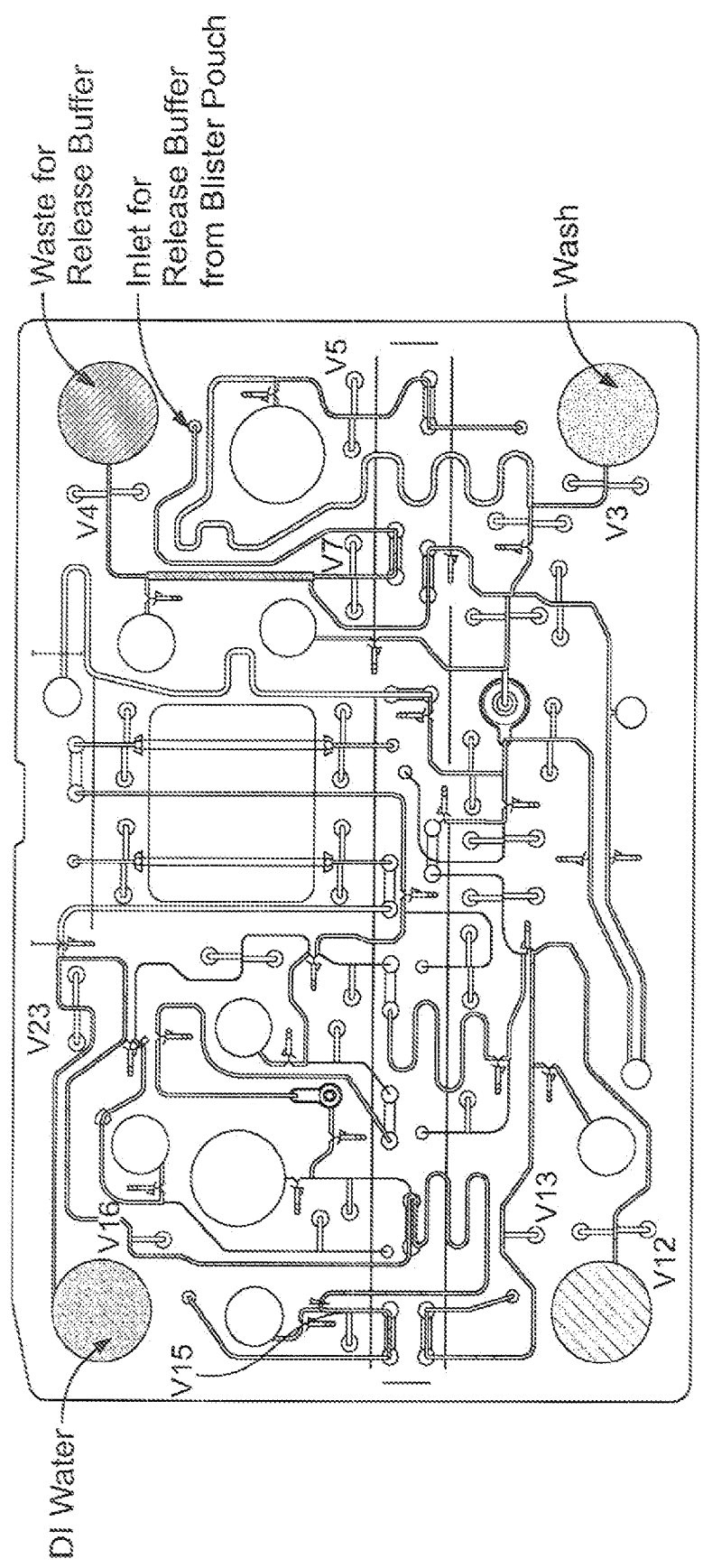
FIGS. 50A-50J highlight various elements of the microfluidic cartridge shown in FIGS. 15A and 15B.
Figure 50B:
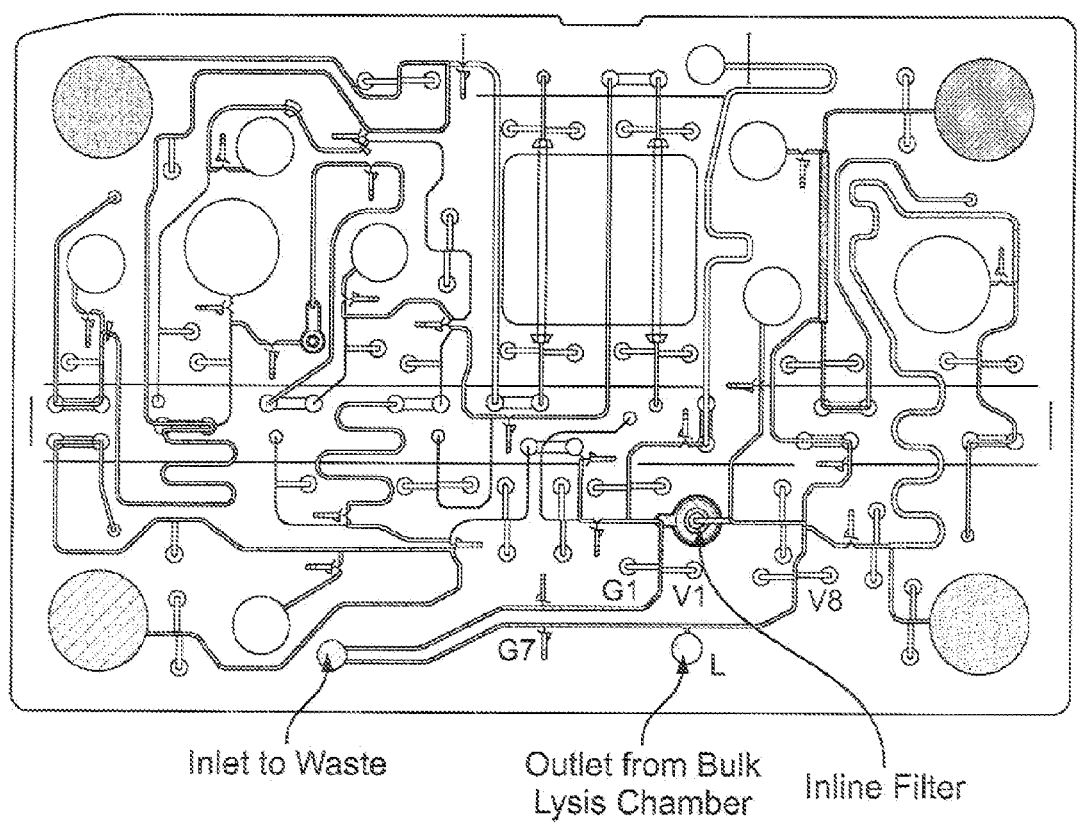

In various embodiments, the apparatus 800 may perform any or all of the following steps. In referring to FIGS. 50A-50J in the following, various elements can also be located with the same designators in FIGS. 15A and 15B. Referring to FIG. 50A, valves (V3, V4, V5, V7, V12, V13, V15, V16, V23) on either ends of the channel holding the 4 reagents may be closed and the bulk lysis lamp may be activated to heat the bulk lysis chamber, for example, to 60° C. for 7 minutes (e.g., using temperature sensor L in FIG. 50B for feedback). Referring to FIG. 50B, Gate G1 can be opened to drain, for a predetermined amount of time (e.g., 2-5 minutes depending on the sample type), the liquid (containing lysate, DNA bound to DNA-affinity beads, etc) through the bead capture filter into the waste chamber. DNA-beads may be trapped against the inline filter while other liquid flows to the waste chamber. Gate G7 can be opened to vent the excess liquid and/or pressure in the lysis chamber into the waste chamber. Valves V1 and V8 may be closed to block the lysis chamber and the waste chamber, respectively.

Figure 50C:
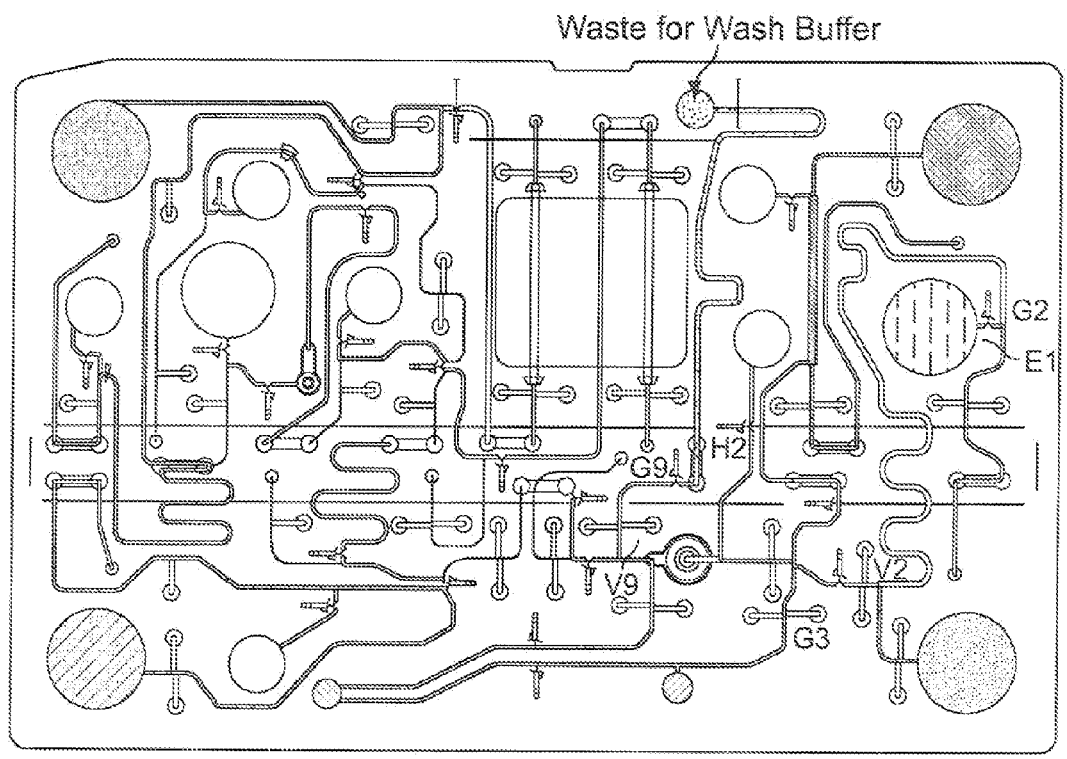

Referring to FIG. 50C, in some examples, trapped beads may be washed by pumping wash buffer through the bead column using pump E1 and opening gates G2, G3, and G9 to position wash buffer downstream of hydrophobic vent H2. The valves isolating the wash buffer channel (e.g., V2) and the wash buffer waste (e.g., V9) may be closed.

Figure 50D:
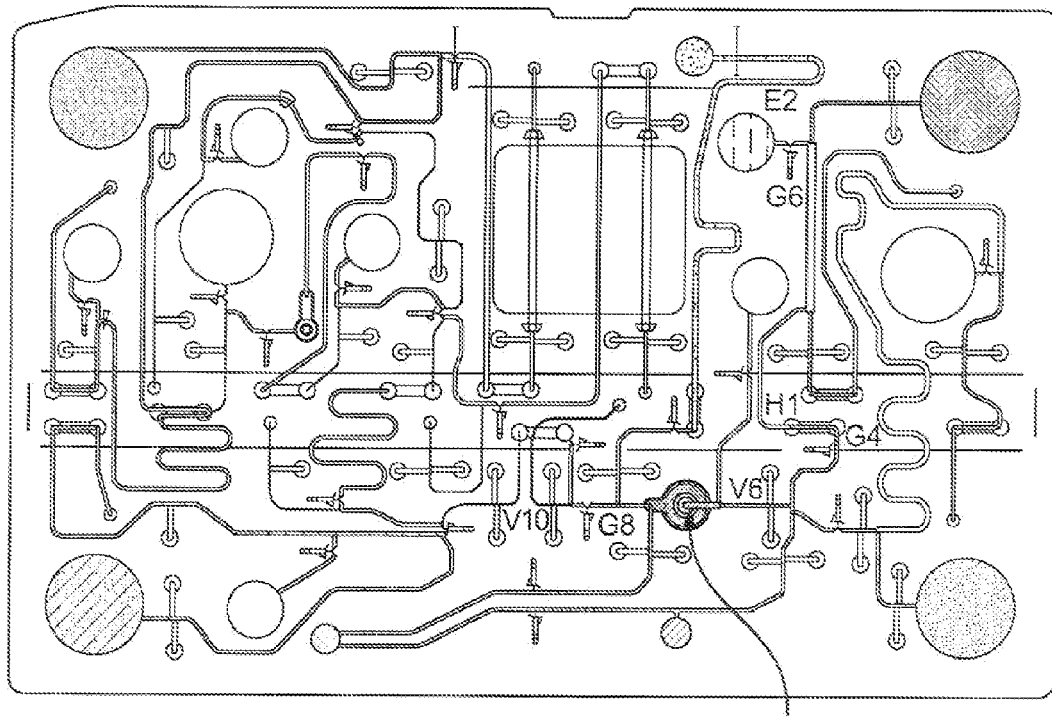

Referring to FIG. 50D, release buffer can be pumped, by using pump E2 and opening gates G6, G4, and G8 to fill up a bead column and position release buffer downstream of air vent H1. The valves blocking the release buffer channel (e.g., V6) and channel downstream of the bead column (e.g., V10) can be closed and the beads heated to, for example, 70 C. for 2 minutes which may release the DNA from the DNA-affinity beads.

Figure 50E:
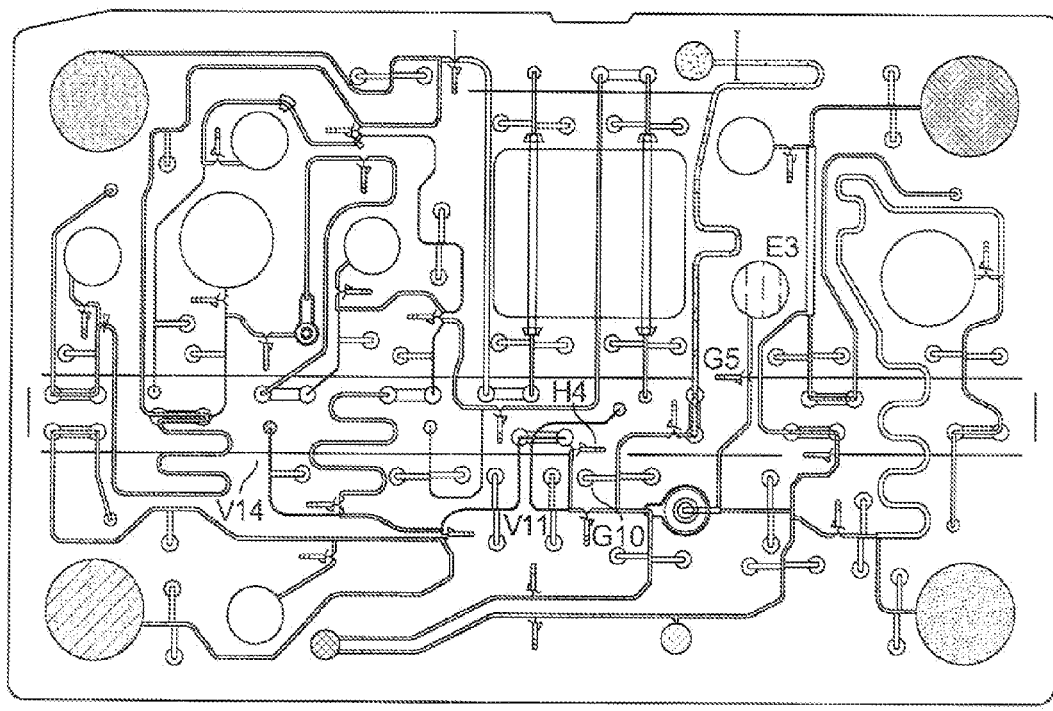
Figure 50F:
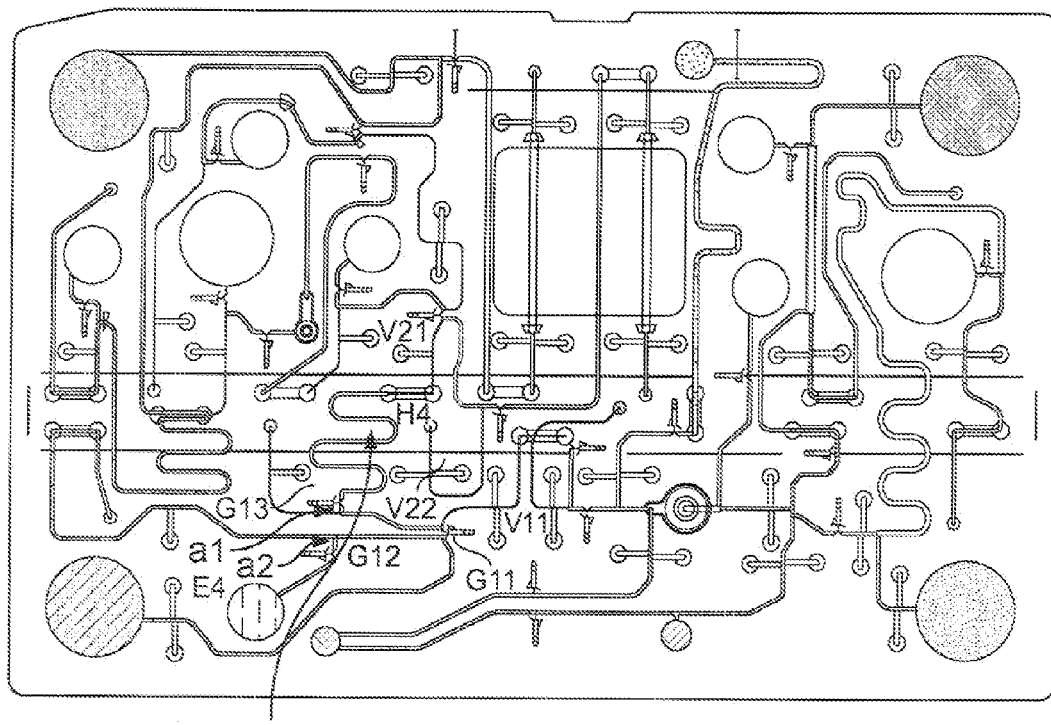
Figure 50G:
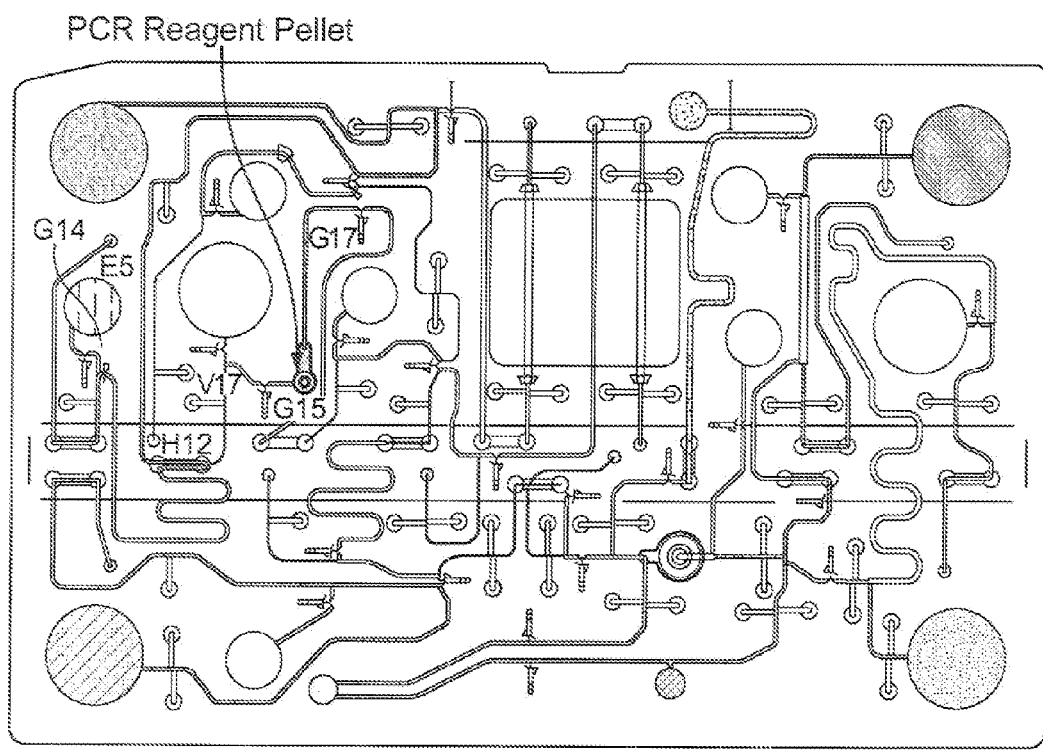

Referring to FIG. 50E, the released DNA can be pumped, using pump E3 and opening gates G5 and G10 to a position downstream of the hydrophobic vent H4, at which time the valves V11 and V14 can be closed. Referring to FIG. 50F, a portion of the released DNA (between junction G11 and a1) and portion of the neutralization buffer (between G11 and a2) can be mixed by using pump E4 and opening gates G12, G11, and G13. Mixing of the composite liquid plug between a1 and a2 may happen after it can be pumped through the neutralization mix channel and positioned downstream of the hydrophobic vent H4. G11 may be a zero-dead volume gate that brings two liquid channels close to each other without trapping air bubbles during the merging of the two liquid plugs. The two valves (V21 and V22) on the ends of the neutralized sample can be closed and, now referring to FIG. 50G, DI water may be pumped using pump E5 and opening gates G14, G15, and G17 to dissolve PCR-reagent pellet. The liquid may be positioned using hydrophobic vent H12. After a period of time long enough for complete dissolution of the lyophilized PCR reagent pellet (e.g., approximately one minute) valve V17 may be closed.

Figure 50H:
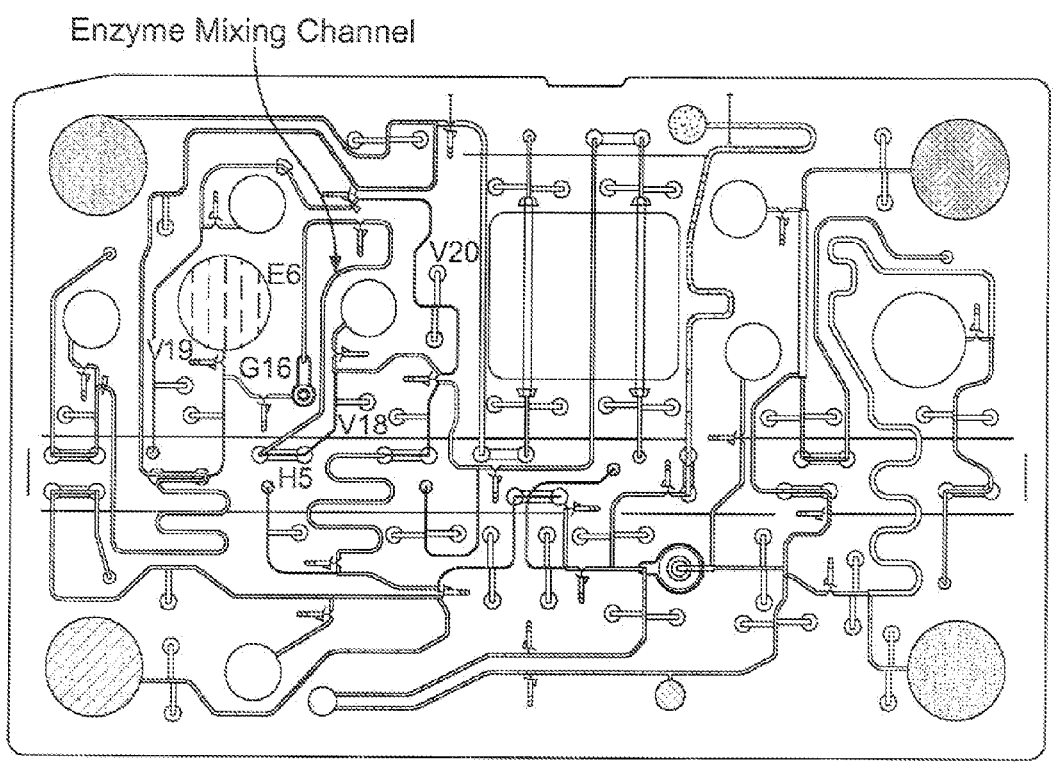

Referring to FIG. 50H, dissolved enzyme can be pumped through the enzyme mixing channel by using pump E6, opening gate G16, and using hydrophobic vent H5 to assist in placement of the fluid. In various embodiments, the mixed enzyme may be distributed (e.g., in 2 equal parts) for multiple reactions to the sample PCR mix section as well as negative PCR mix section, at which time, valves V18, V20, and V19 may be closed.

Figure 50I:
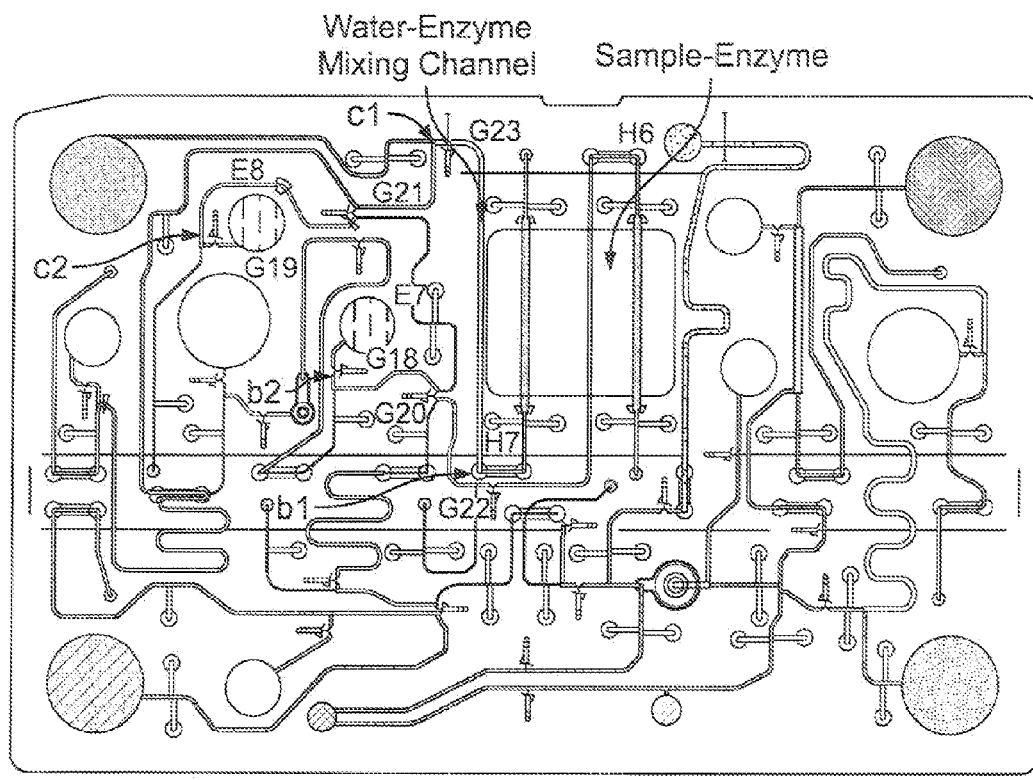

In various embodiments, referring to FIG. 50I, a portion of the neutralized DNA (between junction G20 and b1) and portion of the enzyme (between G20 and b2) may be mixed by using pump E7 and opening gates G18, G20, and G22. Mixing of the composite liquid plug between a1 and a2 can occur after it can be pumped through the neutralization mix channel and positioned downstream of the hydrophobic vent H6. A portion of the DI water (between junction G21 and c1) and a portion of the enzyme (between G21 and c2) can be mixed by using pump E8 and opening gates G19, G21, and G23. Mixing of the composite liquid plug can occur between c1 and c2, after it can be pumped through the neutralization mix channel and positioned downstream of the hydrophobic vent H7.

Figure 50J:
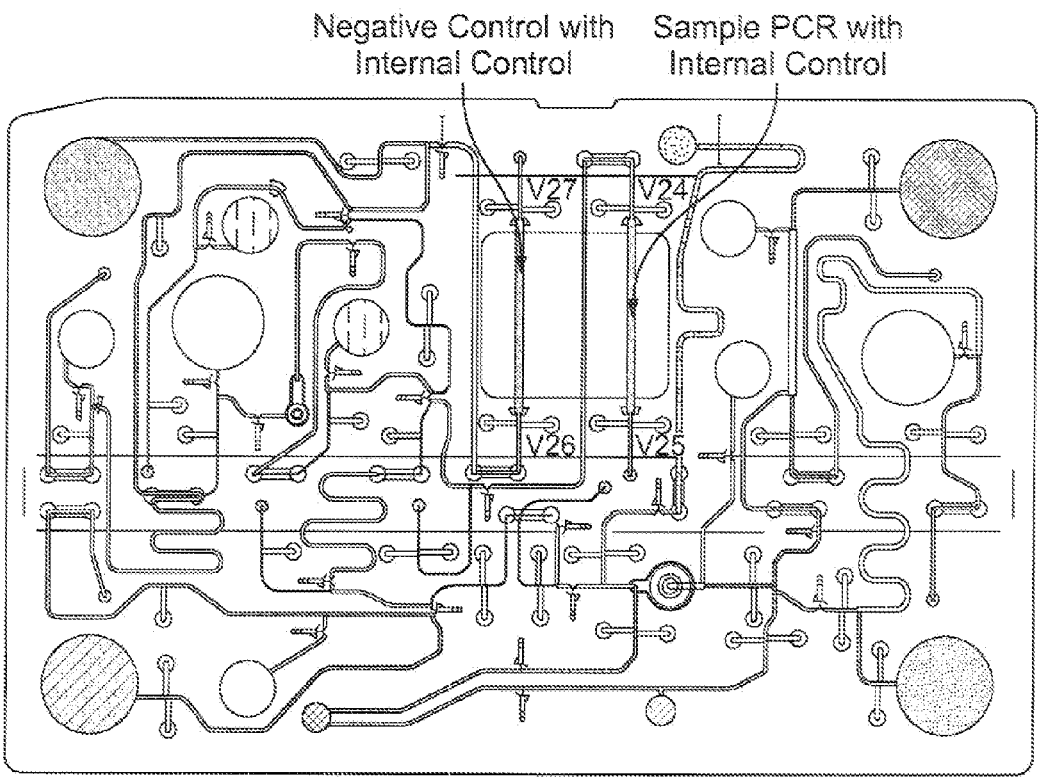

Referring to FIG. 50J, PCR valves V24, 25, 26, 27, in some examples, can be closed to perform sample PCR and Negative control PCR. In various embodiments, light (e.g., fluorescence) can be detected using the optical system in the slider. In some examples, the software can determine the presence of target (e.g., GBS) in the sample based on fluorescence data and may report the results.

Example 6

Apparatus for Polynucleotide Processing

This non-limiting example shows CAD views of various exemplary embodiments of the apparatus, system, microfluidic cartridge, kit, methods and computer program product, as further described herein.

Figure 51:
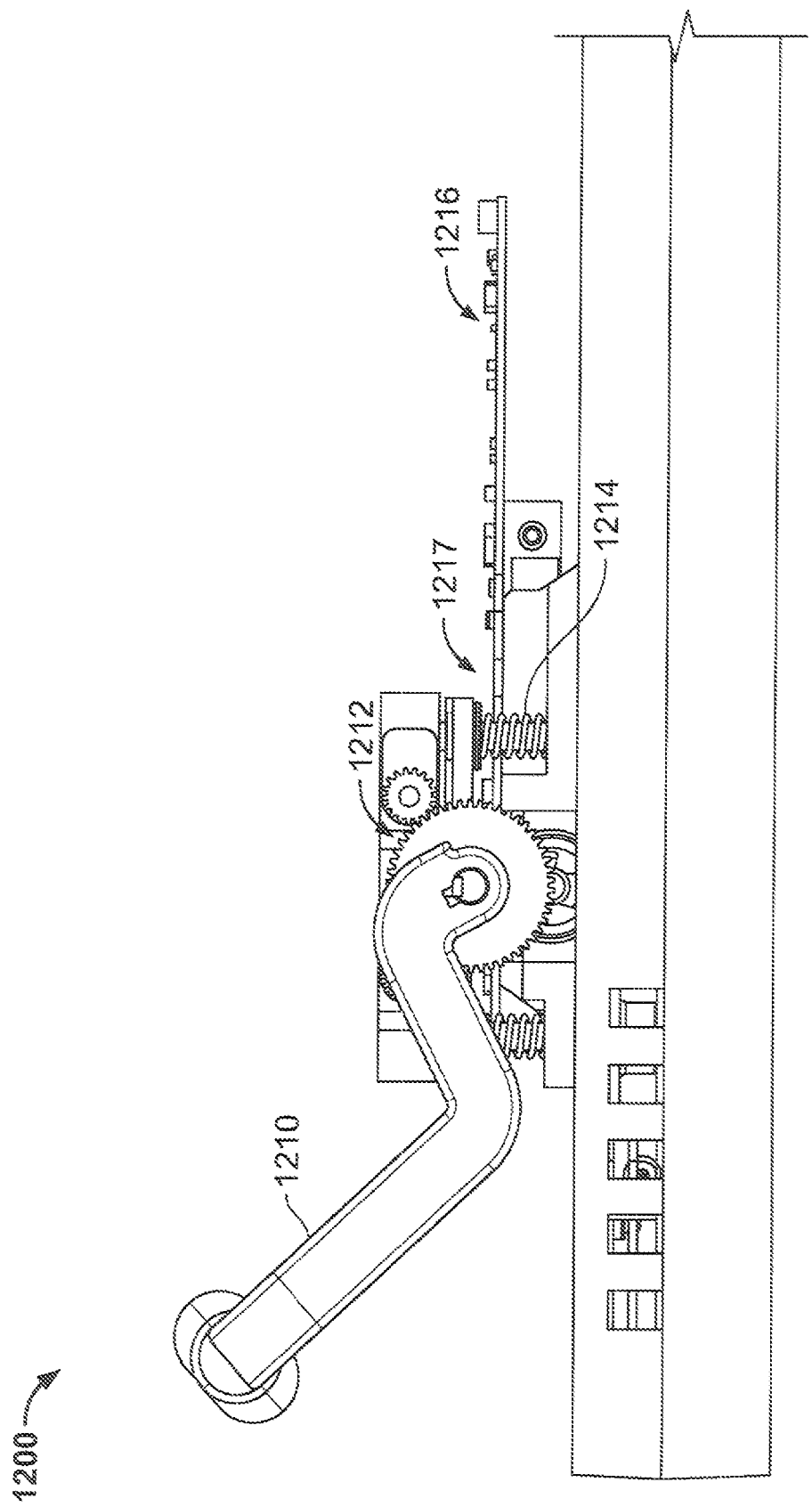
FIG. 51 is a side view of a lever assembly 1200, with lever 1210, gear unit 1212, and force member 1214.

FIG. 51 shows a side view of a lever assembly 1200, with lever 1210, gear unit 1212, and force member 1214. Assembly 1200 can be used to close the lid of the apparatus and (through force members 1214) apply force to a microfluidic cartridge 1216 in the receiving bay 1217. One force member is visible in this cut away view, but any number, for example four can be used. The force members can be, for example, a manual spring loaded actuator as shown, an automatic mechanical actuator, a material with sufficient mechanical compliance and stiffness (e.g., a hard elastomeric plug), and the like. The force applied to the microfluidic cartridge 1216 can result in a pressure at the surface of the microfluidic cartridge 1216 of at least about 0.7 psi to about 7 psi (between about 5 and about 50 kilopascals), or in some embodiments about 2 psi (about 14 kilopascals.

Figure 52:
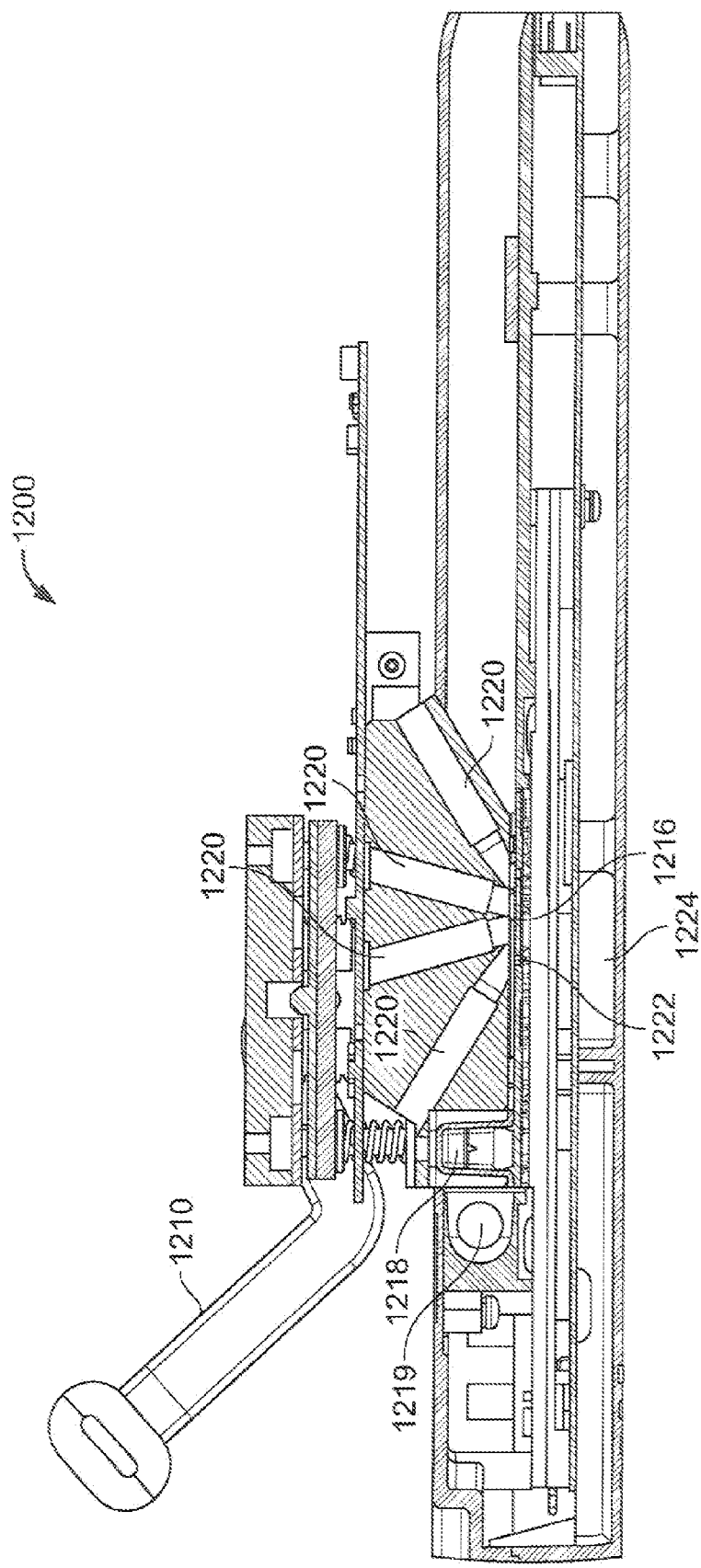
FIG. 52 shows a side view of lever assembly 1200, with a microfluidic cartridge in a receiving bay.

FIG. 52 shows a side view of lever assembly 1200, with microfluidic cartridge 1216 in the receiving bay 1217. A heat pump 1219 (for example, a xenon bulb as shown) can function as a radiant heat source directed at a sample inlet reservoir 1218, where the heat can lyse cells in reservoir 1218. A thermally conductive, mechanically compliant layer 1222 can lie at an interface between microfluidic cartridge 1216 and thermal stage 1224. Typically, microfluidic cartridge 1216 and thermal stage 1224 can be planar at their respective interface surfaces, e.g., planar within about 100 microns, or more typically within about 25 microns. Layer 1222 can improve thermal coupling between microfluidic cartridge 1216 and thermal stage 1224. Optical detector elements 1220 can be directed at the top surface of microfluidic cartridge 1216.

Figure 53:
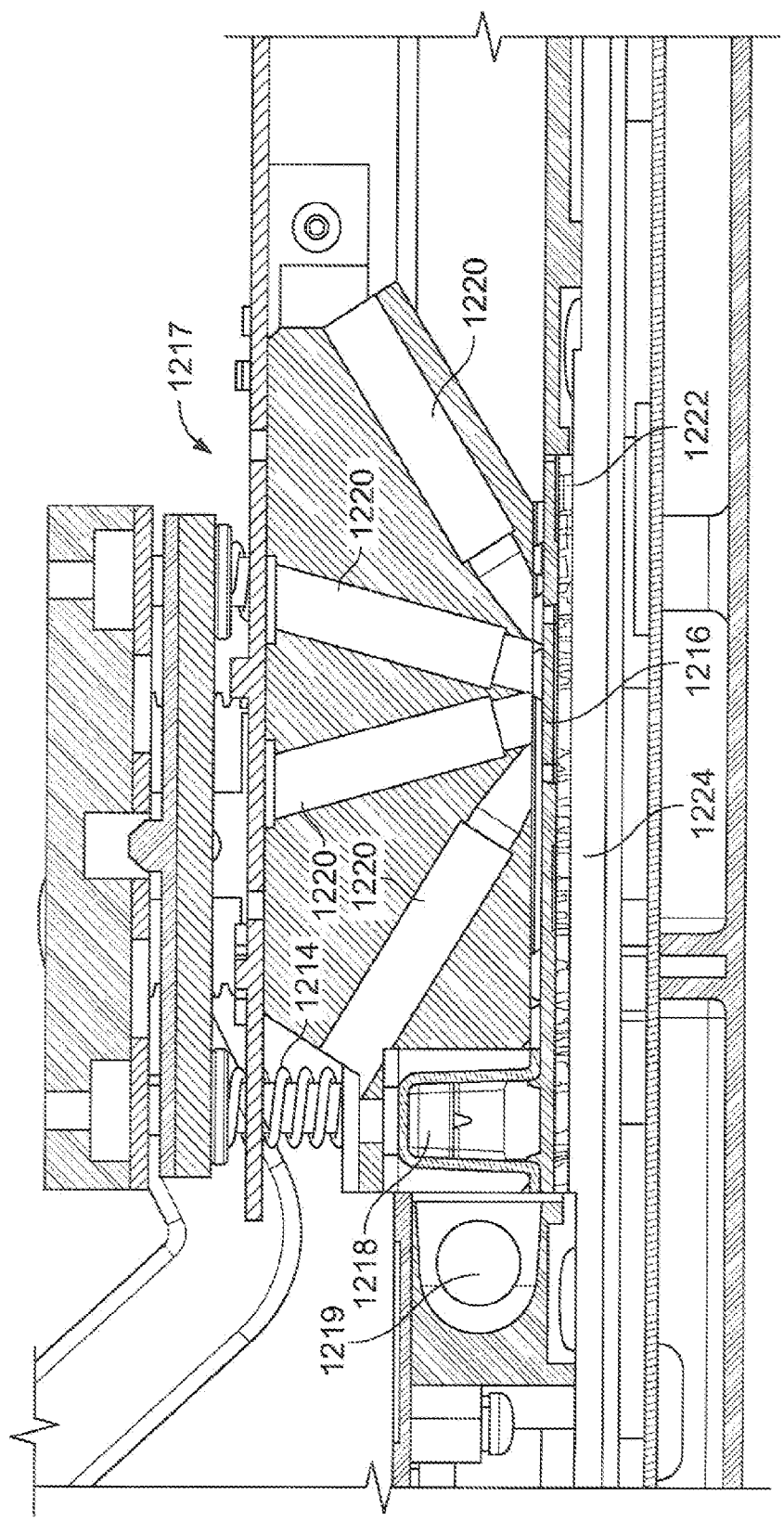
FIG. 53 shows a close-up of a receiving bay.

FIG. 53 shows a close-up of receiving bay 1217.

Figure 54:
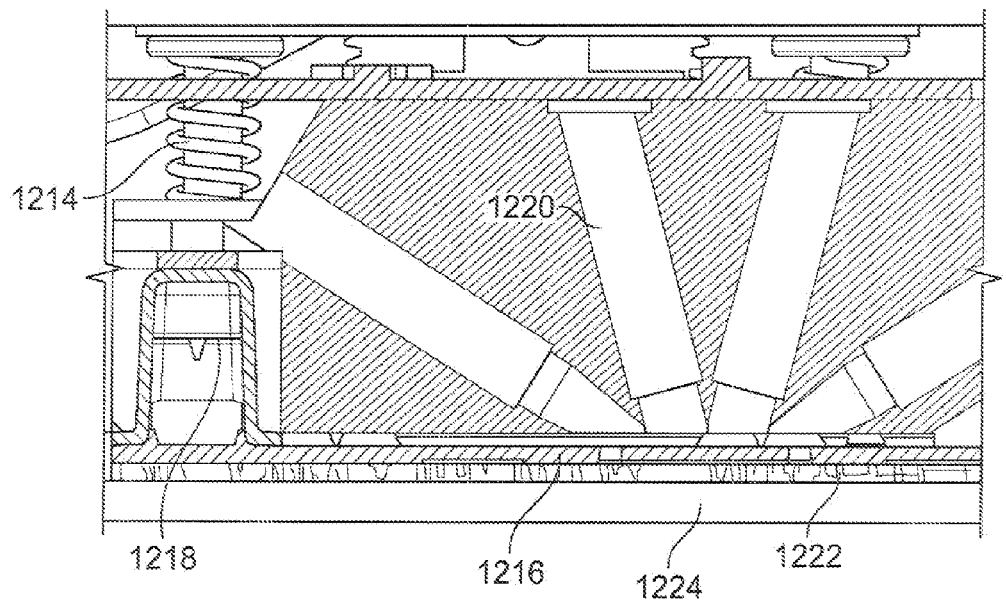
FIG. 54 shows a close-up of the interface between a microfluidic cartridge, thermally conductive, mechanically compliant layer, and a thermal stage.

FIG. 54 shows a close-up of the interface between microfluidic cartridge 1216, thermally conductive, mechanically compliant layer 1222, and thermal stage 1224.

Figure 55:
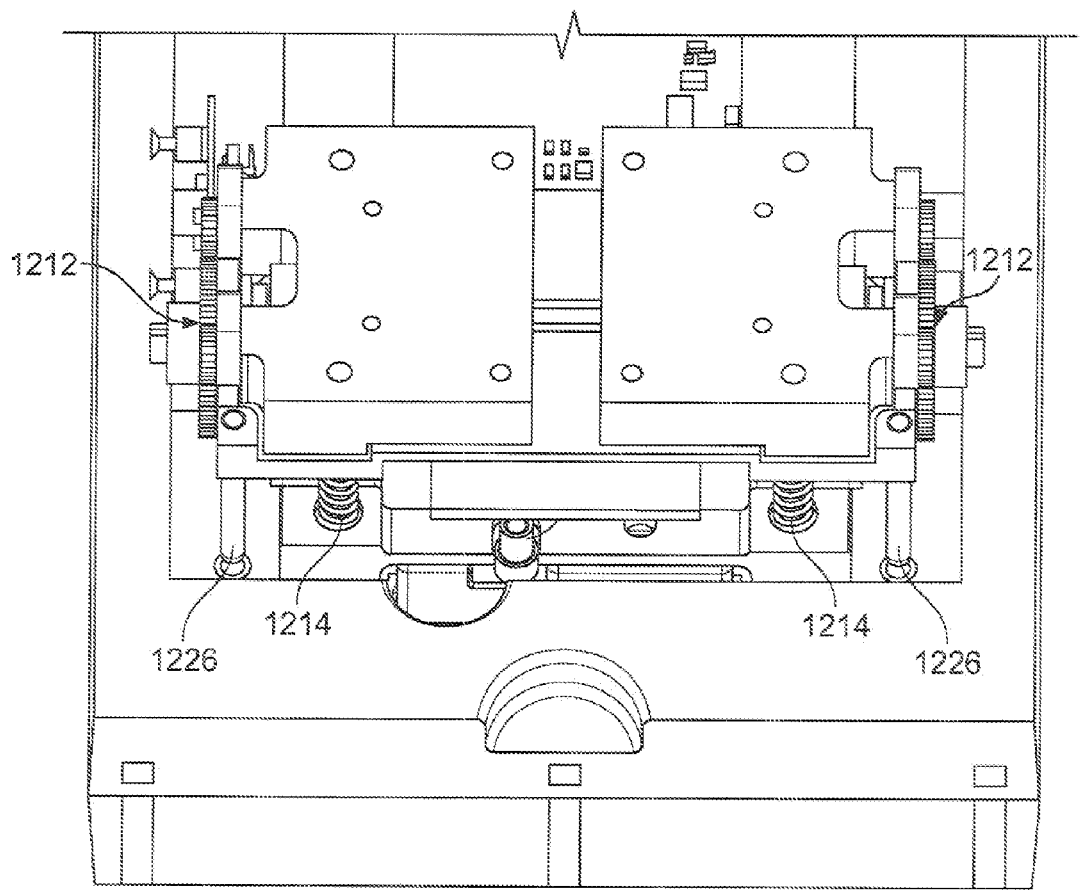
FIG. 55 shows a top view of assembly 1200.

FIG. 55 shows a top view of assembly 1200. In addition to mechanical members 1214, guide members 1226 can be employed.

Figure 56:
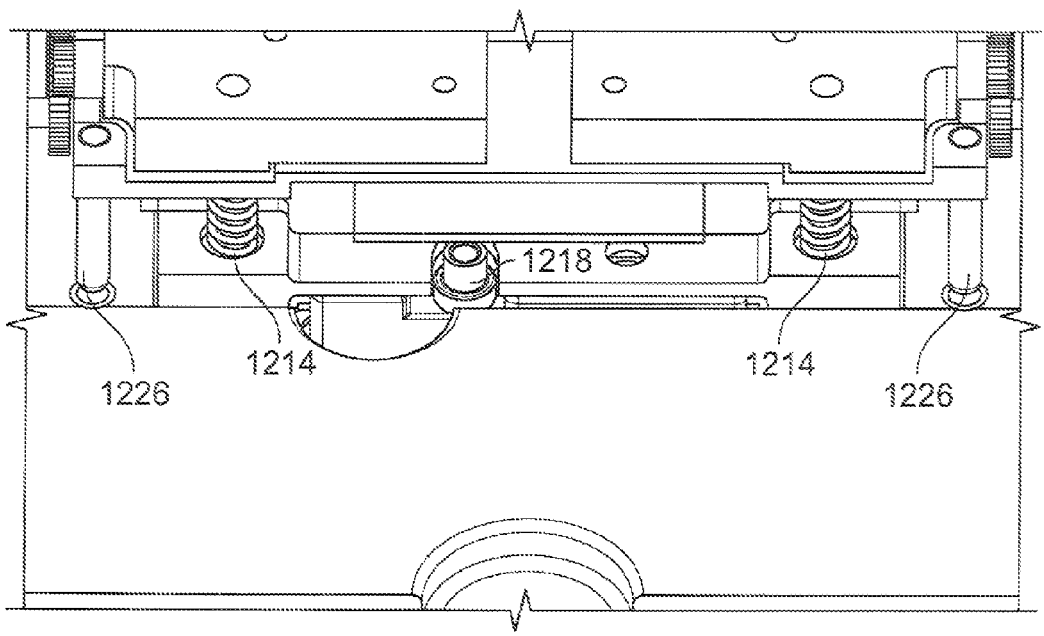
FIG. 56 is a close-up of FIG. 55.

FIG. 56 is a close-up of FIG. 55.

Figure 57:
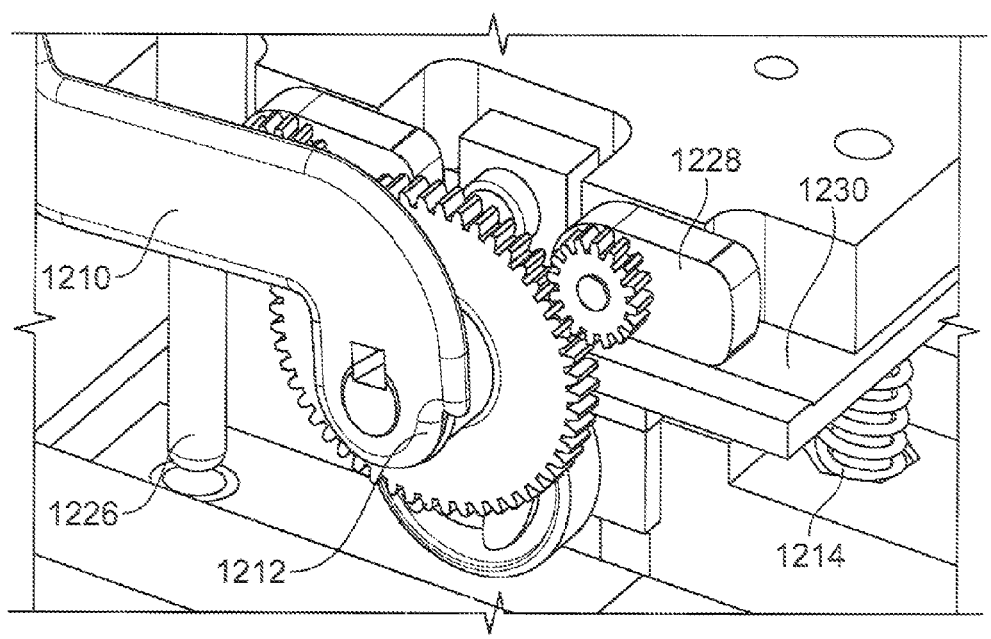
FIGS. 57-59 are a series of pictures of lever 1210 in action. Shown in addition in gear assembly 1212 can be cam 1228, which enables lever 1210 to apply force to plate 1230 coupled to force members 1214.
Figure 58:
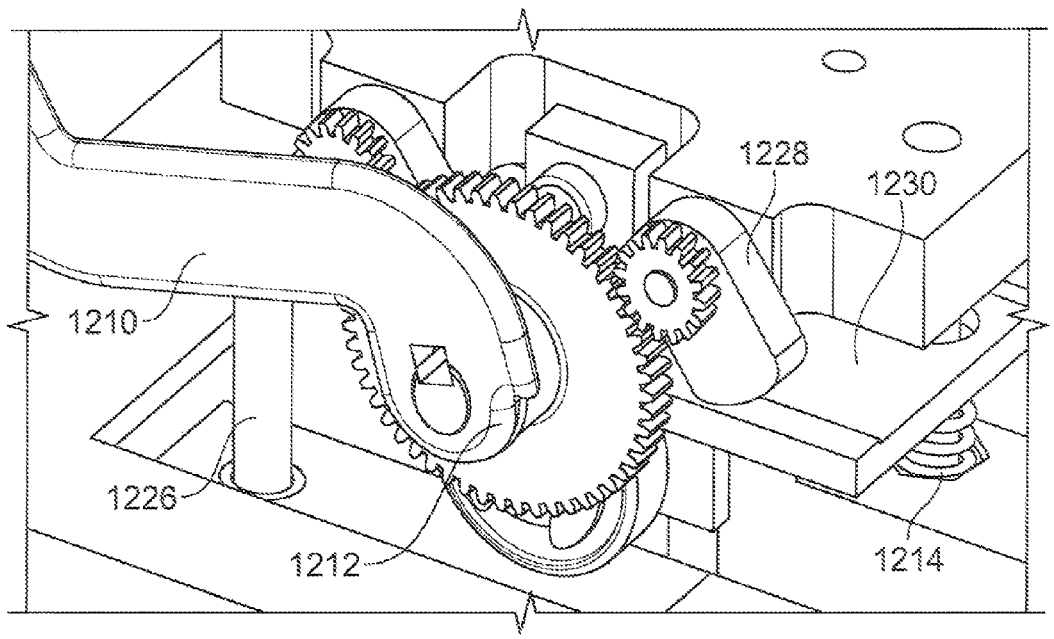
Figure 59:
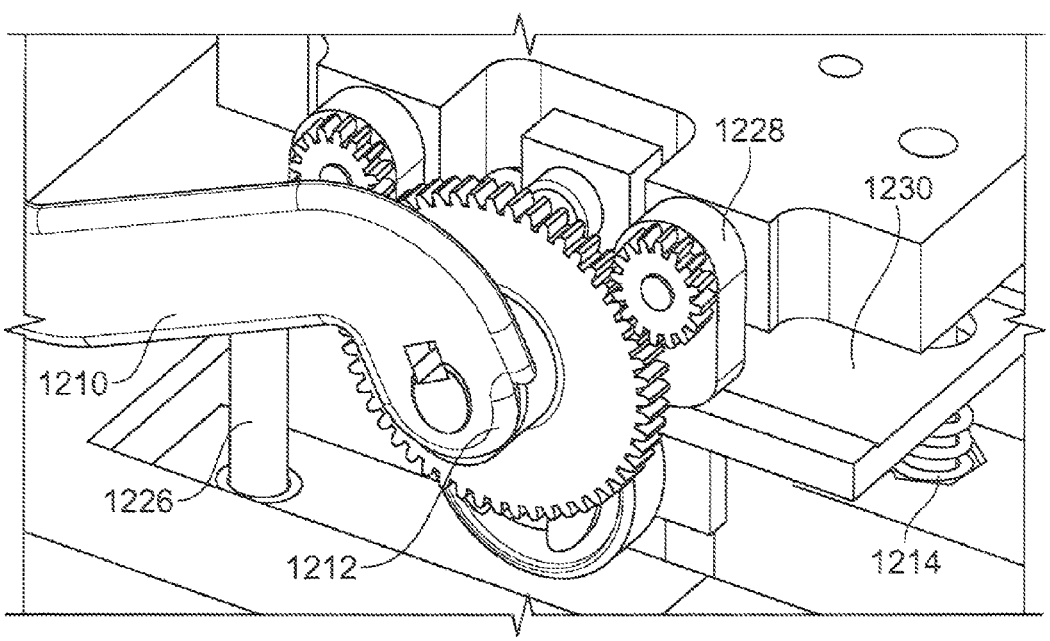

FIGS. 57-59 are a series of pictures of lever 1210 in action. Shown in addition in gear assembly 1212 can be cam 1228, which enables lever 1210 to apply force to plate 1230 coupled to force members 1214.

Figure 60:
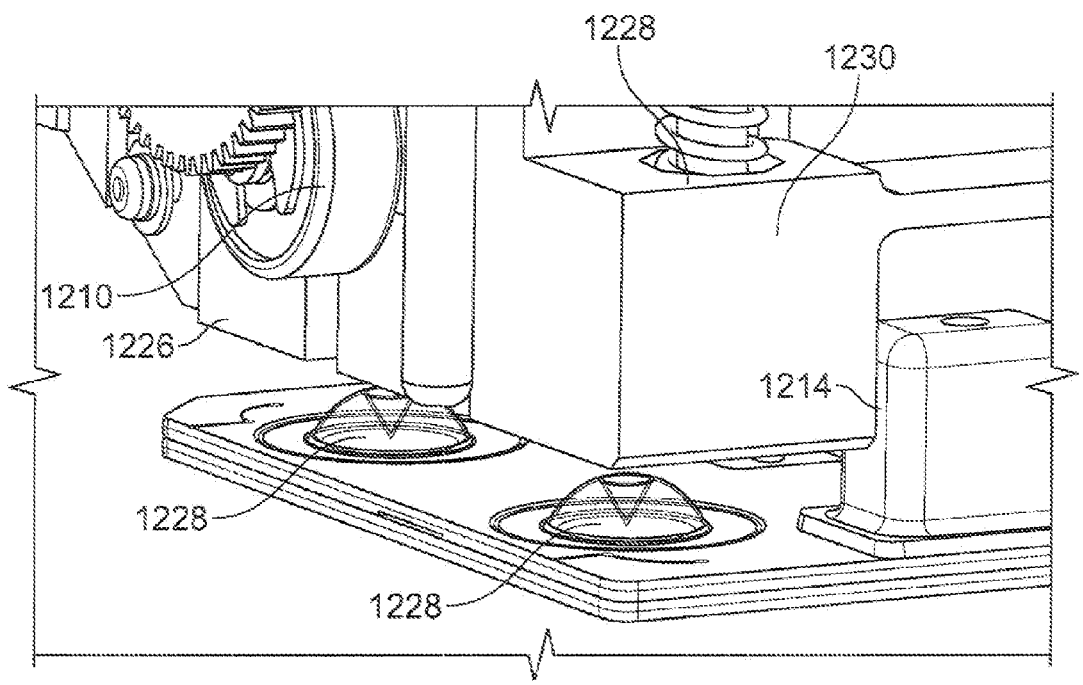
FIGS. 60 and 61 show views of a microfluidic cartridge with self-piercable reservoirs 1228 and mechanical members 1230 for actuating the self piercing reservoirs.
Figure 61:
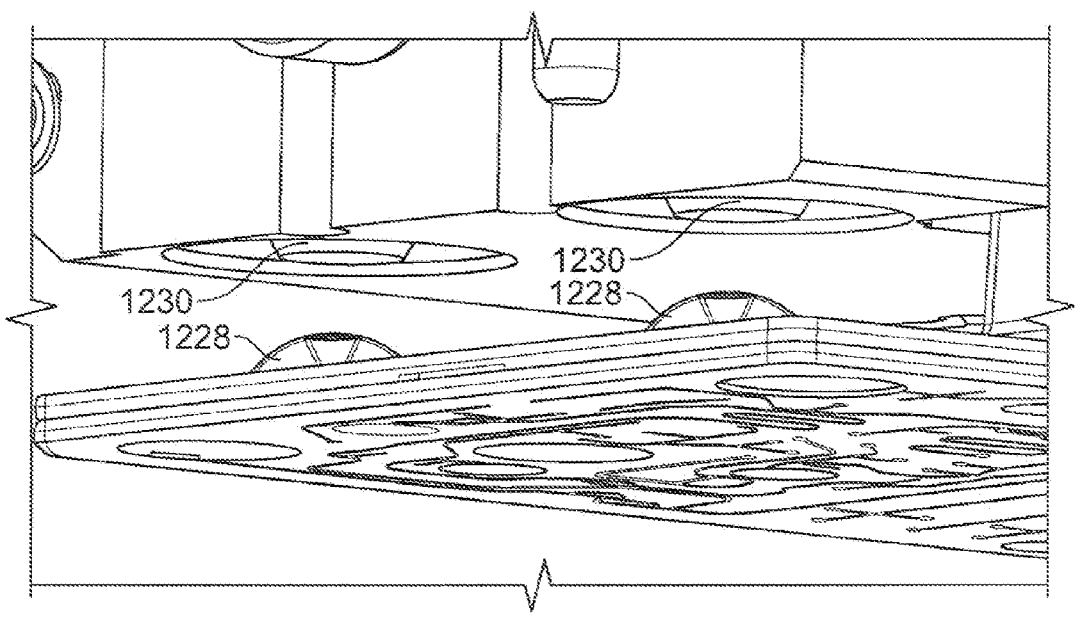

FIGS. 60 and 61 show views of microfluidic cartridge 1216 with self-piercable reservoirs 1228 and mechanical members 1230 for actuating the self piercing reservoirs.

Figure 62:
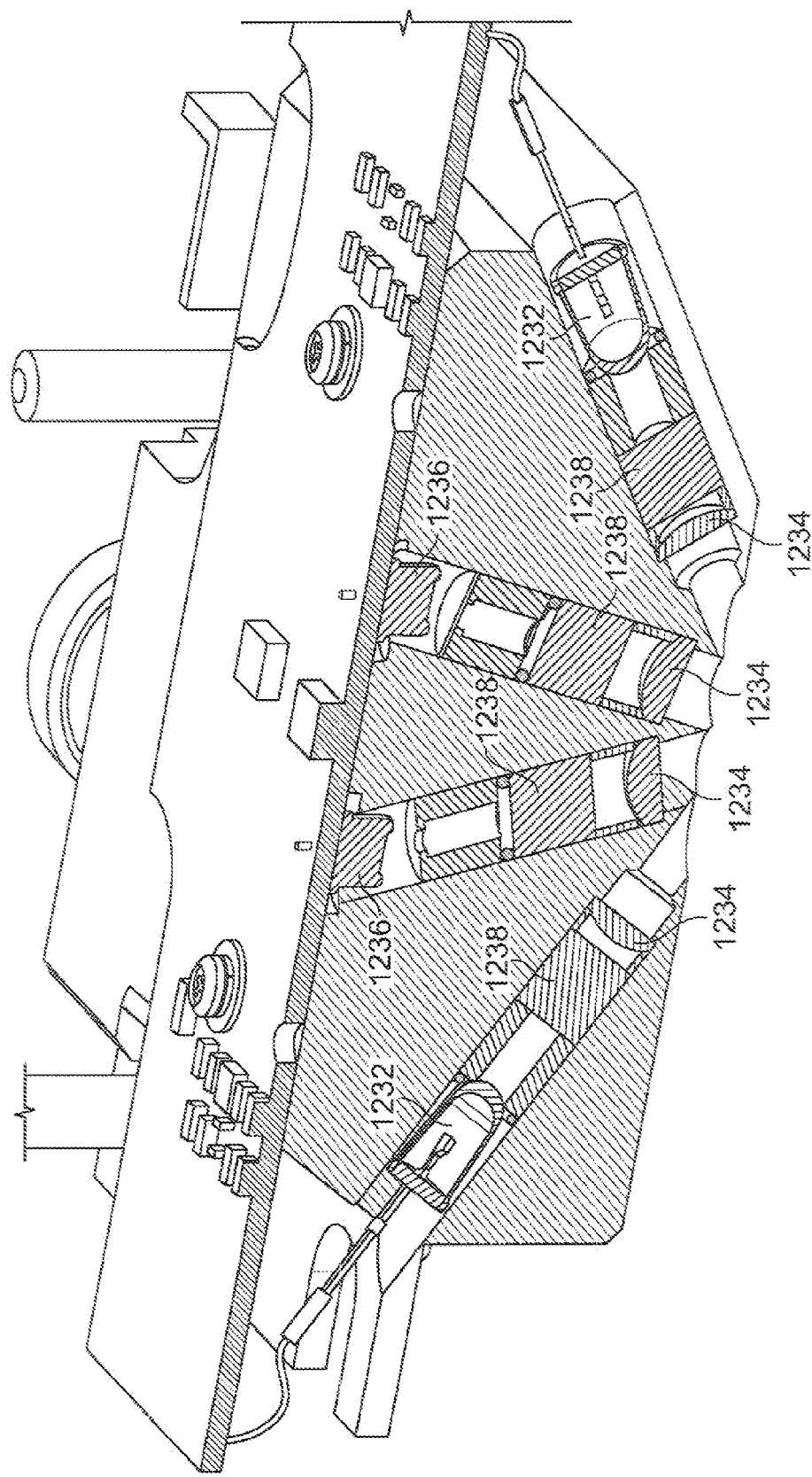
FIGS. 62 and 63 show elements of optical detector elements 1220 including light sources 1232 (for example, light emitting diodes), lenses 1234, light detectors 1236 (for example, photodiodes) and filters 1238.
Figure 63:
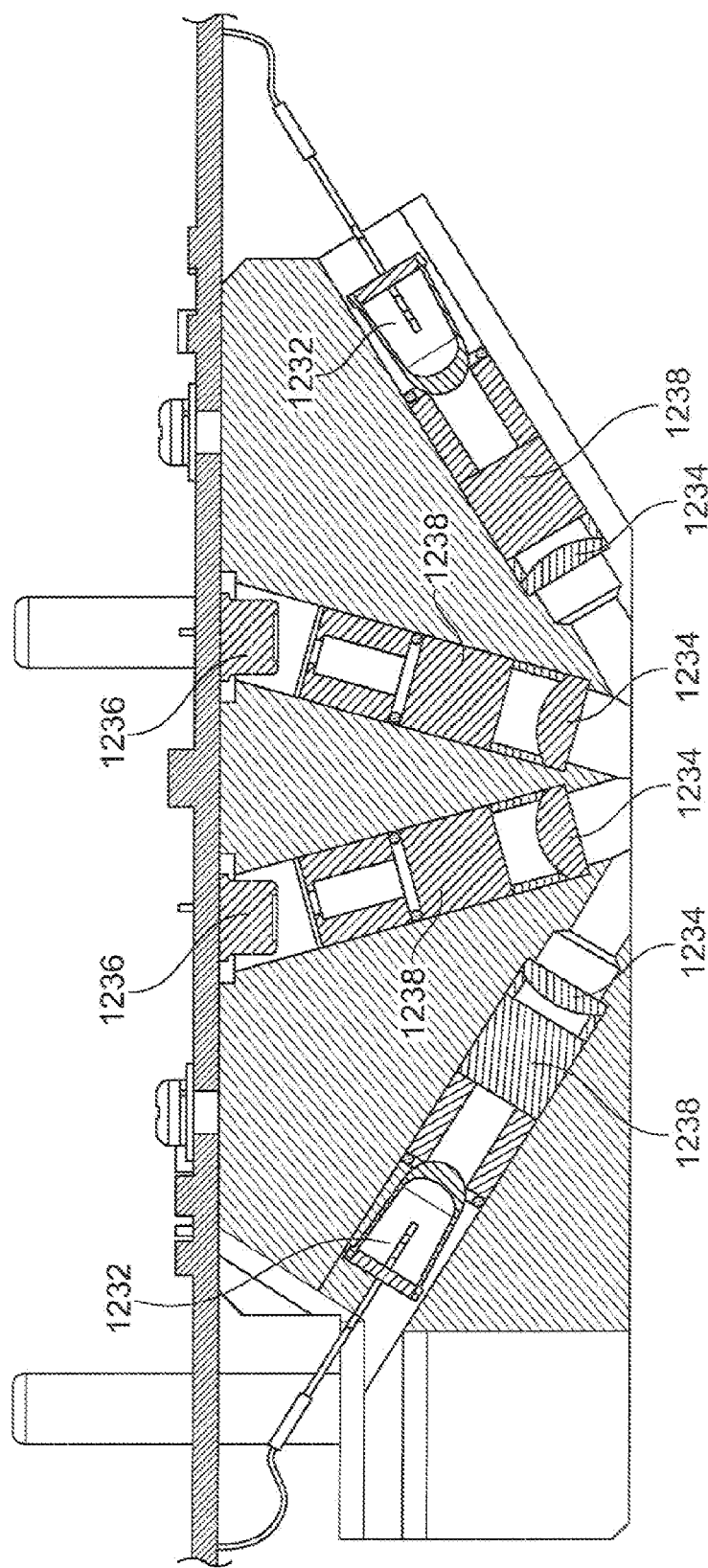

FIGS. 62 and 63 show elements of optical detector elements 1220 including light sources 1232 (for example, light emitting diodes), lenses 1234, light detectors 1236 (for example, photodiodes) and filters 1238. The filters can be, for example, bandpass filters, the filters at the light sources corresponding to the absorption band of one or more fluorogenic probes and the filters at the detectors corresponding to the emission band of the fluorogenic probes.

Example 7

Preparing Retention Member

Carboxylate surface magnetic beads (Sera-Mag Magnetic Carboxylate modified, Part #3008050250, Seradyn) at a concentration of about $10^{11}$ mL$^1$ were activated for 30 minutes using N-hydroxylsuccinimide (NHS) and 1-ethyl-3-(3-dimethylaminopropyl)carbodiimide (EDAC) in a pH 6.1 500 mM 2-(N-Morpholinio)-ethanesulfonic acid (MES) buffer solution. Activated beads were incubated with 3,000 Da or 300,000 Da average molecular weight poly-L-lysine (PLL). After 2 washes to remove unbound PLL, beads were ready for use.

Example 8

Microfluidic Cartridge

Figure 64:
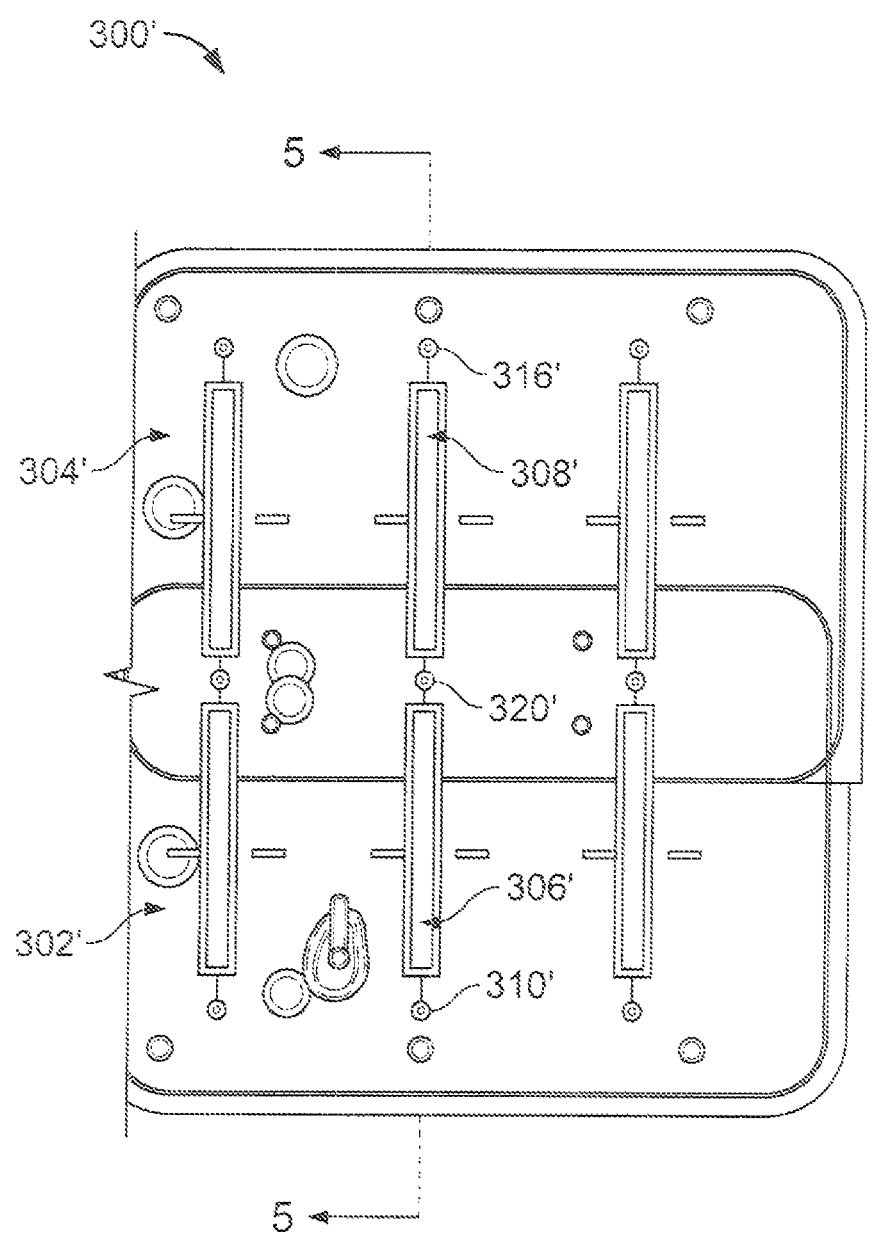
FIG. 64 illustrates a microfluidic device.
Figure 65:
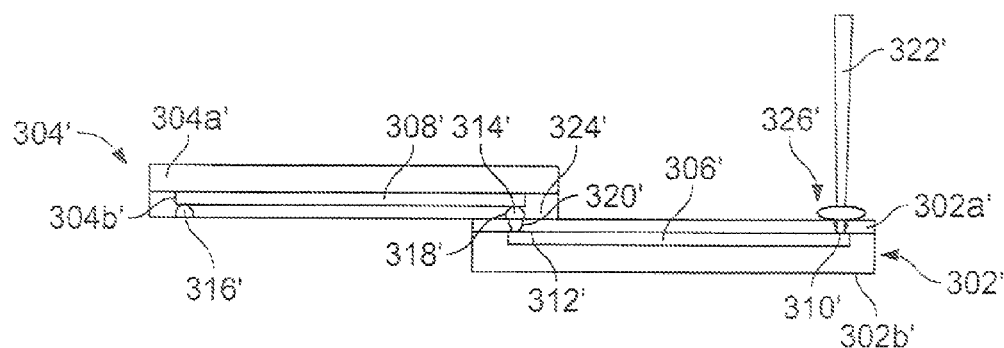
FIG. 65 is a cross-section of the microfluidic device of FIG. 64 taken along 5.

Referring to FIGS. 64 and 65, a microfluidic cartridge 300 was fabricated to demonstrate separation of polynucleotides from inhibitors. Cartridge 300 comprises first and second substrate portions 302', 304', which respectively comprise first and second layers 302a', 302b' and 304a', 304b'. First and second layers 302a', 302b' define a channel 306' comprising an inlet 310' and an outlet 312'. First and second layers 304a', 304b' define a channel 308' comprising an inlet 314' and an outlet 316'. First and second substrate portions 302', 304' were mated using adhesive 324' so that outlet 312' communicated with inlet 314' with a filter 318' positioned therebetween. A portion of outlet 312' was filed with the activated beads prepared above to provide a processing region 320' comprising a retention member (the beads). A pipette 322' (FIG. 66) secured by adhesive 326' facilitated sample introduction.

In use, sample introduced via inlet 310' passed along channel and through processing region 320'. Excess sample material passed along channel 308' and exited device 300' via outlet 316'. Polynucleotides were preferentially retained by the beads as compared to inhibitors. Once sample had been introduced, additional liquids, e.g., a wash liquid and/or a liquid for use in releasing the retained polynucleotides were introduced via inlet 326'.

Example 9

Retention of DNA

Retention of polynucleotides by the poly-L-lysine modified beads of device 300' was demonstrated by preparing respective devices comprising processing regions having a volume of about 1 µL including about 1000 beads. The beads were modified with poly-L-lysine of between about 15,000 and 30,000 Da. Each processing region was filled with a liquid comprising herring sperm DNA (about 20 uL of sample with a concentration of about 20 mg/mL) thereby placing the beads and liquid in contact. After the liquid and beads had been in contact for 10 minutes, the liquid was removed from each processing region and subjected to quantitative real-time PCR to determine the amount of herring sperm DNA present in the liquid.

Two controls were performed. First, an otherwise identical processing region was packed with unmodified beads, i.e., beads that were identical with the poly-L-lysine beads except for the activation and poly-L-lysine incubation steps. The liquid comprising herring sperm DNA was contacted with these beads, allowed to stand for 10 minutes, removed, and subjected to quantitative real-time PCR. Second, the liquid comprising the herring sperm DNA ("the unprocessed liquid") was subjected to quantitative real-time PCR.

Figure 66:
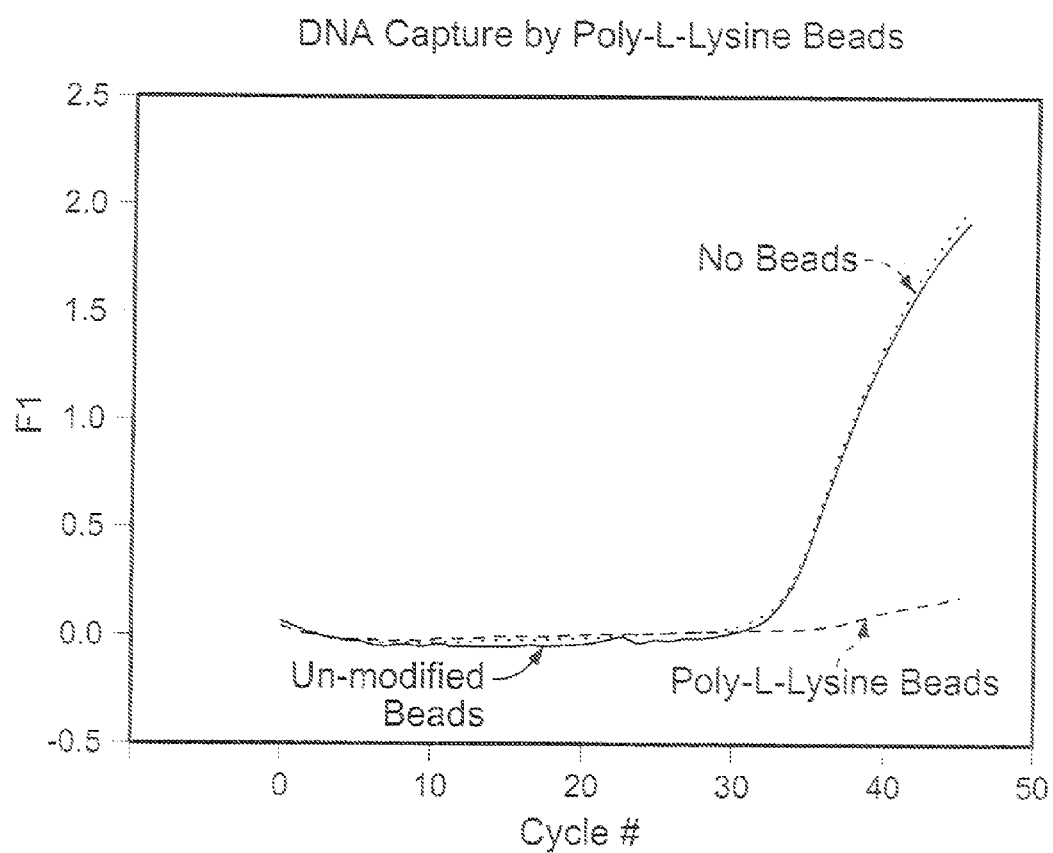
FIG. 66 illustrates the retention of herring sperm DNA.

Referring to FIG. 66, the first and second controls exhibited essentially identical responses indicating the presence of herring sperm DNA in the liquid contacted with the unmodified beads and in the unprocessed liquid. The liquid that had contacted the 3,000 poly-L-lysine beads exhibited a lower response indicating that the modified beads had retained substantially all of the herring sperm DNA. The PCR response of the liquid that had contacted the 300,000 Da poly-L-lysine beads exhibited an amplification response that was at least about 50% greater than for the 3,000 Da beads indicating that the lower molecular weight surface modification was more efficient at retaining the herring sperm DNA.

Example 10

Releasing DNA from Poly-L-Lysine Modified Beads

Devices having processing regions were packed with 3,000 Da poly-L-lysine modified beads. Liquid comprising polynucleotides obtained from group B *streptococci* (GBS) was contacted with the beads and incubated for 10 minutes as above for the herring sperm DNA. This liquid had been obtained by subjecting about 10,000 GBS bacteria in 10 µl of 20 mM Tris pH 8, 1 mM EDTA, 1% Triton X-100 buffer to thermal lysing at 97° C. for 3 min.

After 10 minutes, the liquid in contact with the beads was removed by flowing about 10 µl of wash solution (Tris-EDTA pH 8.0 with 1% Triton X 100) through the processing region. Subsequently, about 1 µl of 5 mM NaOH solution was added to the processing region. This process left the packed processing region filled with the NaOH solution in contact with the beads. The solution in contact with the beads was heated to 95° C. After 5 minutes of heating at 95° C., the solution in contact with the beads was removed by eluting the processing region with a volume of solution equal to three times the void volume of the processing region.

Figure 67:
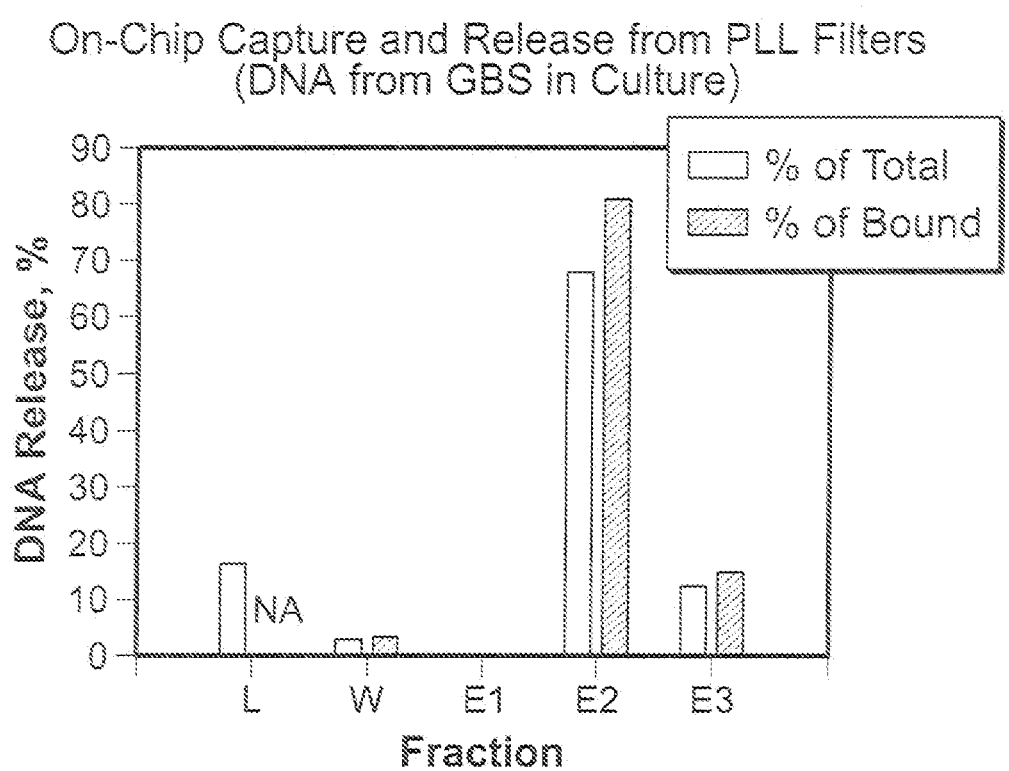
FIG. 67 illustrates the retention and release of DNA from group B *streptococci;*

Referring to FIG. 67, five aliquots of solution were subjected to quantitative real-time PCR amplification. Aliquots E1, E2, and E3 each contained about 1 µl of liquid. Aliquot L was corresponds to liquid of the original sample that had passed through the processing region. Aliquot W was liquid obtained from wash solution without heating. Aliquot E1 corresponds to the dead volume of device 300, about equal to the volume of channel 308. Thus, liquid of aliquot E1 was present in channel 308 and not in contact with the beads during heating. This liquid had passed through the processing region prior to heating. Aliquot E2 comprises liquid that was present within the processing region and in contact with the beads during heating. Aliquot E3 comprises liquid used to remove aliquot E2 from the processing region.

As seen in FIG. 67, more than 65% of the GBS DNA present in the initial sample was retained by and released from the beads (Aliquot E2). Aliquot E2 also demonstrates the release of more than 80% of the DNA that had been retained by the beads. Less than about 18% of the GBS DNA passed through the processing region without being captured. The wash solution without heating comprised less than 5% of the GBS DNA (Aliquot W).

Example 11

Separation of Polynucleotides and Inhibitors

Buccal cells from the lining of the cheeks provide a source of human genetic material (DNA) that may be used for single nucleotide polymorphism (SNP) detection. A sample comprising buccal cells was subjected to thermal lysing to release DNA from within the cells. Device 300 was used to separate the DNA from concomitant inhibitors as described above. A cleaned-up sample corresponding to aliquot E2 of FIG. 67 was subjected to polymerase chain reaction. A control or crude sample as obtained from the thermal lysing was also amplified.

Figure 68:
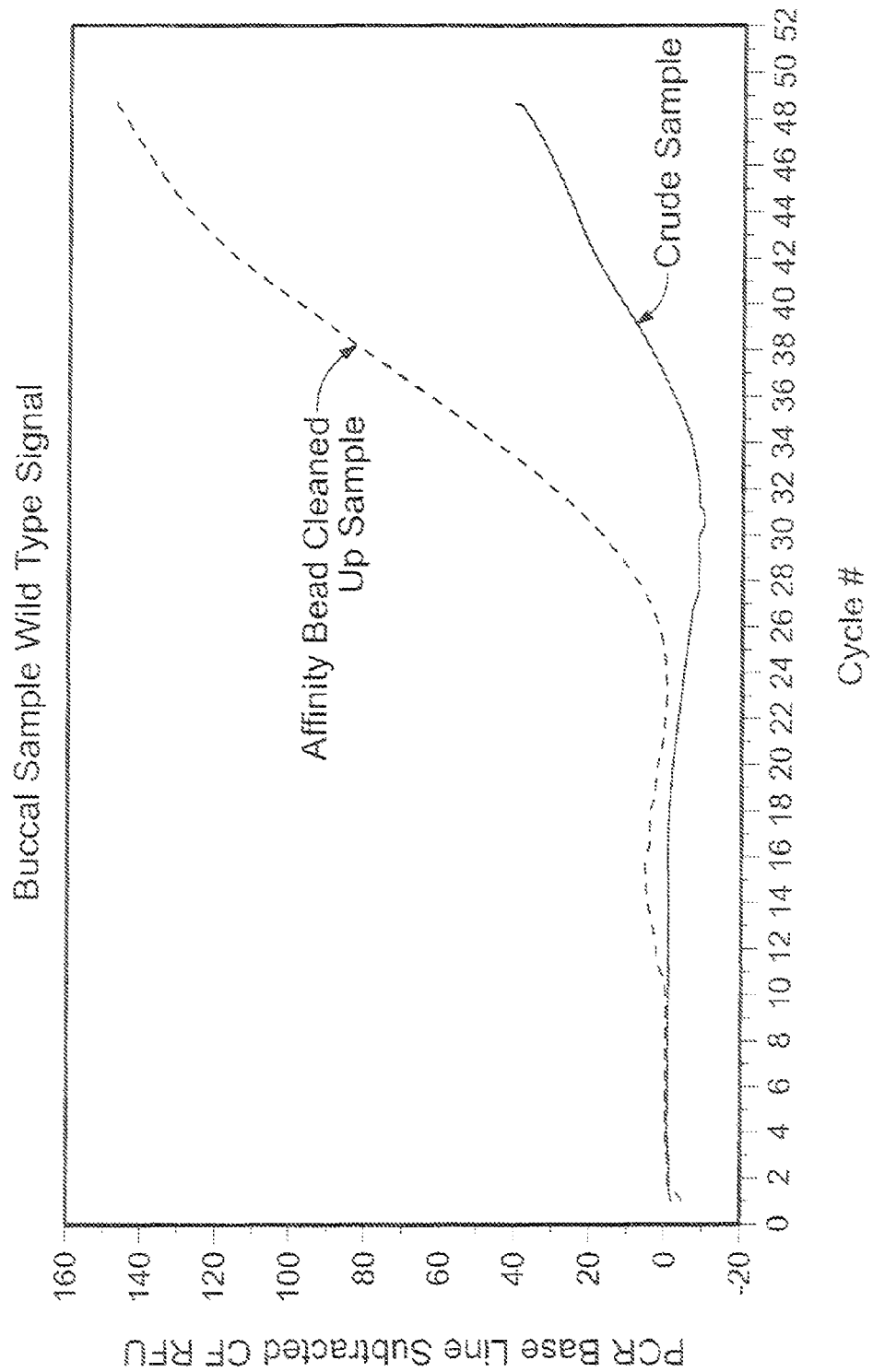
FIG. 68 illustrates the PCR response of a sample from which inhibitors had been removed and of a sample from which inhibitors had not been removed.

Referring to FIG. 68, the cleaned-up sample exhibited substantially higher PCR response in fewer cycles than did the control sample. For example, the clean-up sample exceeded a response of 20 within 32 cycles whereas the control sample required about 45 cycles to achieve the sample response.

Blood acts as a sample matrix in variety of diagnostic tests including detection of infectious disease agents, cancer markers and other genetic markers. Hemoglobin present in blood samples is a documented potent inhibitor of PCR. Two 5 ml blood samples were lysed in 20 mM Tris pH 8, 1 mM EDTA, 1% SDS buffer and introduced to respective devices 300, which were operated as described above to prepare two clean-up samples. A third 5 ml blood sample was lysed and prepared using a commercial DNA extraction method Puregene, Gentra Systems, MN. The respective cleaned-up samples and sample subjected to the commercial extraction method were used for a Allelic discrimination analysis (CYP2D6*4 reagents, Applied Biosystems, CA). Each sample contained an amount of DNA corresponding to about 1 ml of blood.

Figure 69:
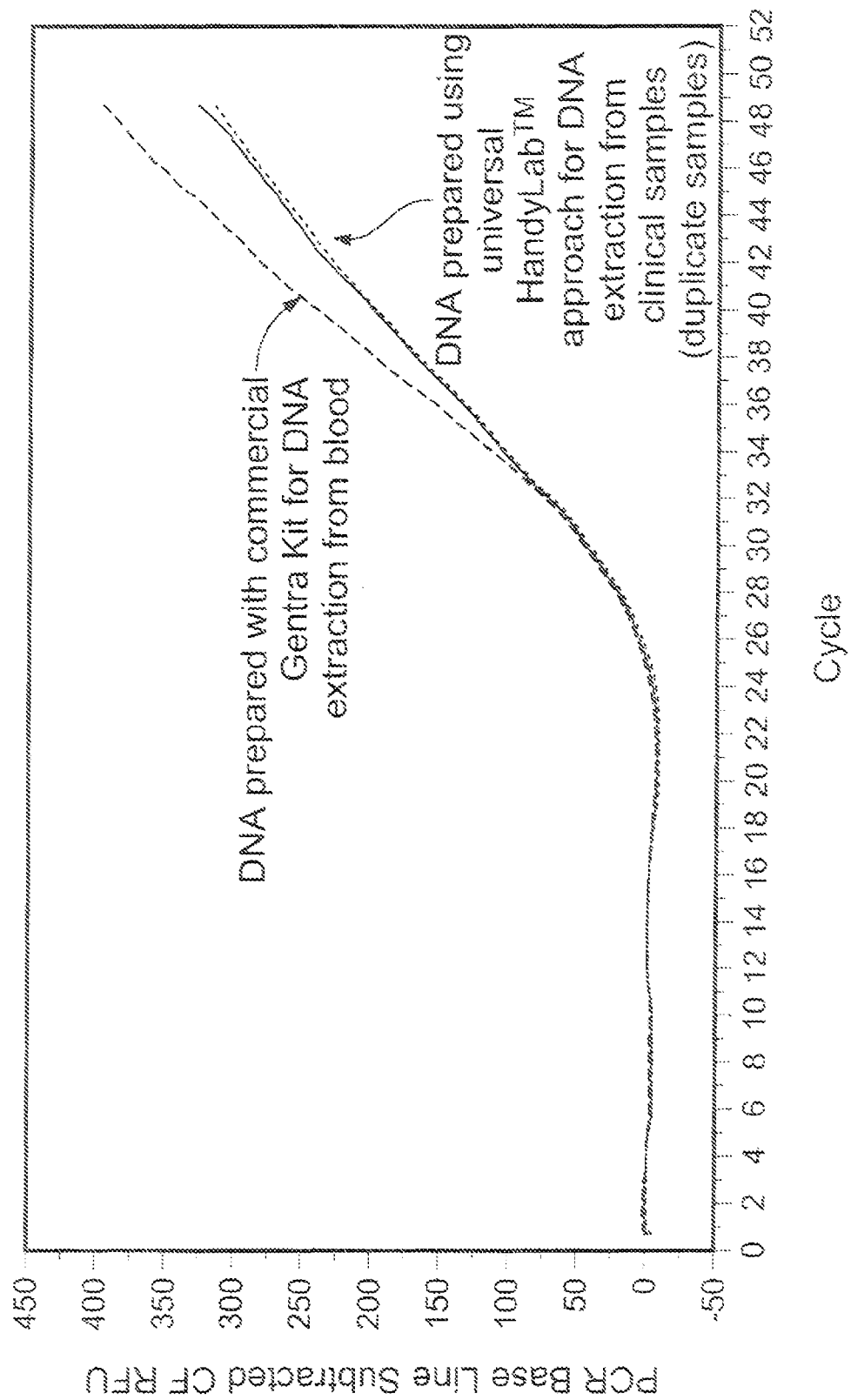
FIG. 69 illustrates the PCR response of a sample prepared in accord with the technology described herein and a sample prepared using a commercial DNA extraction method.

Referring to FIG. 69, the cleaned-up and commercially extracted samples exhibited similar PCR response demonstrating that the processing region of device 300' efficiently removed inhibitors from the blood samples.

Example 12

Protease Resistant Retention Member

The preparation of polynucleotide samples for further processing often includes subjecting the samples to protease treatment in which a protease cleaves peptide bonds of proteins in the sample. An exemplary protease is pronase, a mixture of endo- and exo-proteases. Pronase cleaves most peptide bonds. Certain ligands, such as poly-L-lysine can be susceptible to rupture by pronase and other proteases. Thus, samples are generally not subjected to protease treatment in the presence of the retention member if the ligands bound thereto are susceptible to the proteases.

Poly-D-lysine, the dextro enantiomer of poly-lysine resists cleavage by pronase and other proteases. The ability of a retention member comprising bound poly-D-lysine to retain DNA even when subjected to a protease treatment was studied.

Eight (8) samples were prepared. A first group of 4 samples contained 1000 GBS cells in 10 µl buffer. A second group of 4 samples contained 100 GBS cells in 10 µl buffer. Each of the 8 samples was heated to 97° C. for 3 min to lyse the GBS cells. Four (4) sample sets were created from the heated samples. Each sample set contained 1 sample from each of the first and second groups. The samples of each sample sets were treated as follows.

Figure 70A:
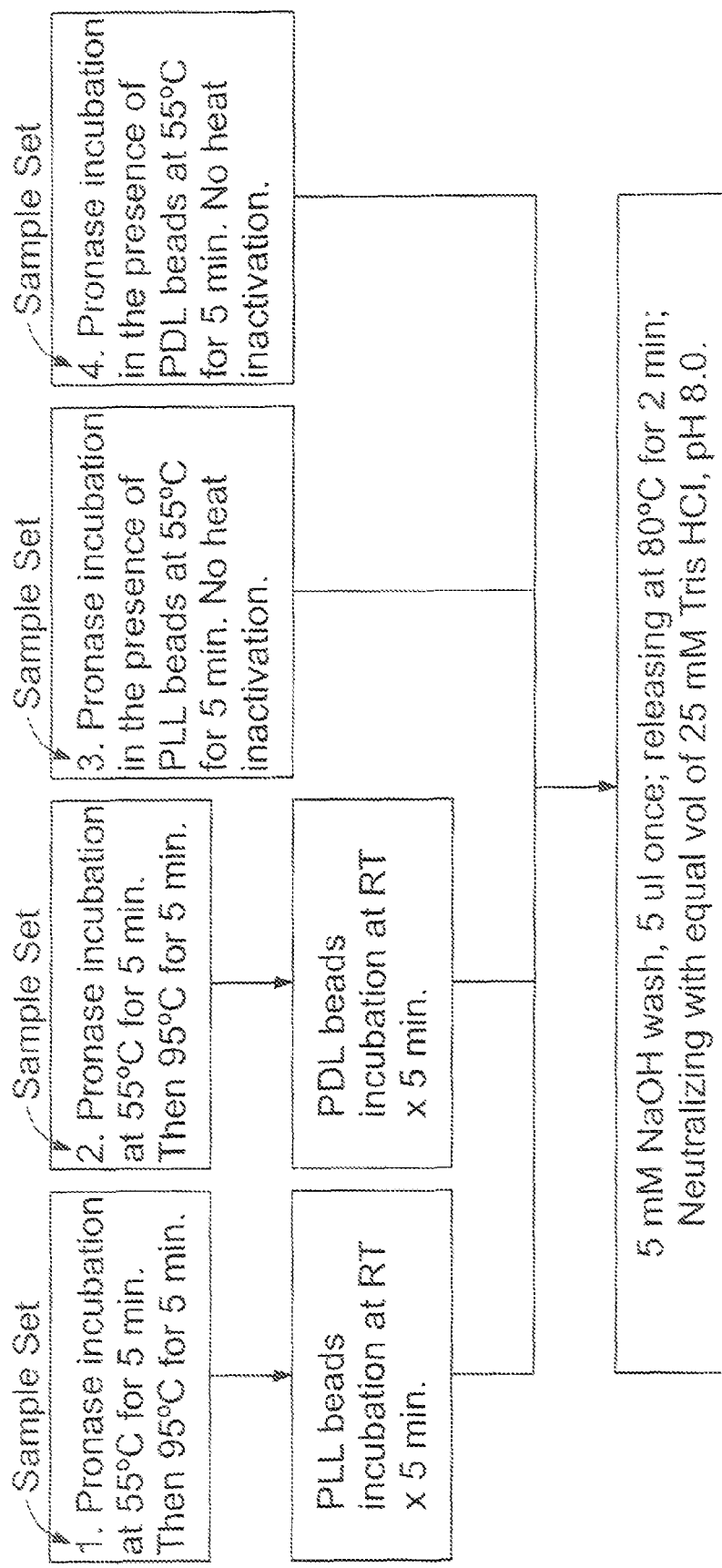
FIG. 70A illustrates a flow chart showing steps performed during a method for separating polynucleotides and inhibitors.

Referring to FIG. 70A, the samples of sample set 1 were subjected to pronase incubation to prepare respective protein cleaved samples, which were then heated to inactivate the proteases. The protein-cleaved, heated samples were contacted with respective retention members each comprising a set of poly-L-lysine modified beads. After 5 minutes, the respective sets of beads were washed with 5 microliters of a 5 mM NaOH solution to separate inhibitors and products of protein cleavage from the bound DNA. The respective sets of beads were each contacted with a second aliquot of NaOH solution and heated to 80° C. for 2 minutes to release the DNA. The solutions with released DNA were neutralized with an equal volume of buffer. The neutralized solutions were analyzed to determine the efficiency of DNA recovery. The results were averaged and shown in FIG. 70B.

The samples of sample set 2 were subjected to pronase incubation to prepare respective protein cleaved samples, which were then heated to inactivate the proteases. The protein-cleaved, heated samples were contacted with respective retention members each comprising a set of poly-D-lysine modified beads. After 5 minutes, the respective sets of beads were washed with 5 microliters of a 5 mM NaOH solution to separate inhibitors and products of protein cleavage from the bound DNA. The respective sets of beads were each contacted with a second aliquot of NaOH solution and heated to 80 (eighty) ° C. for 2 minutes to release the DNA. The solutions with released DNA were neutralized with an equal volume of buffer. The neutralized solutions were analyzed to determine the efficiency of DNA recovery. The results were averaged and shown in FIG. 70B.

The samples of sample set 3 were subjected to pronase incubation to prepare respective protein cleaved samples. The proteases were not deactivated either thermally or chemically. The protein-cleaved samples were contacted with respective retention members each comprising a set of poly-L-lysine modified beads. After 5 minutes, the respective sets of beads were washed with 5 microliters of a 5 mM NaOH solution to separate inhibitors and products of protein cleavage from the bound DNA. The respective sets of beads were each contacted with a second aliquot of NaOH solution and heated to 80 (eighty) ° C. for 2 minutes to release the DNA. The solutions with released polynucleotides were each neutralized with an equal volume of buffer. The neutralized solutions were analyzed to determine the efficiency of DNA recovery. The results were averaged and shown in FIG. 70B.

The samples of sample set 4 were subjected to pronase incubation to prepare respective protein cleaved samples. The proteases were not deactivated either thermally or chemically. The protein-cleaved samples were contacted with respective retention members each comprising a set of poly- D-lysine modified beads. After 5 minutes, the respective sets of beads were washed with 5 microliters of a 5 mM NaOH solution to separate inhibitors and products of protein cleavage from the bound DNA. The respective sets of beads were each contacted with a second aliquot of NaOH solution and heated to 80 (eighty) ° C. for 2 minutes to release the DNA. The solutions with released polynucleotides were each neutralized with an equal volume of buffer. The neutralized solutions were analyzed to determine the efficiency of DNA recovery. The results were averaged and shown in FIG. 70B.

Figure 70B:
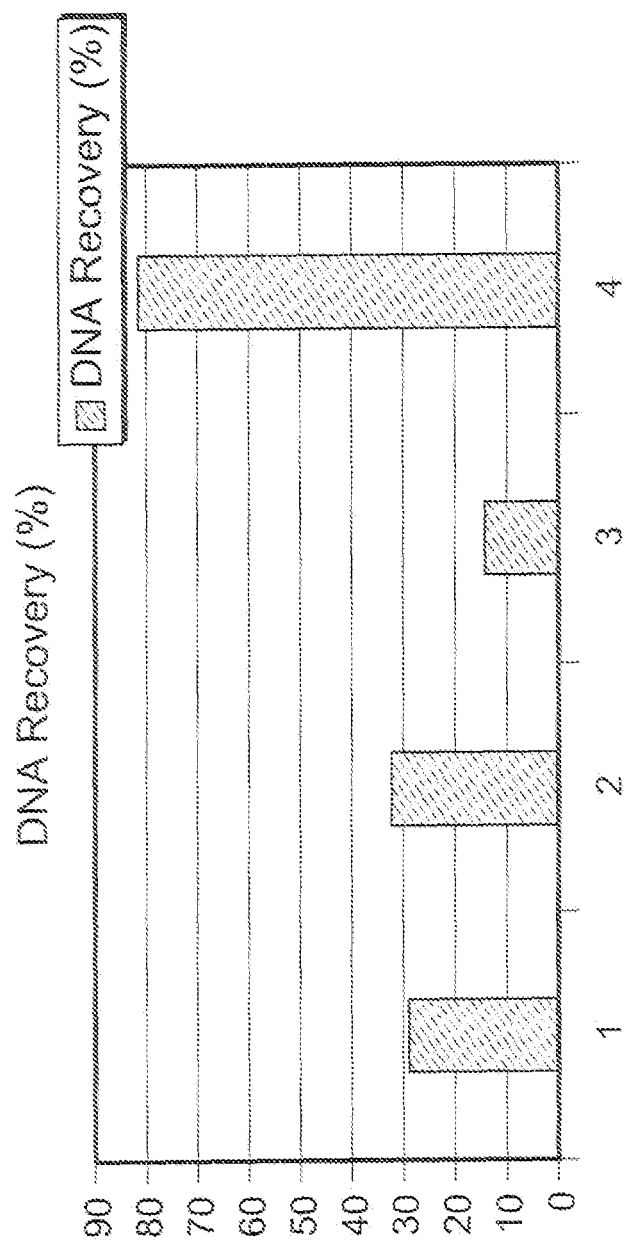
FIG. 70B illustrates DNA from samples subjected to the method of FIG. 26A.

As seen in FIG. 70B, an average of more than 80% of DNA from the GBS cells was recovered using sample set 4 in which the samples were contacted with poly-D-lysine modified beads and subjected to pronase incubation in the presence of the beads without protease inactivation. The recovery efficiency for sample set 4 can be more than twice as high as for any of the other samples. Specifically, the recovery efficiencies for sample sets 1, 2, 3, and 4, were 29%, 32%, 14%, and 81.5%, respectively. The efficiencies demonstrate that high recovery efficiencies can be obtained for samples subjected to protease incubation in the presence of a retention member that retains DNA.

Example 13

Operator's Manual for Apparatus for Polynucleotide Processing

This non-limiting example describes, in the form of an operator's manual, various embodiments of the claimed apparatus, microfluidic cartridge, kit, methods, and computer program product, in particular directed to a single cartridge system including a microfluidic PCR assay for the qualitative detection of microorganisms, such as Group B *Streptococcus* (GBS). Further descriptions pertinent to GBS analysis are presented in Example 14.
Sample Preparation Kit, which may Include
    Sample vial containing buffer and preservative
    Collection Swab with instructions for patient self-collection.
    A number (e.g., 25) of syringes with filter
    Vials containing buffer.
    Patient ID labels for the collection vials
    3 cc syringes.
    Microfluidic cartridge, as further described herein.
External Control Sample Kits, which may Include
    Positive Control Swab specimen containing Limit of Detection sample of, e.g., GBS bacteria in dehydrated form;
        Vials containing buffer with POSITIVE identification on vial;
        Vials containing buffer with NEGATIVE identification on vial; and
        Syringes.
Equipment:
    System with Barcode reader, both of which as further described herein, fitted with, e.g., a 115V or 220V power cord.
Additional Optional Equipment:
Printer with USB connection
Hospital Network connection
Exemplary Use & Indications for Use
    The description in this example, is suitable to test samples for presence of GBS, further details of which are provided in Example 14.
Explanation of Test Application
    The apparatus and materials can be used to test for a variety of pathogens and micro-organisms, as further described herein. One example is to test for GBS, as further described in Example 14. The tests can be performed in the near-patient setting by clinicians who are not extensively trained in laboratory procedures. A QC routine can be built into the User Interface of the system in order provide continued Quality Assurance for the GBS test. The test can also be performed in a central hospital "stat" laboratory, provided that the sample testing occurs within the time-frame required by the physician requesting the test.
Exemplary Warnings & Precautions
    Other warnings and precautions specific to GBS are presented in Example 14.
        In some embodiments, if a patient is currently being treated with antibiotics, the test may be a unreliable indicator of a disease state.
        Typically, avoid use of the cartridge/sample kit beyond expiration date.
        Typically, avoid using cartridge that was previously opened. Air & moisture exposure can degrade the reagents. Avoid opening the cartridge until after the sample is ready to be injected.
        Typically, use new syringe materials for sample preparation.
        Typically, use swabs and buffer provided in test kit. In some embodiments, other brands of collection swabs may interfere with the test performance
        When a specimen must be stored, refrigeration at 4° C. for a duration of up to 24 hours is typically indicated.
        Typically, use protective clothing and disposable gloves while handling the components of the system and specimen.
        Typically, use aseptic technique. It can be especially important to use new disposable gloves to avoid contamination of the test specimen or test materials.
        Typically, avoid injecting the sample with high pressure. Gentle injection is preferred.
        Typically, handle specimens using Universal Precautions in accordance with safe hospital procedures for potentially infectious specimens.
        Typically, use recommended cleaning agents when cleaning the system.
        Typically, avoid cleaning the test cartridge with any cleaning chemical if spill occurs. If necessary, use a dry lab tissue to remove liquids.
Typical Storage and Stability Conditions

| Product Description | Storage/Use Condition | Stability | Transport condition |
|---|---|---|---|
| System | 15-35° C., operational range | NA | −10° C. to 65° C. |
| GBS Sampling Kits | 4-40° C. Do not freeze. | Expiration date | Temp >4° C. |
| Patient or QC Specimen in buffer (wet) | @ 15-30° C. | 8 hours | |
| Patient Specimen or QC in buffer (wet) | @ 4° C. | 24 hours | |
| Patient Specimen in container (dry) | @ 15-30° C. | 24 hours | |
| Patient Specimen in container (dry) | @ 4° C. | | |
| GBS Car-fridges - unopened | 4-30° C. Do not freeze, | Expiration date | Temp >4° C. |

| Product Description | Storage/Use Condition | Stability | Transport condition |
|---|---|---|---|
| GBS Cartridges - unopened | Do not use. | 60 minutes maximum | |
| GBS Control Kits | 15-30° C. | Expiration date | Protection TBD |

Exemplary Specimen Collection
  Precaution: Avoid touching Dacron® end of swab with fingers.
  Remove swab from packaging
  Wipe away excess vaginal secretions.
  Insert swab 2 cm into vagina. (front passage).
  Insert same swab 1 cm into anus. (back passage)
  Place swab in transport package if stored dry.
Exemplary Specimen Preparation
  Use aseptic technique when handling test materials and specimen.
  Confirm sample buffer is not expired.
  Dip swab vigorously 20 times into vial containing 1 cc buffer
  Remove and discard swab.
  Label vial with Patient ID and time of collection, if required by clinical standard procedure.
  Precaution: Avoid opening cartridge package until ready to use. Onboard reagents may be sensitive to light and moisture.
Exemplary System Operation Instructions
  System Ready screen may be shown.
  Touch the screen to stop the screen saver.
  Raise the Handle and Open Lid of the System to begin.
  A self-test of the system may begin once the lid is fully opened and an "open" indicator, if present, is on.
  Inspect the system for any used cartridges remaining from a previous test.
  Log-in with User ID and Password.
  Scan sample collection vial bar-code.
  Open test cartridge. Scan cartridge barcode.
  System may present an error message if materials are expired and/or if specimen vial and test materials are not appropriately matched
  Confirm sample ID with patient information.
  Enter the patient ID and other hospital identifying information, if requested.
Exemplary Instructions for Transferring Sample to Cartridge:
  Put on a new pair of gloves.
  Place sample vial on counter.
  Attach tip onto syringe. Draw entire sample into syringe. Draw in additional 2 cc of air into the syringe.
  Remove tip and attach filter.
  Inject. 1 cc sample into cartridge using syringe and an additional 2 cc air.
  Precaution: use gentle pressure to inject sample to avoid backsplash from sample.
  Exemplary instructions for performing test:
  Gently rock the cartridge back and forth until pellets are dissolved.
  Place Cartridge on the System
  Close Cover of the System
  (Test may begin automatically)
  Results
  When test is complete, results may be available for display or print out.
  Disposal of Materials: Used Cartridge and collection kit can be treated as biohazard Preparing Materials for Shipment
  Cartridge should typically be packaged in biohazard protective materials as described by the International Standards.
Exemplary Cleaning Procedure for System
  A solution of 10% bleach (0.5% sodium hypochlorite), followed by a clean water rinse can be used to disinfect as well as reduced potential DNA contamination.
  DNA contamination can typically be accomplished by cleaning with bleach or materials suitable for eliminating DNA contamination. Chemicon™ Nucleic acid removers can also be used to be used after cleaning with ordinary disinfectants.
  Typically, alcohol or ordinary sanitary wipes will not reduce DNA contamination of the instrument.
Exemplary Reagent Lot Verification
  Purpose—Assessment of cartridge and sample kit lots and verification of total system performance.
  Recommendation: Upon receipt of a new lot of cartridges or sample kits, a quality control set can be run to confirm, for example, whether the reagent set includes (1) external control and (1) negative external control.
Exemplary Quality Control Routine
  The external positive control serves to monitor and calibrate the sensitivity of the specimen preparation steps and the assay, and can be used to minimize the risk of false negative results. If the test fails, it may invalidate the results from that batch of cartridges, and should be reported to the supplier.
  Purpose—Verification of total system performance including assessment of sample handling technique. Test can be performed at a User selected preset interval.
  Recommendation: When test is performed, run a QC set including (1) Positive external control and (1) Negative external control, If QC test fails to yield expected results, contact manufacturer.
Exemplary Quality Control Routine Directions
  Go to Quality Control Screen
  Enter User ID
  Select QC Tech verification, New Reagent Lot, Daily QC
    Run samples as directed on screens.
System Self-Test
  The System may perform a System initiation test when it is powered up. As the Start Up Routine of each Patient Test Sample or QC Sample, the System may run a self-test to determine if, for example, the electronics, optical system, heaters and temperature sensors are functioning as intended.
Exemplary Internal Controls (On-Cartridge)
  Reagents which can be used in the assay may be included on the cartridge to reduce the potential for user handling errors and contamination. Two types of on-cartridge positive and negative controls strategies can be incorporated within each microfluidic cartridge to monitor individual PCR assay performance. Two examples are:
  1) Positive Internal control plasmid (ICP): An internal control plasmid can provide a control for integrity of the PCR assay reagents as well as being an indicator for presence of PCR inhibitory substances in the specimen, i.e. it can be a control for false negative results. During thermocycling, amplification of this region may produce a distinct fluorogenic signal in both PCR lanes. Failure to amplify the internal control sequence, in the absence of a positive sample, can be indicative of either a failure of the reagent mix or presence of PCR inhibitors in the specimen. This can invalidate the results of the test as indicated by an error code on the instrument. "IND" can be displayed to report an indeterminate result.
  2) Negative Internal control PCR lane: A parallel lane can be used to run a second PCR with reagents from the same mix without any sample. This can provide a control against false positive results due to contamination of the reagents. A failed result in the negative control lane can invalidate the result and can be indicated by an error code on the instrument. "IND" can be displayed to report an indeterminate result.

Exemplary Real time PCR for GBS DNA Detection

In various embodiments, the test can use real-time Polymerase Chain Reaction (PCR) for the amplification of a cfb gene sequence of GBS recovered from clinical samples and fluorogenic target-specific hybridization for the detection of the amplified DNA. The cfb gene encodes the CAMP factor, a diffusible extracellular protein which is typically present in GBS isolates. The Group B *Streptococcus* (GBS) detection test can be an integrated, raw-sample-to-result type of nucleic acid amplification assay. A TaqMan fluorogenic probe may be used to detect the PCR amplicons. Reagents used in the assay may be included on the cartridge to reduce potential for user handling errors and contamination.

Exemplary Potential Precautions

In some embodiments, the test system may not be qualified for identifying targets such as GBS DNA, in specimens other than vaginal and/or rectal specimens. Urine and Blood specimens may not be qualified.

In some embodiments, a patient undergoing antibiotic treatment may not be able to obtain a correct diagnosis with this or other diagnostic tests.

In some embodiments, the test may not yield a GBS culture suitable for direct identification of the bacteria by a microbiologist. In some embodiments, the test may not provide susceptibility results that are needed to recommend a treatment for penicillin-allergic persons.

Exemplary Potential Interfering Substances

In some embodiments, urine and vaginal secretions if present in very large quantities, may interfere with the test.

Typically, contaminants such as blood, meconium, and amniotic fluid contamination of the samples is not likely to interfere with the test.

Typically, drug interference (such as present in vaginal and rectal secretions), other than antibiotics, are not known at this time to interfere with PCR.

Exemplary Performance Characteristics and Interpretation

Figure 71:
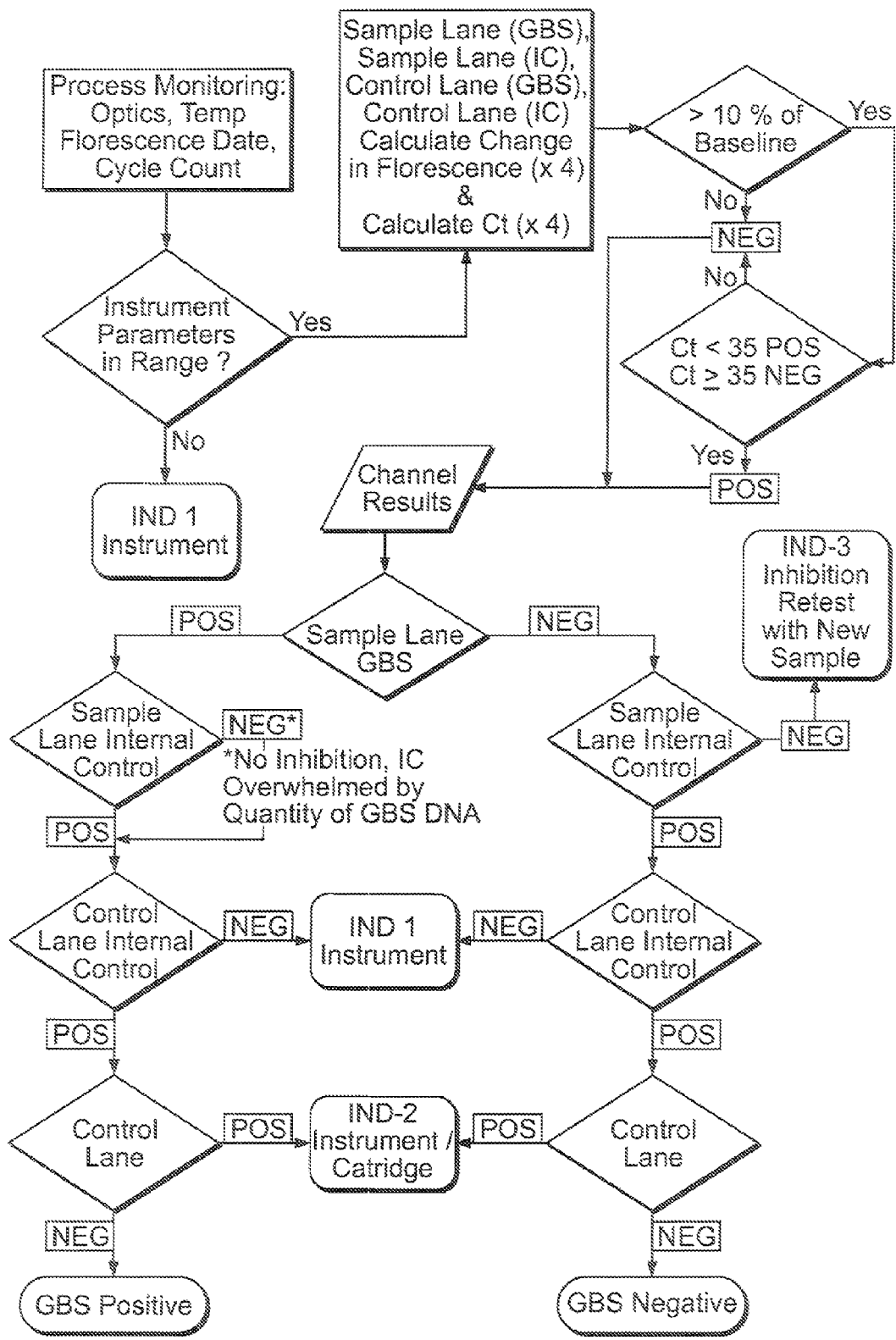
FIG. 71 is a flow chart that outlines an exemplary set of criteria which may be used by the decision algorithm in apparatus 800 to interpret the results, as described in Example 13.

The flow chart in FIG. 71 outlines an exemplary set of criteria which may be used by the decision algorithm in the instrument to interpret the results. PCR reactions (Sample and Control) may be interpreted as positive or negative for the target in question. A logical algorithm may be used to determine if sample is definitively Positive or Negative or Indeterminate.

Exemplary Cross Reacting Substances

Specificity of the primers and probes can be tested with real-time PCR (Taqman assay) using genomic DNAs isolated from the following organisms: nine GBS serotypes (serotype 1*a*, 1*b*, 1*c*, II, III, IV, V, VI and VII; American Type Culture Collection and National Center for *Streptococcus*, Canada); 10 clinical GBS isolates; 60 clinical samples; a wide variety of gram-positive and gram-negative bacterial strains as well as two yeast strains and RSV type I and 2.

Exemplary Microorganisms

| PATHOGEN | TYPE |
|---|---|
| *Pseudomones aeruginosa* | Gram – Bacteria |
| *Proteus mirabilis* | Gram – Bacteria |
| *Kiebsiella oxytoca* | Gram – Bacteria |
| *Kiebsiefla pneurnoniae* | Gram – Bacteria |
| *Escherichia cot* (clinical isolate 1) | Gram – Bacteria |
| *Escherichia coli* (clinical isolate 2) | Gram – Bacteria |
| *Acinetobacter baumannd* | Gram – Bacteria |
| *Serra. marcescens* | Gram – Bacteria |
| *Entembacter aerugenes* | Gram + Bacteria |
| *Enterococcus Maclean* | Gram + Bacteria |
| *Staphylococcus aureus* (clinical isolate 1) | Gram + Bacteria |
| *Staphylococcus aureus* (clinical isolate 2) | Gram + Bacteria |
| *Streptococcus pyogenes* | Gram + Bacteria |
| *Streptococcus viridans* | Gram + Bacteria |
| *Listena monocytogenes* | Gram + Bacteria |
| *Enterococcus* sps. | Gram + Bacteria |
| *Cendida glabrata* | Yeast |
| *Candida albicans* | Yeast |
| *Streptococcus* Group C | Gram + Bacteria |
| *Streptococcus* Group G | Gram + Bacteria |
| *Streptococcus* Group F | Gram + Bacteria |
| *Enterococcus feecalis* | Gram + Bacteria |
| *Streptococcus pneumoniae* | Gram + Bacteria |
| *Staphylococcus epidermidis* (C–) | Gram + Bacteria |
| *Gardenerella vaginalis* | Gram + Bacteria |
| *Micrococcus spa* | Gram + Bacteria |
| *Haemophilus influenza*° | Gram – Bacteria |
| *Neisseria gonorrhoeae* | Gram – Bacteria |
| *Moraxella catarrahlis* | Gram – Bacteria |
| *Salmonella* sps. | Gram – Bacteria |
| *Chlamytha trechomatis* | Gram – Bacteria |
| *Peptostreptococcus product.* | Gram + Bacteria |
| *Peptostreptococcus anaerobe.* | Gram + Bacteria |
| *Lactobacillus lennentum* | Gram + Bacteria |
| *Eubacterium lentum* | Gram + Bacteria |
| Herpes Simplex Virus I (HSV I) | Virus |
| Herpes Simplex Virus ll (HSV II) | Virus |

Exemplary Troubleshooting Chart

| Problem | Possible Cause | Possible Action |
|---|---|---|
| Positive Control reads negative re-suit. No other indication. | Sample not processed adequately. | Review sampling method. Retest. |
| | Bulk Lysis not performed, re-agents degraded. | Test new lot of cartridge. Review storage location of cartridge (<30C). Contact HandyLab. |
| Negative Control reads positive. No other indication. | Contamination | Clean Instrument. Review sampling method. Retest. |
| Error: IND (indeterminant result - IC fail) | IC fail, PCR not performed. | Test new lot of cartridge. |

-continued

| Problem | Possible Cause | Possible Action |
| --- | --- | --- |
| Error: IND (indeterminant result) | Borderline result - IC passed. | Retest with new patient sample. |

Example 14

Operator's Manual for Apparatus for Polynucleotide Processing

This non-limiting example describes, in the form of user instructions, various embodiments of the claimed apparatus, microfluidic cartridge, kit, methods, and computer program product, in particular directed to a microfluidic cartridge for use in a microfluidic PCR assays including the qualitative detection of microorganisms such as Group B *Streptococcus*.

Presence of Group B *Streptococci* (GBS) remains a leading cause of serious neonatal infection despite great progress in prevention since the 1990's with sepsis, pneumonia, and meningitis affecting the baby after birth. The GBS test system can be used for the rapid, qualitative detection of Group B *streptococcus* (GBS) DNA in vaginal/rectal samples.

Exemplary Use and Indications for Use

In various embodiments, the GBS test system can be used for the rapid, qualitative detection of microorganisms in clinical samples, such as Group B *streptococcus* (GBS) DNA in vaginal/rectal samples.

Typical indications for use of the GBS test include, for example, a rapid screening test in the prenatal care regimen for the maternity patient to determine the need for antibiotic treatment during labor, as described by the CDC guidelines (Centers for Disease Control and Prevention. Prevention of Perinatal Group B *Streptococcal* Disease: Revised Guideline from CDC. Morbidity and Mortality Weekly Report, Aug. 16, 2002; 51 (No. RR-11); 1-24). The test can provide rapid results at the point of care or in a central laboratory with rapid turnaround service during the intrapartum and prepartum phase of the maternity patient. The test can also be used to detect GBS DNA in vaginal or rectal samples of any subject suspected of GBS infection. See also Mark A. Burns, Brian N. Johnson, Sundaresh N. Brahmasandra, Kalyan Handique, James R. Webster, Madhavi Krishnan, Timothy S. Sammarco, Piu M. Man, Darren Jones, Dylan Heldsinger, Carlos H. Mastrangelo, David T. Burke "An Integrated Nanoliter DNA Analysis Device" *Science*, Vol. 282, 16 Oct. 1998.

Explanation of Test Application

The Center for Disease Control and Prevention recommends universal prenatal screening for vaginal/rectal GBS colonization of all women at 35-37 weeks gestation in order to determine the need for prophylactic antibiotics during labor and delivery. The current CDC recommendation is the culture-based test method (Standard Culture Method), from which results are typically available in 48-72 hours, compared to about 30 minutes for the present test. The test can utilize automated sample preparation and real-time PCR to identify the cfb gene in the GBS genome which is an established identification sequence that encodes the CAMP factor. The CAMP factor is an extra cellular protein typically present in GBS isolates. The CAMP factor can be used for the presumptive identification of GBS bacteria in clinical samples by the culture method. This test can be performed in the near-patient setting by clinicians who are not extensively trained in laboratory procedures. A QC routine can be built into the User Interface in order provide continued Quality Assurance for the GBS test. The test can also be performed in a central hospital "stat" laboratory provided that the sample testing occurs within the time-frame required by the maternity department.

Possible Contraindications

The GBS test may be contraindicated for persons with allergy to polyester contained in the specimen collection swab.

Exemplary Warnings & Precautions

Warnings herein may be additional to those of general application shown in Example 13, herein.

GBS test may not provide susceptibility results that are recommended for penicillin-allergic women.

Because IV antibiotics typically need to be started at least 4 hours before delivery, and in the absence of prepartum GBS data, it may be important to collect samples and start the GBS test as soon as possible after the patient enters the Labor and Delivery area of the hospital.

In some embodiments, if a patient is currently being treated with antibiotics, the test may be a unreliable indicator of disease state.

Buffer may contain Sodium Azide as a preservative. Health Hazard if ingested.

Typically, test the specimen within, for example, 8 hours of the sampling and storage in the buffer. In the situation where a specimen must be stored, refrigeration at 4 C for a duration of up to 24 hours may be used.

Typically, avoid use of the test materials beyond the expiration date.

Typically, avoid opening the cartridge until after the sample is ready to be injected. Typically, avoid using a cartridge if the protective, metallized bag is opened. In some embodiments, light, air and moisture exposure may degrade the reagents.

Typically, use swabs, syringe and buffer provided in test kit. In some embodiments, other brands of GBS collection swab may interfere with the test performance.

Typically, materials are single use only; reusing materials may give erroneous results.

Avoid opening cartridge package until ready to test. Onboard reagents may be sensitive to light and moisture. Avoid use if package seal is broken and foil pouch is no longer expanded (puffy).

Exemplary Sample Collection Kit

A. Swabs

B. Tubes containing sample collection buffer.

C. Cannula tips

D. Syringes (e.g., 3 cc)

E. Syringe filters

F. GBS microfluidic cartridge

Exemplary Specimen Collection & Buffer Suspension Instructions

Caution: Typically, use only collection kit; avoid touching end of swab with fingers.

Remove swab from packaging.

Wipe away excess vaginal secretions.

Insert swab 2 cm into vagina (front passage).

Insert same swab 1 cm into anus (back passage).

Confirm Vial of Sample buffer (B) is not expired.

Dip swab (A) vigorously up and down 20 times into vial containing buffer.
Remove and discard swab.
Label vial with patient ID information
Exemplary Preparation of Sample for Testing
　Cannula tip (C) can be attached to the syringe (D)
　Draw some or all of sample into syringe.
　May draw in additional air (e.g., 2 ml).
　Cannula tip (C) may be replaced with filter (E).
　Cartridge Package can be opened at the tear points marked on the package.
　Barcodes of the Sample vial (B) and Cartridge (F) can be scanned with the System scanner. System may warn if materials are expired.
　Patient identification information can be entered, if needed.
　Can lay cartridge on flat surface or hold it flat with luer in upright position. Typically, assure that the the cartridge remains label side up during the procedure.
　Sample (including excess air) can be injected into cartridge using syringe/filter assembly. Gentle injection pressure can be used to avoid backsplash from sample.
　Syringe/filter assembly can be removed from cartridge.
　Cartridge can be gently rocked side-to-side about 10 times until the pellets inside the sample chamber are dissolved and mixed.
　Cartridge can be placed on the System
Cover of the System can be closed and handle can be locked in down position. (Test may begin automatically)
Results
　When test is complete, results may be clearly displayed. Results can be printed or stored as determined by lab procedures.
Exemplary Disposal of Materials
　Cartridge and collection kit should be treated as biohazard.
Exemplary Recommended Lab Quality Control Routine
Exemplary Test Verification
　On a weekly basis, (1) positive external control and (1) negative external control can be run. A QC set to confirm system total system performance. This procedure is also recommended when training new users.
Exemplary Quality Control Routine Directions:
　May run samples as directed on display screens. If a QC test fails to yield expected results, manufacturer can be contacted.
　The external positive control can include a lyophilized aliquot of *Streptococcus agalactiae* (GBS) cells that are reconstituted at run-time with sample collection buffer. The number of GBS cells in the external positive control may be approximately equal to the Minimum Detectable Limit (MDL) of the test.
　Exemplary quality control tests also include an System Self-test QC, as described in Example 14.
Exemplary Internal Controls (On-Cartridge)
　Typical reagents for the assay may be included on the cartridge to reduce the potential for user handling errors and contamination. Two types of on-cartridge positive and negative controls strategies may be incorporated within each microfluidic cartridge to monitor individual PCR assay performance.
　An exemplary positive internal control plasmid for GBS is a double stranded circular DNA molecule containing a 96 bp region comprised of a unique 39 bp artificial DNA sequence flanked by the forward and reverse sequences from the cfb gene can be included in the lyophilized master mix along with a second distinct fluorogenic probe specific to this unique sequence. The Failure to amplify the internal control sequence, in the absence of a positive GBS sample, can be indicative of either a failure of the reagent mix or presence of PCR inhibitors in the specimen.

Exemplary Real Time PCR for GBS DNA Detection
　The test can utilize real-time Polymerase Chain Reaction (PCR) for the amplification of a cfb gene sequence of GBS recovered from clinical samples. A fluorogenic target-specific Tacman® probe can be used for the detection of the amplified DNA. The cfb gene encodes the CAMP factor, a diffusible extracellular protein which is typically present in GBS isolates. The Group B *Streptococcus* (GBS) detection test may be an integrated, raw-sample-to-result type of nucleic acid amplification assay. Typical reagents for the assay can be included on the cartridge to reduce potential for user handling errors and cross contamination.

Exemplary Possible Test Limitations
　In some embodiments, the test system may not be qualified for identifying GBS DNA in specimens other than vaginal/rectal specimens. For example, urine and blood specimens may not be qualified in some embodiments.
　In some embodiments, a patient undergoing antibiotic treatment may not be able to obtain a correct GBS diagnosis.
　In some embodiments, the test may not yield a GBS culture suitable for direct identification of the bacteria by a microbiologist.

Exemplary Performance Characteristics and Interpretation
　10-30% of pregnant women are colonized with GBS. The GBS colonization cut-off is determined to be approximately 1000 copies of DNA/sample determined by amplification of the cfb gene sequence. The user is referred to the flow-chart of FIG. 71 for application of exemplary criteria for result interpretation, where the target in question is GBS and IC plasmid.

Exemplary Possible Interfering Substances
　In some embodiments, urine or vaginal secretions, or mucus, if present in large quantities, may interfere with test.
　In some embodiments, blood, meconium, or amniotic fluid contamination of the samples is typically not likely to interfere with the test.
　In some embodiments, drug interference (present in vaginal and rectal secretions), other than antibiotics, are typically not known at this time to interfere with PCR.

Exemplary Results Interpretation and Expected Values
　10-30% of pregnant women can be colonized with GBS. The GBS colonization cut-off can be determined to be approximately 1000 copies of DNA/sample determined by amplification of the cfb gene sequence.
　PCR reactions can be interpreted as positive or negative for GBS and Internal control. A logical algorithm may be used to determine if sample is Positive or Negative or Indeterminate.

Exemplary Storage and Stability Information

| Description | Storage/Use Condition | Stability |
| --- | --- | --- |
| Patient Specimen in buffer (wet) | @ 15-30° C. | 8 hours |
| Patient Specimen in buffer (wet) | @ 4° C. | 24 hours |
| Patient Specimen (dry storage) | @ 15-30° C. | 24 hours |
| GBS Cartridges - unopened | 4-30° C. | Expiration date |
| GBS Cartridges - opened | Do not use. | 60 minutes max. |

Each reference cited herein is incorporated by reference in its entirety, including: U.S. Pat. Nos. 6,057,149, 6,048,734, 6,130,098, 6,271,021, 6,911,183, CA2,294,819, 6,575,188, 6,692,700, 6,852,287, and Canadian patent application no. CA 2,294,819.
　A number of embodiments of the technology have been described. Nevertheless, it will be understood that various modifications may be made without departing from the spirit and scope of the technology. Accordingly, other embodiments are within the scope of the following claims.

What is claimed is:

1. An apparatus, comprising:
a receiving bay configured to receive an insertable multi-lane microfluidic cartridge comprising a plurality of PCR reaction zones, each reaction zone configured to accept a polynucleotide-containing sample, each lane comprising one of the plurality of PCR reaction zones;
a processor;
a memory in communication with the processor;
a plurality of heater sets fixed in position in the receiving bay, each heater set configured to thermally couple to one of the plurality of PCR reaction zones in the multi-lane cartridge, each heater set comprising a plurality of heat sources, the memory comprising instructions that direct the processor to independently control the temperature of the plurality of heat sources in each heater set to cyclically heat one of the plurality of PCR reaction zones in a series of heating phases without moving the plurality of heat sources relative to each other, the memory further comprising instructions that direct the processor to control the temperature of the plurality of heat sources to maintain a substantially uniform temperature throughout one of the plurality of PCR reaction zones during each heating phase without moving the plurality of heat sources relative to each other, the memory further comprising instructions that direct the processor to perform independent PCR reactions on polynucleotide-containing samples in the multi-lane cartridge; and
a detector configured to detect the presence of one or more amplified polynucleotides on the multi-lane microfluidic cartridge.

2. The apparatus of claim 1, further comprising a registration member that is complementary to the multi-lane microfluidic cartridge, whereby the receiving bay receives the multi-lane microfluidic cartridge in a single orientation.

3. The apparatus of claim 1, further comprising a sensor coupled to the processor, the sensor configured to sense whether the multi-lane microfluidic cartridge is received.

4. The apparatus of claim 1, wherein the detector is an optical detector.

5. The apparatus of claim 4, wherein the optical detector comprises a light source configured to emit light in an absorption band of a fluorescent dye, and wherein the optical detector further comprises a light detector configured to detect light in an emission band of the fluorescent dye, wherein the fluorescent dye corresponds to a fluorescent polynucleotide probe or a fragment thereof.

6. The apparatus of claim 4, wherein the optical detector is configured to independently detect a plurality of fluorescent dyes at a plurality of different locations of the multi-lane microfluidic cartridge, wherein each fluorescent dye corresponds to a fluorescent polynucleotide probe or a fragment thereof.

7. The apparatus of claim 1, wherein the processor is programmable to operate the detector to detect a polynucleotide or a probe thereof in the multi-lane microfluidic cartridge.

8. The apparatus of claim 1, wherein each of the plurality of heater sets comprises at least two contact heat sources.

9. The apparatus of claim 8, wherein at least one of the at least two contact heat sources is selected from a group consisting of: a resistive heater, a radiator, a fluidic heat exchanger, and a Peltier device.

10. The apparatus of claim 8, wherein the at least two contact heat sources are configured to be in direct physical contact with the multi-lane microfluidic cartridge when the multi-lane microfluidic cartridge is inserted into the receiving bay.

11. The apparatus of claim 1, wherein at least one of the plurality of heater sets has a heating area of between about 1 $mm^2$ and about 225 $mm^2$.

12. The apparatus of claim 11, wherein the heating area is between about 1 $mm^2$ and about 100 $mm^2$.

13. The apparatus of claim 8, further comprising a compliant layer at the at least two contact heat sources, wherein the compliant layer is configured to thermally couple the at least two contact heat sources with one or more selected regions of the multi-lane microfluidic cartridge.

14. The apparatus of claim 13, wherein the compliant layer has a thickness of between about 0.05 and about 2 millimeters and a Shore hardness of between about 25 and about 100.

15. The apparatus of claim 1, wherein at least one of the plurality of heat sources is a resistive heater.

16. The apparatus of claim 1, further comprising a heating stage configured to be removable from the apparatus wherein at least one of the plurality of heat sources is located in the heating stage.

17. The apparatus of claim 1, further comprising a lid at the receiving bay, the lid being operable to at least partially exclude ambient light from the receiving bay.

18. The apparatus of claim 17, wherein the lid is a sliding lid.

19. The apparatus of claim 1, wherein the plurality of heater sets comprise a plurality of resistive heaters.

20. The apparatus of claim 19, wherein the plurality of resistive heaters in each heater set align with one PCR reaction zone in one lane of the multi-lane microfluidic cartridge when the multi-lane microfluidic cartridge is inserted into the receiving bay.

21. The apparatus of claim 1, wherein the apparatus is configured to direct, under the control of the processor, electrical signals to each of the plurality of heat sources in each heater set independently.

22. The apparatus of claim 1, further comprising one or more force members configured to apply force to at least a portion of the multi-lane microfluidic cartridge.

23. The apparatus of claim 22, wherein the one or more force members are configured to operate a mechanical member at the multi-lane microfluidic cartridge.

24. The apparatus of claim 23, wherein the mechanical member is a pierceable reservoir.

25. The apparatus of claim 22, wherein the one or more force members are configured to apply force to a plurality of locations in the multi-lane microfluidic cartridge.

26. The apparatus of claim 22, wherein the force applied by the one or more force members results in an average pressure at an interface between a portion of the receiving bay and a portion of the multi-lane microfluidic cartridge of between about 5 kilopascals and about 50 kilopascals.

27. The apparatus of claim 26, wherein the average pressure is at least about 14 kilopascals.

28. The apparatus of claim 22, wherein at least one of the one or more force members is manually operated.

29. The apparatus of claim 22, wherein at least one of the one or more force members is mechanically coupled to a lid at the receiving bay, whereby operation of the lid operates the force member.

30. The apparatus of claim 1, further comprising at least one input device coupled to the processor, the at least one input device being selected from a group consisting of a keyboard, a touch-sensitive surface, a microphone, a trackpad, a retinal scanner, a fingerprint reader, and a mouse.

31. The apparatus of claim 1, further comprising a data storage medium configured to receive data from one or more of a processor, an input device, or a communication interface, the data storage medium being selected from a group consisting of: a hard disk drive, an optical disk drive, a flash-card, and a CD-Rom.

32. The apparatus of claim 1, further comprising a communication interface coupled to the processor, the communication interface being selected from a group consisting of: a serial connection, a parallel connection, a wireless network connection, and a wired network connection.

33. The apparatus of claim 1, further comprising at least one sample identifier coupled to the processor, the at least one sample identifier being selected from a group consisting of: an optical character reader, a bar code reader, and a radio frequency tag reader.

34. The apparatus of claim 33, wherein the at least one sample identifier is a handheld bar code reader.

35. The apparatus of claim 1, further comprising at least one output device coupled to the processor, the at least one output device being selected from a group consisting of: a visual display, a printer, and a speaker.

36. The apparatus of claim 1, wherein the detector is configured to detect the presence of one or more amplified polynucleotides that are amplified by a method selected from a group consisting of: polymerase chain reaction; TMA; SDA; NASBA; LCR; and Rolling-Cycle Amplifications.

37. A system comprising the apparatus of claim 1 and a multi-lane microfluidic cartridge inserted into the receiving bay of the apparatus, wherein the multi-lane microfluidic cartridge comprises:
   a sample inlet for receiving a quantity of biological sample containing one or more polynucleotides; and
   a port permitting detection of one or more amplified polynucleotides.

38. A system comprising the apparatus of claim 1 and a multi-lane microfluidic cartridge inserted into the receiving bay of the apparatus, wherein the multi-lane microfluidic cartridge comprises:
   one or more reagents configured to:
   lyse cells in the sample;
   prepare the polynucleotides for amplification; and
   amplify the polynucleotides.

39. The system of claim 38, wherein the one or more reagents are held in one or more reagent retention vessels.

40. The system of claim 38, wherein the one or more reagents are held in a microfluidic chamber or a channel.

41. A system comprising the apparatus of claim 1 and a multi-lane microfluidic cartridge inserted into the receiving bay of the apparatus, wherein the multi-lane microfluidic cartridge comprises: one or more microfluidic components configured to act on microfluidic volumes of polynucleotide containing sample before, during and after amplification of one or more polynucleotides from the sample, the one or more microfluidic components being selected from a group consisting of: one or more channels configured to permit passage of the microfluidic volumes; one or more actuators configured to move the microfluidic volumes; one or more chambers configured to hold the microfluidic volumes; and one or more components configured to inhibit motion of the microfluidic volumes.

42. The system of claim 41, wherein the one or more components configured to inhibit motion of the microfluidic volumes comprise:
   a microfluidic valve configured to transform from an open to a closed state or
   a microfluidic gate configured to transform from a closed to an open state.

43. The system of claim 38, wherein the one or more reagents are in freeze-dried form.

44. The system of claim 37, wherein the multi-lane microfluidic cartridge further comprises a waste reservoir for storing waste generated during sample processing and waste from the biological sample.

45. The apparatus of claim 1, wherein the plurality of heat sources are configured to maintain a temperature gradient of less than 1° C. across a width of one of the plurality of PCR reaction zones at any point along a length of one PCR reaction zone.

46. The apparatus of claim 1, wherein the plurality of heat sources comprises four heaters configured to thermally couple to four sides of one of the plurality of PCR reaction zones.

47. The apparatus of claim 1, wherein each heater set further comprises one or more temperature sensors configured to control power supplied to the plurality of heat sources, the one or more temperature sensors further configured to transmit temperature information to the processor.

48. An apparatus, comprising:
   a receiving bay configured to receive an insertable multi-lane microfluidic cartridge, the receiving bay comprising a plurality of contact heating zones, each of the plurality of contact heating zones configured to be independently thermally coupled to a distinct location in one lane of the multi-lane microfluidic cartridge;
   a processor;
   a memory in communication with the processor and comprising instructions;
   a plurality of heater sets fixed in position in the receiving bay, each heater set thermally coupled to one of the plurality of contact heating zones, each heater set comprising a plurality of heat sources, the memory comprising instructions that direct the processor to independently control the temperature of the plurality of heat sources in each heater set to cyclically heat one of the plurality of contact heating zones in a series of heating phases without moving the plurality of heat sources relative to each other, the memory further comprising instructions that direct the processor to control the temperature of the plurality of heat sources to maintain a substantially uniform temperature throughout one of the plurality of contact heating zones during each heating phase without moving the plurality of heat sources relative to each other, the memory further comprising instructions that independently operate each of the plurality of contact heating zones to carry out nucleic acid amplification on polynucleotide-containing samples in the multi-lane microfluidic cartridge; and
   a detector configured to detect the presence of one or more amplified polynucleotides on the multi-lane cartridge.

49. The apparatus of claim 48, wherein one of the plurality of heater sets comprises four heaters configured to thermally couple to one of the plurality of contact heating zones.

50. The apparatus of claim 48, wherein each of the plurality of heater sets comprises at least two contact heat sources, and wherein at least one of the at least two contact heat sources is selected from a group consisting of: a resistive heater, a radiator, a fluidic heat exchanger, and a Peltier device.

51. The apparatus of claim 50, wherein the at least two contact heat sources are configured to be in direct physical contact with one of the plurality of contact heating zones.

52. The apparatus of claim 50, wherein at least one of the plurality of heater sets has a heating area for contacting one of the plurality of contact heating zones of between about 1 mm$^2$ and about 225 mm$^2$.

* * * * *